(12) United States Patent
Tange et al.

(10) Patent No.: US 11,299,717 B2
(45) Date of Patent: Apr. 12, 2022

(54) PRODUCTION OF CITRONELLAL AND CITRONELLOL IN RECOMBINANT HOSTS

(71) Applicants: Evolva SA, Reinach (CH); Takasago International Corporation, Tokyo (JP)

(72) Inventors: Thomas Oestergaard Tange, Reihen (CH); Johannes Haerle, Reinach (CH); Fanny Delegrange, Hagenthal le Haut (FR); Julien Denis Vivian De Block, Allschwil (CH); Robert Charles Allan, Basel (CH); Philipp Friedrich Berninger, Basel (CH); Christophe Folly, Basel (CH); Davide Antonio Ravasio, Breitenbach (CH); Ludivine Labagnere, Saint Louis (FR); Federico Brianza, Riehen (CH); Curt Aimé Friis Nielsen, Reinach (CH); Jørgen Hansen, Frederiksberg (DK); Nora Weber, Leymen (FR); Samantha Jessica Capewell, Basel (CH)

( * ) Notice: Subject to any disclaimer, the term of this patent is extended or adjusted under 35 U.S.C. 154(b) by 0 days.

(21) Appl. No.: 16/338,186

(22) PCT Filed: Oct. 11, 2017

(86) PCT No.: PCT/EP2017/075995
§ 371 (c)(1),
(2) Date: Mar. 29, 2019

(87) PCT Pub. No.: WO2018/069418
PCT Pub. Date: Apr. 19, 2018

(65) Prior Publication Data
US 2019/0225945 A1 Jul. 25, 2019

Related U.S. Application Data

(60) Provisional application No. 62/406,906, filed on Oct. 11, 2016.

(51) Int. Cl.
*C12P 7/00* (2006.01)
*C12N 9/02* (2006.01)
(Continued)

(52) U.S. Cl.
CPC .............. *C12N 9/001* (2013.01); *C12N 9/00* (2013.01); *C12N 9/0006* (2013.01);
(Continued)

(58) Field of Classification Search
CPC ........ C12N 9/001; C12N 9/1085; C12N 9/16; C12N 9/0006; C12P 5/007
See application file for complete search history.

(56) References Cited

U.S. PATENT DOCUMENTS

2010/0112671 A1   5/2010   Keasling et al.

FOREIGN PATENT DOCUMENTS

| WO | WO 2014/027118 A1 | 2/2014 | |
|---|---|---|---|
| WO | WO 2016/008883 A1 | 1/2016 | |
| WO | WO-2016108236 A1 * | 7/2016 | ............. A01N 43/90 |

OTHER PUBLICATIONS

Pardo. De novo production of six key grape aroma monoterpenes by a geraniol synthase-engineered S. cerevisiae wine strain. Microb Cell Fact. 2015; 14: 136. Published online Sep. 16, 2015.*

(Continued)

*Primary Examiner* — Yong D Pak
(74) *Attorney, Agent, or Firm* — McDonnell Boehnen Hulbert & Berghoff LLP

(57) ABSTRACT

The invention relates to recombinant microorganisms and methods of producing citronellal, citronellol, citronellic acid, and/or citronellal/citronellol pathway intermediates and precursors.

6 Claims, 35 Drawing Sheets

Specification includes a Sequence Listing.

(51) Int. Cl.
| | |
|---|---|
| *C12N 9/04* | (2006.01) |
| *C12N 9/10* | (2006.01) |
| *C12N 9/16* | (2006.01) |
| *C12N 15/52* | (2006.01) |
| *C12P 7/24* | (2006.01) |
| *C12P 7/40* | (2006.01) |
| *C12N 9/00* | (2006.01) |
| *C12P 5/00* | (2006.01) |
| *C12P 7/04* | (2006.01) |

(52) U.S. Cl.
CPC ......... *C12N 9/0008* (2013.01); *C12N 9/0036* (2013.01); *C12N 9/104* (2013.01); *C12N 9/1085* (2013.01); *C12N 9/16* (2013.01); *C12N 15/52* (2013.01); *C12P 5/007* (2013.01); *C12P 7/24* (2013.01); *C12P 7/40* (2013.01); *C12Y 101/01021* (2013.01); *C12Y 101/01183* (2013.01); *C12Y 102/99006* (2013.01); *C12Y 103/01031* (2013.01); *C12Y 205/01001* (2013.01); *C12Y 301/07011* (2015.07); *C12P 7/04* (2013.01)

(56) References Cited

OTHER PUBLICATIONS

Alagna. Identification and Characterization of the Iridoid Synthase Involved in Oleuropein Biosynthesis in Olive (*Olea europaea*) Fruits. J Biol Chern. Mar. 11, 2016; 291(11): 5542-5554. Published online Dec. 26, 2015.*

Liu. Engineering *Escherichia coli* for high-yield geraniol production with biotransformation of geranyl acetate to geraniol under fed-batch culture. Biotechnol Biofuels (2016) 9:58. Published online : Mar. 11, 2016.*

GenBank. No. AY362553.1. 2004 and No. AF513112. 2002.*

Simkin. Characterization of the plastidial geraniol synthase from Madagascar periwinkle which initiates the monoterpenoid branch of the alkaloid pathway in internal phloem associated parenchyma. Phytochemistry 85 (2013) 36-43.*

Chaparro-Riggers. Comparison of Three Enoate Reductases and their PotentialUse for Biotransformations. Adv. Synth. Catal. 2007, 349, 1521-1531.*

Yang. Metabolic engineering of *Escherichia coli* for the biosynthesis of alpha-pinene. Biotechnology for Biofuels 2013, 6:60.*

A0A0K2YIV5_9NOCA. UniProtKB/TrEMBL. Nov. 11, 2015.*

International Preliminary Report on Patentability dated Apr. 16, 2019 in connection with International Application No. PCT/EP2017/075995, filed on Oct. 11, 2017, 13 pages.

International Search Report dated Apr. 14, 2018 in connection with International Application No. PCT/EP2017/075995, filed on Oct. 11, 2017, 9 pages.

Written Opinion of the International Searching Authority dated Apr. 14, 2018 in connection with International Application No. PCT/EP2017/075995, filed on Oct. 11, 2017, 12 pages.

Ziga, Z., et al. "Towards synthesis of monoterpenes and derivatives using synthetic biology," Current Opinion in Chemical Biology, Jun. 13, 2016, 34:37-43.

\* cited by examiner

PRODUCTION OF CITRONELLAL AND CITRONELLOL IN RECOMBINANT HOSTS

CROSS REFERENCE

This application is a U.S. National Stage Application of International Application No. PCT/EP2017/075995, filed on Oct. 11, 2017, and claims the benefit of U.S. Provisional Application No. 62/406,906, filed on Oct. 11, 2016, the disclosures of each of which are explicitly incorporated by reference herein in their entirety.

BACKGROUND OF THE INVENTION

Field of the Invention

This disclosure relates to production of citronellal and citronellol in recombinant hosts. In particular, this disclosure relates to the synthesis of citronellal, citronellol and citronellic acid precursors in recombinant hosts.

Description of Related Art

Citronellal is a monoterpenoid that provides a lemon scent that is commonly associated with citronella oil. In addition to providing a lemon-scented fragrance, citronellal has been shown to repel insects, including but not limited to mosquitos, and to have antifungal properties. Citronellal is also useful as a starting material for the asymmetric synthesis of related chiral compounds.

Citronellal is predominantly formed by the secondary metabolism of plants. Citronellal can be extracted from the oils of plants such as *Corymbia citriodora*, *Cymbopogon nardus*, and *Cymbopogon winterianus*. Citronellal is most commonly isolated by steam distillation or solvent extraction as a non-racemic mixture of its R- and S-enantiomers.

Citronellal can be reductively bioconverted to citronellol. Citronellol synthesis is usually done by hydrogenation of geraniol (trans) or nerol (cis). Similar to citronellal, citronellol is commonly used in the fragrance industry, acts as an insect repellent, and can be used as an intermediate in the synthesis of several natural terpenoids.

Because robust production of both citronellal and citronellol in, for example, the fragrance and pharmaceutical industries, significant agricultural resources in terms of land, equipment, and biomass generation are required to meet current industry needs. However, identifying alternative, highly efficient, and renewable sources of these compounds remains difficult. Moreover, greater purity of citronellal and citronellol compounds is needed but difficult to obtain from plant sources without additional processing steps. Therefore, there remains a need to develop alternative approaches for obtaining scalable amounts of highly pure citronellal and citronellol.

SUMMARY OF THE INVENTION

It is against the above background that the present invention provides certain advantages and advancements over the prior art. In particular, as set forth herein, the use of recombinant microorganisms: bacteria or yeast, to make citronellal and citronellol is disclosed.

Although this invention disclosed herein is not limited to specific advantages or functionalities the invention provides a recombinant host cell capable of producing a citronellal or a citronellic acid, comprising:

(a) a gene encoding a geranyl diphosphate synthase (GPPS) polypeptide;
(b) a gene encoding a geraniol synthase (GES) polypeptide;
(c) a gene encoding a geraniol dehydrogenase (GeDH) polypeptide; and
(d) a gene encoding a enoate reductase (ENR) polypeptide;

wherein at least one of the genes is a recombinant gene.

The invention also provides a recombinant host cell capable of producing a citronellal, a citronellol, or a citronellic acid, comprising:

(a) a gene encoding a geranyl diphosphate synthase (GPPS) polypeptide;
(b) a gene encoding a geraniol synthase (GES) polypeptide;
(c) a gene encoding a geraniol dehydrogenase (GeDH) polypeptide;
(d) a gene encoding a enoate reductase (ENR) polypeptide; and
(e) a gene encoding aldehyde reductase (AR) polypeptide;

wherein at least one of the genes is a recombinant gene.

In one aspect of the recombinant host cells disclosed herein:

(a) the ENR polypeptide catalyzes the formation of citronellal from geranial and/or neral; and
(b) the AR polypeptide catalyzes the formation of nerol from neral and/or citronellol from citronellal.

In one aspect of the recombinant host cells disclosed herein, the GES polypeptide catalyzes the formation of geraniol from geranyl diphosphate (GPP), wherein the GPP is produced by the GPPS polypeptide converting isopentyl pyrophosphate (IPP) and dimethylallyl pyrophosphate (DMAPP) from a mevalonate pathway and/or a methylerythritol 4-phosphate (MEP) pathway.

In one aspect of the recombinant host cells disclosed herein, the mevalonate pathway is an endogenous pathway or a recombinant pathway.

In one aspect of the recombinant host cells disclosed herein:

(a) the GPPS polypeptide comprises a polypeptide having at least 50% sequence identity to the amino acid sequence set forth in any one of SEQ ID NOs:17, 59-62, or 87-88;
(b) the GES polypeptide comprises a polypeptide having at least 40% sequence identity to the amino acid sequence set forth in any one of SEQ ID NOs:18 or 63-66;
(c) the GeDH polypeptide comprises a polypeptide having at least 45% sequence identity to the amino acid sequence set forth in any one of SEQ ID NOs:1-6, 19, 20, or 24-32;
(d) the ENR polypeptide comprises a polypeptide having at least 50% sequence identity to the amino acid sequence set forth in any one of SEQ ID NOs:7-9, 21, 22, 33, 34, 37, 44-48, 54, 55, or 67; and
(e) the AR polypeptide comprises a polypeptide having at least 90% sequence identity to the amino acid sequence set forth in any one of SEQ ID NOs: 31-32, 68, or 83-86.

The invention also provides a recombinant host cell capable of producing a citronellal, a citronellol, or a citronellic acid, comprising:

(a) a gene encoding a neryl diphosphate synthase (NPPS) polypeptide;
(b) a gene encoding a nerol synthase (NES) polypeptide;

(c) a gene encoding a nerol dehydrogenase (NeDH) polypeptide; and
(d) a gene encoding a enoate reductase (ENR) polypeptide;
wherein at least one of the genes is a recombinant gene.

The invention also provides a recombinant host cell capable of producing a citronellal, a citronellol, or a citronellic acid, comprising:
(a) a gene encoding a neryl diphosphate synthase (NPPS) polypeptide;
(b) a gene encoding a nerol synthase (NES) polypeptide;
(c) a gene encoding a nerol dehydrogenase (NeDH) polypeptide;
(d) a gene encoding a enoate reductase (ENR) polypeptide; and
(e) a gene encoding aldehyde reductase (AR) polypeptide;
wherein at least one of the genes is a recombinant gene.

In one aspect of the recombinant host cells disclosed herein:
(a) the ENR polypeptide catalyzes the formation of citronellal from geranial and/or neral; and
(b) the AR polypeptide catalyzes the formation of geraniol from geranial and/or citronellol from citronellal.

In one aspect of the recombinant host cells disclosed herein:
(a) the NPPS polypeptide comprises a polypeptide having at least 45% sequence identity to the amino acid sequence set forth in any one of SEQ ID NO:53 or 74-75;
(b) the NES polypeptide comprises a polypeptide having at least 45% sequence identity to the amino acid sequence set forth in any one of SEQ ID NOs:56-58 or 77-79;
(c) the NeDH polypeptide comprises a polypeptide having at least 50% sequence identity to the amino acid sequence set forth in any one of SEQ ID NOs:1-6, 19, 20, or 24-32;
(d) the ENR polypeptide comprises a polypeptide having at least 50% sequence identity to the amino acid sequence set forth in any one of SEQ ID NOs:7-9, 21, 22, 33, 34, 37, 44-48, 54-55, or 67;
(e) the AR polypeptide comprises a polypeptide having at least 90% sequence identity to the amino acid sequence set forth in any one of SEQ ID NOs:31, 32, or 83-86; and
(f) the ADH polypeptide comprises a polypeptide having at least 45% sequence identity to the amino acid sequence set for in SEQ ID NO:68.

The invention also provides a recombinant host cell capable of producing a citronellal and/or a citronellol, comprising:
(a) a gene encoding a geranyl diphosphate synthase (GPPS) polypeptide or a gene encoding a neryl diphosphate synthase (NPPS) polypeptide; and
(b) a gene encoding a geraniol synthase (GES) polypeptide or a gene encoding a neryl synthase (NES) polypeptide;
wherein the recombinant host cell further comprises a gene encoding a iridoid synthase (ISY) polypeptide or a gene encoding a enoate reductase (ENR) polypeptide; and wherein at least one of the genes is a recombinant gene.

The invention also provides a recombinant host cell capable of producing a citronellal, a citronellol, or a citronellic acid, comprising:
(a) a gene encoding a geranyl diphosphate synthase (GPPS) polypeptide or a gene encoding a neryl diphosphate synthase (NPPS) polypeptide, and;
(b) a gene encoding a geraniol synthase (GES) polypeptide or a gene encoding a neryl synthase (NES) polypeptide;
wherein the recombinant host cell further comprises a gene encoding a iridoid synthase (ISY) polypeptide and a gene encoding a citronellal/citronellol dehydrogenase (CiDH) polypeptide, and wherein at least one of the genes is a recombinant gene.

In one aspect of the recombinant host cells disclosed herein:
(a) the GPPS polypeptide comprises a polypeptide having at least 50% sequence identity to the amino acid sequence set forth in any one of SEQ ID NOs:17, 59-62, 87, or 88;
(b) the NPPS polypeptide comprises a polypeptide having at least 45% sequence identity to the amino acid sequence set forth in any one of SEQ ID NO:53, 74, or 75;
(c) the GES polypeptide comprises a polypeptide having at least 40% sequence identity to the amino acid sequence set forth in any one of SEQ ID NOs:18 or 63-66;
(d) the NES polypeptide comprises a polypeptide having at least 45% sequence identity to the amino acid sequence set forth in any one of SEQ ID NOs:56-58;
(e) the ISY polypeptide comprises a polypeptide having at least 50% sequence identity to the amino acid sequence set forth in any one of SEQ ID NOs:54 or 55;
(f) the ENR polypeptide comprises a polypeptide having at least 50% sequence identity to the amino acid sequence set forth in any one of SEQ ID NOs:7-9, 21, 22, 33, 34, 37, 44-48, 54, 55, or 67; and
(g) the CiDH polypeptide comprises a polypeptide having at least 80% sequence identity to the amino acid sequence set forth in any one of SEQ ID NOs:49-52.

In one aspect of the recombinant host cells disclosed herein, the citronellal is d-citronellal, l-citronellal, or a combination thereof.

In one aspect of the recombinant host cells disclosed herein, the citronellol is d-citronellol, l-citronellol, or a combination thereof.

In one aspect of the recombinant host cells disclosed herein, the recombinant host cell comprises a plant cell, a mammalian cell, an insect cell, a fungal cell, an algal cell, or a bacterial cell.

In one aspect of the recombinant host cells disclosed herein, the recombinant host cell is a bacterial cell.

In one aspect of the recombinant host cells disclosed herein, the bacterial cell is *Escherichia* cells, *Lactobacillus* cells, *Lactococcus* cells, *Corynebacterium* cells, *Acetobacter* cells, *Acinetobacter* cells, or *Pseudomonas* cells.

In one aspect of the recombinant host cells disclosed herein, the recombinant host cell is a yeast cell further comprising the deletion of one or more of ADH6, RFX1, GRE2, ARI1, GCY1, and AYR1.

In one aspect of the recombinant host cells disclosed herein, the yeast comprises:
(a) a deletion of ADH6, RFX1, GRE2, ARI1, GCY1, and AYR1; or
(b) a deletion of ADH6, RFX1, GRE2, and ARI1.

In one aspect of the recombinant host cells disclosed herein, the recombinant host cell is a yeast cell further comprising a gene encoding a heterologous NADH oxidase polypeptide.

In one aspect of the recombinant host cells disclosed herein, the heterologous NADH oxidase polypeptide comprises a polypeptide having at least 90% sequence identity to the amino acid sequence set forth in SEQ ID NO:69.

In one aspect of the recombinant host cells disclosed herein, the heterologous NADH oxidase polypeptide has the amino acid sequence set forth in SEQ ID NO:69.

In one aspect of the recombinant host cells disclosed herein, the recombinant host cell is a yeast cell further comprising a gene encoding a carboxylic acid reductase (CAR) polypeptide.

In one aspect of the recombinant host cells disclosed herein, the CAR polypeptide comprises a polypeptide having at least 75% sequence identity to the amino acid sequence set forth in SEQ ID NO:70.

In one aspect of the recombinant host cells disclosed herein, the CAR polypeptide has the amino acid sequence set forth in SEQ ID NO:70.

In one aspect of the recombinant host cells disclosed herein, the recombinant yeast cell further comprises a gene encoding a phosphopaneine transferase (PPTase) polypeptide.

In one aspect of the recombinant host cells disclosed herein, the PPTase polypeptide comprises a polypeptide having at least 75% sequence identity to the amino acid sequence set forth in SEQ ID NO:71.

In one aspect of the recombinant host cells disclosed herein, the PPTase polypeptide has the amino acid sequence set forth in SEQ ID NO:71

In one aspect of the recombinant host cells disclosed herein, the yeast cell is a *Saccharomyces cerevisiae* cell.

In one aspect of the recombinant host cells disclosed herein, the *Saccharomyces cerevisiae* cell contains a farnesyl pyrophosphate synthase (ERG20) gene that is transcriptionally downregulated or mutated to provide lower than wild type farnesyl pyrophosphate synthase activity.

The invention also provides a method of producing a citronellal, a citronellol, or a citronellic acid, comprising growing the recombinant host cells disclosed herein in a cell culture broth, under conditions in which the genes are expressed, wherein the citronellal, citronellol, or citronellic acid is produced by the recombinant host cell.

In one aspect of the methods disclosed herein, the recombinant host cell is transformed with one or more plasmids comprising a gene encoding the GPPS polypeptide or a gene encoding the NPPS polypeptide, a gene encoding the GES polypeptide or a gene encoding the NES polypeptide, a gene encoding the GeDH polypeptide or a gene encoding the NeDH polypeptide, a gene encoding the ISY polypeptide, a gene encoding the CiDH polypeptide, and/or a gene encoding the ENR polypeptide; wherein at least one of the genes is a recombinant gene.

In one aspect of the methods disclosed herein, the recombinant host cell is transformed with a gene encoding the GPPS polypeptide or a gene encoding the NPPS polypeptide, a gene encoding the GES polypeptide or a gene encoding the NES polypeptide, a gene encoding the GeDH polypeptide or a gene encoding the NeDH polypeptide, a gene encoding the ISY polypeptide, a gene encoding the CiDH polypeptide, and/or a gene encoding the ENR polypeptide; wherein at least one of the genes is a recombinant gene.

In one aspect of the methods disclosed herein, at least one of the recombinant genes is integrated within the host cell genome.

The invention also provides a method of producing a citronellal or a citronellol, comprising a whole-cell bioconversion of citronellal or citronellol precursors in a cell culture broth using one or more of:

(a) a geranyl diphosphate synthase (GPPS) polypeptide;
(b) a geraniol synthase (GES) polypeptide;
(c) a geraniol dehydrogenase (GeDH) polypeptide;
(d) a neryl diphosphate synthase (NPPS) polypeptide;
(e) a nerol synthase (NES) polypeptide;
(f) a nerol dehydrogenase (NeDH) polypeptide;
(g) a iridoid synthase (ISY) polypeptide;
(h) a citronellal/citronellol dehydrogenase (CiDH) polypeptide;
(i) an enoate reductase (ENR) polypeptide;
(j) an alcohol dehydrogenase (ADH) polypeptide; and/or
(k) an aldehyde reductase (AR) polypeptide;

wherein at least one of the polypeptides is a recombinant polypeptide; and producing the citronellal or the citronellol thereby.

In one aspect of the methods disclosed herein:
(a) the ENR polypeptide reduces geranial to citronellal; and
(b) the ADH and AR polypeptides reduce citronellal to citronellol.

In one aspect of the methods disclosed herein:
(a) the GPPS polypeptide comprises a polypeptide having at least 50% sequence identity to the amino acid sequence set forth in any one of SEQ ID NOs:17, 59-62, 87, or 88;
(b) the GES polypeptide comprises a polypeptide having at least 40% sequence identity to the amino acid sequence set forth in any one of SEQ ID NOs:18 or 63-66;
(c) the GeDH polypeptide comprises a polypeptide having at least 45% sequence identity to the amino acid sequence set forth in any one of SEQ ID NOs:1, 2, 3, 4, 5, 6, 19, 20, or 24-32;
(d) the NPPS polypeptide comprises a polypeptide having at least 45% sequence identity to the amino acid sequence set forth in any one of SEQ ID NOs:53, 74, or 75;
(e) the NES polypeptide comprises a polypeptide having at least 45% sequence identity to the amino acid sequence set forth in any one of SEQ ID NOs:56-58;
(f) the NeDH polypeptide comprises a polypeptide having at least 50% sequence identity to the amino acid sequence set forth in any one of SEQ ID NOs:1-6, 19, 20, or 24-32;
(g) the ISY polypeptide comprises a polypeptide having at least 50% sequence identity to the amino acid sequence set forth in any one of SEQ ID NOs:54 or 55;
(h) the CiDH polypeptide comprises a polypeptide having at least 80% sequence identity to the amino acid sequence set forth in any one of SEQ ID NOs:49-52
(i) the ENR polypeptide comprises a polypeptide having at least 50% sequence identity to the amino acid sequence set forth in any one of SEQ ID NOs:7-9, 21, 22, 33, 34, 37, 44-48, 54, 55, or 67;
(j) the ADH polypeptide comprises a polypeptide having at least 45% sequence identity to the amino acid sequence set for in SEQ ID NO:68; and
(k) the AR polypeptide comprises a polypeptide having at least 90% sequence identity to the amino acid sequence set forth in any one of SEQ ID NO:31, 32, or 83-86.

The invention also provides a method of producing a citronellal or a citronellol, comprising:
(a) providing a recombinant host cell with mevalonate pathway comprising genes capable of converting acetyl-CoA to isopentyl pyrophosphate (IPP) and dimethylallyl pyrophosphate (DMAPP); wherein the recombinant host cell is a bacterial, fungal, algal, or yeast cell;
(b) providing a citronellal plasmid comprising:
   (i) a gene encoding a polypeptide with geranyl diphosphate synthase (GPPS) activity;
   (ii) a gene encoding a geraniol synthase (GES) polypeptide;
   (iii) a gene encoding a geraniol dehydrogenase (GeDH) polypeptide;
   (iv) a gene encoding a enoate reductase (ENR) polypeptide; and/or
   (v) a gene encoding aldehyde reductase (AR) polypeptide;
(c) transforming the recombinant host cell with the citronellal plasmid; and
(d) culturing the recombinant host cell transformed with the citronellal plasmid in a culture broth;
wherein the citronellal or the citronellol is produced by the recombinant host cell.

In one aspect of the methods disclosed herein, the mevalonate pathway is endogenous or exogenous to the host cell, and is subdivided into one or more operons or coordinated gene regulation element.

In one aspect of the methods disclosed herein, a first operon of the one or more operons or coordinated gene regulation element comprises:
(a) a promoter;
(b) a gene encoding a *Escherichia coli* MG1655 Acetyl-CoA acetyltransferase (Ec_atoB) polypeptide;
(c) a gene encoding a *Lactobacillus casei* hydroxymethylglutaryl-CoA synthase (Lc_MvaS) polypeptide; and
(d) a gene encoding a *Lactobacillus casei* hydroxymethylglutaryl-CoA synthase (Lc_MvaA) polypeptide.

In one aspect of the methods disclosed herein, a second operon of the one or more operons or coordinated gene regulation element comprises:
(a) a promoter;
(b) a gene encoding a *Saccharomyces cerevisiae* mevalonate kinase (Sc_erg12) polypeptide or *Methanosarcina mazei* mevalonate kinase (Mm_MK) polypeptide;
(c) a gene encoding a *Saccharomyces cerevisiae* phosphomevalonate kinase (Sc_erg8) polypeptide;
(d) a gene encoding a *Saccharomyces cerevisiae* Diphospomevalonate decarboxylase (Sc_erg19) polypeptide; and
(e) a gene encoding a *Escherichia coli* Isopentenyl diphosphate isomerase (Ec_idi) polypeptide or a *Streptomyces pneumoniae* Isopentyl diphosphate isomerase (Sp_idi) polypeptide.

In one aspect of the methods disclosed herein, the citronellal plasmid comprises:
(a) at least one promoter;
(b) a gene encoding a geranyl diphosphate synthase polypeptide; and
(c) a gene encoding a geraniol synthase polypeptide; and further comprising:
(d) an ENR polypeptide encoded by a gene that is a gene encoding *Kluyveromyces lactis* Yellow Enzyme (Kl_KYE1) polypeptide, Ene reductase (Ps_OYE2.6) polypeptide, *Zymomonas mobilis* ENR (Zm_OYE) polypeptide, *S. cerevisiae* ENR (Sc_OYE2) polypeptide, or Sc_OYE3 polypeptide; or
(e) a GeDH polypeptide encoded by a gene that is a gene encoding *Castellaniella defragrans* geraniol dehydrogenase (Cd_GeDH) polypeptide, *Rhodococcus* sp. RD6.2 geraniol dehydrogenase (Rs_GeDH) polypeptide, *Sphingopyxis macrogoltabida* geraniol dehydrogenase (Sm_GeDH) polypeptide, *Acinetobacter calcoaceticus* geraniol Dehydrogenase (Ac_GeDH) polypeptide, or *Thauera terpenica* 58Eu geraniol dehydrogenase (Tt_GeDH) polypeptide.

In one aspect of the methods disclosed herein, the gene encoding a geranyl diphosphate synthase is *Abies grandis* geranyl diphosphate synthase (Ag_GPPS2) or *Picea glauca* geranyl diphosphate synthase (Pg_GPPS), and the gene encoding a geraniol synthase is *Catharanthus roseus* eraniol Synthase (Cr_GES), *Ocimum basilicum* geraniol synthase (Ob_GES), *Phyla dulcis* geraniol synthase (Pd_GES), or *Valeriana officinalis* geraniol synthase (VO_GES) gene.

In one aspect of the methods disclosed herein, the culture media further comprises nerol and/or geraniol.

In one aspect of the methods disclosed herein, the host cell is contacted with an oxidizing bacteria.

In one aspect of the methods disclosed herein, the oxidizing bacteria is from the genus *Gluconobacter*.

In one aspect of the methods disclosed herein, the oxidizing bacteria is *Gluconobacter cerinus, Gluconobacter frateurii,* or *Gluconobacter oxydans*.

In one aspect, the methods disclosed herein further comprise isolating the produced citronellal, the citronellol, or the citronellic acid alone or a combination thereof.

In one aspect of the methods disclosed herein, isolating step comprises:
(a) providing the cell culture broth comprising the produced citronellal, the citronellol, or the citronellic acid alone or the combination thereof;
(b) separating a liquid phase of the cell culture broth from a solid phase of the cell culture broth to obtain a supernatant comprising the produced citronellal, the citronellol, or the citronellic acid alone or the combination thereof;
(c) providing one or more adsorbent resins in a one or more packed ion exchange or reversed-phase chromatography columns; and
(d) contacting the supernatant of step (b) with the one or more adsorbent resins in the one or more packed ion exchange or reversed-phase chromatography columns in order to obtain at least a portion of the produced citronellal, the citronellol, or the citronellic acid alone or the combination thereof, thereby isolating the produced citronellal, the citronellol, or the citronellic acid alone or the combination thereof.

In one aspect of the methods disclosed herein, isolating step comprises:
(a) providing the cell culture broth comprising the produced citronellal, the citronellol, or the citronellic acid alone or the combination thereof;
(b) separating a liquid phase of the cell culture broth from a solid phase of the cell culture broth to obtain a supernatant comprising the produced citronellal, the citronellol, or the citronellic acid alone or the combination thereof;
(c) crystallizing or extracting one or more of the produced citronellal, the citronellol, or the citronellic acid alone or the combination thereof, thereby isolating the produced citronellal, the citronellol, or the citronellic acid alone or the combination thereof.

In one aspect, the methods disclosed herein further comprise recovering the citronellal, the citronellol, the citronellic acid, or a composition thereof.

In one aspect of the methods disclosed herein, the recovered composition is enriched with an optically pure composition of citronellal or citronellol.

In one aspect of the methods disclosed herein, the recombinant host cell is a bacterial cell.

In one aspect of the methods disclosed herein, the bacterial cell is *Escherichia* cells, *Lactobacillus* cells, *Lactococcus* cells, *Cornebacterium* cells, *Acetobacter* cells, *Acinetobacter* cells, or *Pseudomonas* cells.

In one aspect of the methods disclosed herein, the recombinant host cell is a yeast cell.

In one aspect of the methods disclosed herein, the yeast cell is *Saccharomyces cerevisiae*.

The invention also provides a use of a GeDH polypeptide in the manufacture of geranial, citronellal, citronellol, citronellic acid, or a combination thereof.

The invention also provides a use of a NeDH polypeptide in the manufacture of neral, citronellal, citronellol, or citronellic acid or a combination thereof.

The invention also provides a use of a GeDH polypeptide and/or a NeDH polypeptide for the manufacture of geranial, neral, citronellal, citronellol, or citronellic acid or a combination thereof.

The invention also provides a use of a CiDH polypeptide in the manufacture of citronellal, citronellic acid or a combination thereof.

The invention also provides a use of a GeDH polypeptide in an in vitro or a whole-cell bioconversion manufacture of geranial, citronellal, citronellol, or citronellic acid or a combination thereof.

The invention also provides a use of a NeDH polypeptide in an in vitro or a whole-cell bioconversion manufacture of neral, citronellal, citronellol, or citronellic acid or a combination thereof.

The invention also provides a use of a GeDH polypeptide and a NeDH polypeptide in an in vitro or a whole-cell bioconversion manufacture of geranial, neral, citronellal, citronellol, or citronellic acid or a combination thereof.

The invention also provides a use of a CiDH polypeptide in an in vitro or a whole-cell bioconversion manufacture of citronellal, citronellic acid, or a combination thereof.

In one aspect of the uses disclosed herein, the GeDH polypeptide comprises a polypeptide having at least 45% sequence identity to the amino acid sequence set forth in any one of SEQ ID NOs:1-6, 19, 20, or 24-32.

In one aspect of the uses disclosed herein, the NeDH polypeptide comprises a polypeptide having at least 50% sequence identity to the amino acid sequence set forth in any one of SEQ ID NOs:1-6, 19, 20, or 24-32.

In one aspect of the uses disclosed herein, the CiDH polypeptide comprises a polypeptide having at least 80% sequence identity to the amino acid sequence set forth in any one of SEQ ID NOs:49-52.

The invention also provides a use of a ENR polypeptide in the manufacture of citronellol, citronellal, citronellic acid, or a combination thereof.

The invention also provides a use of a ENR polypeptide in an in vitro or a whole-cell bioconversion manufacture of citronellol, citronellal, citronellic acid, or a combination thereof.

In one aspect of the uses disclosed herein, the ENR polypeptide comprises a polypeptide having at least 50% sequence identity to the amino acid sequence set forth in any one of SEQ ID NOs:7-9, 21, 22, 33, 34, 37, 44-48, 54, 55, or 67.

The invention also provides a use of a ISY polypeptide in the manufacture of citronellol, citronellal, citronellic acid or a combination thereof.

The invention also provides a use of a ISY polypeptide in an in vitro or a whole-cell bioconversion manufacture of citronellol, citronellal, citronellic acid, or a combination thereof.

In one aspect of the uses disclosed herein, the ISY polypeptide comprises a polypeptide having at least 50% sequence identity to the amino acid sequence set forth in any one of SEQ ID NOs:54 or 55.

The invention also provides a use of a AR polypeptide in the manufacture of geraniol, nerol, citronellol, citronellic acid or a combination thereof.

The invention also provides a use of a AR polypeptide in an in vitro or a whole-cell bioconversion manufacture of geraniol, nerol, citronellol, citronellic acid or a combination thereof.

In one aspect of the uses disclosed herein, the AR polypeptide comprises a polypeptide having at least 50% sequence identity to the amino acid sequence set forth in any one of SEQ ID NOs:31, 32, or 83-86.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1A:
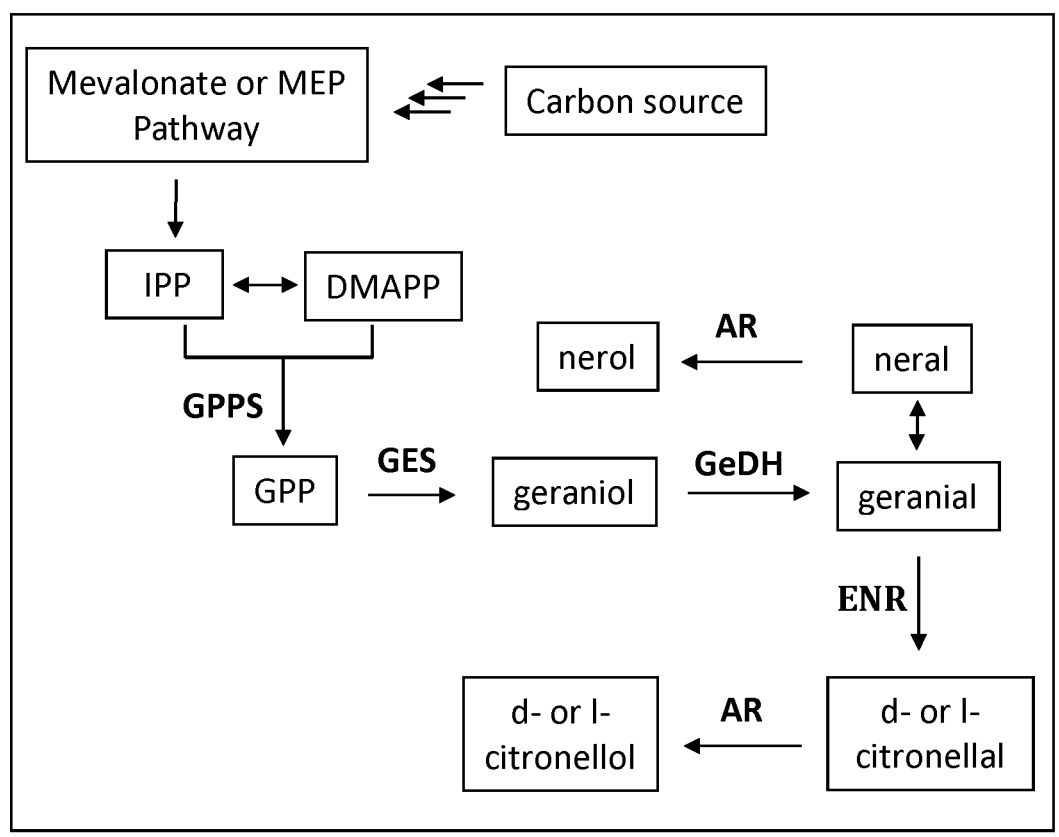
FIG. 1a shows a schematic of the citronellal biosynthetic pathway. Enzymes are indicated where applicable at each reaction.

Skilled artisans will appreciate that elements in the Figures are illustrated for simplicity and clarity and have not necessarily been drawn to scale. For example, the dimensions of some of the elements in the Figures can be exaggerated relative to other elements to help improve understanding of the embodiment(s) of the present invention.

DETAILED DESCRIPTION OF THE INVENTION

All publications, patents and patent applications cited herein are hereby expressly incorporated by reference for all purposes.

Before describing the present invention in detail, a number of terms will be defined. As used herein, the singular forms "a," "an," and "the" include plural referents unless the context clearly dictates otherwise. For example, reference to a "nucleic acid" means one or more nucleic acids.

As used herein, the term "about" refers to ±10% of a given value.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Green & Sambrook, 2012, MOLECULAR CLONING: A LABORATORY MANUAL, Fourth Edition, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

As used herein, the terms "polynucleotide," "nucleotide," "oligonucleotide," and "nucleic acid" can be used interchangeably to refer to nucleic acid comprising DNA, RNA, derivatives thereof, or combinations thereof, in either single-stranded or double-stranded embodiments depending on context as understood by the skilled worker.

As used herein, the terms "microorganism," "microorganism host," "microorganism host cell," "recombinant host," and "recombinant host cell" can be used interchangeably. As used herein, the term "recombinant host" is intended to refer to a host, the genome of which has been augmented by at least one DNA sequence. Such DNA sequences include but are not limited to genes that are not naturally present, DNA sequences that are not normally transcribed into RNA or translated into a protein ("expressed"), and other genes or DNA sequences which one desires to introduce into a host. It will be appreciated that typically the genome of a recombinant host described herein is augmented through stable introduction of one or more recombinant genes. Generally, introduced DNA is not originally resident in the host that is the recipient of the DNA, but it is within the scope of this disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms.

As used herein, the term "recombinant gene" or "recombinant DNA sequence" refers to a gene or DNA sequence that is not wild type in the host. Recombinant genes and recombinant DNA sequences can be introduced from another species into a recipient host, or can be derived from a wild type gene or DNA sequence such that a DNA sequence already present in the host has been augmented, modified or mutated through genetic engineering by mutagenesis and/or recombinant methods to form a recombinant host. Examples of a recombinant gene or recombinant DNA sequence include, but are not limited to, an exogenous gene introduced into a host, an endogenous gene modified or mutated so as to result in a variant displaying altered activity or functionality of the gene product, a chimeric gene (such as created by domain-swapping of proteins) a codon-optimized gene, an endogenous or heterologous gene linked to or under the control of a different transcriptional regulator such as promoter, operator, repressor or terminator. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA, such that the recombinant host comprises endogenous genes present in a higher copy number than the wild type host cell. In some embodiments, recombinant genes are synthetic and/or codon-optimized for expression in a host cell (for example, S. cerevisiae (SEQ ID NO:1-9) or E. coli (SEQ ID NO:10-22).

As used herein, the term "engineered biosynthetic pathway" refers to a biosynthetic pathway comprising at least one recombinant gene or recombinant DNA sequence in a recombinant host, as described herein. In some aspects, one or more steps of the biosynthetic pathway do not naturally occur in an unmodified (wild type) host. In some embodiments, a heterologous version of a gene is introduced into a host that comprises an endogenous version of the gene.

As used herein, the term "endogenous" gene refers to a gene that originates from and is produced or synthesized within a particular organism, tissue, or cell. In some embodiments, the endogenous gene is a yeast gene. In some embodiments, the gene is endogenous to S. cerevisiae, including, but not limited to S. cerevisiae strain S288C.

In some embodiments, an endogenous yeast gene is overexpressed in a recombinant host. As used herein, the term "overexpress" is used to refer to the expression of a gene in an organism at levels higher than the level of gene expression in a wild type organism. See, e.g., Prelich, 2012, Genetics 190:841-54.

In some embodiments, an endogenous yeast gene, for example ADH, is deleted or is transcriptionally downregulated. See, e.g., Giaever & Nislow, 2014, Genetics 197(2): 451-65. As used herein, the terms "deletion," "deleted," "knockout," and "knocked out" can be used interchangeably to refer to an endogenous gene that has been manipulated to no longer be expressed in an organism, including, but not limited to, S. cerevisiae.

As used herein, the term "heterologous" gene describes a gene derived from a species other than the recombinant host. In some embodiments, the recombinant host is S. cerevisiae, and a heterologous gene is derived from an organism other than S. cerevisiae. A gene coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

A "selectable marker" can be one of any number of genes that complement host cell auxotrophy, provide antibiotic resistance, or result in a color change. Linearized DNA fragments of the gene replacement vector then are introduced into the cells using methods well known in the art (see below). Integration of the linear fragments into the genome and the disruption of the gene can be determined based on the selection marker and can be verified by, for example, PCR or Southern blot analysis. Subsequent to its use in selection, a selectable marker can be removed from the genome of the host cell by, e.g., Cre-LoxP systems (see, e.g., Gossen et al., 2002, *Ann. Rev. Genetics* 36:153-173 and U.S. 2006/0014264). Alternatively, a gene replacement vector can be constructed in such a way as to include a portion of the gene to be disrupted, where the portion is devoid of any endogenous gene promoter sequence and encodes none, or an inactive fragment of, the coding sequence of the gene.

As used herein, the terms "variant" and "mutant" are used to describe a protein sequence that has been modified at one or more amino acids, compared to the wild-type sequence of a particular protein.

As used herein, the term "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of a gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene with inactivation thereof.

As used herein, the terms "mevalonate pathway", "isoprenoid pathway" and the "HMG-CoA reductase pathway" can be used interchangeably and refer to a metabolic pathway that synthesizes isopentyl pyrophosphate (IPP) and/or dimethylallyl pyrophosphate (DMAPP). IPP and/or DMAPP are typically utilised by cells in the production of isoprenoids. The primary substrate for the mevalonate pathway is acetyl coenzyme A (acetyl-CoA), which is generated by cells in the breakdown of a carbon source (such as but not limited to glucose, acetate, ethanol) for example by glycolysis, or the breakdown of fatty acids through β-oxidation. IPP and DMAPP are five-carbon intermediates which when contacted with a geranyl diphosphate synthase (GPPS) together yield geranyl diphosphate (GPP). Alternatively, the IPP and DMAPP can be contacted with a neryl diphosphate synthase (NPPS) to yield neryl diphosphate (NPP).

As used herein, the term "geranyl diphosphate synthase" (GPPS), refers to an enzyme, polypeptide or fragment thereof that is able to catalyze the production of geranyl diphosphate (GPP) from IPP and DMAPP. For the avoidance of doubt, genes encoding polypeptides with farnesyl pyrophosphate synthase (FPPS) activity can also possess GPPS activity, either natively or as a result of mutation. As non-limiting examples, the FPPS genes ERG20 and of ispA can be mutated to produce enzymes with GPPS activity. For the avoidance of doubt, the term "geranyl diphosphate synthase" (GPPS) as used herein thus encompasses such mutated or otherwise recombinant ERG20 and ispA genes encoding polypeptides or enzymes possessing GPPS activity.

As used herein, the term "contact" is used to refer to any physical interaction between two objects. For example, the term "contact" can refer to the interaction between an enzyme and a substrate. In another example, the term "contact" can refer to the interaction between a liquid (e.g., a supernatant) and an adsorbent resin.

As used herein, the terms "isopentenyl pyrophosphate", "IPP", "isopentenyl diphosphate" and "IDP" can be used interchangeably. The term IPP refers to a product of the mevalonate pathway.

As used herein, the term "dimethylallyl pyrophosphate", "dimethylallyl diphosphate", "DMAPP" and "DMADP" can be used interchangeably. The term DMAPP refers to an isomer of IPP. DMAPP is isomerized from IPP by the enzyme isopentenyl pyrophosphate isomerase.

As used herein, the terms "aldehyde reductase", "AR" and "aldose reductase" can be used interchangeably. Aldehyde reductase refers to a NAD(P)H-dependent oxidoreductase that catalyzes the reduction of aldehydes and carbonyls.

As used herein the term "citronellal/citronellol pathway" refers to the biosynthetic engineered pathway for the expression of citronellal, citronellol, and/or citronellic acid. In some aspects, the citronellal/citronellol pathway can be initiated by geraniol synthase (GES), which catalyzes the reaction of GPP or NPP to geraniol.

In some aspects, a geraniol synthase catalyzes the conversion of GPP into geraniol and in some aspects, a geraniol synthase catalyzes the conversion of GPP into geraniol. Geraniol is then oxidized by geraniol dehydrogenase (GeDH) to produce geranial. The third step of the citronellal/citronellol pathway is the reduction of geranial to citronellal via an enoate reductase (ENR) (see FIG. 1a).

Alternatively, the citronellal/citronellol pathway can be initiated by nerol synthase (NES), which catalyzes the conversion of NPP or GPP into nerol. In some aspects, a nerol synthase catalyzes the conversion of GPP into nerol and in some aspects, a nerol synthase catalyzes the conversion of GPP into nerol. Nerol is then oxidized by neral dehydrogenase (NeDH) to produce neral. Neral is then converted to 1-citronellal by an enoate reductase (ENR) activity (see FIG. 1b).

As used herein, the terms "geraniol dehydrogenase" (GeDH) and "nerol dehydrogenase" (NeDH) refer to enzymes, polypeptides and fragments thereof with the ability to synthesize geranial from geraniol, and neral from nerol, respectively. In some embodiments, the same polypeptide can exhibit one or both activities. For example, the gene product of Rs_GeDH is a polypeptide exhibiting both GeDH and NeDH activities.

As used herein, the terms "citronellol precursor", "citronellol precursors", "citronellic acid precursors" and "citronellal/citronellol intermediates" refer to intermediates in the mevalonate pathway such IPP and DMAPP and intermediates in the citronellal/citronellol pathway, such as GPP, geraniol, geranial and/or citronellal.

In one embodiment, isomerisation of neral to geranial can happen via keto-enol tautomerization. As used herein, the term "keto-enol tautomerization" refers to the conversion of a keto form to an enol form.

The fourth step of this process reduces citronellal to citronellol by alcohol dehydrogenase/aldehyde reductase activity in the host cell. The dehydrogenase can be selected from *Castellaniella defragrans* geraniol dehydrogenase (Cd_GeDH), *Thauera terpenica* 58Eu geraniol dehydrogenase (Tt_GeDH), *Spingopyxis macrogoltabida* geraniol dehydrogenase (Sm_GeDH) and, *Acinetobacter calcoaceticus* geraniol dehydrogenase (Ac_GeDH), or other geraniol dehydrogenases not listed. The aldehyde reductase (AR) activity can be a result of endogenous or exogenous aldehyde reductase enzyme activity. Additionally, the aldehyde reductase that converts neral to nerol, geranial to geraniol, or citronellal to citronellol can be the same or different (see FIGS. 1a and 1b).

Alternatively, the citronellal/citronellol pathway can produce citronellol via conversion of NPP or GPP to nerol or geraniol by NES or GES activity, respectively. In this embodiment, Enoate reductase (ENR) or Iridoid synthase (ISY) activity converts nerol or geraniol to l- or d-citronellol, respectively. D- or l-citronellol is then oxidized by citronellal/citronellol dehydrogenase (CiDH) to yield d- or l-citronellal, respectively (see FIG. 1c).

As used herein, the term "synthase" refers to an enzyme that catalyses a synthesis process typically involving the linkage of two or more molecules, (for example, the reaction in which acetyl-CoA condenses with acetoacetyl-CoA to form 3-hydroxy-3-methylglutaryl-CoA is catalysed by HMG-CoA synthase.

As used herein, the term "kinase" refers to an enzyme that catalyses the transfer of phosphate groups from high-energy, phosphate-donating molecules to specific substrates, such as mevalonate kinase (MK) and phosphomevalonate kinase (PMK).

As used herein the terms "enantiomer", "enantiomers", "optical isomer", "stereoisomer" or "optical isomers" refer to a chiral molecule or chiral molecules that are mirror images of one another. These molecules are non-superimposable on one another and are distinguished by those skilled in through the use of prefixes. There are three major nomenclature systems with equivalence as follows: the +/− optical activity system (+ and −) based on the ability of a pure isomer to rotate plane polarized light clockwise or anticlockwise; the d/l system otherwise known as the dextrorotation- and levorotation-system based on direct translation into Latin (dexter for right and laevus for left). Thus "l" is equivalent to "−", and "d" is equivalent to "+". The two systems are herein used interchangeably. For the avoidance of doubt, the related R/S system based on the Latin language (rectus for proper and sinister for straight) is used to characterize the absolute configuration of a specific stereocenter, of which there can be more than one in a molecule, though it can also be used to characterize an entire molecule if it comprises a single stereocenter. As used herein the term "d-enantiomer" refers to a molecule having a chiral carbon in which the higher polarity group is located on the right of the Fischer projection (D-enantiomers rotate plane polarized light clockwise (+)). As used herein the term "l-enantiomer" refers to a molecule having a chiral carbon in which the higher polarity group is located on the left of the Fischer projection (L-enantiomers rotate plane polarized light counterclockwise (−)).

As used herein, the terms "optical purity" and "enantiomeric excess" can be used interchangeably. Optical purity refers to a measure of purity used for chiral substances. For example, if the optical purity is 100% then only one enantiomer (either d- or l-) was produced. Additionally, if the pathway produces 90% d-citronellal and 10% l-citronellal then the optical purity of d-citronellal is 90%-10%=80% enantiomeric excess (ee).

As used herein, the term "isomerase" refers to an enzyme which converts a molecule from one isomer to another. An isomerase can facilitate the intramolecular rearrangement in which bonds are broken and formed or they can catalyze conformational changes, such as isopentenyl diphosphate isomerase.

As used herein, the term "reductase" refers to an enzyme that acts as a reducing agent. Reductases include but are not limited to HMG-CoA reductase and enoate reductase (ENR). As used herein, the terms "enoate reductase" and "ene reductase" are used interchangeably, and also comprise the yeast Old Yellow Enzymes (OYE) class of flavoproteins. For the avoidance of doubt, Iridoid synthases (such as, but not limited to, Oe_ISY and Cr_ISY) can possess enoate reductase activity and such enzymes are thus encompassed by the term "enoate reductase" as used herein.

As used herein, the term "derivative" refers to a molecule or compound that is derived from a similar compound by some chemical or physical process.

As used herein, the term "nerol" refers to a monoterpene with a fresh sweet rose odor originally isolated from neroli oil, but also present in essential oils from lemongrass and hops. Nerol is the cis-trans isomer of geraniol.

As used herein, the terms "citronellol" or "dihydrogeraniol" refer to a natural acyclic monoterpenoid that can be produced by the hydrogenation of geraniol (trans).

As used herein, the terms "neral" and "geranial" refer to a liquid aldehydes that are constituents of citral, an essential oil naturally derived from such plants as lemon myrtle, *Litsea citrata, Litsea cubeba*, lemongrass, lemon tea-tree. Citral, also known as 3,7-dimethyl-2,6-dienal or lemonal, is a blend of isomeric terpenoids in which the E-isomer (citral A) is geranial providing a strong lemon citrus odor and the Z-isomer (citral B) is neral providing sweeter but less intense lemon odor. Citral is used commercially as an antimicrobial, a fragrance, fragrance component, a flavoring agent, to fortify lemon, and in the synthesis of vitamin A.

As used herein, the term "geraniol" refers to a monoterpenoid alcohol with a rose-like scent naturally present in rose oil, germanioum oil, palmarosa oil, lemon oil and citronella oil. Geraniol is used commercially a fragrance component in perfumes, typically with flavors such as peach, raspberry, grapefruit, red apple, plum, lime, orange, lemon, watermelon, pineapple, and blueberry.

As used herein, the terms "citronellal", "rhodinal" or "3,7-dimethyloct-6-en-1-al" refer to a monoterpenoid that is the main component in citronella oil and provides its distinctive lemon scent. Citronellal can be present as an l or d enantiomer.

As used herein, the term "dehydrogenase" refers to an enzyme that oxidizes a substrate by a reduction reaction that removes one or more hydrogen molecules from a substrate to an electron acceptor, such as geraniol dehydrogenase or alcohol dehydrogenase.

As used herein, the terms "mevalonate plasmid" and "pMev" can be used interchangeably. The term mevalonate plasmid refers to a plasmid transformed into *E. coli* that can result in the production of IPP and DMAPP from acetyl-CoA and/or malonyl-CoA. The genes included in the mevalonate plasmid can be endogenous or exogenous. The first three genes; *Escherichia coli* MG1655 Acetyl-CoA acetyltransferase (Ec_atoB), *Staphylococcus aureus* HMG-CoA synthase (Sa_mvaS), *Staphylococcus aureus* HMG-CoA reductase (Sa_mvaA) are under control of one promoter and the last four genes: *Saccharomyces cerevisiae* Mevalonate Kinase (Sc_erg12), *Saccharomyces cerevisiae* Phosphomevalonate kinase (Sc_erg8), *Saccharomyces cerevisiae* Diphospomevalonate decarboxylase (Sc_erg19), and *Escherichia coli* Isopentenyl diphosphate isomerase (Ec_idi) are under control of another promoter. Each operon is terminated by a transcriptional terminator. The seven genes are located on a p15-based replicative plasmid backbone and the kanamycin selection marker. All genes except Ec_IDI are heterologous and were synthesized by Thermo Fisher Scientific GENEART™ GmbH (Regensburg, Germany) as *Escherichia coli* codon optimized variants. Ec_a- toB was a recombinant gene produced by codon optimization for *E. coli* of the endogenous gene of the *E. coli* wild type host (the wild type gene was modified because it did not extensively use the preferred codons for expression in *E. coli*).

As used herein, the terms "citronellal plasmid", "pCitro plasmid" and "pCitro" can be used interchangeably. The term citronellal plasmid refers to a plasmid that following transformation into a host cells can result in the production of citronellal from IPP and DMAPP. The genes in the citronellal plasmid can be either endogenous or exogenous. In one non-limiting example disclosed herein, the 4 enzymes: geranyl diphosphate synthase, geraniol synthase, ene reductase and geraniol dehydrogenase encoded by the heterologous genes Ag_GPPS2, Cr_GES, Kl_KYE1 (alternatively Ps_OYE2.6) and Cd_GeDH (alternatively Rs_GeDH), were subdivided on two operons. The first three genes are under the control of a promoter and terminated by a transcriptional terminator. The last gene is under the control of another promoter and terminator. The 4 genes are located on a pBR322-based replicative plasmid backbone and ampicillin selection marker, though any suitable plasmid (preferably a high copy number plasmid) and selection marker can be used. All genes were synthesized by Thermo Fisher Scientific GENEART™ GmbH (Regensburg, Germany). Since the species of host cell in this instance was chosen to be *Escherichia coli*, the genes in this example were codon optimized variants (except Rs_GeDH which was codon optimized for *Saccharomyces cerevisiae*).

As used herein, the terms "operon" and "operons" and "coordinated gene regulation element" are functionally equivalent, are used interchangeably, and refer to a genetic regulator system comprising a functioning unit of DNA containing more than one gene under the control of a single promoter. Although highly prevalent as a means of coordinated gene regulation, operons are not ubiquitous. For example, in yeast (such as *Saccharomyces cerevisiae*) coordinated gene regulation is frequently achieved by linking opposite DNA strand genes using a common promoter element, or by concatenating more than one functional domain into a single peptide to provide chimeric proteins. All of the above systems using a single promoter to regulate more than one functional activity are observed in wild type host cells of one species or another, and have inspired the engineering of multi-enzyme pathways under coordinated expression using recombinant DNA techniques.

As used herein, the term "plasmid" or "plasmids" refer to a small, circular, double-stranded DNA molecule that is distinct from the chromosomal DNA of a cell. Plasmids have a wide range of lengths and offer several genetic advantages. Plasmids are one form of "vector" and are particularly useful for introducing and maintain foreign (exogenous) DNA within a host cell. Choice of plasmid for a particular application is typically dictated by the ability to be maintained in one or more host cell species at a chosen copy number of plasmids per host cell.

As used herein, the terms "acetyltransferase" and "transacetylase" can be used interchangeably. "Acetyltransferase" (such as acetyl-CoA acetyltransferase) refers to a type of transferase that transfers an acetyl group from an acetyl-CoA to a recipient compound, such as for example, a lysine amino acid.

Exemplary UniProt Numbers for specific embodiments of such enzymes include: H1ZV38 (SEQ ID NO:1), A0AOE4B3N6 (SEQ ID NO:2), A0A0P0DQG4 (SEQ ID NO:3), Q59096 (SEQ ID NO:4), C9E0G2 (SEQ ID NO:5), D5MPF3 (SEQ ID NO:6), P40952 (SEQ ID NO:7), A3LT82 (SEQ ID NO:8), Q9FEW9 (SEQ ID NO:67), Q03558 (SEQ ID NO:33), G1FCG0 (SEQ ID NO:34), Q88NF7 (SEQ ID NO:37), Q5NLA1 (SEQ ID NO:9), Q6I7B7 (SEQ ID NO:44), G6XL43 (SEQ ID NO:45), A0A0D6MPY3 (SEQ ID NO:46), F8EUA7 (SEQ ID NO:47), B7L5K3 (SEQ ID NO:48, Q1WF68 (SEQ ID NO:49), Q1WF63 (SEQ ID NO:50), J1IP19 (SEQ ID NO:51), U1H7S9 (SEQ ID NO:52), C1K5M2 (SEQ ID NO:53), A0A0U3J294 (SEQ ID NO:54), K7WDL7 (SEQ ID NO:55), R4HEK6 (SEQ ID NO:56), T2DP90 (SEQ ID NO:57), J7JYU1 (SEQ ID NO:58), P76461 (SEQ ID NO:10), Q9FD87 (SEQ ID NO:11), Q9FD86 (SEQ ID NO:12), P07277 (SEQ ID NO:13), P24521 (SEQ ID NO:14), P32377 (SEQ ID NO:15), Q46822 (SEQ ID NO:16), P40952 (SEQ ID NO:7), A3LT82 (SEQ ID NO:22), A0A0M2H8A0 (SEQ ID NO:30), P27250 (SEQ ID NO:31), P75691 (SEQ ID NO:32), B2N194 (SEQ ID NO:24), D2WKD9 (SEQ ID NO:25), Q2KNL5 (SEQ ID NO:26), AOAOE4B3N6 (SEQ ID NO:27), C9E0G2 (SEQ ID NO:28), A0A0X8R1M5 (SEQ ID NO:29), J9PZR5 (SEQ ID NO:18), Q6USK1 (SEQ ID NO:63), E9JGT2 (SEQ ID NO:64), C0KWV4 (SEQ ID NO:65), V9ZAD7 (SEQ ID NO:66), Q04894 (SEQ ID NO:68).

In one embodiment, the present invention contemplates in vivo and in vitro production of one or more of citronellal, citronellol, citronellic acid, or citronellal precursors. In a further embodiment, the present invention contemplates a combination of in vivo and in vitro steps for the production one or more of citronellal, citronellol, citronellic acid, or citronellal precursors. In one particular embodiment, the present invention provides recombinant hosts containing an engineered biosynthetic pathway capable of producing one or more of citronellal, citronellol, citronellic acid, or citronellal precursors, said engineered biosynthetic pathway including one or more expressed and functional heterologous enzymes.

For example, in some aspects the present invention provides recombinant microorganism (such as a yeast or bacterial) cells capable of producing in vivo citronellol precursors. In particular, recombinant yeast or bacterial cells as provided herein are capable of expressing one or more dehydrogenases and/or other proteins capable of converting geraniol to geranial and citronellal to citronellol. Sources for dehydrogenases include but are not limited to bacteria, including several species of *Rhizobium, Streptomyces, Pseudomonas, Escherichia* and *Bacillus* that naturally express these enzymes. In other particular embodiments, dehydrogenases used herein can be derived from yeast, fungi, plants, and/or animals.

In another embodiment, the invention provides recombinant microorganism (such as a yeast or bacterial) cells capable of expressing one or more reductases and/or other proteins capable of converting geranial to citronellal.

In another embodiment, the invention provides recombinant microorganism (such as a yeast or bacterial) cells capable of expressing one or more reductases and/or other proteins capable of converting neral to citronellal.

In another embodiment, the invention provides recombinant microorganism (such as a yeast or bacterial) cells capable of expressing one or more synthases and/or other proteins capable of converting IPP and DMAPP to GPP or GPP to geraniol.

In another embodiment, the invention provides recombinant microorganism (such as a yeast or bacterial) cells capable of expressing one or more synthases and/or other proteins capable of converting IPP and DMAPP to NPP or NPP to nerol.

In another embodiment, the recombinant microorganism (such as a yeast or bacterial) cells capable of producing citronellol precursors can be further modified to increase citronellol precursor production by increasing IPP and DMAPP levels via the replacement of the native farnesyl pyrophosphate synthase promoter with a weaker promoter, resulting in the transcriptional downregulation of the native farnesyl pyrophosphate synthase. As a non-limiting example, the yeast ERG20 gene encodes the yeast farnesyl pyrophosphate synthase, which acts to catalyse the formation of farnesyl diphosphate from GPP and IPP, and it is possible to increase IPP and DMAPP in yeast by replacing the ERG20 promoter with the KEX2 promoter, resulting in the transcriptional downregulation of ERG20.

In another embodiment, the recombinant microorganism (such as a yeast or bacterial) cells with elevated levels of IPP and DMAPP are well suited for the introduction and/or integration of pathway expression cassettes for the genes necessary to yield citronellal and/or citronellol. For example, Ag_GPPS2 can be under the control of the TEF1 promoter, Cr_GES can be under the control of PGK1 promoter, Rs_GeDH can be under the control of PGK1 promoter and Kl_KYE1 can be under the control of the TPI1 promoter. In some aspects, expression cassettes can contain flanking regions homologous to regions of the host genome, so as to allow targeted integrated in the host cell genome (for example *Saccharomyces cerevisiae* or *Escherichia coli*) by homologous recombination (see e.g., WO 2014/027118 which is incorporated by reference in its entirety).

In another embodiment, elevated levels of IPP and DMAPP can be achieved in *E. coli* host cells using one or more operons collectively comprising genes required for the mevalonate pathway having one or more mevalonate pathway genes optimized for *E. coli*. In a certain embodiment, the seven genes comprising the mevalonate pathway can be present on one or more plasmids and/or integrated into the genomic DNA of the host. For example, in one embodiment the mevalonate pathway can be introduced and maintained in *E. coli* subdivided into two operons on a single plasmid: Ec_atoB, Sa_mvaS, and Sa_mvaA can be driven by one promoter and Sc_erg12, Sc_erg8, Sc_erg19 and Ec_idi can be driven by another promoter. In this instance, all mevalonate pathway genes except Ec_atoB are heterologous genes optimized for *E. coli*. Optimization of genes for heterologous expression in a particular host species typically makes use of the understanding of preferred codon usage patterns.

In another embodiment, recombinant protein expression of citronellal, citronellol and/or citronellic acid in *E. coli* can occur via a citronellal plasmid comprising *E. coli* optimized genes. For example, transcription of Ag_GPPS2, Cr_GES, Kl-KYE1 and Cd_GeDH can be driven by one or more promoters. In some embodiments, the promoters are constitutive promoters. A constitutive promoter refers to a promoter not regulated by transcription factors, that allows for continual transcription of the coding sequence or gene under its control. Examples of constitutive promoters include, but are not limited to, PT7, PTrc, PTac and PLac without their operator, PGapA, PGadE). In other embodiments, the promoters are inducible promoters that allow for chemical or physical transcriptional regulation of the gene under regulation. A positively regulated inducible promoter refers to a promoter that allows for elevated transcription of the coding sequence or gene under its control in the presence of a biotic or abiotic factor. In further embodiments, induction of the gene to higher rates of transcription can be induced by the addition of a factor that inactivates a transcriptional repressor molecule. In yet further embodiments, activators and repressors can function in multi-regulated inducible promoters. Examples of inducible promoters include, but are not limited to, alcA.

In another embodiment, recombinant protein expression of citronellal, citronellol and/or citronellic acid in *E. coli* can occur via a citronellal plasmid comprising one or more *E. coli* optimized genes. Transcription of Ag_tGPPs, Cr_GES, Ps_OYE2.6 and Rs_GeDH can be driven by one or more promoters, such as the trc-promoter. In one example, the Ag_tGPPs, Cr_GES and Ps_OYE2.6 genes are optimised for *E. coli*.

For example, the present invention provides recombinant microorganism (such as a yeast or bacterial) cells capable of producing in vivo one or more of citronellal, citronellol or citronellic acid. In particular, recombinant yeast or bacterial cells as provided herein are capable of expressing one or more dehydrogenases, reductases and/or other proteins capable of converting geraniol to citronellal, citronellol and/or citronellic acid.

In another embodiment, the recombinant microorganism (such as a yeast or bacterial) cells disclosed herein are capable of expressing one or more geraniol dehydrogenases capable of catalysing the formation of geraniol to geranial, and/or citronellal to citronellol.

In a further embodiment, the recombinant microorganism (such as a yeast or bacterial) cells disclosed herein are capable of expressing one or more ene reductases capable of reducing geranial to citronellal.

As used herein, the terms "detectable amount," "detectable concentration," "measurable amount," and "measurable concentration" refer to a level of a specific product to be measured (for example, geraniol, geranial, citronellal, citronellol, citronellic acid, or citronellal/citronellol intermediates and/or citronellal/citronellol precursors). The product can be measured in AUC, $\mu M/OD_{600}$, mg/L, $\mu M$, or mM. Geraniol, geranial, citronellal, citronellol, citronellic acid, citronellal/citronellol intermediate and/or citronellal/citronellol precursor production (i.e., total, supernatant, organic phase, and/or intracellular geraniol, geranial, and/or citronellal levels) can be detected and/or analyzed by techniques generally available to one skilled in the art, for example, but not limited to, liquid chromatography-mass spectrometry (LC-MS), thin layer chromatography (TLC), high-performance liquid chromatography (HPLC), ultraviolet-visible spectroscopy/spectrophotometry (UV-Vis), mass spectrometry (MS), and NMR.

As used herein, the term "undetectable concentration" refers to a level of a compound that is too low to be measured and/or analyzed by techniques such as TLC, HPLC, UV-Vis, MS, or NMR. In some embodiments, a compound at an "undetectable concentration" (<1 ppm) is not present.

As used herein, the terms "or" and "and/or" is utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." In some embodiments, "and/or" is used to refer to the exogenous nucleic acids that a recombinant cell comprises, wherein a recombinant cell comprises one or more exogenous nucleic acids selected from a group. In certain embodiments, "and/or" is used to refer to production of geraniol, geranial, citronellal and/or citronellol, wherein one or more geraniol, geranial, citronellol and/or citronellol are produced. In yet another embodiment, "and/or" is used to refer to production of geraniol, geranial, citronellal, citronellol and/or citronellic acid wherein one or more geraniol, geranial, citronellal, citronellol and/or citronellic acid are produced through one or more of the following steps: culturing a recombinant microorganism, producing one or more geraniol, geranial, citronellal, citronellol and/or citronellic acid in a recombinant microorganism, and/or isolating one or more geraniol, geranial, citronellal citronellol and/or citronellic acid.

Functional Homologs

Functional homologs of the polypeptides described herein are also suitable for use in producing citronellol, citronellal, citronellic acid and/or precursors thereof in a recombinant host.

A functional homolog refers to a polypeptide that has sequence similarity to a reference polypeptide, and that carries out one or more of the biochemical or physiological function(s) of the reference polypeptide. A functional homolog and the reference polypeptide can be a natural occurring polypeptide, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of citronellol and citronellol precursor biosynthesis polypeptides. Sequence analysis can involve BLAST, Reciprocal BLAST, or PSI-BLAST analysis of non-redundant databases using any sequence disclosed herein as a reference sequence for a database search for homologs. Amino acid sequence can be, in some instances, deduced from the nucleotide sequence. Those polypeptides in the database that have greater than 40% sequence identity are candidates for further evaluation for suitability as a citronellol and citronellol precursor biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in citronellol and citronellol precursor biosynthesis polypeptides, e.g., conserved functional domains. In some embodiments, nucleic acids and polypeptides are identified from transcriptome data based on expression levels rather than by using BLAST analysis.

Conserved regions can be identified by locating a region within the primary amino acid sequence of citronellol and citronellol precursor biosynthesis polypeptides that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., *Nucl. Acids Res.*, 26:320-322 (1998); Sonnhammer et al., Proteins, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate to identify such homologs.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 90%, 91%, 92%, 93%, 94%, 95%, 96%, 97%, 98%, or 99% amino acid sequence identity.

For example, polypeptides suitable for producing citronellol and/or citronellol precursors in a recombinant host include functional homologs of Ag_GPPS2, Cr_GES, Kl_KYE1, Cd_GeDH, Tt_GeDH, Rs_GeDH, Sm_GeDH, Ac_GeDH, Pp_GeDH, Ps_OYE2.6, Zm_OYE, Ec_atoB, Sa_mvaS, Sa_mvaA, Sc_erg12, Sc_erg8, Sc_erg19, Lc_MVA, Ef_MVA, Sp_IDI, ScIDI and Ec_idi.

Methods to modify the substrate specificity of, are known to those skilled in the art, and include without limitation site-directed/rational mutagenesis approaches, random directed evolution approaches and combinations in which random mutagenesis/saturation techniques are performed near the active site of the enzyme. For example see Labrou N E., *Curr Protein Pept Sci.* 11(1):91-100.

A candidate sequence typically has a length that is from 80% to 200% of the length of the reference sequence, e.g., 82, 85, 87, 89, 90, 93, 95, 97, 99, 100, 105, 110, 115, 120, 130, 140, 150, 160, 170, 180, 190, or 200% of the length of the reference sequence. A functional homolog polypeptide typically has a length that is from 95% to 105% of the length of the reference sequence, e.g., 90, 93, 95, 97, 99, 100, 105, 110, 115, or 120% of the length of the reference sequence, or any range between. A percent (%) identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using a computer program (for example, ClustalW (version 1.83, default parameters), or the Needleman-Wunsch algorithm), which allows alignments of nucleic acid or polypeptide sequences to be carried out across their entire length (global alignment). Chenna et al., 2003, *Nucleic Acids Res.* 31(13):3497-500.

Clustal Omega calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method:

percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The Clustal Omega output is a sequence alignment that reflects the relationship between sequences. Clustal Omega can be run, for example, at the Baylor College of Medicine Search Launcher site on the World Wide Web (searchlauncher.bcm.tmc.edu/multi-align/multi-align.html) and at the European Bioinformatics Institute site on the World Wide Web_www.ebi.ac.uk/Tools/msa/clustalo/.

To determine a percent identity of a candidate nucleic acid or amino acid sequence to a reference sequence, the sequences are aligned using Clustal Omega, the number of identical matches in the alignment is divided by the length of the reference sequence, and the result is multiplied by 100. It is noted that the % identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

To determine a percent identity of a candidate amino acid sequence to a reference sequence, the sequences are aligned using ClustalW, the number of identical matches in the alignment is divided by the length of the reference sequence, and the result is multiplied by 100. It is noted that the % identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that geraniol dehydrogenase, geraniol dehydrogenase-like proteins, enoate (ene) reductase, ene reductase-like proteins, acetyl-CoA acetyltransferase and acetyl-CoA acetyltransferase-like proteins, HMG-CoA synthase and HMG-CoA synthase-like proteins, mevalonate kinase and mevalonate kinase-like proteins, phosphomevalonate kinase and phosphor mevalonate kinase-like proteins, isopentenyl diphosphate isomerase and isopentenyl diphosphate isomerase-like proteins, geranyl diphosphate synthase and geranyl diphosphate synthase-like proteins, geraniol synthase and geraniol synthase-like proteins can include additional amino acids that are not involved in the enzymatic activities carried out by the enzymes.

It will be appreciated that functional dehydrogenase, reductase, synthase, acetyltransferase, kinase, decarboxylase and isomerase proteins can include additional amino acids that are not involved in the enzymatic activities carried out by the enzymes. The terms "chimera," "fusion polypeptide," "fusion protein," "fusion enzyme," "fusion construct," "chimeric protein," "chimeric polypeptide," "chimeric construct," and "chimeric enzyme" can be used interchangeably herein to refer to proteins engineered through the joining of two or more genes that code for different proteins.

In some embodiments, a nucleic acid sequence encoding a geraniol dehydrogenase, an ene reductase, a geranial diphosphate synthase, a HMG-CoA synthase, a HMG-CoA reductase, an acetyl-CoA acetyltransferase, a phosphomevalonate kinase, a mevalonate kinase, di phosphomevalonate decarboxylase or an isopentenyl diphosphate isomerase polypeptide can include a tag sequence that encodes a "tag" designed to facilitate subsequent manipulation (e.g., to facilitate purification or detection), solubility, secretion, or localization of the encoded polypeptide. Tag sequences can be inserted in the nucleic acid sequence encoding the polypeptide such that the encoded tag is located at either the carboxyl or amino terminus of the polypeptide. Non-limiting examples of encoded tags include green fluorescent protein (GFP), human influenza hemagglutinin (HA), glutathione S transferase (GST), polyhistidine-tag (HIS tag), disulfide oxiodoreductase (DsbA), maltose binding protein (MBP), N-utilization substance (NusA), small ubiquitin-like modifier (SUMO), and Flag™ tag (Kodak, New Haven, Conn.). Other examples of tags include a chloroplast transit peptide, a mitochondrial transit peptide, an amyloplast peptide, signal peptide, or a secretion tag.

In some embodiments, a fusion protein is a protein altered by domain swapping. As used herein, the term "domain swapping" is used to describe the process of replacing a domain of a first protein with a domain of a second protein. In some embodiments, the domain of the first protein and the domain of the second protein are functionally identical or functionally similar. In some embodiments, the structure and/or sequence of the domain of the second protein differs from the structure and/or sequence of the domain of the first protein.

Citronellol and Citronellol Precursor Biosynthesis Nucleic Acids

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. "Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also can include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region can be present, e.g., introns, enhancers, upstream activation regions, transcription terminators, and inducible elements.

One or more genes can be combined in a recombinant nucleic acid construct in "modules" useful for a discrete aspect of citronellal/citronellol production. Combining a plurality of genes in a module, particularly a polycistronic module, facilitates the use of the module in a variety of species. For example, a citronellal/citronellol biosynthesis gene cluster, or a mevalonate pathway gene cluster, can be combined in a polycistronic module such that, after insertion of a suitable regulatory region, the module can be introduced into a wide variety of species. As another example, citronellal/citronellol gene cluster can be combined such that each citronellal/citronellol coding sequence is operably linked to a separate regulatory region, to form a citronellal/citronellol module. Such a module can be used in those species for which monocistronic expression is necessary or desirable. In addition to genes useful for citronellal/citronellol production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

In some cases, it is desirable to inhibit one or more functions of an endogenous polypeptide in order to divert metabolic intermediates towards citronellol or citronellol precursor biosynthesis. For example, it can be desirable to downregulate synthesis of farnesyl pyrophosphate in a yeast strain in order to further increase IPP and DMAPP production necessary to produce GPP, e.g., by downregulating farnesyl pyrophosphate synthase. In such cases, a nucleic acid that overexpresses the polypeptide or gene product can be included in a recombinant construct that is transformed into the strain. Alternatively, mutagenesis can be used to generate mutants in genes for which it is desired to increase or enhance function.

In one embodiment, the GPPS polypeptide for use in any one of the recombinant host cells, methods and/or uses of the present invention has an amino acid sequence shown in any one of SEQ ID NO:17, or 59-62 or has an amino acid sequence which has at least 50% identity therewith, preferably at least 75% identity therewith, preferably at least 80%, preferably at least 85%, preferably at least 95%, preferably at least 98% identity therewith.

In one embodiment, the GES polypeptide for use in any one of the recombinant host cells, methods and/or uses of the present invention has an amino acid sequence shown in any one of SEQ ID NO:18, or 63-66 or has an amino acid sequence which has at least 40% identity therewith, preferably at least 75% identity therewith, preferably at least 80%, preferably at least 85%, preferably at least 95%, preferably at least 98% identity therewith.

In one embodiment, the GeDH polypeptide for use in any one of the recombinant host cells, methods and/or uses of the present invention has an amino acid sequence of any one of SEQ ID NO:1-6, 19, 20, or 24-32 or has an amino acid sequence which has at least 45% identity therewith, preferably at least 75% identity therewith, preferably at least 80%, preferably at least 85%, preferably at least 95%, preferably at least 98% identity therewith.

In one embodiment, the ENR polypeptide for use in any one of the recombinant host cells, methods and/or uses of the present invention has an amino acid sequence shown in any one of SEQ ID NO:7-9, 21, 22, 33, 34, 37, 44-48, or 67 or has an amino acid sequence which has at least 50% identity therewith, preferably at least 75% identity therewith, preferably at least 80%, preferably at least 85%, preferably at least 95%, preferably at least 98% identity therewith.

In one embodiment, the AR polypeptide for use in any one of the recombinant host cells, methods and/or uses of the present invention has an amino acid sequence shown in any one of SEQ ID NO:31, 32, or 83-86 or has an amino acid sequence which has at least 85% identity therewith, preferably 90% identity therewith, preferably at least 95%, preferably at least 98% identity therewith.

In one embodiment, the NPPS polypeptide for use in any one of the recombinant host cells, methods and/or uses of the present invention has an amino acid sequence shown in any one of SEQ ID NO:53, 74, or 75, or has an amino acid sequence which has at least 45% identity therewith, preferably at least 75% identity therewith, preferably at least 80%, preferably at least 85%, preferably at least 95%, preferably at least 98% identity therewith.

In one embodiment the NES polypeptide for use in any one of the recombinant host cells, methods and/or uses of the present invention has an amino acid sequence shown in any one of SEQ ID NO:56-58 or 77-79 has an amino acid sequence which has at least 45% identity therewith, preferably at least 75% identity therewith, preferably at least 80%, preferably at least 85%, preferably at least 95%, preferably at least 98% identity therewith.

In one embodiment the NeDH polypeptide for use in any one of the recombinant host cells, methods and/or uses of the present invention has an amino acid sequence shown in any one of SEQ ID NOs:1-6, 19, 20, or 24-32 has an amino acid sequence which has at least 50% identity therewith, preferably at least 75% identity therewith, preferably at least 80%, preferably at least 85%, preferably at least 95%, preferably at least 98% identity therewith.

In one embodiment the ADH polypeptide for use in any one of the recombinant host cells, methods and/or uses of the present invention has an amino acid sequence shown in SEQ ID NO:68, or has an amino acid sequence which has at least 45% identity therewith, preferably at least 75% identity therewith, preferably at least 80%, preferably at least 85%, preferably at least 95%, preferably at least 98% identity therewith.

In one embodiment, the ISY polypeptide for use in any one of the recombinant host cells, methods and/or uses of the present invention has an amino acid sequence shown in any one of SEQ ID NO:54 or 55, or has an amino acid sequence which has at least 50% identity therewith, preferably at least 75% identity therewith, preferably at least 80%, preferably at least 85%, preferably at least 95%, preferably at least 98% identity therewith.

In one embodiment, the CiDH polypeptide for use in any one of the recombinant host cells, methods and/or uses of the present invention has an amino acid sequence shown in any one of SEQ ID NO:49-52, or has an amino acid sequence which has at least 80% identity therewith, preferably at least 85%, preferably at least 95%, preferably at least 98% identity therewith.

Host Microorganisms

Recombinant hosts can be used to express polypeptides for producing citronellal, citronellol, citronellic acid and/or their precursors, including fungal, bacterial, yeast, mammalian, insect, and plant.

A number of prokaryotes and eukaryotes are particularly suitable for use in constructing the recombinant microorganisms described herein, e.g., gram-negative bacteria (such as *E. coli*), yeast (such as *S. cerevisiae*), and fungi. A species and strain selected for use as a citronellal and citronellol precursor production strain is first analyzed to determine which production genes are endogenous to the strain and which genes are not present. Genes for which an endogenous counterpart is not present in the strain are advantageously assembled in one or more recombinant constructs, which are then transformed into the strain in order to supply the missing function(s).

Typically, the recombinant microorganism is grown in a fermenter at a temperature(s) for a period of time, wherein the temperature and period of time facilitate production of citronellal, citronellol, citronellic acid, and/or their precursors. The constructed and genetically engineered microorganisms provided by the invention can be cultivated using conventional fermentation processes, including, inter alia, chemostat, batch, fed-batch cultivations, semi-continuous fermentations such as draw and fill, continuous perfusion fermentation, and continuous perfusion cell culture. Depending on the particular microorganism used in the method, other recombinant genes such as isopentenyl biosynthesis genes and terpene synthase and cyclase genes can also be present and expressed. Levels of substrates and intermediates, e.g., isopentenyl diphosphate, dimethylallyl diphosphate, geranyl diphosphate, geranial, geraniol, citronellal, citronellol, and/or citronellic acid can be determined by extracting samples from culture media for analysis according to published methods.

Carbon sources of use in the instant method can include any molecule that can be metabolized by the recombinant host cell to facilitate growth and/or production of the citronellal/citronellol. Examples of suitable carbon sources include, but are not limited to, sucrose (e.g., as found in molasses), fructose, xylose, ethanol, acetate, glycerol, glucose, cellulose, starch, cellobiose or other glucose-comprising polymer. In embodiments employing yeast as a host, for example, carbon sources such as sucrose, fructose, xylose, ethanol, glycerol, and glucose can be preferred. The carbon source can be provided to the host organism according to any feeding regimen commonly used by those skilled in the art of culturing the appropriate host cell species.

After the recombinant microorganism has been grown in culture for a period of time, wherein the culturing conditions and period of time facilitate production of citronellal, citronellol, citronellic acid, and/or one or more citronellal/citronellol precursors which can then be recovered from the culture medium, off-gas and/or recombinant microorganisms using various techniques known in the art. For example, citronellal, citronellol, citronellic acid, and their precursors diffuse and/or are transported out of the host cell by host transporters. In some embodiments, a permeabilizing agent can be added to aid the feedstock entering into the host and product getting out. In some embodiments, citronellal, citronellol, citronelic acid, and their precursors can be trapped outside by a solvent phase (of which isopropylmyristate, IPM, is a non-limiting example) added directly to the culture medium, or they can be trapped in solvent phase (of which IPM is again a non-limiting example) in a collection container in an off-gas trapping system connected to the fermenter.

A non-limiting example of an off-gas trapping system comprises leading the off gas from the headspace above the fermentation medium in the fermenter into a cooling unit (such as a Dimroth condenser) that cools the temperature of the off-gas to below the condensation point of water vapor and citronellal or citronellol gas. The condensed water, citronellol and/or citronellal is drained and/or pumped into a collection container containing a solvent phase (such as IPM) that traps citronellal and/or citronellol. The condensed water vapor is present in the collection container as a second phase (aqueous phase), which can be drained periodically or continuously so as to increase the citronellol and/or citronellol content in the collection container. In some embodiments, the gaseous headspace of the collection container is attached to a second cooling unit (such as a Dimroth condenser) that cools any citronellal and/or citronellol gas and water vapor that escaped condensation in the first cooling unit, and collects the condensates in a second collection container containing a solvent phase and an aqueous phase. Citronellal and/or citronellol can then be enriched, purified or isolated from the solvent phase by evaporation of the solvent or precipitation (such as by temperature or pH adjustment).

In another embodiment, a crude lysate of the cultured microorganism can be centrifuged to obtain a supernatant, which can then be applied to a chromatography column (e.g., a C-18 column), washed with water to remove hydrophilic compounds, then elution of the compound(s) of interest performed with a suitable solvent (a non-limiting example of which is methanol). The compound(s) can then be further purified by preparative HPLC, (relevant techniques of which are taught in, for example, WO 2009/140394).

It will be appreciated that the various genes and modules discussed herein can be present in two or more recombinant hosts or host cells rather than a single host. When a plurality of recombinant hosts is used, they can be grown in a mixed culture to accumulate citronellal, citronellol, and/or citronellic acid.

Alternatively, the two or more hosts each can be grown in a separate culture medium and the product of the first culture medium, e.g., IPP and DMAPP, can be introduced into second culture medium to be converted into a subsequent intermediate such as GPP, or into an end product such as, for example, one or more of citronellal, citronellol or citronellic acid. For example, citronellol produced by recombinant microorganisms (such as the recombinant yeast or *E. coli* taught herein) can be contacted with oxidizing bacteria (for example, the *Gluconobacter* sp., e.g., *Gluconobacter oxydans, Gluconobacter cerinus*, or *Gluconobacter frateurii*) to permit the bioconversion of citronellol into citronellal and/or citronellic acid. The product produced by the second, or final host is then recovered. It will also be appreciated that in some embodiments, a recombinant host can be grown using nutrient sources other than a culture medium and utilizing a system other than a fermenter.

As used herein, the terms "bioconversion" or "biotransformation" refer to the conversion of organic materials, into usable products by biological processes or agents, such as certain microorganisms. In some embodiments, citronellal, citronellol, or citronellic acid, can be produced by bioconversion using oxidizing bacteria. For bioconversion to occur, an oxidizing bacteria modifies a precursor, and/or an intermediate thereof, to the citronellol, citronellal, or citronellic acid produced by a recombinant host cell expressing one or more enzymes involved in the citronellal/citronellol pathway. Following modification in vivo, the citronellol, citronellal, or citronellic acid remains in the cell and/or is excreted into the culture medium. For example, a recombinant host cell comprising an operative engineered biosynthetic pathway, comprising: a gene encoding a geranyl diphosphate synthase (GPPS) polypeptide; a gene encoding a geraniol synthase (GES) polypeptide; a gene encoding a geraniol dehydrogenase (GeDH) polypeptide; a gene encoding a enoate reductase (ENR) polypeptide; and a gene encoding aldehyde reductase (AR) polypeptide wherein the recombinant host cell is capable of producing one or more of citronellol, citronellal, or citronellic acid is contacted with oxidizing bacteria to convert citronellol to citronellal and/or citronellic acid. In certain embodiments, bioconversion is regarded as an advantage because an efficient self-sustained bioconversion system can significantly lower the scale-up costs.

Exemplary prokaryotic and eukaryotic species are described in more detail below. However, it will be appreciated that other species can be suitable. For example, suitable species can be in a genus such as *Abies, Acinetobactor, Castellaniella, Catharanthus, Gluconobacter, Escherichia, Kluyveromyces, Pichia, Pseudomonas, Rhodococcus, Saccharomyces, Staphylococcus, Sphingopyxis, Thauera*, or *Zymomonas*. Exemplary species from such genera include *Abies grandis, Acinetobacter calcoaceticus, Castellaniella defragrans, Catharanthus roseus, Gluconobacter oxydans, Gluconobacter cerinus, Gluconobacter frateurii, Escherichia coli, Kluyveromyces lactis, Pichia stipitis, Pseudomonas putida, Rhodococcus* sp. RD6.2, *Saccharomyces cerevisiae, Staphylococcus aureus, Sphingopyxis macrogoltabida, Thauera terpenica* 58Eu, and *Zymomonas mobilis* subsp. *mobilis*.

In some embodiments, a microorganism can be a prokaryote, such as bacteria, for example, *Escherichia coli, Lactobacillus, Lactococcus, Cornebacterium, Acetobacter, Acinetobacter*, or *Pseudomonas*.

In other embodiments, a microorganism can be a fungus, such as an Ascomycete, for example, *Gibberella fujikuroi, Kluyveromyces lactis, Schizosaccharomyces pombe, Aspergillus niger, Yarrowia lipolytica, Ashbya gossypii*, or *Saccharomyces cerevisiae*.

In certain embodiments, a microorganism can be an algal cell, for example, *Blakeslea trispora, Dunaliella salina, Haematococcus pluvialis, Chlorella* sp., *Undaria pinnatifida, Sargassum, Laminaria japonica*, or *Scenedesmus almeriensis* species.

In some embodiments, a microorganism can be a cyanobacterial cell, for example, *Blakeslea trispora, Dunaliella salina, Haematococcus pluvialis, Chlorella* sp., *Undaria pinnatifida, Sargassum, Laminaria japonica*, or *Scenedesmus almeriensis*.

*Saccharomyces* spp.

*Saccharomyces* is a well-studied and widely used chassis organism in synthetic biology, and can be used as the recombinant microorganism platform. For example, there are libraries of mutants, plasmids, detailed computer models of metabolism and other information available for *S. cerevisiae*, allowing for rational design of various modules to enhance product yield. Methods are known for making recombinant microorganisms.

*Abies grandis*

*Abies grandis* is a fir native to the Pacific Northwest and Northern California of North America, occurring at altitudes of sea level to 1,800 m. It is a major constituent of the Grand Fir/Douglas Fir Ecoregion of the Cascade Range. The tree typically grows to 40-70 m in height. There are two varieties, the taller coast grand fir, found west of the Cascade Mountains, and the shorter interior grand fir, found east of the Cascades.

*Aspergillus* spp.

*Aspergillus* species such as *A. oryzae, A. niger* and *A. sojae* are widely used microorganisms in food production and can also be used as the recombinant microorganism platform. Nucleotide sequences are available for genomes of *A. nidulans, A. fumigatus, A. oryzae, A. clavatus, A. flavus, A. niger*, and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for producing citronellol and citronellol precursors.

*E. coli*

*E. coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Castellaniella defragrans*

*Castellaniella defragrans* is a Betaproteobacterium capable of coupling the oxidation of monoterpenes with denitrification.

*Acinetobacter calcoaceticus*

*Acinetobacter calcoaceticus* is a non-motile, gram negative coccobacillus. It grows under aerobic conditions, is catalase positive and oxidase negative.

*Agaricus, Gibberella*, and *Phanerochaete* spp.

*Agaricus, Gibberella*, and *Phanerochaete* spp. can be useful because they are known to produce large amounts of isoprenoids in culture. Thus, the terpene precursors for producing large amounts of citronellol are already produced by endogenous genes. Thus, modules comprising recombinant genes for citronellol biosynthesis polypeptides can be introduced into species from such genera without the necessity of introducing mevalonate or MEP pathway genes.

Arxula adeninivorans (Blastobotrys adeninivorans)

Arxula adeninivorans is dimorphic yeast (it grows as a budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

Yarrowia lipolytica

Yarrowia lipolytica is dimorphic yeast (see Arxula adeninivorans) and belongs to the family Hemiascomycetes. The entire genome of Yarrowia lipolytica is known. Yarrowia species is aerobic and considered to be non-pathogenic. Yarrowia is efficient in using hydrophobic substrates (e.g. alkanes, fatty acids, oils) and can grow on sugars. It has a high potential for industrial applications and is an oleaginous microorganism. Yarrowia lipolyptica can accumulate lipid content to approximately 40% of its dry cell weight and is a model organism for lipid accumulation and remobilization. See e.g., Nicaud, 2012, Yeast 29(10):409-18; Beopoulos et al., 2009, Biochimie 91(6):692-6; Bankar et al., 2009, Appl Microbiol Biotechnol. 84 (5): 847-65.

Rhodotorula sp.

Rhodotorula is unicellular, pigmented yeast. The oleaginous red yeast, Rhodotorula glutinis, has been shown to produce lipids and carotenoids from crude glycerol (Saenge et al., 2011, Process Biochemistry 46(1):210-8). Rhodotorula toruloides strains have been shown to be an efficient fed-batch fermentation system for improved biomass and lipid productivity (Li et al., 2007, Enzyme and Microbial Technology 41:312-7).

Rhodosporidium Toruloides

Rhodosporidium toruloides is oleaginous yeast and useful for engineering lipid-production pathways (See e.g., Zhu et al., 2013, Nature Commun. 3:1112; Ageitos et al., 2011, Applied Microbiology and Biotechnology 90(4): 1219-27).

Candida boidinii

Candida boidinii is methylotrophic yeast (it can grow on methanol). Like other methylotrophic species such as Hansenula polymorpha and Pichia pastoris, it provides an excellent platform for producing heterologous proteins. Yields in a multigram range of a secreted foreign protein have been reported. A computational method, IPRO, recently predicted mutations that experimentally switched the cofactor specificity of Candida boidinii xylose reductase from NADPH to NADH. See, e.g., Mattanovich et al., 2012, Methods Mol Biol. 824:329-58; Khoury et al., 2009, Protein Sci. 18(10):2125-38.

Hansenula polymorpha (Pichia angusta)

Hansenula polymorpha is methylotrophic yeast (see Candida boidinii). It can furthermore grow on a wide range of other substrates; it is thermo-tolerant and can assimilate nitrate (see also Kluyveromyces lactis). It has been applied to producing hepatitis B vaccines, insulin and interferon alpha-2a for the treatment of hepatitis C, furthermore to a range of technical enzymes. See, e.g., Xu et al., 2014, Virol Sin. 29(6):403-9.

Kluyveromyces lactis

Kluyveromyces lactis is yeast regularly applied to the production of kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale. See, e.g., van Ooyen et al., 2006, FEMS Yeast Res. 6(3):381-92.

Pichia pastoris

Pichia pastoris is methylotrophic yeast (see Candida boidinii and Hansenula polymorpha). It provides an efficient platform for producing foreign proteins. Platform elements are available as a kit and it is worldwide used in academia for producing proteins. Strains have been engineered that can produce complex human N-glycan (yeast glycans are similar but not identical to those found in humans). See, e.g., Piirainen et al., 2014, N Biotechnol. 31(6):532-7.

Physcomitrella spp.

Physcomitrella mosses, when grown in suspension culture, have characteristics similar to yeast or other fungal cultures. This genera can be used for producing plant secondary metabolites, which can be difficult to produce in other types of cells.

Catharanthus roseus

Catharanthus roseus is a species of flowering plant in the dogbane family Apocynaceae. It is native and endemic to Madagascar, but grown elsewhere as an ornamental and medicinal plant, a source of the drugs vincristine and vinblastine, used to treat cancer.

Rhodococcus sp.

Rhodococcus is a genus of aerobic, nonsporulating, non-motile Gram-positive bacteria closely related to Mycobacterium and Corynebacterium. Though a number of species have been shown to have pathogenic properties, many are benign, and have been found to survive in a wide range of environments, including soil, water, and eukaryotic cells.

Staphylococcus aureus

Staphylococcus aureus is a gram-positive coccal bacterium that is a member of the Firmicutes, and is frequently found in the nose, respiratory tract, and on the skin. It is often positive for catalase and nitrate reduction. Although S. aureus is not always pathogenic, it is a common cause of skin infections such as abscesses, respiratory infections such as sinusitis, and food poisoning.

Zymomonas mobilis

Zymomonas mobilis is a Gram negative, facultative anaerobic, non-sporulating, polarly-flagellated, rod-shaped bacterium. It has notable bioethanol-producing capabilities, which surpass yeast in some aspects. It was originally isolated from alcoholic beverages like the African palm wine, the Mexican pulque, and also as a contaminant of cider and beer (cider sickness and beer spoilage) in European countries.

Pseudomonas putida

Pseudomonas putida is a Gram-negative, rod-shaped, saprotrophic soil bacterium. It demonstrates a very diverse metabolism, including the ability to degrade organic solvents such as toluene. This ability has been put to use in bioremediation, or the use of microorganisms to biodegrade oil.

Gluconobacter sp.

Gluconobacter sp are gram-negative rod or oval shaped bacteria. They tend to have a small genome size and limited metabolic abilities. These abilities include partially oxidizing carbohydrates and alcohols through the process of oxidative fermentation. They are obligately aerobic, and have a strict respiratory type of metabolism with oxygen as the terminal electron acceptor. Gluconobacter strains prefer sugar-enriched environments. Examples include, but are not limited to, Gluconobacter oxydans, Gluconobacter cerinus, and Gluconobacter frateurii.

Citronellal/Citronellol Compositions

Significant agricultural resources in terms of land, equipment, and biomass generation are required to meet current industry needs for citronellol, citronellal, and citronellic acid. It is therefore desirable to have the ability to obtain scalable amounts of highly pure citronellol, citronellal, and citronellic acid. Recombinant hosts described herein can produce compositions that are selectively enriched for citronellol, citronellal, and/or citronellic acid. As used herein, the term "enriched" is used to describe a citronellol, citronellal, and/or citronellic acid composition with an increased proportion of a particular citronellol, citronellal, and/or citronellic acid, compared to citronellol, citronellal, and/or citronellic acid (extract) from the oils of plants such as *Corymbia citriodora*, *Cymbopogon nardus*, and *Cymbopogon winterianus*. Thus, the recombinant hosts described herein can facilitate the production of compositions that are tailored to meet the profile desired for a given product and that have a proportion of each citronellol, citronellal, and/or citronellic acid that is consistent from batch to batch. In some embodiments, recombinant hosts described herein do not produce or produce a reduced amount of an undesired citronellol, citronellal, and/or citronellic acid precursor and/or intermediate or by-product found in plant extracts. Thus, compositions comprising citronellol, citronellal, and/or citronellic acid produced by the recombinant hosts described herein are distinguishable from compositions derived from plants. In some embodiments, a citronellol, citronellal, and/or citronellic acid composition can be produced in vitro, in vivo, or by bioconversion.

The amount of an individual desired product (e.g., citronellol, citronellal, or citronellic acid) accumulated can be from about 1 to about 7,000 mg/L, e.g., about 1 to about 10 mg/L, about 3 to about 10 mg/L, about 5 to about 20 mg/L, about 10 to about 50 mg/L, about 10 to about 100 mg/L, about 25 to about 500 mg/L, about 100 to about 1,500 mg/L, or about 200 to about 1,000 mg/L, at least about 1,000 mg/L, at least about 1,200 mg/L, at least about at least 1,400 mg/L, at least about 1,600 mg/L, at least about 1,800 mg/L, at least about 2,800 mg/L, or at least about 7,000 mg/L. In some aspects, the amount of citronellol, citronellal, or citronellic acid can exceed 7,000 mg/L. The amount of a combination of citronellol, citronellal, and citronellic acid accumulated can be from about 1 mg/L to about 7,000 mg/L, e.g., about 200 to about 1,500, at least about 2,000 mg/L, at least about 3,000 mg/L, at least about 4,000 mg/L, at least about 5,000 mg/L, at least about 6,000 mg/L, or at least about 7,000 mg/L. In some aspects, the amount of a combination of citronellol, citronellal, and citronellic acid can exceed 7,000 mg/L. In general, longer culture times will lead to greater amounts of product. Thus, the recombinant host microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce citronellol, citronellal, and/or citronellic acid. For example, a first microorganism can comprise one or more biosynthesis genes for producing a citronellol, citronellal, and/or citronellic acid precursor, while a second microorganism comprises citronellol, citronellal, and/or citronellic acid biosynthesis genes. The product produced by the second, or final microorganism is then recovered. It will also be appreciated that in some embodiments, a recombinant microorganism is grown using nutrient sources other than a culture medium and utilizing a system other than a fermenter.

Alternatively, the two or more microorganisms each can be grown in a separate culture medium and the product of the first culture medium, e.g., IPP and/or DMAPP, or geraniol or nerol, can be introduced into second culture medium to be converted into a subsequent intermediate, or into an end product such as citronellal. The product produced by the second, or final microorganism is then recovered. It will also be appreciated that in some embodiments, a recombinant microorganism is grown using nutrient sources other than a culture medium and utilizing a system other than a fermenter.

Citronellol, citronellal, and/or citronellic acid and compositions obtained by the methods disclosed herein can be used to make any number of commonly used products in the fragrance industry, such as an insect repellent, and they can also be used as an intermediate in the synthesis of several natural terpenoids. For example, substantially pure citronellol, citronellal, and/or citronellic acid can be included in products such as candles, lotions, perfumes, deodorants, toothpaste, chewing gum and oils. Substantially pure citronellol, citronellal, and/or citronellic acid can also be included. Alternatively, a mixture of citronellol, citronellal, and/or citronellic acid can be made by culturing recombinant microorganisms separately, each producing a specific citronellol, citronellal, and/or citronellic acid, recovering the citronellol, citronellal, and/or citronellic acid in substantially pure form from each microorganism and then combining the compounds to obtain a mixture comprising each compound in the desired proportion. The recombinant microorganisms described herein permit more precise and consistent mixtures to be obtained compared to current citronellol, citronellal, and/or citronellic acid products.

Compositions produced by a recombinant microorganism described herein can be incorporated into a number of products. For example, a citronellol, citronellal, and/or citronellic acid compositions produced by a recombinant microorganism can be incorporated into a product in an amount ranging from about 20 mg citronellol, citronellal, and/or citronellic acid/kg of product to about 1800 mg citronellol, citronellal, and/or citronellic acid/kg of product on a dry weight basis, depending on the type of citronellol, citronellal, and/or citronellic acid and product. For example, a citronellol composition can have from 90-99 weight % citronellol and an undetectable amount of plant-derived contaminants, and be incorporated into a product at from 25-1600 mg/kg, e.g., 100-500 mg/kg, 25-100 mg/kg, 250-1000 mg/kg, 50-500 mg/kg or 500-1000 mg/kg on a dry weight basis.

A citronellal composition can be a citronellal composition having greater than 3 weight % citronellal and be incorporated into the product such that the amount of citronellal in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the citronellal composition has an undetectable amount of plant-derived contaminants.

A citronellic acid composition can be a citronellic acid composition having greater than 3 weight % citronellic acid and be incorporated into the product such that the amount of citronellic acid in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the citronellic acid composition has an undetectable amount of plant-derived contaminants.

The invention will be further described in the following examples, which do not limit the scope of the invention described in the claims.

EXAMPLES

The Examples that follow are illustrative of specific embodiments of the invention, and various uses thereof. They are set forth for explanatory purposes only, and are not to be taken as limiting the invention.

Example 1. Analysis of Monoterpenes in In Vivo Samples

Isopropyl myristate (IPM) was recovered from biphasic culture by centrifugation at 4000 g for 5 minutes. 20 µl of IPM was diluted 20× in hexane before quantification. 2 µl of diluted sample was injected on a Waters Acquity UPC² system (Milford, USA) coupled to a Waters Acquity UPC² PDA eLambda detector. Separation of the compounds was achieved on a Waters Acquity UPC² HSS C18 SB column (1.8 µm, 3.0 mm×100 mm), kept at 40° C. Mobile phases A and B were CO2 and acetonitrile, respectively. A flow of 2.0 ml/min was used. The gradient profile was as follow: 0.2 min constant at 1% B, a linear gradient from 1% B to 10% B in 1.8 min, a wash for 1 min at 10% B and back to the initial condition. The Automatic Back-Pressure Regulator (ABPR) pressure was kept at 2000 psi on the Water Acquity CO2 convergence manager.

Monoterpenes, including citronellal, geranial, citronellol and geraniol, were analyzed by recording their UV 210 nm absorbance. Detected monoterpene compounds were quantified using a linear calibration curve with authentic standards (ranging from 0.625 mg/l to 320 mg/l; Sigma-Aldrich, Buchs, Switzerland) using Waters TargetLynx software.

Example 2. Analysis of Monoterpenes in In Vitro Samples

100 µl in vitro assay samples were extracted by liquid-liquid extraction with 300 µl Methyl tert-butyl ether (MTBE) or hexane. MTBE or hexane was recovered by quick centrifugation at 12000×g and placed in injection vials prior analysis.

1 µl sample was injected on an Agilent 7890A GC system (Santa Clara, USA) equipped with an Agilent flame ionization detector. Separation of the compounds was achieved on a Restek Rtx®-Wax column (30 m×0.25 mm, 0.25 µm film thickness). The oven temperature was initially held at 50° C. for 0.6 min, raised to 180° C. at 20° C./min, them programmed from 180° C. to 250° C. at 60° C./min and finally held at 250° C. for 0.6 min. Hydrogen was used as carrier gas with a constant flow of 2 ml/min. The injector and detector were held at 250° C. and 260° C., respectively.

Monoterpenes, including citronellal, geranial, citronellol and geraniol, were quantified using a linear calibration curve with authentic standards (ranging from 0.078 mg/l to 40 mg/l; Sigma-Aldrich, Buchs, Switzerland) using Agilent Masshunter Quantitative Analysis software.

Example 3. Strain Engineering

Recombinant yeast strains capable of producing citronellal/citronellol pathway intermediates and citronellol were engineered using precursor strains (see e.g., WO 2014027118, which is incorporated by reference in its entirety) by incorporating one or more copies of a recombinant gene encoding an *Abies grandis* GPPS polypeptide (SEQ ID NO:17), a recombinant gene encoding a *Catharanthus roseus* GES polypeptide (SEQ ID NO:18), a recombinant gene encoding a *Kluyveromyces lactis* ENR polypeptide (SEQ ID NO:21), *Pichia stipitis* ENR polypeptide (SEQ ID NO:8), *Zymomonas mobilis* ENR polypeptide (SEQ ID NO:9), a recombinant gene encoding a recombinant *Castellaniella defragrans* GeDH polypeptide (SEQ ID NO:1, SEQ ID NO:19), a recombinant gene encoding a *Thaurera terpenica* 58Eu GeDH polypeptide (SEQ ID NO:5), a recombinant gene encoding a *Rhodococcus* sp. RD6.2 GeDH polypeptide (SEQ ID NO:2), a recombinant gene encoding a *Sphingopyxis macrogoltabida* GeDH polypeptide (SEQ ID NO:3), a recombinant gene encoding an *Acinetobacter calcoaceticus* GeDH polypeptide (SEQ ID NO:4), and/or a recombinant gene encoding a *Pseudomonas putida* GeDH polypeptide (SEQ ID NO:6).

Example 4. Citronellal/Citronellol Pathway Production in Yeast and Bacteria Via Geraniol An exemplary heterologous or endogenous pathway in yeast and bacteria for the production of d- or l-citronellal and d- or l-citronellol is shown in FIG. 1a. The mevalonate pathway or 2C-methyl-D-erythritol-4-phosphate (MEP) pathway can lead to the production of isopentenyl diphosphate (IPP) and dimethylally pyrophosphate (DMAPP). IPP and DMAPP can then be condensed by Geranyl diphosphate synthase (GPPS) to produce geranyl diphosphate (GPP), which can be a starting substrate for the citronellal/citronellol pathway. GPP can then be converted into geraniol by geraniol synthase (GES). Geraniol can then be oxidized by geraniol dehydrogenase (GeDH) to produce geranial. Ene reductase (ENR, also called enoate reductases) can then be used to reduce geranial into d-citronellal. Citronellal can then be reduced to citronellol by aldehyde reductase (AR) activity in the host cell in addition to reverse activity of GeDH from the oxidation of geraniol. The specificity of the ENR and its substrate can determine the production of d- or l-citronellal (see FIG. 1a).

An additional aspect of the citronellal/citronellol pathway can be the isomerization of geranial to neral. This step can occur chemically due to keto-enol tautomerization. Neral can then be converted to nerol by AR activity in the host cell in addition to reverse activity of GeDH from the oxidation of geraniol.

Figure 1B:
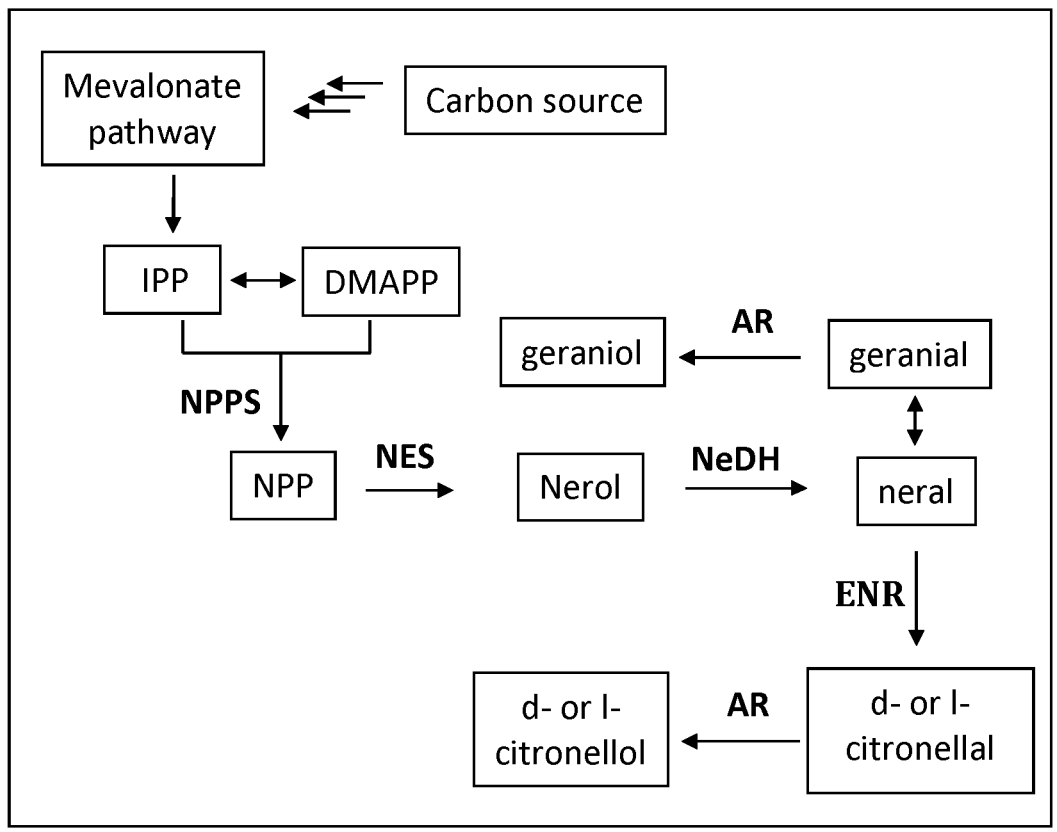
FIG. 1b shows an alternative citronellal/citronellol pathway with indicated enzymes and products.

Example 5. Citronellal/Citronellol Pathway Production in Yeast and Bacteria Via Nerol An exemplary heterologous or endogenous pathway in yeast and bacterial for the production of d- or l-citronellal and d- or l-citronellol is shown in FIG. 1b. The mevalonate pathway or MEP pathway can lead to the production of IPP and DMAPP. IPP and DMAPP can then be converted by neryl diphosphate synthase (NPPS) to produce neryl diphosphate (NPP), which can be a starting substrate for the citronellal/citronellol pathway. NPP can then be converted into nerol by neryl synthase (NES). Nerol can then be oxidized by neral dehydrogenase (NeDH) to produce neral. ENR can then reduce neral into l-citronellal. Citronellal can then be reduced to citronellol by AR activity in the host cell in addition to reverse activity of NeDH from the oxidation of nerol. The specificity of the ENR and its substrate can determine the production of d- or l-citronellal (see FIG. 1b).

Figure 1C:
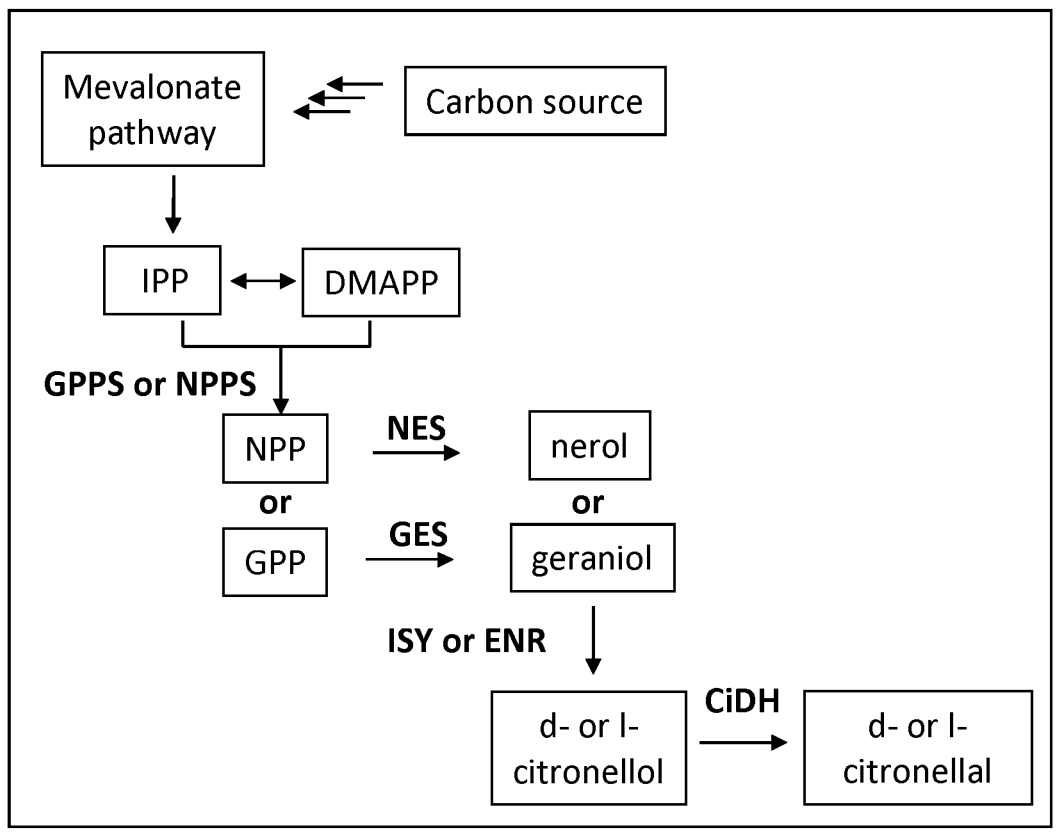
FIG. 1c shows yet another alternative citronellal/citronellol pathway with indicated enzymes and products.

Example 6. Citronellal/Citronellol Pathway Production in Yeast and Bacteria Via Direct Conversion of Nerol or Geraniol to Citronellol An exemplary heterologous or endogenous pathway in yeast and bacterial for the production of d- or l-citronellal and d- or l-citronellol is shown in FIG. 1c. The mevalonate pathway or MEP pathway can lead to the production of IPP and DMAPP. IPP and DMAPP can then be condensed by GPPS or NPPS to produce GPP or NPP, respectively. GPP or NPP can be converted to geraniol or nerol, respectively. Geraniol or nerol can then be converted to d-citronellol or l-citronellol, respectively, by an enoate reductase (ENR) or an iridoid synthase (ISY). D- or l-citronellol can then be oxidized to d- or l-citronellal, respectively, by citronellol dehydrogenase (CiDH).

Example 7. Citronellal/Citronellol Pathway Production in Yeast

In vivo expression of heterologous genes that establish the citronellal/citronellol pathway on plasmid in *S. cerevisiae* was tested using a yeast strain with elevated levels of isopentenyl diphosphate (IPP) and dimethylally pyrophosphate (DMAPP), caused by a transcriptional downregulation of ERG20 to increase the production of geranyl diphosphate by the overexpression of Ag_GPPS2 (see e.g., WO 2014027118 which is incorporated by reference in its entirety).

The yeast strain was transformed with plasmids containing autonomously replicating sequence (ARS) and a yeast centromere (CEN) (ARS-CEN plasmids) with co-expression of *Abies grandis* geranyl diphosphate synthase (Ag_GPPS2), *Catharanthus roseus* geranial synthase (Cr_GES), and/or *Kluyveromyces lactis* Yellow Enzyme (Kl_KYE1) and *Castellaniella defragrans* geranial dehydrogenase (Cd_GeDH). The ARS-CEN plasmid was under the control of constitutive promoters. Synthetic Complete (SC) media with 2% glucose was used for culturing. Cultures were supplemented with 10% v/v isopropylmyristate secondary phase during the culturing to help extract and trap targeted molecules produced by the activation of the pathway. Cultures were grown for 120 hours.

All genes listed above were synthesized by Thermo Fisher Scientific GENEART™ GmbH (Regensburg, Germany) as *S. cerevisiae* codon optimized variants and IPM samples were analyzed by UPCs-UV.

Figure 2:
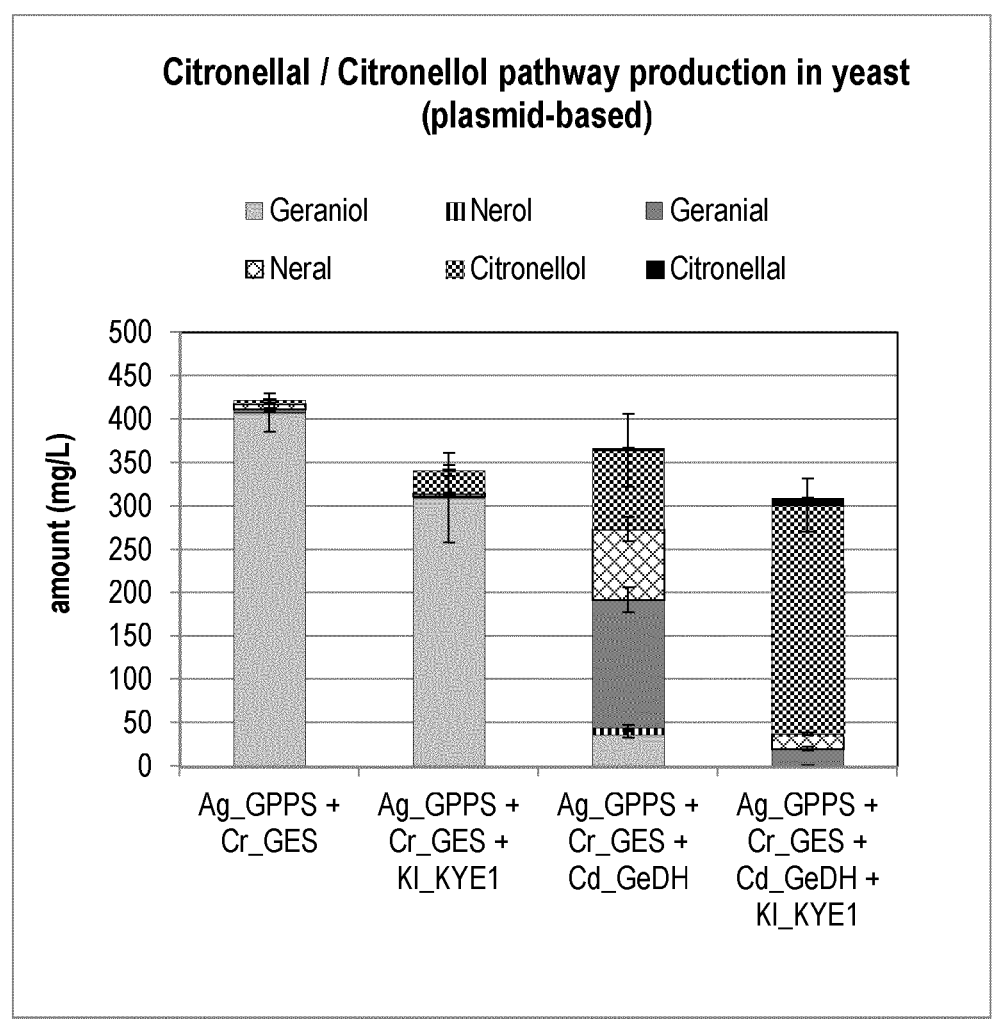
FIG. 2 shows the plasmid-based citronellal/citronellol pathway production in yeast. Expression of heterologous genes that initiate the citronellal/citronellol pathway in vivo in yeast by co-expressing *Abies grandis*_Geranyl diphosphate synthase (Ag_GPPS2), *Catharanthus roseus*_geraniol Synthase (Cr_GES), *Castellaniella defragrans*_Geraniol Dehydrogenase (Cd_GeDH), and *Kluyveromyces lactis*_Yellow Enzyme (Kl_KYE1).

Co-expression of Ag_GPPS2+Cr_GES resulted in production of about 400 mg/L of geraniol, the first intermediate in the pathway. Co-expression of Ag_GPPS2+Cr_GES+ Kl_KYE1 led to the production about 300 mg/L of geraniol and a minor accumulation of geranial (about 10 mg/L) and citronellol (about 25 mg/L). Expression of Ag_GPPS2+ Cr_GES+Cd_GeDH led to accumulation of varying amounts of geraniol (about 30 mg/L), geranial (about 150 mg/L), citronellol (about 100 mg/L), neral (about 75 mg/L), and less than 5 mg/L of citronellal and nerol. These results demonstrate that geraniol is converted to geranial by Cd_GeDH and then further converted transiently to citronellal by endogenous ene reductase activity (Sc_OYE2). Some of the geranial is interconverted to neral by keto-enol tautomerisation and some of the neral is reduced to nerol by AR activity. Following the production of citronellal, alcohol dehydrogenase/aldehyde reductase activity yields citronellol. Expression of Ag_GPPS2, Cr_GES, Cd_GeDH and Kl_KYE1 led to the establishment of the full citronellal/citronellol pathway with production of citronellol (via citronellal). Expression of Kl_KYE1 and Cd_GeDH genes on the plasmid suggest their role in the production of intermediates and/or the end product of the citronellal/citronellol pathway. The predominant direction of the pathway was revealed by the stepwise addition of pathway steps. GPP→geraniol/nerol→geranial/neral→citronellal→citronellol (see FIGS. 1 and 2).

Example 8. Production of Nerol as a Substrate for the Citronellal/Citronellol Pathway In vivo expression of heterologous genes that establish the production of nerol via activation of the citronellal/citronellol pathway on plasmids in *S. cerevisiae* was tested using a yeast strain with elevated levels of isopentenyl diphosphate (IPP) and dimethylally pyrophosphate (DMAPP), caused by a transcriptional downregulation of ERG20.

The yeast strain was transformed with plasmids containing autonomously replicating sequence (ARS) and a yeast centromere (CEN) (ARS-CEN plasmids) with co-expression of *Abies grandis*_geranyl diphosphate synthase (Ag_GPPS2) and *Glycine max*_nerol synthase (Gm_NES; SEQ ID NO:56) or *Solanum lycopersicum*_neryl diphosphate synthase (Sl_NDPS1; SEQ ID NO:53) and Gm_NES. The ARS-CEN plasmid was under the control of constitutive promoters. Synthetic Complete (SC) media with 2% glucose was used for culturing. Cultures were supplemented with 10% v/v isopropylmyristate secondary phase during the culturing to help extract and trap targeted molecules produced by the activation of the pathway. Cultures were grown for 120 hours.

Figure 3:
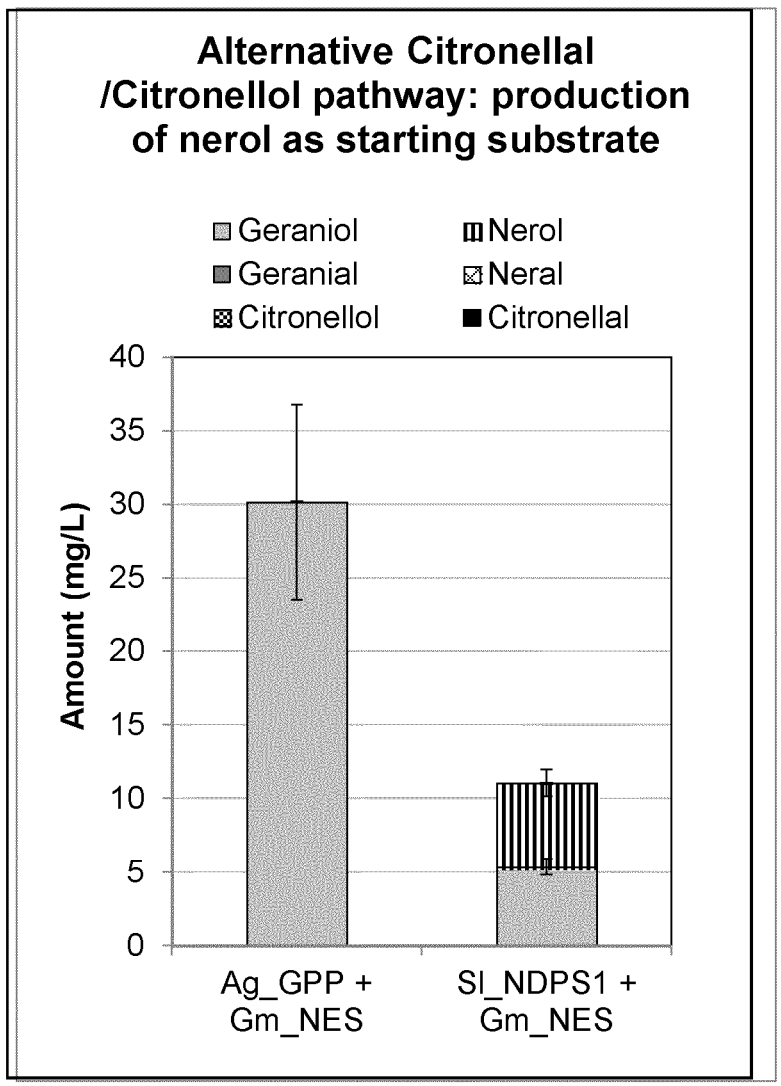
FIG. 3 shows plasmid-based nerol production in yeast, which can be an alternative starting substrate for the citronellal/citronellol pathway. Expression of heterologous genes that initiate the citronellal/citronellol pathway in vivo in yeast by co-expressing *Abies grandis*_Geranyl diphosphate synthase (Ag_GPPS2), *Glycine max*_nerol synthase (Gm_NES), or *Solanum lycopersicum*_neryl diphosphate synthase (Sl_NDPS1) and *Glycine max*_nerol synthase (Gm_NES).

All genes listed above were synthesized by Thermo Fisher Scientific GENEART™ GmbH (Regensburg, Germany) as *S. cerevisiae* codon optimized variants and IPM samples were analyzed by UPCs-UV. Expression of Ag_GPPS2 and Gm_NES resulted in the production of geraniol only (about 30 mg/L) while the expression of Sl_NDPS1 and Gm_NES yielded about 5 mg/L of nerol and geraniol (see FIG. 3). The production of nerol in this example indicates production of NPP by Sl_NDPS1 and that NPP was converted to nerol by the expression of Gm_NES.

Example 9. Production of Citronellal Via the Conversion of Geraniol to Citronellol In vivo expression of heterologous genes that establish the citronellal/citronellol pathway on plasmids in *S. cerevisiae* was tested using a yeast strain with elevated levels of isopentenyl diphosphate (IPP) and dimethylally pyrophosphate (DMAPP), caused by a transcriptional downregulation of ERG20.

The yeast strain was transformed with plasmids containing autonomously replicating sequence (ARS) and a yeast centromere (CEN) (ARS-CEN plasmids) with co-expression of *Abies grandis* geranyl diphosphate synthase (Ag_GPPS2) and *Catharanthus roseus* geranial synthase (Cr_GES), co-expression of Ag_GPPS2, Cr_GES, and *Olea europaea* Iridoid synthase (Oe_ISY), or co-expression of Ag_GPPS2, Cr_GES, Oe_ISY, and *Bradyrhizobium* sp. DFCI-1_citronellol/citronellal dehydrogenase (Bs_CiDH). The ARS-CEN plasmid was under the control of constitutive promoters. Synthetic Complete (SC) media with 2% glucose was used for culturing. Cultures were supplemented with 10% v/v isopropylmyristate secondary phase during the culturing to help extract and trap targeted molecules produced by the activation of the pathway. Cultures were grown for 120 hours.

All genes listed above were synthesized by Thermo Fisher Scientific GENEART™ GmbH (Regensburg, Germany) as *S. cerevisiae* codon optimized variants and IPM samples were analyzed by UPCs-UV.

Figure 4:
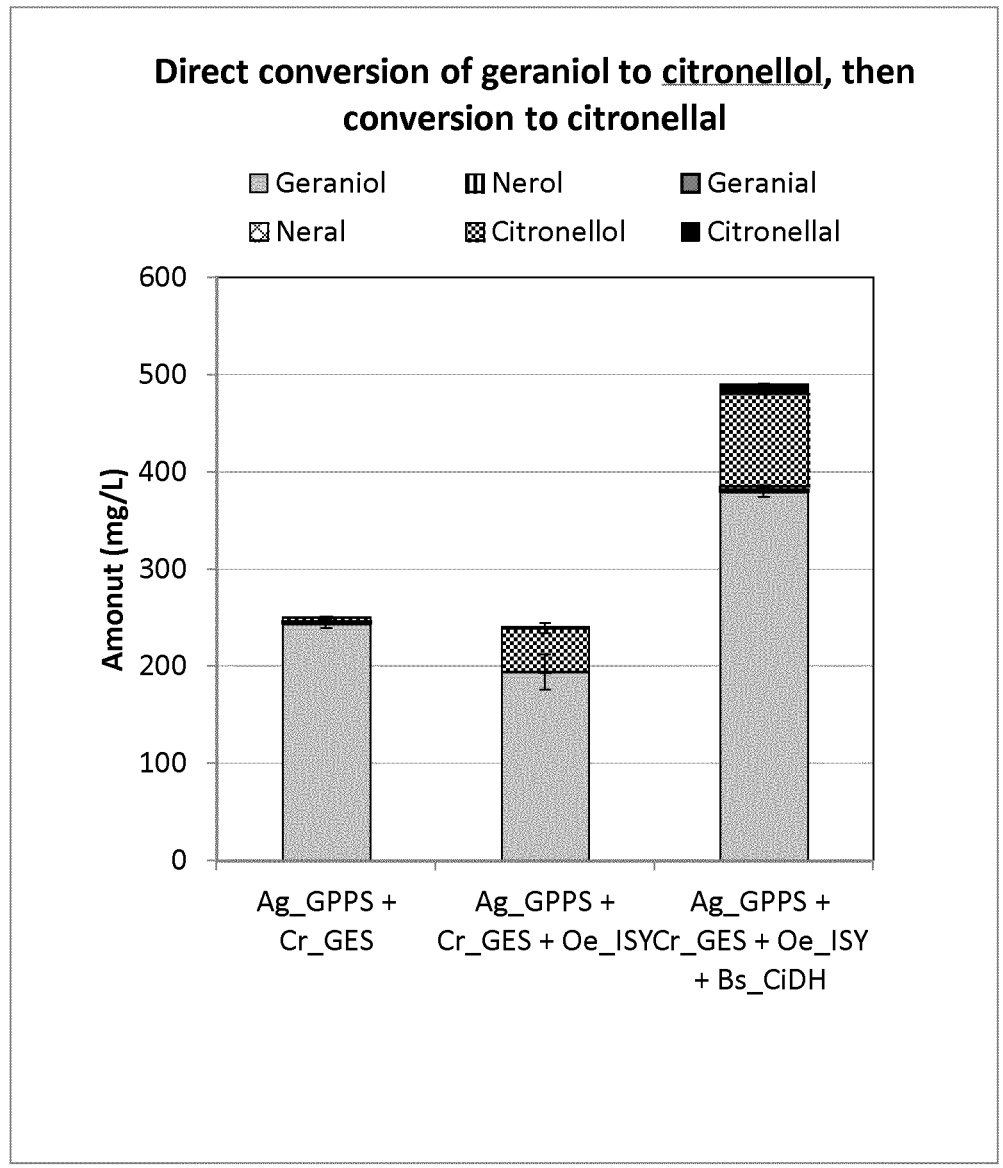
FIG. 4 shows plasmid-based citronellal/citronellol pathway production in yeast via the conversion of geraniol to citronellol, then citronellol to citronellal. Expression of heterologous genes that initiate the citronellal/citronellol pathway in vivo in yeast by co-expressing *Abies grandis*_ Geranyl diphosphate synthase (Ag_GPPS2), *Catharanthus roseus*_Geraniol Synthase (Cr_GES), or Ag_GPPS2, Cr_GES, and *Olea europaea*_Iridoid synthase (Oe_ISY), or Ag_GPPS2, Cr_GES, Oe_ISY, and *Bradyrhizobium* sp. DFCI-1_citronellal/citronellol dehydrogenase (Bs_CiDH).

Expression of Ag_GPPS2 and Cr_GES resulted in the production of about 230 mg/L of geraniol. Expression of Ag_GPPS2, Cr_GES and Oe_ISY lead to the production of about 200 mg/L geraniol, about 50 mg/L citronellol and less than 10 mg/L citronellal. Expression of Ag_GPPS2, Cr_GES, Oe_ISY, and Bs_CiDH yielded 375 mg/L geraniol, 100 mg/L citronellol, less than 50 mg/L citronellal, and less than 20 mg/L geranial. Results indicate that Oe_ISY converts geraniol directly to citronellol and that co-expression of Bs_CiDH in a yeast strain with geraniol leads to the accumulation of a small amount of citronellal (see FIG. 4).

Example 10. Citronellal/Citronellol Pathway Integrated in *S. cerevisiae*

*S. cerevisiae* yeast strain with full chromosomal integration of citronellal/citronellol pathway genes *Abies grandis* geranyl diphosphate synthase (Ag_tGPPS) *Catharanthus roseus* geranial synthase (Cr_GES) *Kluyveromyces lactis* Yellow Enzyme (Kl_KYE1), and *Castellaniella defragrans* geranial dehydrogenase (Cd_GeDH) was developed and tested to identify which citronellal/citronellol pathway intermediates and/or end product would be produced.

A yeast strain with elevated levels of isopentenyl diphosphate (IPP) and dimethyl allyl pyrophosphate (DMAPP), caused by transcriptional downregulation of ERG20, was used for integration of pathway expression cassettes (see e.g., WO 2014027118 which is incorporated by reference in its entirety). TEF1 promoter in front of Ag_GPPS2 PGK1 promoter in front of Cr_GES and Cd_GeDH, and TPI1 promoter in front of Kl_KYE1. The expression cassettes containing flanking regions were integrated in the yeast genome by homologous recombination The integration construct consists of an expression cassette and a selection marker (promoter-ORF-terminator-selection marker) with flanking sequences upstream and downstream (about 3-400 nucleotides) that are homologous to specific intergenic sequences in the *S. cerevisiae* genome. The homologous sequences target the integration construct to these sequences in the genome, and the construct integrates by homologous recombination. Yeast clones with integrated expression cassette and selection marker can be selected by means of selection marker.

Yeast extract Peptone Dextrose (YPD) media with 2% glucose was used for culturing. The cultures were supplemented with 10% v/v isopropyl myristate (IPM) secondary phase during culturing to help extract and trap molecules produced by the activation of the pathway. Cultures were grown for 120 hours. All genes were synthesized by Thermo Fisher Scientific GENEART™ GmbH (Regensburg, Germany) as *S. cerevisiae* codon optimized variants. IPM samples were analyzed by UPC2-UV. IPM samples were analysed by chiral GC to measure optical purity of citronellal and citronellol (enantiomer excess; ee %).

Expression of the integrated pathway resulted in the production of citronellol (about 175 mg/L) as the only major product. Specifically, the integrated pathway yielded about 100 ee % of d-citronellol (see FIG. 5).

Example 11. Citronellal/Citronellol Pathway Production in Yeast with Different GeDH Genes The active geraniol dehydrogenases in the citronellal/citronellol pathway in yeast include *Castellaniella defragrans* geraniol dehydrogenase (Cd_GeDH), *Thauera terpenica* 58Eu geraniol dehydrogenase (Tt_GeDH), *Rhodococcus* sp. RD6.2 geraniol dehydrogenase (Rs_GeDH), *Spingopyxis macrogoltabida* geraniol dehydrogenase (Sm_GeDH), *Acinetobacter calcoaceticus* geraniol dehydrogenase (Ac_GeDH), and *Pseudomonas putida* geraniol dehydrogenase (Pp_GeDH).

In order to initiate the citronellal/citronellol pathway, a yeast strain with elevated levels of IPP and DMAPP, caused by a transcriptional downregulation of ERG20 was used to yield elevated levels of GPP. The yeast strain was transformed with ARS-CEN plasmids with *Abies grandis* geranyl diphosphate synthase (Ag_GPPS2), *Catharanthus roseus* geranial synthase (Cr_GES), and *Kluyveromyces lactis* Yellow Enzyme (Kl_KYE1), and a geraniol dehydrogenase gene selected from the following: *Castellaniella defragrans* geraniol dehydrogenase (Cd_GeDH; SEQ ID NO:1), *Thauera terpenica* 58Eu geraniol dehydrogenase (Tt_GeDH; SEQ ID NO:5), *Rhodococcus* sp. RD6.2_geraniol dehydrogenase (Rs_GeDH; SEQ ID NO:2), *Spingopyxis macrogoltabida* geraniol dehydrogenase (Sm_GeDH; SEQ ID NO:3), and *Acinetobacter calcoaceticus* geraniol dehydrogenase (Ac_GeDH; SEQ ID NO:4), *Pseudomonas putida* geraniol dehydrogenase (Pp_GeDH; SEQ ID NO:6). The heterologous genes are under control of constitutive promoters; TEF1 promoter in front of Ag_GPPS2, PGK1 promoter in front of Cr_GES, TPI1 promoter in front of Kl_KYE1 and PGK1 promoter in front of each of the different GeDHs. Synthetic Complete (SC) media with 2% glucose was used for culturing. Cultures were supplemented with 10% v/v isopropylmyristate secondary phase during the culturing to help extract and trap targeted molecules coming from the pathway. Cultures were grown for 120 hours. All genes were synthesized by Thermo Fisher Scientific GENEART™ GmbH (Regensburg, Germany) as *S. cerevisiae* codon optimized variants and IPM samples were analyzed by UPCs-UV.

Figure 6A:
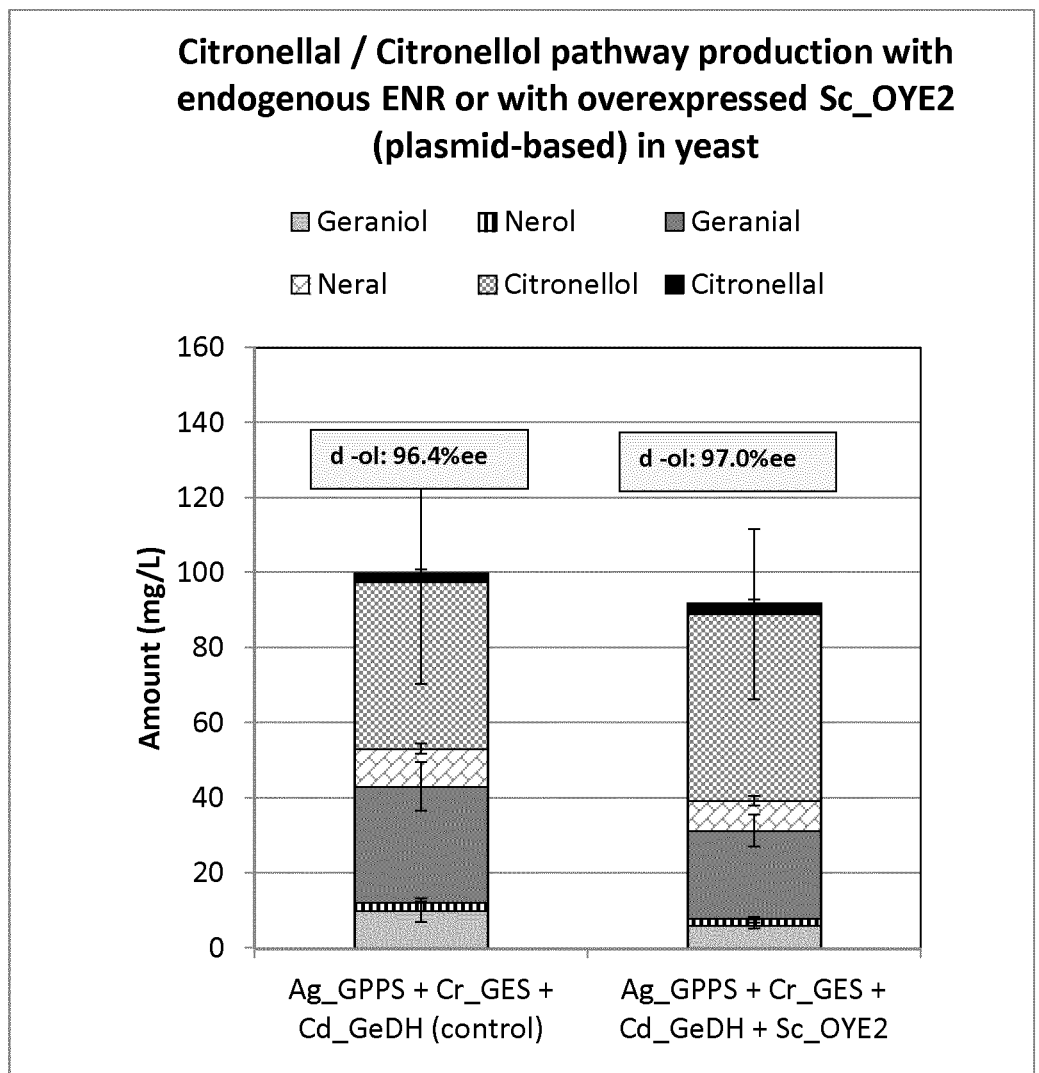
FIG. 6a shows the citronellal/citronellol pathway production with endogenous ENR or with overexpressed *S. cerevisiae*_ENR (Sc_OYE2) in yeast.
Figure 6B:
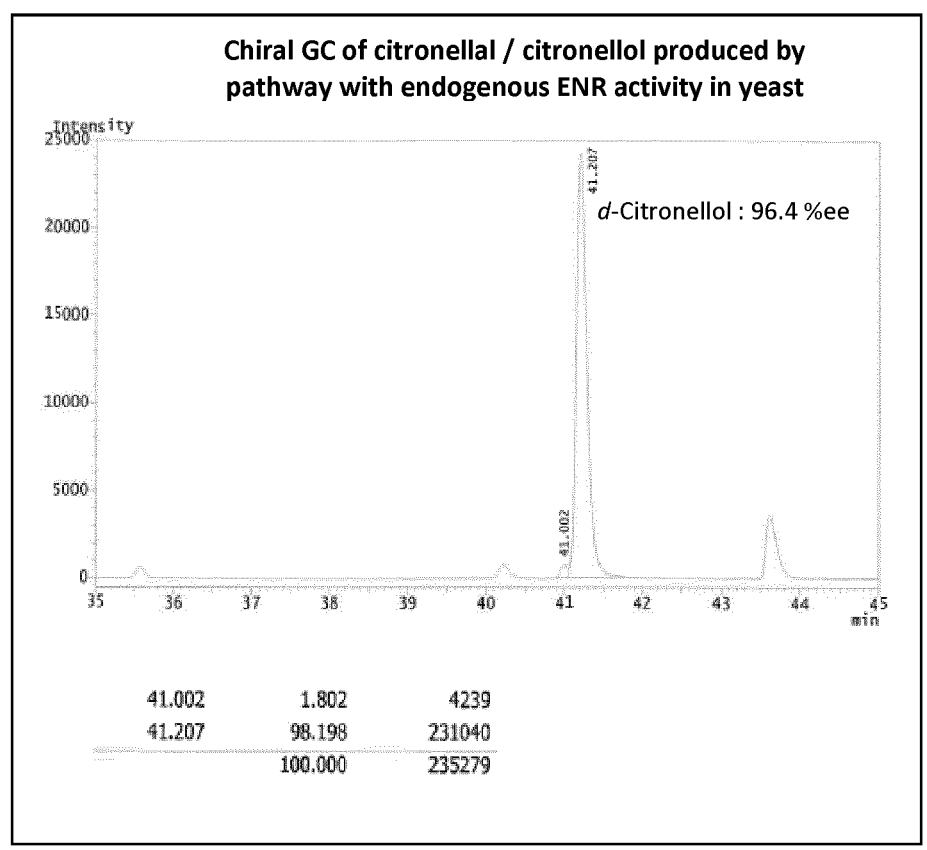
FIG. 6b shows the chiral GC of citronellal/citronellol produced in yeast with endogenous ENR activity.
Figure 6C:
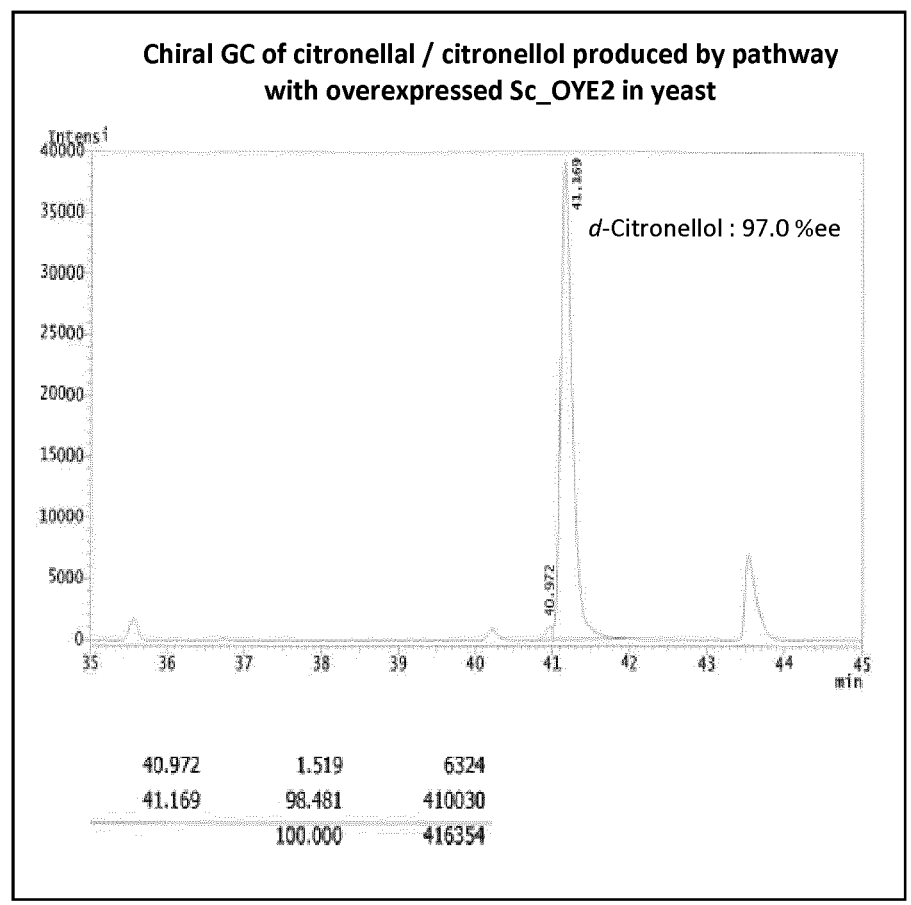
FIG. 6c shows the chiral GC of citronellal/citronellol produced in yeast with overexpressed Sc_OYE2 activity.
Figure 7:
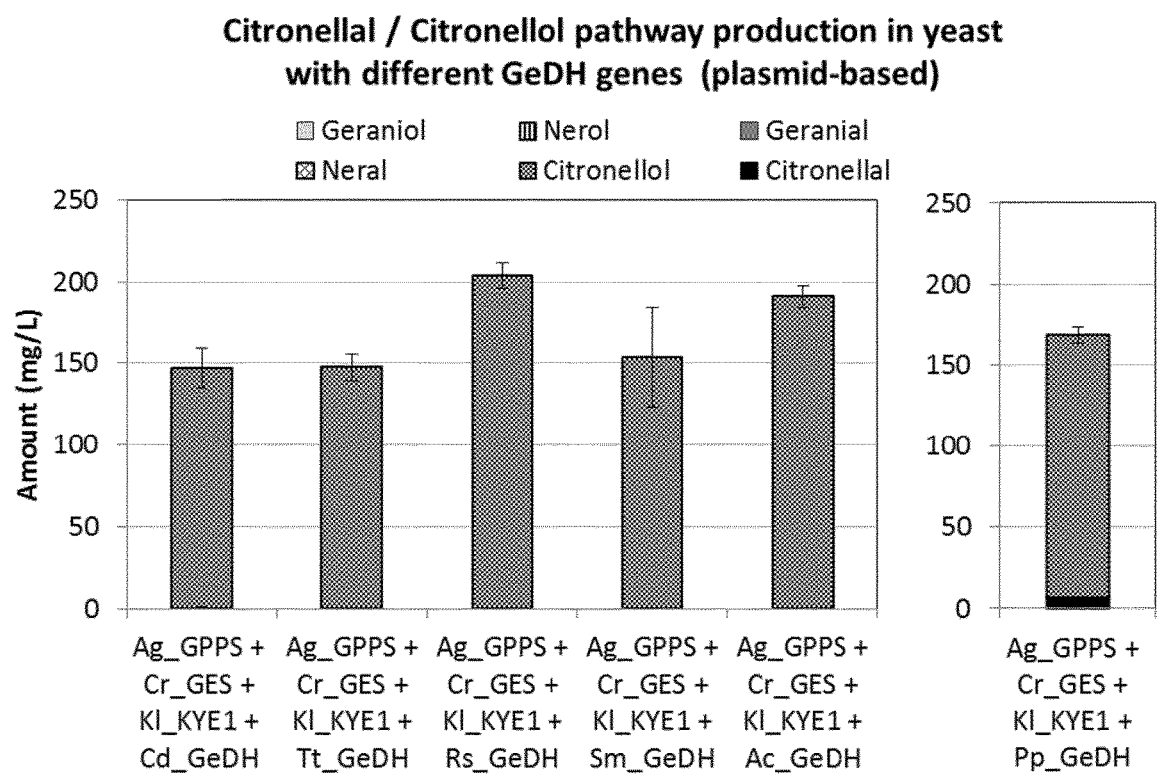
FIG. 7 shows GeDH active in citronellal/citronellol pathway in yeast. Expression of each Geraniol Dehydrogenase (GeDH), *Castellaniella defragrans*_Geraniol dehydrogenase (Cd_GeDH), *Thauera terpenica*_58Eu_Geraniol dehydrogenase (Tt_GeDH), *Rhodococcus* sp. RD6.2_Geraniol dehydrogenase (Rs_GeDH), *Sphingopyxis macrogoltabida*_Geraniol dehydrogenase (Sm_GeDH), and *Acinetobacter calcoaceticus*_Geraniol Dehydrogenase (Ac_GeDH) and *Pseudomonas putida*_Geraniol dehydrogenase (Pp_GeDH) with *Abies grandis*_Geranyl Diphosphate Synthase (Ag_GPPS2), *Catharanthus roseus*_Geraniol Synthase (Cr_GES) and *Kluyveromyces lactis*_Yellow Enzyme (Kl_KYE1) in vivo in yeast.

Various combinations of Cd_GeDH, Tt_GeDH, Rs_GeDH, Sm_GeDH, Pp_GeDH, and Ac_GeDH enzymes tested in this experiment yielded various amounts of citronellol (see FIG. 6). Pathway intermediates including citronellal were converted by all combinations of Cd_GeDH, Tt_GeDH, Rs_GeDH, Sm_GeDH, Pp_GeDH, and Ac_GeDH enzymes tested to citronellol with only negligible amounts of geraniol or geranial produced. The co-expression of Ag_GPPS2, Cr_GES, Kl_KYE1, and Rs_GeDH and Ag_GPPS2, Cr_GES, Kl_KYE1, and Ac_GeDH yielded the highest amount of citronellol (about 200 mg/L). When Ac_GeDH expression was replaced with Pp_GeDH, about 10 mg/L citronellal was produced and about 150 mg/L citronellol was produced (see FIG. 7).

Example 12. Optical Purity Produced by Endogenous ENR and Overexpressed Sc_OYE2 in Yeast Citronellal/citronellol pathway production was carried out in yeast that overexpressed endogenous ENR or Sc_OYE2 (plasmid-based). The yeast strain was transformed with plasmids containing autonomously replicating sequence (ARS) and a yeast centromere (CEN) (ARS-CEN plasmids) with co-expression of *Abies grandis* geranyl diphosphate synthase (Ag_GPPS2), *Catharanthus roseus* geranial synthase (Cr_GES), and *Castellaniella defragrans* geranial dehydrogenase (Cd_GeDH)(control) or Ag_GPPS2, Cr_GES, Cd_GeDH, and *S. cerevisiae* ENR (Sc_OYE2; SEQ ID NO:33). The ARS-CEN plasmid was under the control of constitutive promoters. Synthetic Complete (SC) media with 2% glucose was used for culturing. Cultures were supplemented with 10% v/v isopropylmyristate secondary phase during the culturing to help extract and trap targeted molecules produced by the activation of the pathway. Cultures were grown for 120 hours.

All genes listed above were synthesized by Thermo Fisher Scientific GENEART GmbH (Regensburg, Germany) as *S. cerevisiae* codon optimized variants and IPM samples were analyzed by UPCs-UV. IPM samples were analyzed by chiral GC to measure optical purity of citronellal and citronellol.

The expression of Ag_tGGPS, Cr_GES and Cd_GeDH yielded about 10 mg/L geraniol, less than 5 mg/L nerol, about 30 mg/L geranial, about 10 mg/L neral, about 45 mg/L citronellol, and less than 5 mg/L citronellal. Endogenous ENR activity resulted in the production of 96.4% ee d-citronellol. The overexpression of Sc_OYE2 produced about 10 mg/L geraniol, less than 5 mg/L nerol, about 25 mg/L geranial, about 10 mg/L neral, about 50 mg/L citronellol, and less than 5 mg/L citronellal. D-citronellol with an ee of 97.0% was produced (see FIG. 6).

Example 13. Geraniol Conversion in Yeast Cell Lysates Containing GeDH Enzymes

A variety of GeDH genes were expressed in yeast cultures that were used for preparing yeast cell lysate. The lysate was used for feeding experiments with geraniol to observe the amount of citronellal/citronellol pathway products produced.

Yeast cell lysates (YCL) from yeast cultures expressing Cd_GeDH, Tt_GeDH, Rs_GeDH, Sm_GeDH, Pp_GeDH, or Ac_GeDH were harvested and diluted to similar protein concentrations. Following harvesting, in vitro reactions were initiated by feeding geraniol and NAD as substrates to the lysates to establish the citronellal/citronellol pathway. To measure background activity that was not a result of the expression of GeDH, the YCLs were harvested from cells only containing an empty vector (see "Empty"). In vitro reactions were stopped by extracting with Methyl-tert-butylether (MTBE) after 1, 15, and 90 minutes of incubation at 30° C. and levels of geranial, citronellal and citronellol were analyzed by gas chromatography-flame ionization detector (GC-FID). All genes were synthesized by Thermo Fisher Scientific GENEART™ GmbH (Regensburg, Germany) as *S. cerevisiae* codon optimized variants.

Figure 5A:
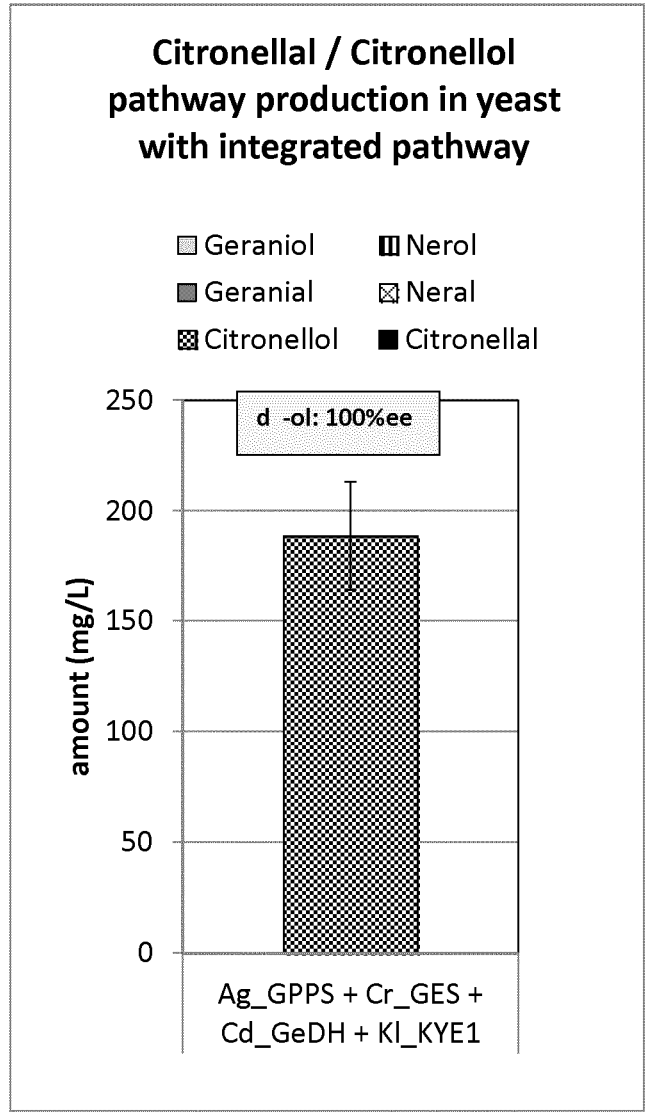
FIG. 5a shows the full chromosomal integration in *S. cerevisiae* of citronellal/citronellol pathway genes: *Abies grandis*_Geranyl diphosphate synthase (Ag_GPPS2), *Catharanthus roseus*_Geraniol Synthase (Cr_GES), *Castellaniella defragrans*_Geraniol Dehydrogenase (Cd_GeDH), and *Kluyveromyces lactis*_Yellow Enzyme (Kl_KYE1), in *S. cerevisiae*.
Figure 5B:
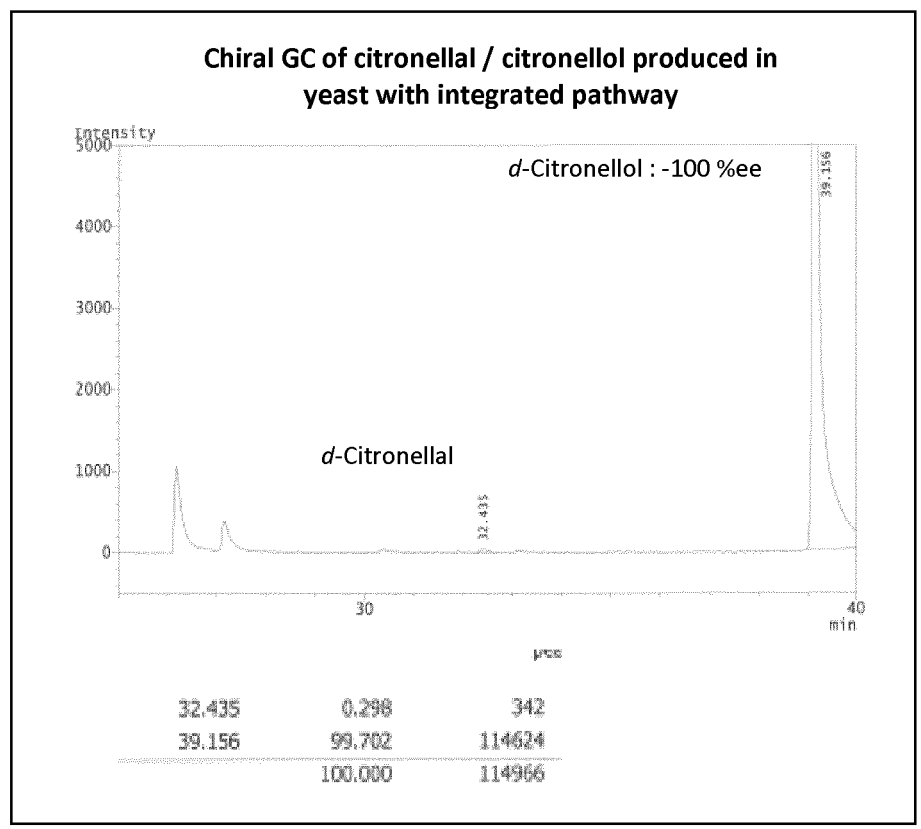
FIG. 5b shows the chiral GC of citronellal/citronellol produced in yeast with the integrated pathway.
Figure 10:
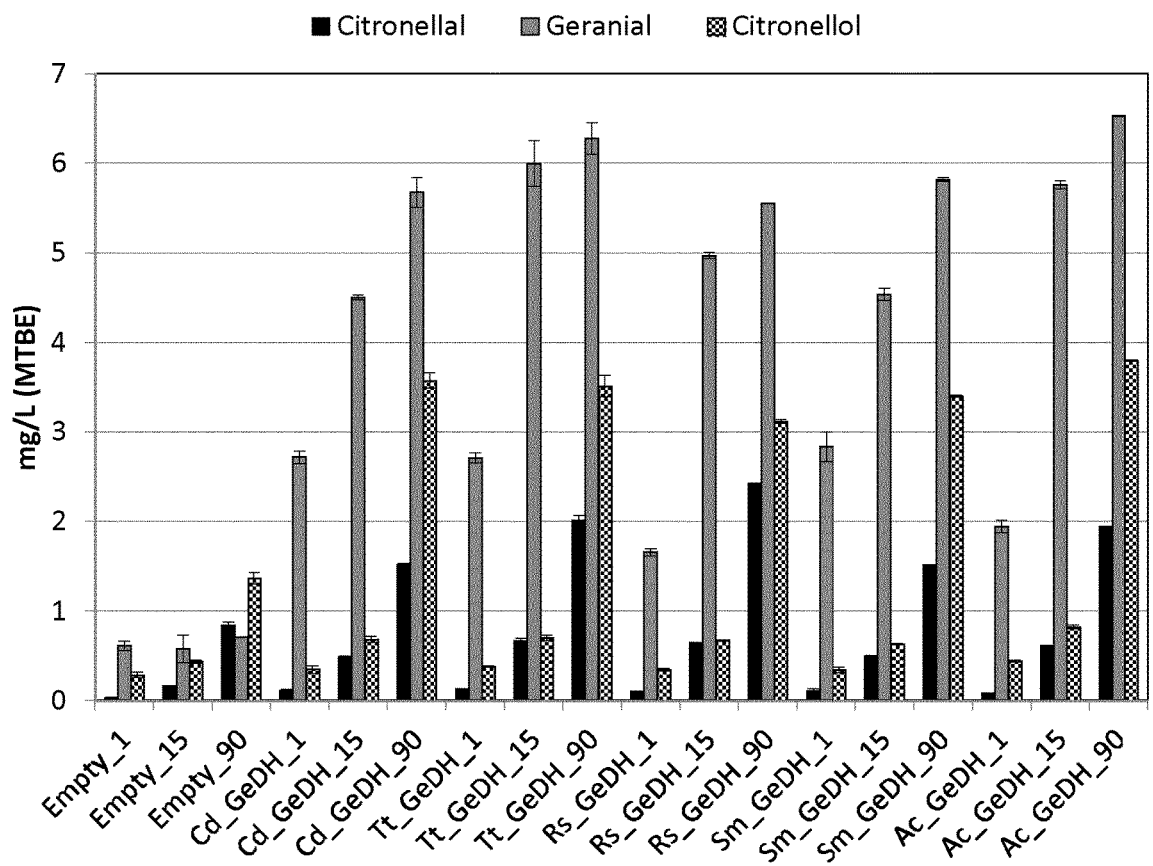
FIG. 10 shows geraniol conversion in yeast cell lysates containing Geraniol Dehydrogenases (GeDH); *Castellaniella defragrans*_Geraniol dehydrogenase (Cd_GeDH), *Thauera terpenica* 58Eu_Geraniol dehydrogenase (Tt_GeDH), *Rhodococcus* sp. RD6.2_Geraniol Dehydrogenase (Rs_GeDH), *Sphingopyxis macrogoltabida*_Geraniol Dehydrogenase (Sm_GeDH), and *Acinetobacter calcoaceticus*_Geraniol dehydrogenase (Ac_GeDH). Citronellal, geraniol and citronellol signals were measured in yeast cell lysates containing each of the GeDHs listed above at 1 minute, 15 minutes and 90 minutes.

All YCLs harvested from cells expressing a GeDH showed higher signals of geranial, citronellal, and citronellol than YCL harvested from cells expressing the empty vector (compare "X_GeDH" vs. "Empty") (see FIG. 5). All GeDH enzymes were successful in converting geraniol to geranial, which was then further converted to citronellal and citronellol by endogenous activity. Highest citronellal (about 2.5 mg/L) and lowest citronellol (about 3 mg/L) signals were detected in YCLs harvested from cells expressing Rs_GeDH when compared to other samples at 90 minutes (see FIG. 10).

Example 14. Optical Purity Produced by Kl_KYE1 and Zm_OYE in Yeast

Overexpression of ENRs Kl_KYE1 (SEQ ID NO:7) and *Zymomonas mobilis* ENR (Zm_OYE; SEQ ID NO:9) was carried out in yeast produced citronellol of high purity. The yeast strain was transformed with plasmids containing autonomously replicating sequence (ARS) and a yeast centromere (CEN) (ARS-CEN plasmids) with co-expression of *Abies grandis* geranyl diphosphate synthase (Ag_GPPS2), *Catharanthus roseus* geranial synthase (Cr_GES), and *Castellaniella defragrans* geranial dehydrogenase (Cd_GeDH) (control) or Ag_GPPS2, Cr_GES, Cd_GeDH, and, Cd_GeDH, and Zm_OYE. The ARS-CEN plasmid was under the control of constitutive promoters. Synthetic Complete (SC) media with 2% glucose was used for culturing. Cultures were supplemented with 10% v/v isopropylmyristate secondary phase during the culturing to help extract and trap targeted molecules produced by the activation of the pathway. Cultures were grown for 120 hours.

All genes listed above were synthesized by Thermo Fisher Scientific GENEART™ GmbH (Regensburg, Germany) as *S. cerevisiae* codon optimized variants and IPM samples were analyzed by UPCs-UV. IPM samples were analyzed by chiral GC to measure optical purity of citronellal and citronellol.

Figure 8A:
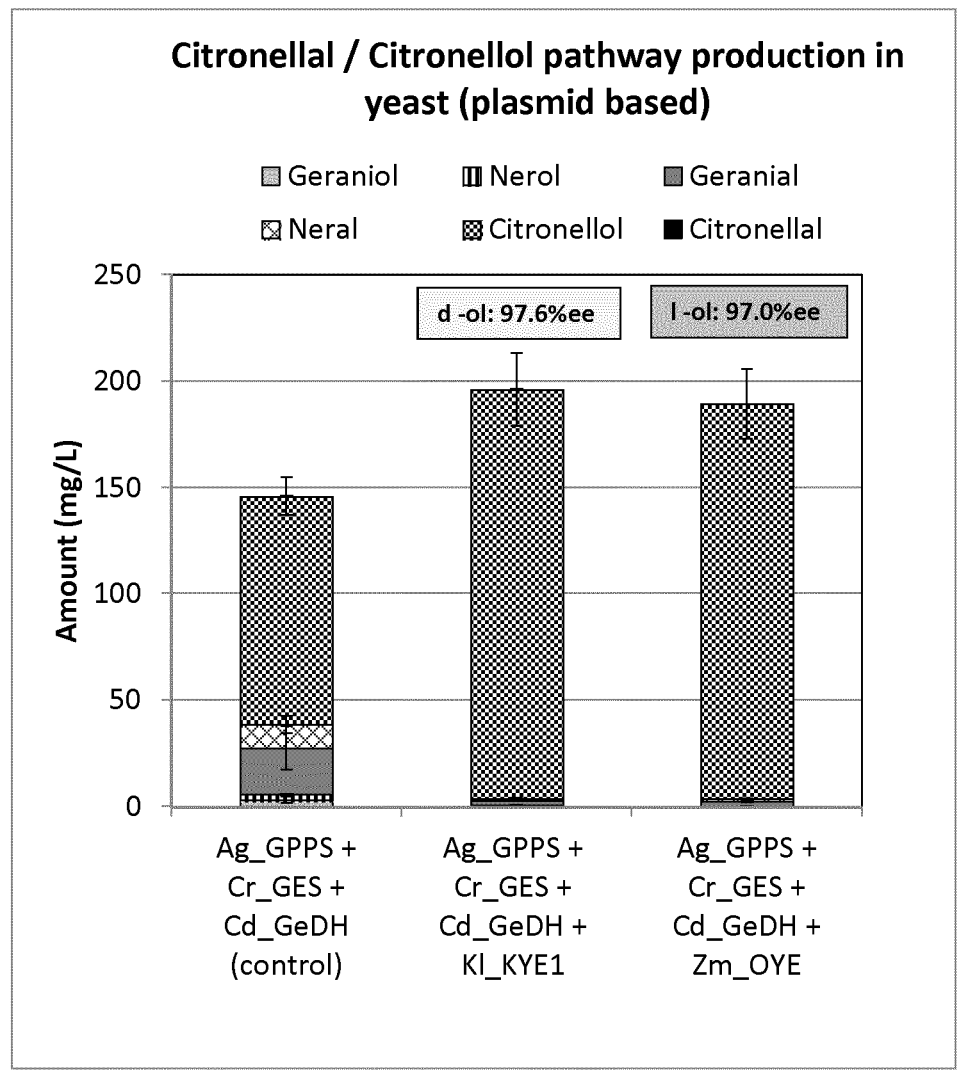
FIG. 8a shows the plasmid-based citronellal/citronellol production in yeast under control conditions and when either Kl_KYE1 or *Zymomonas mobilis*_ENR (Zm_OYE) is overexpressed.
Figure 8B:
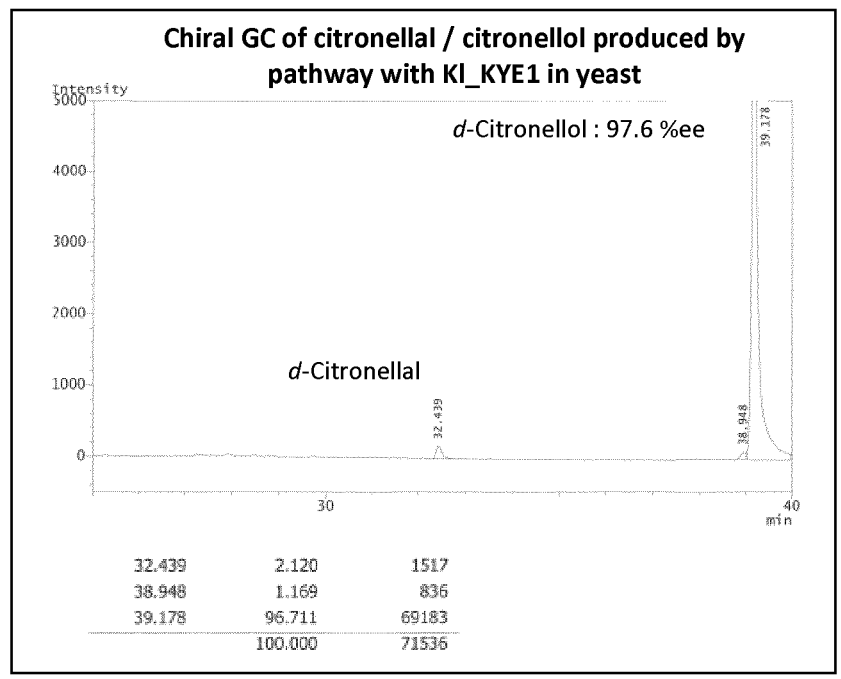
FIG. 8b shows the chiral GC of citronellal/citronellol produced in yeast with overexpressed Kl_KYE1 activity.
Figure 8C:
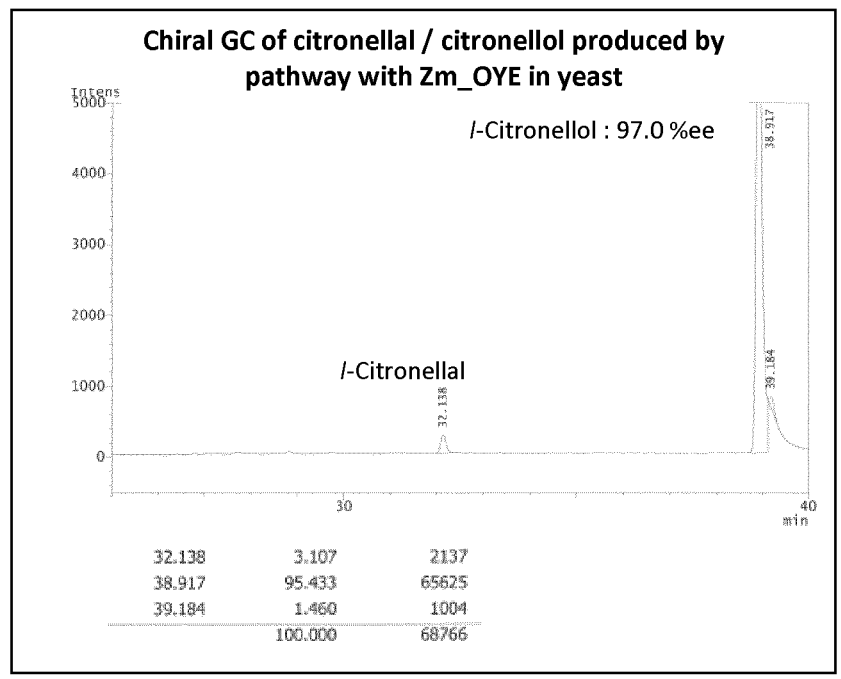
FIG. 8c shows the chiral GC of citronellal/citronellol produced in yeast with overexpressed Zm_OYE activity.

Expression of the control genes in the plasmid-based citronellal/citronellal production pathway in yeast yielded less than 5 mg/L nerol, about 20 mg/L geranial, about 10 mg/L neral, and about 100 mg/L citronellol. Overexpression of Kl_KYE1 resulted in about 5 mg/L neral and about 200 mg/L d-citronellol (97.6% ee). Overexpression of Zm_OYE also produced about 5 mg/L neral and about 200 mg/L l-citronellol (97% ee) (see FIG. 8).

Example 15. Rs_GeDH Catalyzes the Conversion of Geraniol to Geranial in Yeast Lysates GeDHs described in FIG. 10, were tested to examine their propensity to catalyze the conversion of citronellal to citronellol in yeast cell lysates. Yeast cell lysates (YCL) from yeast cultures expressing Cd_GeDH or Rs_GeDH were harvested and diluted to similar protein concentrations. In vitro reactions were then started by feeding citronellal and NAD as substrates to the lysates. In an effort to measure the background activity, the YCL was harvested from cells not expressing a heterologous GeDH but only containing an empty vector (see "Empty" in FIG. 6). In vitro reactions were stopped by extracting with Methyl-tert-butylether (MTBE) after 10, 60, 180, and 480 minutes of incubation with the GeDHs. MTBE samples were analyzed by Gas Chromatography-Flame Ionization Detector (GC-FID).

Figure 11:
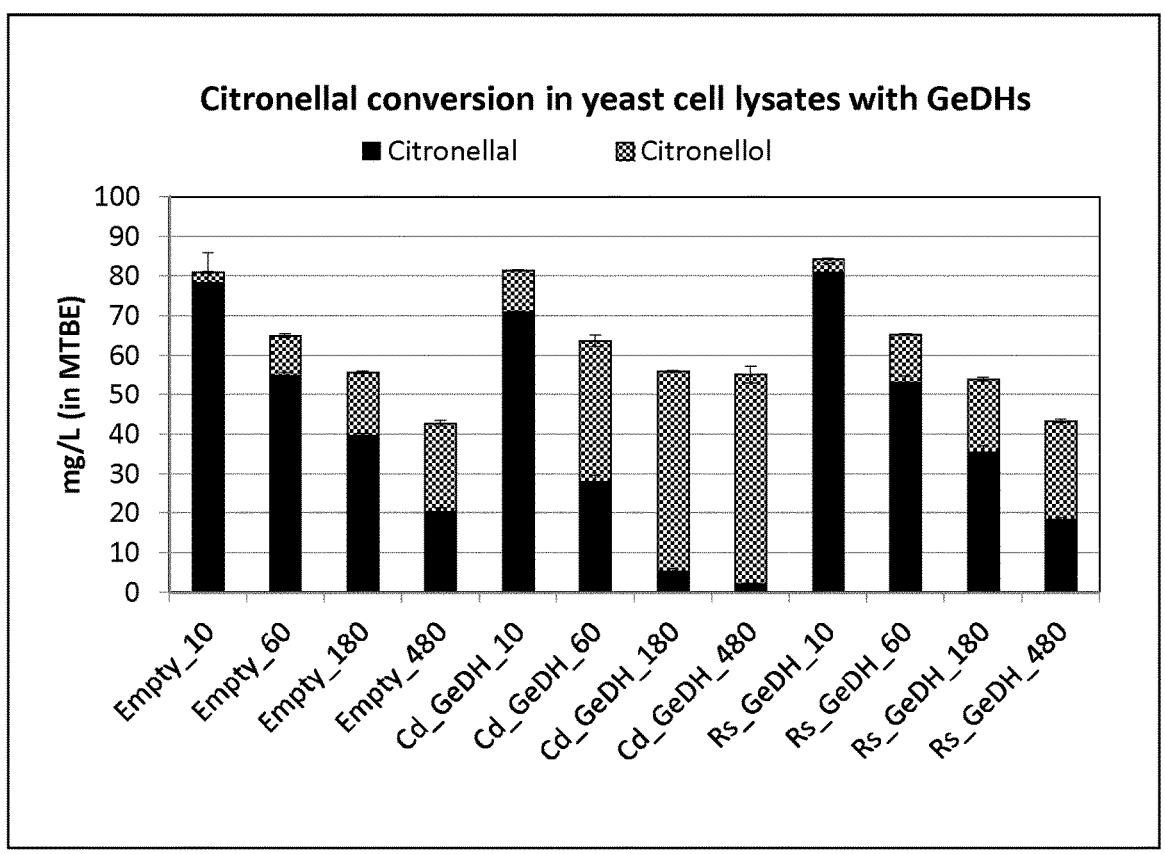
FIG. 11 shows that Rs_GeDH primarily catalyzes the conversion of geraniol to geranial.

Citronellal to citronellol conversion was detected in all in vitro reactions (see FIG. 6). The highest citronellal to citronellol conversion levels were detected in YCL harvested from cells expressing the Cd_GeDH indicative of its potential role in yielding the final product of the citronellal/citronellol pathway. YCLs harvested from cells expressing empty vector or Rs_GeDH showed the same citronellal to citronellol conversion (compare citronellol in "Empty" vs. "Rs_GeDH" in FIG. 6), indicating that Rs_GeDH does not convert citronellal to citronellol (see FIG. 11).

Figure 9:
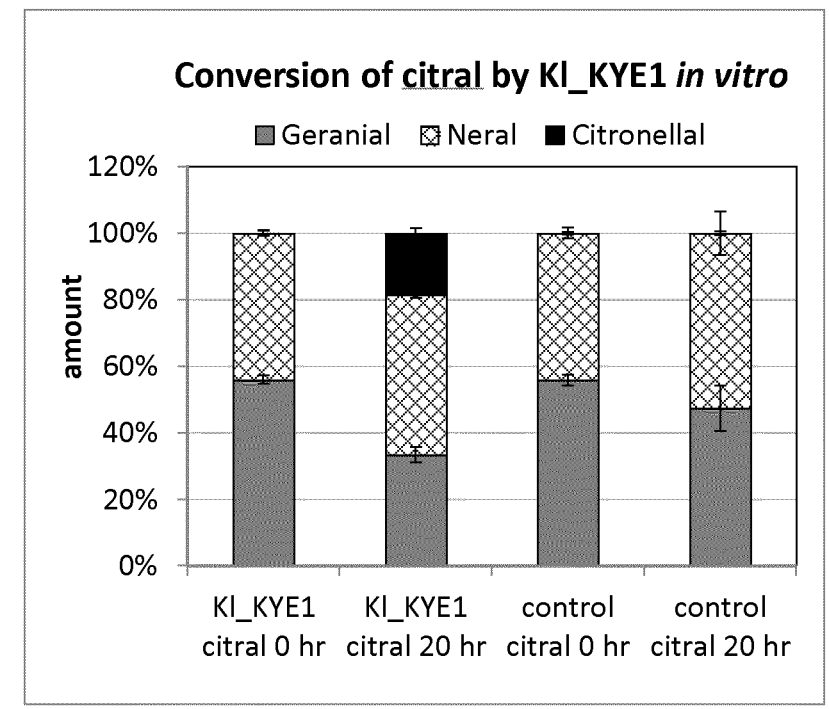
FIG. 9 shows in vitro conversion of citral by K_KYE1 (top) or Zm_OYE (bottom).
Figure 9:
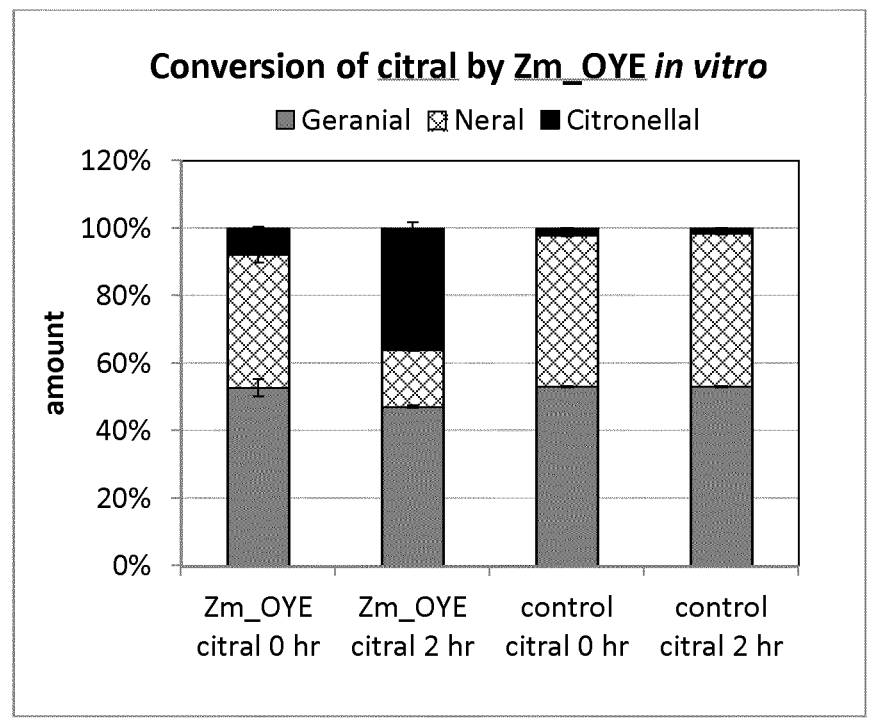

Example 16. Substrate-Mediated Conversion of d-Citronellal and l-Citronellal by ENR Activity In vitro testing of substrate specificity of two different ENRs, Kl_KYE1 (SEQ ID NO:21) and Zm_OYE (SEQ ID NO:9), yielded citronellal/citronellol pathway products (see FIG. 9). Kl_KYE1 and Zm_OYE were overexpressed and purified from *E. coli* as GST fusions. Proteins were then incubated with citral (neral:geranial about 50:50) at 30° C. in vitro with NADPH regeneration system (20 mM Tris/HCL [pH7.5], 0.2 mg/mL GST-fusion, 1 mM NADP+, 20 mM G6P and 10 μg/mL GDH and 5 mM citral (Sigma Aldrich) for the indicated time period (0, 2, or 20 hrs). Reactions were extracted with hexane and analyzed by UPC2-UV to detect reaction products.

In vitro incubation of citral (50% geranial:50% neral) with KI_KYE1 alone yielded about 50% geranial and about 50% neral, while 20 hrs of citral incubation with KI_KYE1 overexpression yielded about 30% geranial, about 50% neral, and about 20% citronellal. Primarily, the geranial component is converted to citronellal when KI_KYE is expressed. Under control conditions (without KI_KYE1), without citral incubation, about 50% geranial, and about 50% neral was produced and at 20 hours following citral incubation, about 45% geranial was produced and about 55% neral was produced. The control reaction without KI_KYE was largely unchanged.

In vitro incubation of citral (50% geranial:50% neral) with Zm_OYE alone yielded about 50% geranial, about 40% neral, and about 10% citronellal, while 2 hr incubation yielded about 45% geranial, about 10% neral, and about 45% citronellal. Primarily, the neral component is converted to citronellal. Under control conditions (without Zm_OYE), without citral incubation, and following 2 hours of citral incubation, yielded about 50% geranial, about 45% neral, and about 5% citronellal. The control reaction without Zm_OYE was largely unchanged.

Example 17. Design of the pMev Plasmid for IPP+ DMAPP Production in E. coli

Figure 12:
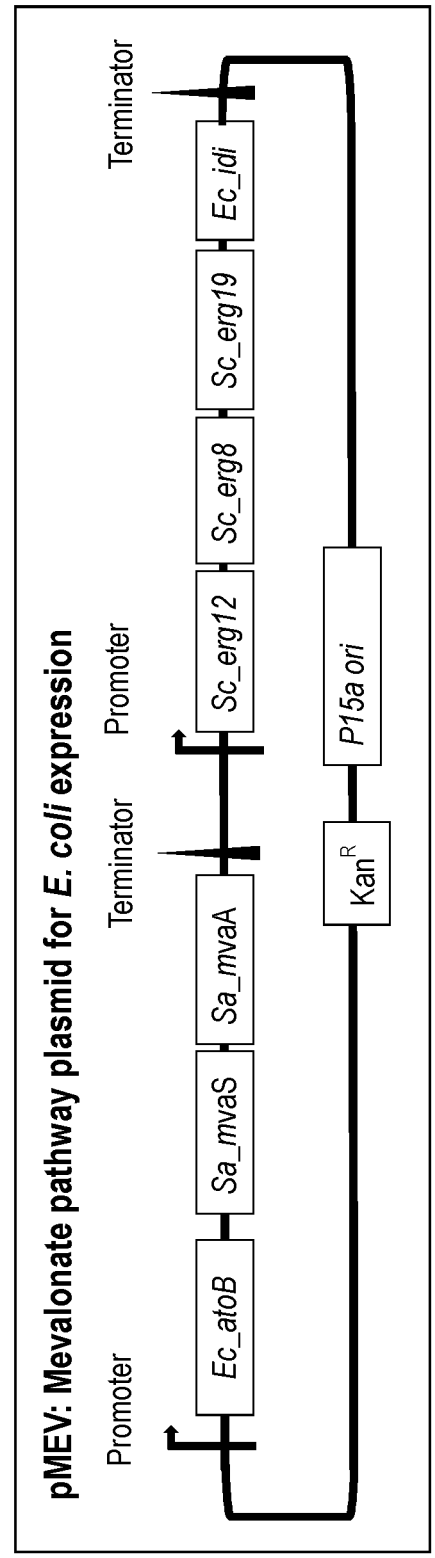
FIG. 12 shows a schematic of the design of the mevalonate plasmid (pMev plasmid) for isopentenyl diphosphate (IPP) and dimethylally pyrophosphate (DMAPP) production in *E. coli*.

A mevalonate plasmid for the expression of IPP and DMAPP in E. coli was constructed. Seven genes (Ec_atoB (SEQ ID NO:10), Sa_mvaS (SEQ ID NO:11), Sa_mvaA (SEQ ID NO:12), Sc_Erg12 (SEQ ID NO:13), Sc_erg8 (SEQ ID NO:14), Sc_erg19 (SEQ ID NO:15), and Ec_idi (SEQ ID NO:16)) were subdivided on two operons. The first three genes were placed under one promoter and the last four genes were placed under another promoter. Each operon was engineered to contain a transcriptional terminator. The 7 genes are located on a p15-based replicative plasmid backbone encoding the LacI protein and a kanamycin selection marker. All genes except Ec_idi were heterologous and were synthesized by Thermo Fisher Scientific GENEART™ GmbH (Regensburg, Germany) as Escherichia coli codon optimized variants (see FIG. 12). Ec_atoB was a recombinant gene produced by codon optimization for E. coli of the endogenous gene of the E. coli wild type host (the wild type gene was modified because it did not extensively use the preferred codons for expression in E. coli) synthesized by Thermo Fisher Scientific GENEART™ GmbH (Regensburg, Germany) to provide a codon optimized variant for E. coli.

Figure 13:
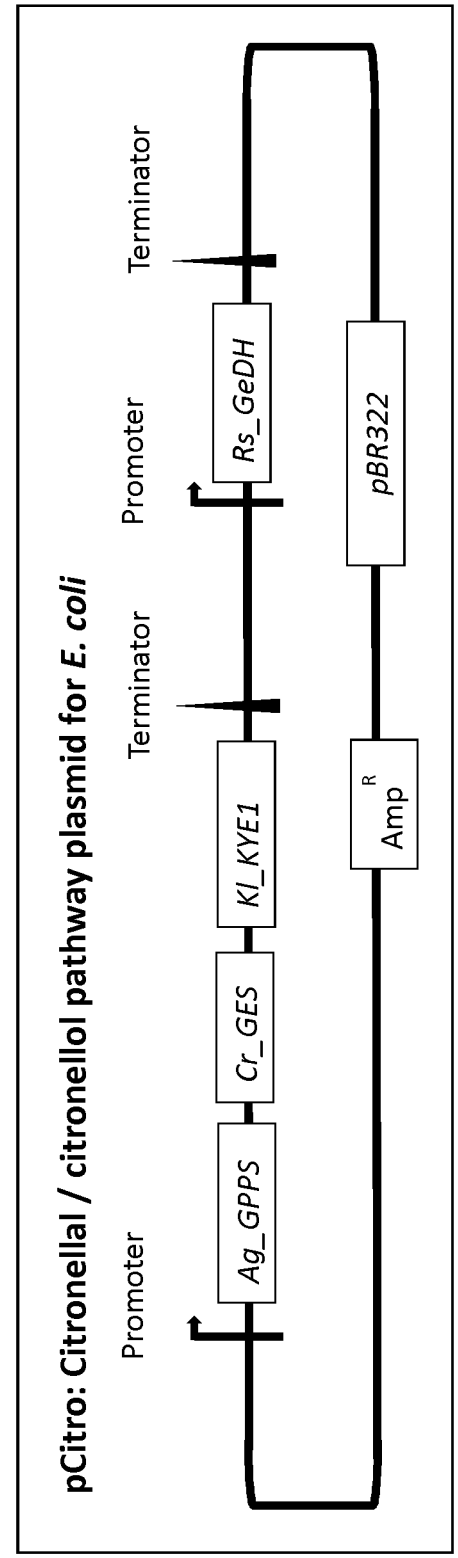
FIG. 13 shows a schematic of the design of the citronellal plasmid (pCitro plasmid) for citronellal/citronellol production in *E. coli*.

Example 18. Design of the pCitro Plasmid for Citronellal/Citronellol Production in E. coli A plasmid comprising genes for citronellal production from IPP and DMAPP in E. coli was constructed. Four proteins (geranyl diphosphate synthase, geraniol synthase, ene reductase and geraniol dehydrogenase) encoded by Ag_GPPS2, Cr_GES, KI_KYE1, and Cd_GeDH (alternatively another GPPS, GES, GeDH, or ENR gene as disclosed throughout) were subdivided on two operons. The first three genes were under the control of one promoter and the last gene is under the control of another promoter. The 4 genes were located on a pBR322-based replicative plasmid backbone encoding ampicillin selection marker. All genes were synthesized by Thermo Fisher Scientific GENEART™ GmbH (Regensburg, Germany) as E. coli codon optimized variants, except Rs_GeDH which was codon optimized for Saccharomyces cerevisiae (see FIG. 13).

Example 19. Establishing a Citronellal/Citronellol Pathway on Plasmids in E. coli Plasmid constructs from FIGS. 12 and 13 were used to establish the citronellal/citronellol pathway in E. coli. A comparative study was performed to test initiation of the citronellal/citronellol pathway by the activity of Cd_GeDH compared with Rs_GeDH.

Plasmid pMev encoded 7 proteins (Ec_atoB, Sa_mvaS, Sa_mvaA, Sc_Mk, Sc_erg8, Sc_erg19, and Ec_idi) responsible for the conversion of acetyl-CoA to IPP and DMAPP and plasmid pCitro encoded 4 proteins (Ag_GPPS2, Cr_GES, KI_KYE1 and Rs_GeDH or Cd_GeDH) that convert IPP and DMAPP to citronellal/citronellol pathway products. Cultures were grown for 40 hours in LB media containing 1% glucose. Cultures were supplemented with 10% IPM secondary phase to help extract and trap the pathway intermediates. IPM samples were analyzed in triplicates by UltraPerformance Convergence Chromatography (UPC2-UV) (triplicates). IPM samples were analyzed by chiral GC to measure optical purity (enantiomer excess; ee %) of citronellal and citronellol.

Figure 14A:
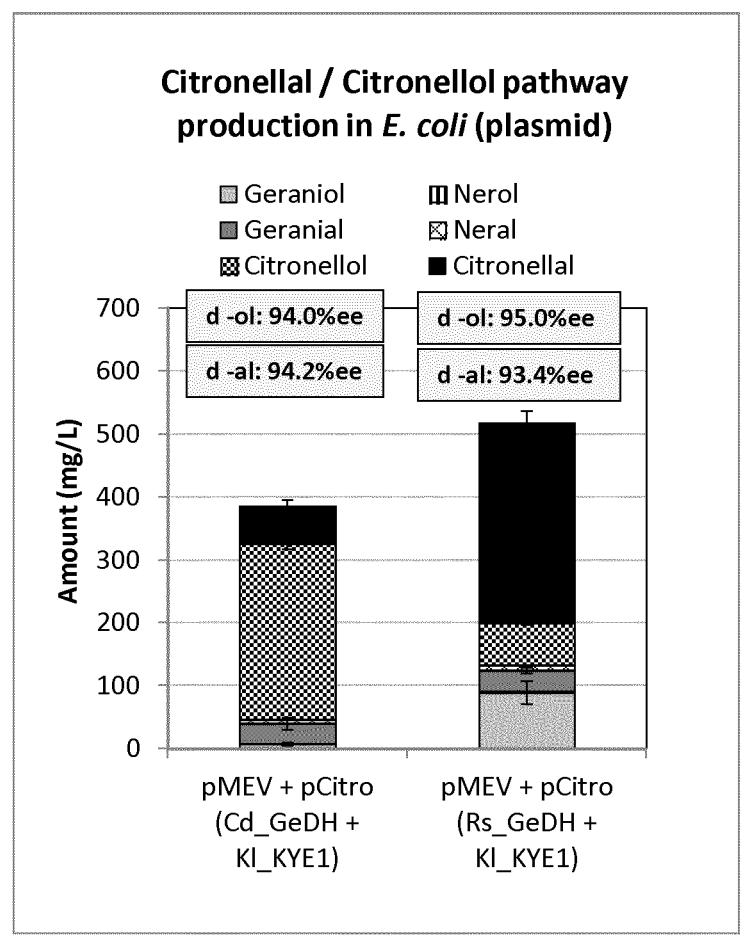
FIG. 14a shows citronellal/citronellol pathway production on pMEV and pCitro (Kl-KYE1) plasmids in *E. coli* using Cd_GeDH or Rs_GeDH.
Figure 14B:
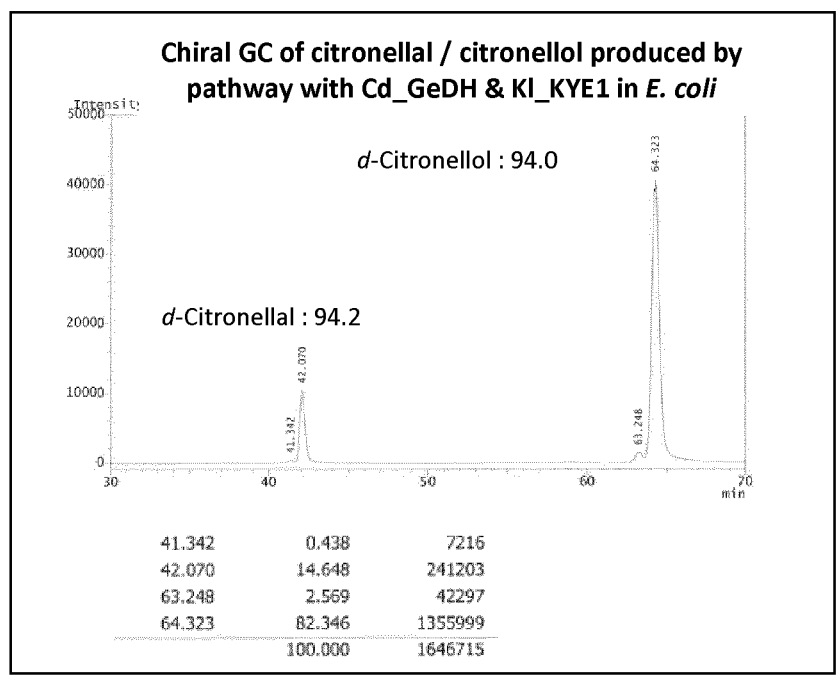
FIG. 14b shows the chiral GC of citronellal/citronellol produced in *E. coli* with Cd_GeDH and Kl_KYE1 activity.
Figure 14C:
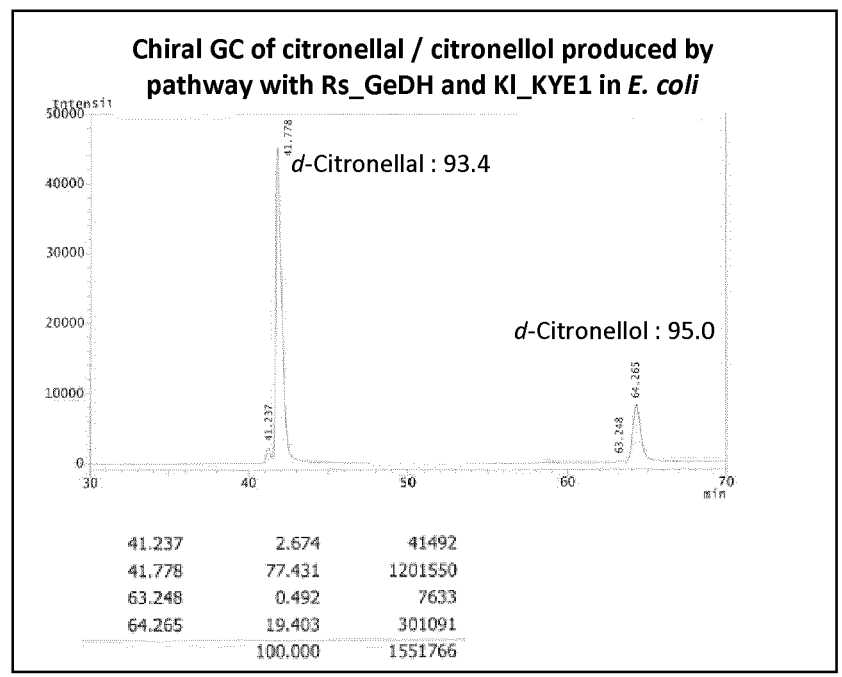
FIG. 14c shows the chiral GC of citronellal/citronellol produced in *E. coli* with Rs_GeDH and Kl_KYE1 activity.

Co-expression of pMev and either pCitro (Cd_GeDH) or pCitro (Rs_GeDH) in E. coli resulted in the production of citronellal/citronellol intermediates and citronellol. About 25 mg/L of geranial, about 5 mg/L nerol, about 350 mg/L d-citronellol (94% ee), and about 40 mg/L d-citronellal (93.4% ee) was produced with the co-expression of pMEV and pCitro (Cd_GeDH+KI_KYE1). When Cd_GeDH was replaced by Rs_GeDH, about 75 mg/L geraniol, about 25 mg/L geranial, about 5 mg/L nerol, about 40 mg/L d-citronellol (95% ee), and about 300 mg/L d-citronellal (94.2% ee) (see FIG. 14).

Example 20. Citronellal/Citronellol Pathway with Zm_OYE on Plasmids in E. coli

Determination of citronellal/citronellol pathway production with overexpression of Zm_OYE on plasmid in E. coli.

Figure 15A:
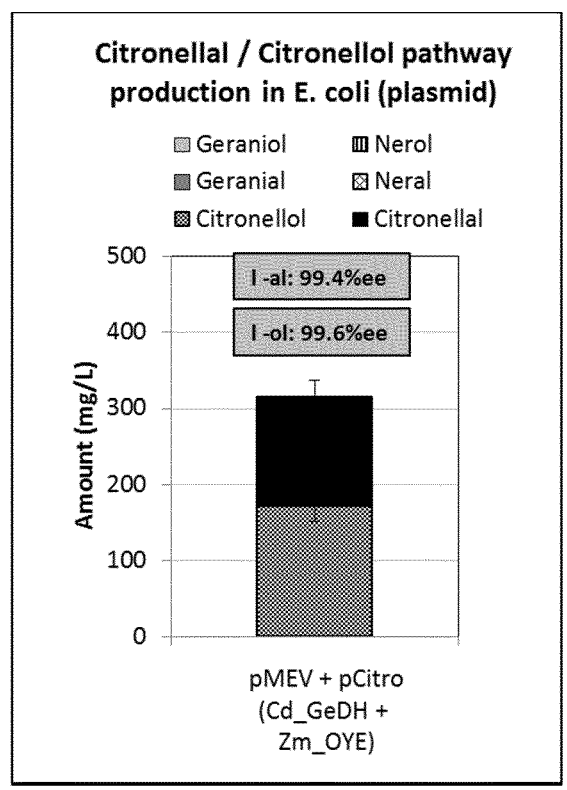
FIG. 15a shows the citronellal/citronellol pathway production on pMEv and pCitro plasmids in *E. coli* expressing Cd_GeDH and Zm_OYE.
Figure 15B:
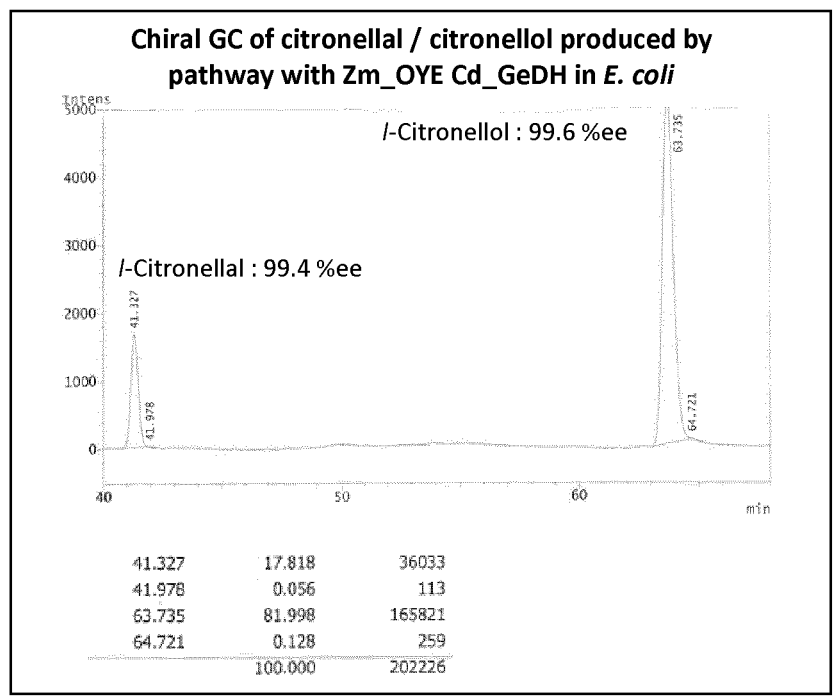
FIG. 15b shows the chiral GC of citronellal/citronellol produced by the pathway with Zm_OYE and Cd_GeDH is overexpressed in *E. coli*.

Plasmid pMev encodes seven genes (Ec_atoB, Sa_mvaS, Sa_mvaA, Sc_MK, Sc_erg8, Sc_erg19, and Ec_idi) which convert acetyl-CoA to IPP and DMAPP and plasmid pCitro encodes four genes; Ag_GPPS2, Cr_GES, Zm_OYE) and Cd_GeDH which convert IPP and DMAPP to citronellal/citronellol. Cultures were grown for 40 hours in LB media containing 1% glucose and supplemented with 10% IPM secondary phase to help extract and trap the pathway intermediates and end product. All pathway products were analyzed in triplicates by UPC2-UV. IPM samples were analyzed by chiral GC to measure optical purity (enantiomer excess (ee %)) of citronellal and citronellol. Co-expression of plasmids pMev and pCitro (Cd_GeDH+Zm_OYE) resulted in the production of about 175 mg/L l-citronellol (99.6% ee) and about 150 mg/L l-citronellal (99.4% ee) (see FIG. 15).

Example 21. Deletion of Endogenous Yeast Genes to Improve Citronellal Accumulation in Yeast Integrated with Citronellal/Citronellol Pathway Endogenous yeast genes that directly or indirectly are involved in aldehyde reductase (AR) activity were deleted in a yeast strain that converts citronellal to citronellol in order to control the amount of citronellal and citronellol produced by the pathway in the yeast. This approach can lead to an increase in the chemical purity of citronellal produced in yeast.

An *S. cerevisiae* yeast strain with elevated levels of IPP and DMAPP (caused by a transcriptional downregulation of ERG20), was used for integration of citronellal/citronellol pathway expression cassettes Ag_GPPS, Cr_GES, Cd_GeDH, KI_KYE1 under control of constitutive promoters (all genes were codon-optimized for expression in *S. cerevisiae* using GENEART™, and expression cassettes were integrated in the yeast genome by homologous recombination). Deletion of combinations of the following yeast genes: ADH6, RFX1, GRE2, ARI1, GCY1 and AYR1, led to an increase in citronellal accumulation. The yeast strains were grown for 96 hours in synthetic complete (SC) media with 2% glucose, supplemented with 10% v/v isopropylmyristate (IPM) secondary phase during culture to promote extraction and trapping of the targeted citronellal/citronellol pathway molecules. IPM samples were analyzed by UPC2-UV and by chiral GC (see FIG. 16a).

Figure 16:
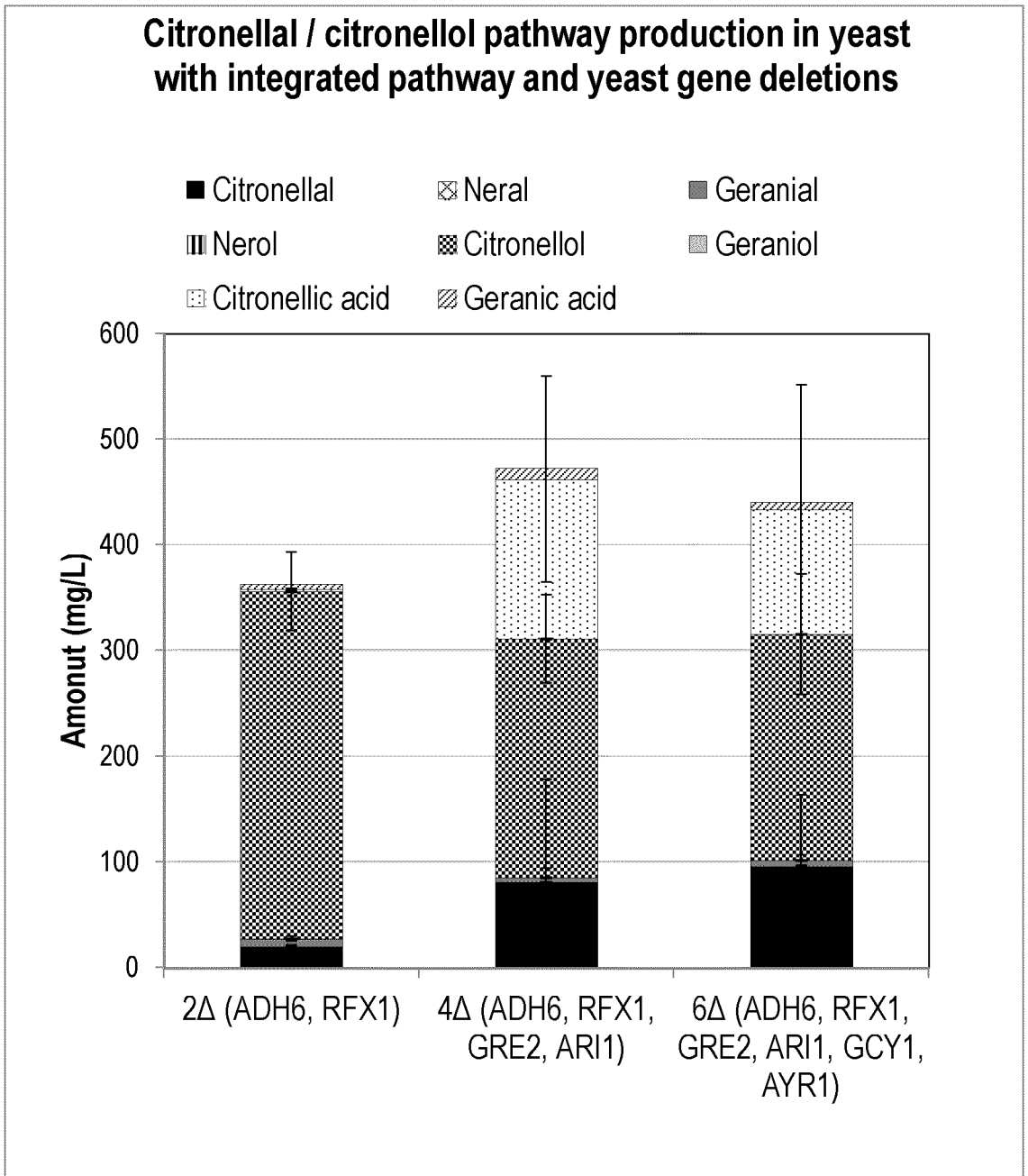
FIG. 16 shows that deletion of yeast endogenous genes ADH6, RFX1, GRE2, ARI1, GCY1, and AYR1 involved in aldehyde reductase (AR) activity in yeast integrated with Citronellal/Citronellol pathway expression cassettes leads to an increase in citronellal accumulation in yeast.

As shown in FIG. 16a, deletion of ADH6, RFX1, GRE2, and ARI1 resulted in accumulation of about 90 mg/L of citronellal compared to the deletion of only ADH6 and RFX1 of only 10 mg/L (reflecting an about 9-fold improvement in citronellal accumulation). Deletion of ADH6, RFX1, GRE2, ARI1, GCY1 and AYR1 resulted in accumulation of about 100 mg/L of citronellal compared to the deletion of only ADH6 and RFX1 of only 10 mg/L (reflecting an about 10-fold improvement in citronellal accumulation).

Example 22. Improvement of Chemical Purity of Citronellal in Yeast by Expression of NADH Oxidase Gene Expression of a heterologous NADH oxidase gene in a yeast strain comprising the citronellal/citronellol pathway reduces citronellol formation. NADH oxidase converts NADH to NAD+, thus lowering NADH levels in the yeast. The lower NADH levels lead to reduced enzymatic activity of aldehyde reductase (AR), and thus less conversion of citronellal to citronellol in yeast. This approach can increase the chemical purity of citronellal produced in yeast by reducing citronellol accumulation.

An *S. cerevisiae* yeast strain with elevated levels of IPP and DMAPP (caused by a transcriptional downregulation of ERG20), was used for integration of citronellal/citronellol pathway expression cassettes Ag_GPPS, Cr_GES, Rs_GeDH, KI_KYE1 under control of constitutive promoters (all genes were codon-optimized for expression in *S. cerevisiae* using GENEART™, and expression cassettes were integrated in the yeast genome by homologous recombination). Expression of Sp_NADHoxi (SEQ ID NO:69), led to reduced accumulation of citronellol and increased chemical purity of citronellal. The yeast strains were grown for 96 hours in synthetic complete (SC) media with 2% glucose, supplemented with 10% v/v isopropylmyristate (IPM) secondary phase during culture to promote extraction and trapping of the targeted citronellal/citronellol pathway molecules. IPM samples were analyzed by UPC2-UV and by chiral GC (see FIG. 17). This example identifies a heterologous NADH oxidase gene that reduces conversion of citronellal to citronellol in yeast, and demonstrates that expression of a heterologous NADH oxidase gene in a yeast strain comprising citronellal/citronellol pathway can reduce citronellol accumulation and increase the chemical purity of citronellal produced by the citronellal/citronellol pathway.

Figure 17:
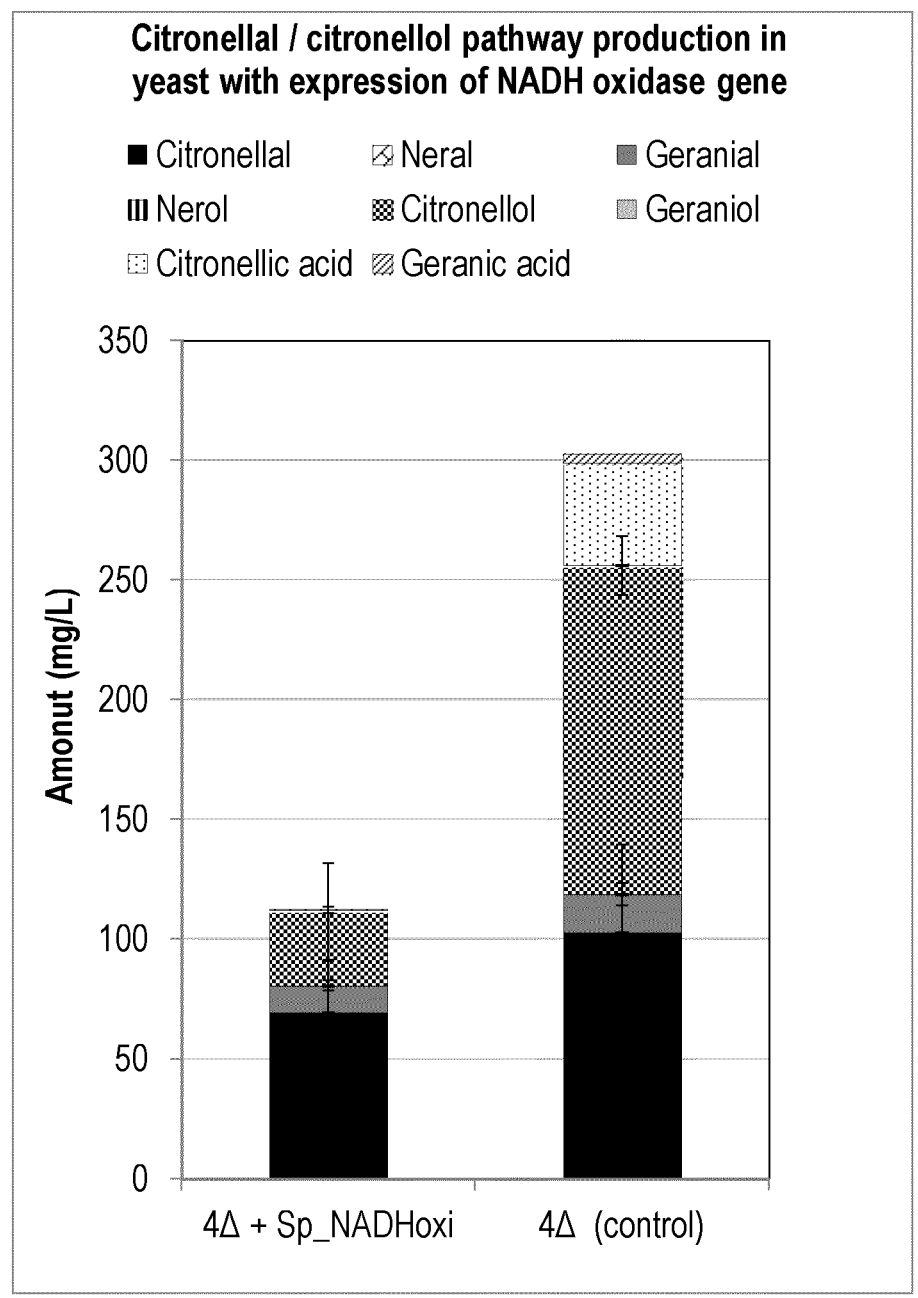
FIG. 17 shows that expression of a heterologous NADH oxidase gene in yeast integrated with Citronellal/Citronellol pathway expression cassettes leads to an increase in chemical purity of citronellal in yeast.

As shown in FIG. 17, constitutive expression of a heterologous NADH oxidase in yeast comprising deletions of ADH6, RFX1, GRE2, and ARI1 resulted in accumulation of about 70 mg/L of citronellal and 30 mg/L of citronellol (a ratio of about 2.3:1 of citronellal to citronellol) compared to a yeast comprising only deletion of ADH6, RFX1, GRE2, and ARI1 that accumulated about 100 mg/L citronellal, and about 150 mg/L citronellol, plus about 50 mg/L of citronellic acid (a ratio of about 0.5:1 of citronellal to citronellol plus citronellic acid). Thus, constitutive expression of a heterologous NADH oxidase in yeast with deletions of ADH6, RFX1, GRE2, and ARI1 resulted in about a 4.5 fold improvement of the chemical purity of citronellal.

Example 23. Improvement of Chemical Purity of Citronellal in Yeast by Expression of a Carboxylic Acid Reductase (CAR) Gene Together with a Phosphopantetheine Transferase (PPTase) Gene Expression of a heterologous carboxylic acid reductase (CAR) gene together with a heterologous phosphopantetheine transferase (PPTase) gene in a yeast strain comprising the citronellal/citronellol pathway reduces citronellic acid accumulation. Expression of a carboxylic acid gene together with phosphopantetheine transferase gene in yeast with citronellal/citronellol pathway can prevent carboxylic acid formation. Expression of a CAR gene and PPTase gene prevents citronellal from being converted to citronellic acid when citronellal accumulates in yeast upon deletion of genes that support aldehyde reductase (AR) activity. Thus, this approach can be used as a means to increase chemical purity of citronellal in yeast.

An *S. cerevisiae* yeast strain with elevated levels of IPP and DMAPP (caused by a transcriptional downregulation of ERG20), was used for integration of citronellal/citronellol pathway expression cassettes Ag_GPPS, Cr_GES, Rs_GeDH, KI_KYE1 under control of constitutive promoters (all genes were codon-optimized for expression in *S. cerevisiae* using GENEART™, and expression cassettes were integrated in the yeast genome by homologous recombination). Expression of Mm_CAR (SEQ ID NO:70) and Bs_SFP (SEQ ID NO:71), led to reduced accumulation of citronellol and increased chemical purity of citronellal. The yeast strains were grown for 96 hours in synthetic complete (SC) media with 2% glucose, supplemented with 10% v/v isopropylmyristate (IPM) secondary phase during culture to promote extraction and trapping of the targeted citronellal/citronellol pathway molecules. IPM samples were analyzed by UPC2-UV and by chiral GC (see FIG. 18). This example identifies a heterologous CAR gene that prevents citronellic acid formation in yeast, and demonstrates that expression of a heterologous CAR gene together with a PPTase gene in a yeast strain comprising citronellal/citronellol pathway can prevent citronellic acid and increase the chemical purity of citronellal produced by the citronellal/citronellol pathway in yeast.

Figure 18:
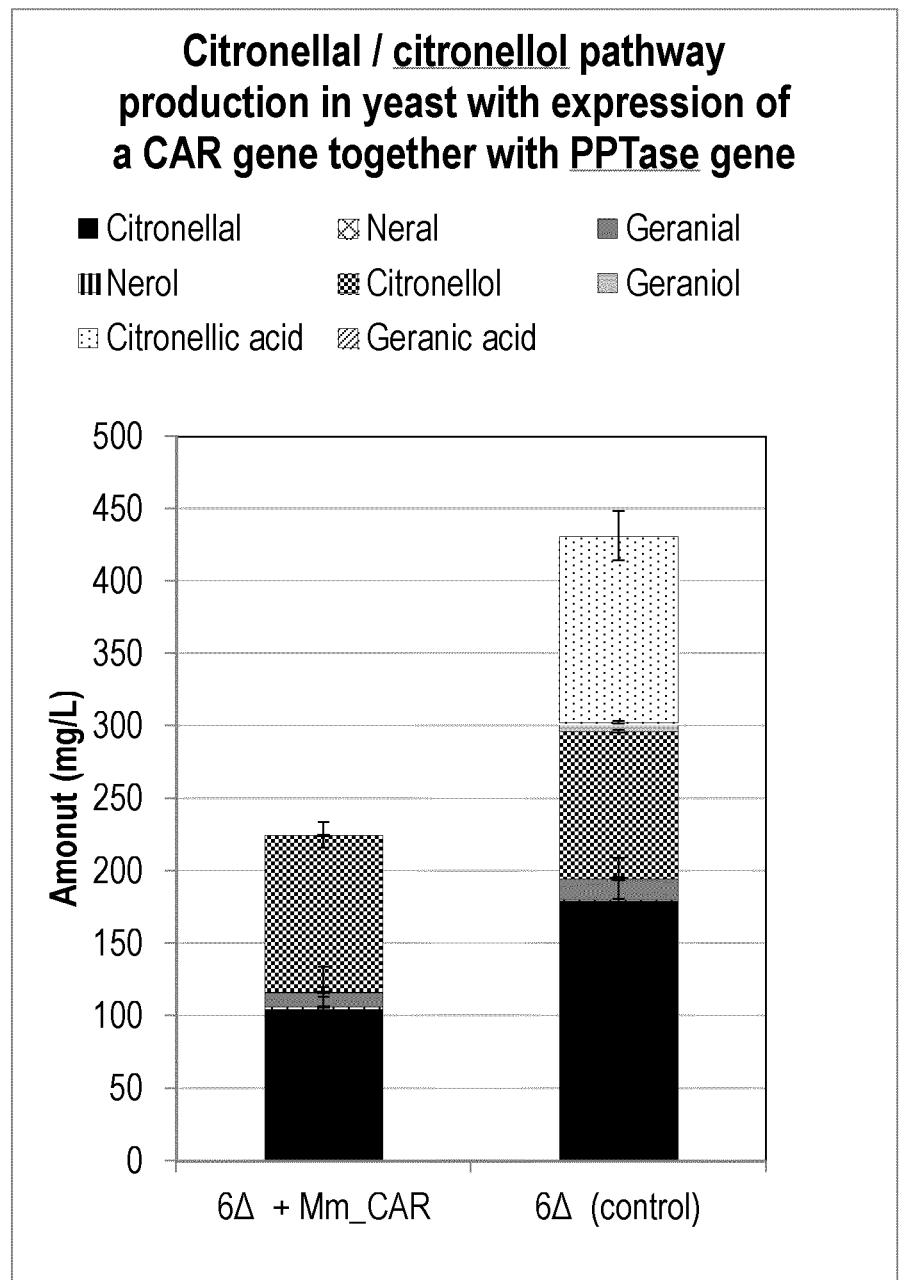
FIG. 18 shows that expression of a heterologous carboxylic acid reductase (CAR) gene together with a heterologous phosphopantetheine transferase (PPTase) in yeast integrated with Citronellal/Citronellol pathway expression cassettes leads to an increase in chemical purity of citronellal in yeast.

As shown in FIG. 18, expression of a heterologous carboxylic acid reductase (CAR) gene together with a heterologous phosphopantetheine transferase (PPTase) gene in a yeast strain comprising deletions of ADH6, RFX1, GRE2, ARI1, GCY1 and AYR1 can increase the chemical purity of citronellal produced by about 1.8-fold (a ratio of about 1:1 of citronellal to citronellol compared to a ratio of about 1.8:1 citronellal to citronellol in the control).

Example 24. Citronellal/Citronellol Pathway Production in Yeast Via Alternative Pathway In vivo expression of heterologous genes that establish a citronellal/citronellol pathway on plasmid was tested in yeast using a *S. cerevisiae* strain with elevated levels of isopentenyl diphosphate (IPP) and dimethylally pyrophosphate (DMAPP), caused by a transcriptional downregulation of ERG20. The yeast strain was further transformed with plasmids expressing *Rhodococcus* sp. geranial dehydrogenase (Rs_GeDH; SEQ ID NO:2) or *Castellaniella defragrans* geranial dehydrogenase (Cd_GeDH; SEQ ID NO:1) and/or *Kluyveromyces lactis*_Yellow Enzyme (KI_KYE1; SEQ ID NO:7), using constitutive promoters, to establish the citronellal/citronellol pathway. All genes listed above were synthesized by Thermo Fisher Scientific GENEART™ GmbH (Regensburg, Germany) as *S. cerevisiae* codon optimized variants. Synthetic Complete (SC) media with 2% glucose and supplemented with 250 mg/L nerol in IPM was used for culturing. Cultures were also supplemented with 10% v/v isopropylmyristate secondary phase during the culturing to help extract and trap targeted molecules produced by the activation of the pathway. Cultures were grown for 96 hours and IPM samples were analyzed by UPCs-UV.

Figure 19:
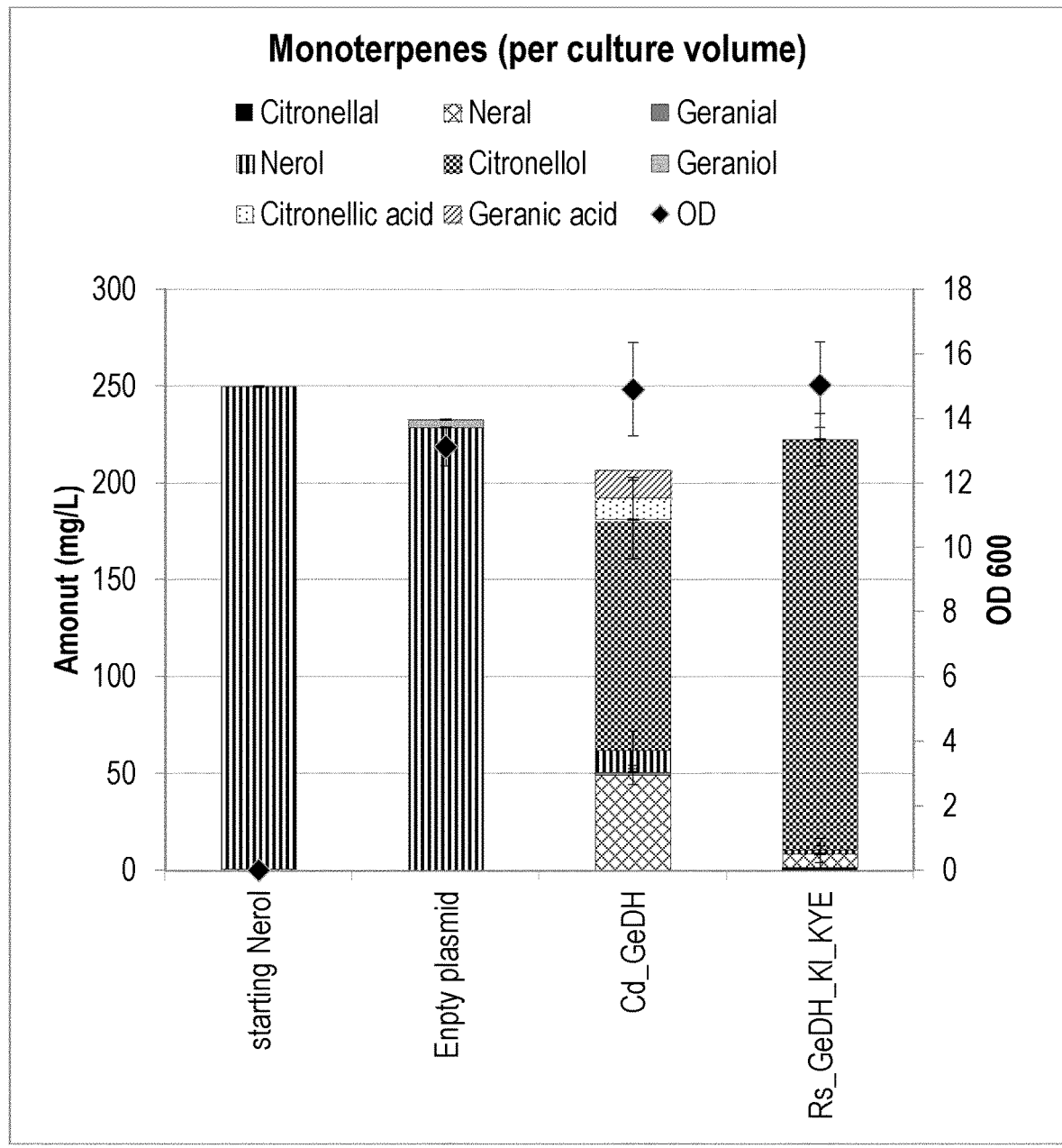
FIG. 19 shows that nerol can be converted to citronellal and citronellol by heterologous genes with Ne/GeDH and ene-reductase activities to produce d- and l-citronellal, and d- and l-citronellol in yeast.

Feeding of nerol to yeast expressing heterologous genes with Ne/GeDH activity and ene reductase activities leads to production of neral, d- and l-citronellal as well as d- and l-citronellol. In a strain containing the geraniol dehydrogenase Cd_GeDH (or Rs_GeDH or others), nerol is converted to neral and then to citronellol via citronellal (being converted to citronellol by ADH background activities). In a strain containing both a geraniol dehydrogenase and the ene reductase KI_KYE, all the nerol is converted to citronellol via citronellal (being converted to citronellol by ADH background activities). This approach shows that nerol can be converted to citronellal and citronellol by heterologous genes with Ne/GeDH and ene-reductase activities, and this approach can be used as an alternative to the main pathway, as described in example 7 above, to produce d- and l-citronellal d- and l-citronellol (see FIG. 19). As shown in FIG. 19, about 115 mg/L of citronellol and about 220 mg/L citronellal were produced in yeast fed nerol and expressing heterologous genes with Ne/GeDH activity and ene reductase.

Example 25. Citronellal/Citronellol Pathway Production in Yeast Via Alternative Pathway In vivo expression of heterologous genes that establish a citronellal/citronellol pathway on plasmid was tested in yeast using a *S. cerevisiae* strain with elevated levels of isopentenyl diphosphate (IPP) and dimethylally pyrophosphate (DMAPP), caused by a transcriptional downregulation of ERG20. The yeast strain was transformed with plasmids expressing an Iridoid synthase (Oe_ISY) (SEQ ID NO:54) and/or a ene reductase (KI_KYE1; SEQ ID NO:7) under control of constitutive promoters. All genes listed above were synthesized by Thermo Fisher Scientific GENEART™ GmbH (Regensburg, Germany) as *S. cerevisiae* codon optimized variants. Synthetic Complete (SC-His) media with 2% glucose and supplemented with 200 mg/L geraniol or 250 mg/L nerol in IPM was used for culturing. Cultures were also supplemented with 10% v/v isopropylmyristate secondary phase during the culturing to help extract and trap targeted molecules produced by the activation of the pathway. Cultures were grown for 96 hours and IPM samples were analyzed by UPCs-UV.

Figure 20A:
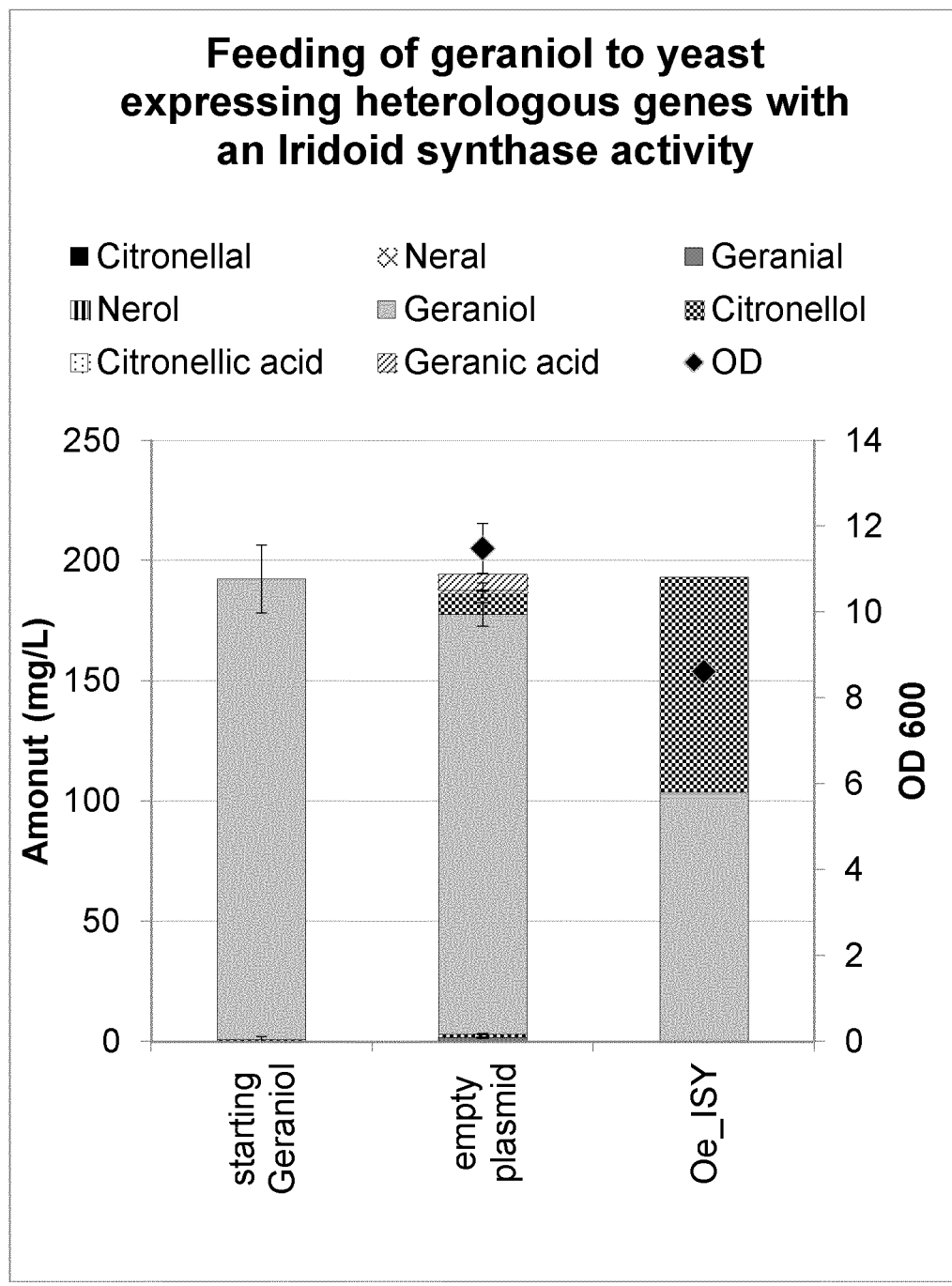
FIG. 20a shows that geraniol can be converted to citronellal and citronellol by a heterologous gene with Iridoid synthase activities to produce d- and l-citronellal, and d- and l-citronellol in yeast.
Figure 20B:
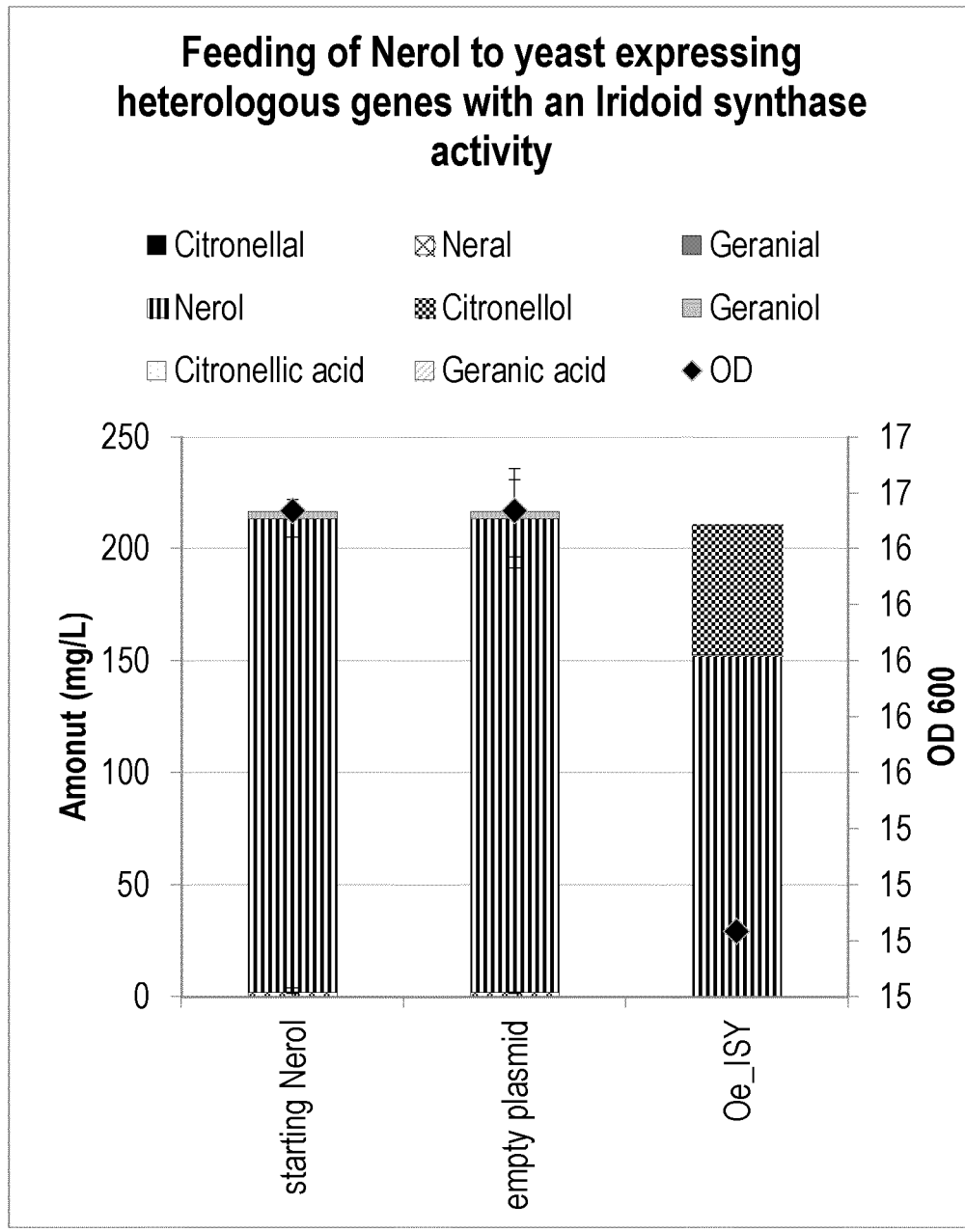
FIG. 20b shows that nerol can be converted to citronellal and citronellol by a heterologous gene with Iridoid synthase to produce d- and l-citronellal, and d- and l-citronellol in yeast.

Feeding of geraniol or nerol to yeast expressing heterologous genes with ene reductase activity (ENR or Iridoid synthase ISY) leads to direct conversion to d- and l-citronellol, respectively. In a strain containing Oe_ISY, geraniol and nerol are converted to citronellol. This approach show that geraniol and nerol can be converted to citronellol by a heterologous a Iridoid synthase gene. This approach can be used as an alternative to the main pathway, as described in example 7 above, to produce d- and l-citronellal, and d- and l-citronellol (see FIG. 20a and FIG. 20b). As shown in FIG. 20a, about 90 mg/L of citronellol was produced in yeast fed geraniol and expressing a heterologous gene with Iridoid synthase activity (compared to about 10 mg/L in the control, representing about a 9-fold improvement). As shown in FIG. 20b, about 60 mg/L of citronellol was produced in yeast fed nerol and expressing a heterologous gene with Iridoid synthase activity (compared to an undetectable amount of citronellol the control, representing about at least a 60-fold improvement).

Example 26. Bioconversion of Citronellol to Citronellal by Oxidizing Bacteria

Citronellol produced by recombinant microorganisms ("strains from NCCB") were contacted with the oxidizing bacteria *Gluconobacter oxydans* or *Gluconobacter cerinus* to perform the bioconversion of citronellol into citronellal. The oxidizing bacteria were cultured in a glycerol medium with 2.5% glycerol, 0.5% yeast extract, and 0.3% peptone. Cultures were harvested and resuspended in 50 mM acetate or phosphate buffer (pH 5 or 6.5), and supplemented with 10% v/v isopropylmyristate secondary phase containing 0.5 g/L citronellol to decrease toxicity of the substrate and the product citronellal or citronellic acid (in some cases, 2.5% glycerol was added to the bioconversion). Bioconversion was performed for 24 to 144 hours. IPM samples were analyzed by UPCs-UV to detect products.

Figure 21A:
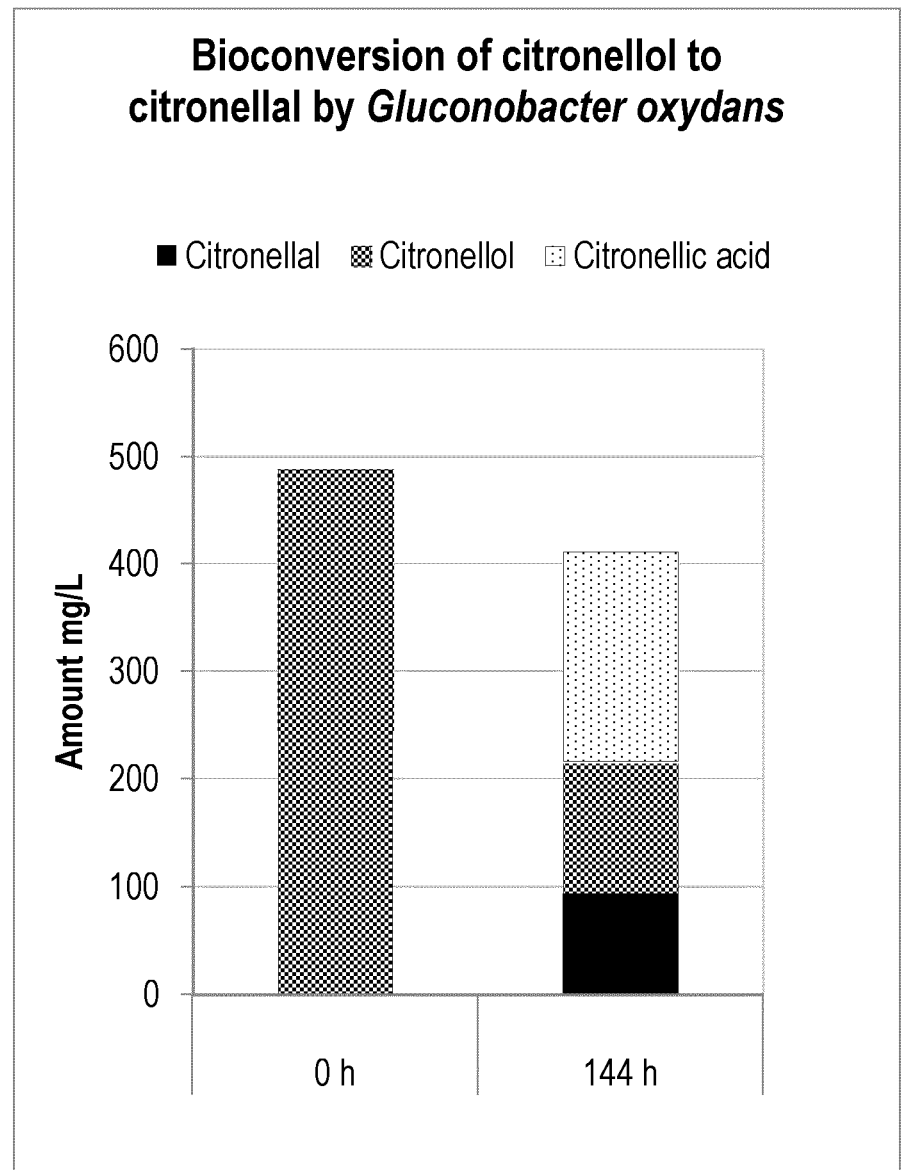
FIG. 21a shows the results from bioconversion of citronellol into citronellal and citronellic acid. The oxidizing bacteria *Gluconobacter oxydans* converted citronellol into citronellal and citronellic acid after 144 hours.
Figure 21B:
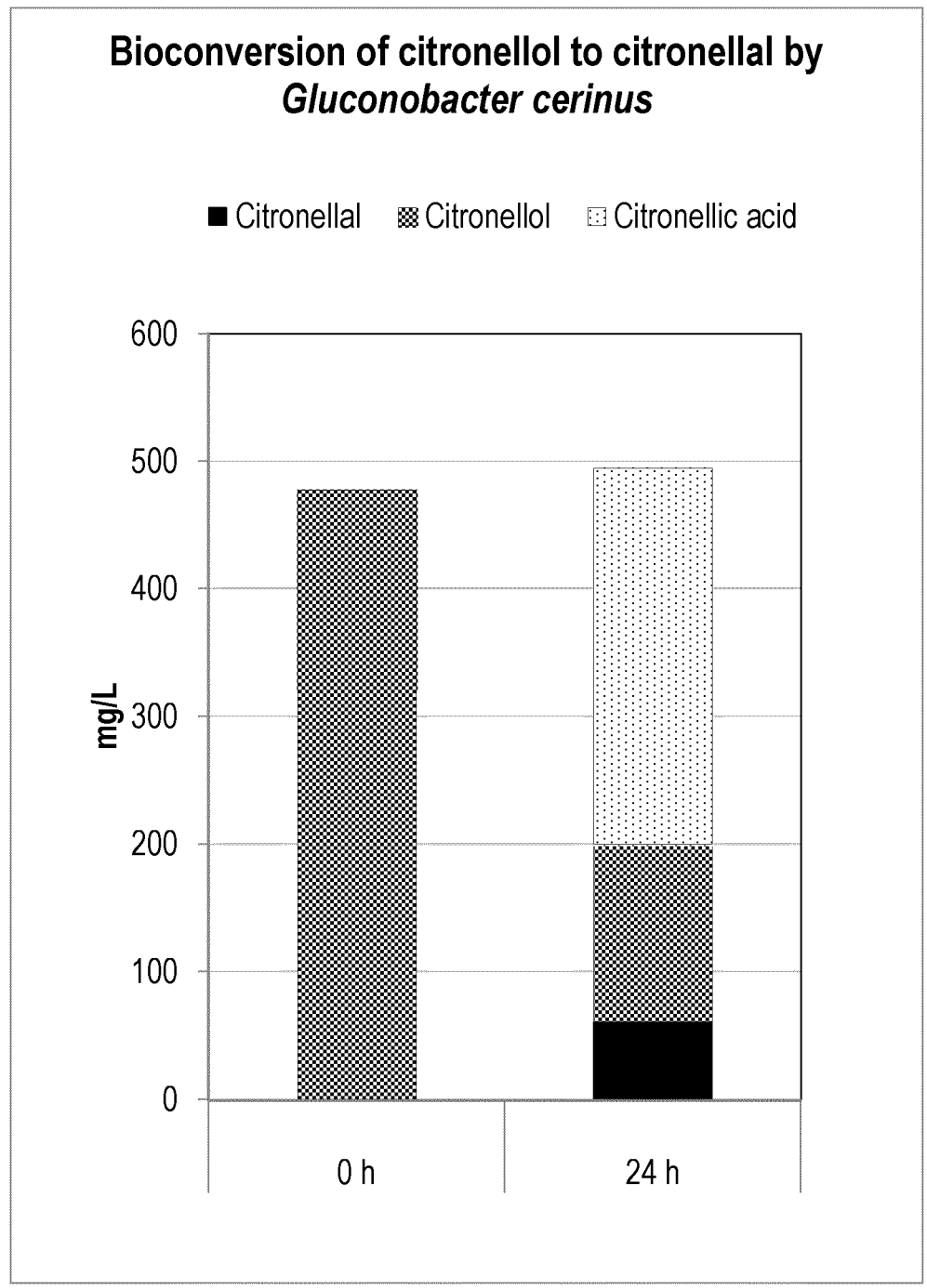
FIG. 21b shows the results from bioconversion of citronellol into citronellal. The oxidizing bacteria *Gluconobacter cerinus* converted citronellol into citronellal after 144 hours.

The example identifies that the oxidizing activity of the oxidizing bacteria *Gluconobacter oxydans* and *Gluconobacter cerinus* converts citronellol produced by recombinant microorganisms into citronellal or citronellic acid, and demonstrates an approach of bioconversion of citronellol into citronellal. The oxidizing bacteria *Gluconobacter oxydans* produced about 100 mg/L of citronellal, and about 200 mg/L of citronellic acid after 144 hours (see FIG. 21a). The oxidizing bacteria *Gluconobacter cerinus* produced about 50 mg/L of citronellal, and about 300 mg/L of citronellic acid after 144 hours (see FIG. 21b).

Example 27. Bioconversion of Citronellal to Citronellic Acid by Oxidizing Bacteria Citronellal produced by recombinant microorganisms ("strains from NCCB") were contacted with the oxidizing bacteria *Gluconobacter cerinus* to perform the bioconversion of citronellal to citronellic acid. The oxidizing bacteria were cultured in a glycerol medium with 2.5% glycerol, 0.5% yeast extract, and 0.3% peptone. Cultures were harvested and resuspended in 50 mM acetate (pH 5), and supplemented with 10% v/v isopropylmyristate secondary phase containing 0.5 g/L citronellal to decrease toxicity of the substrate and the product. Bioconversion was performed for 144 hours. IPM samples were analyzed by UPCs-UV to detect products.

Figure 22:
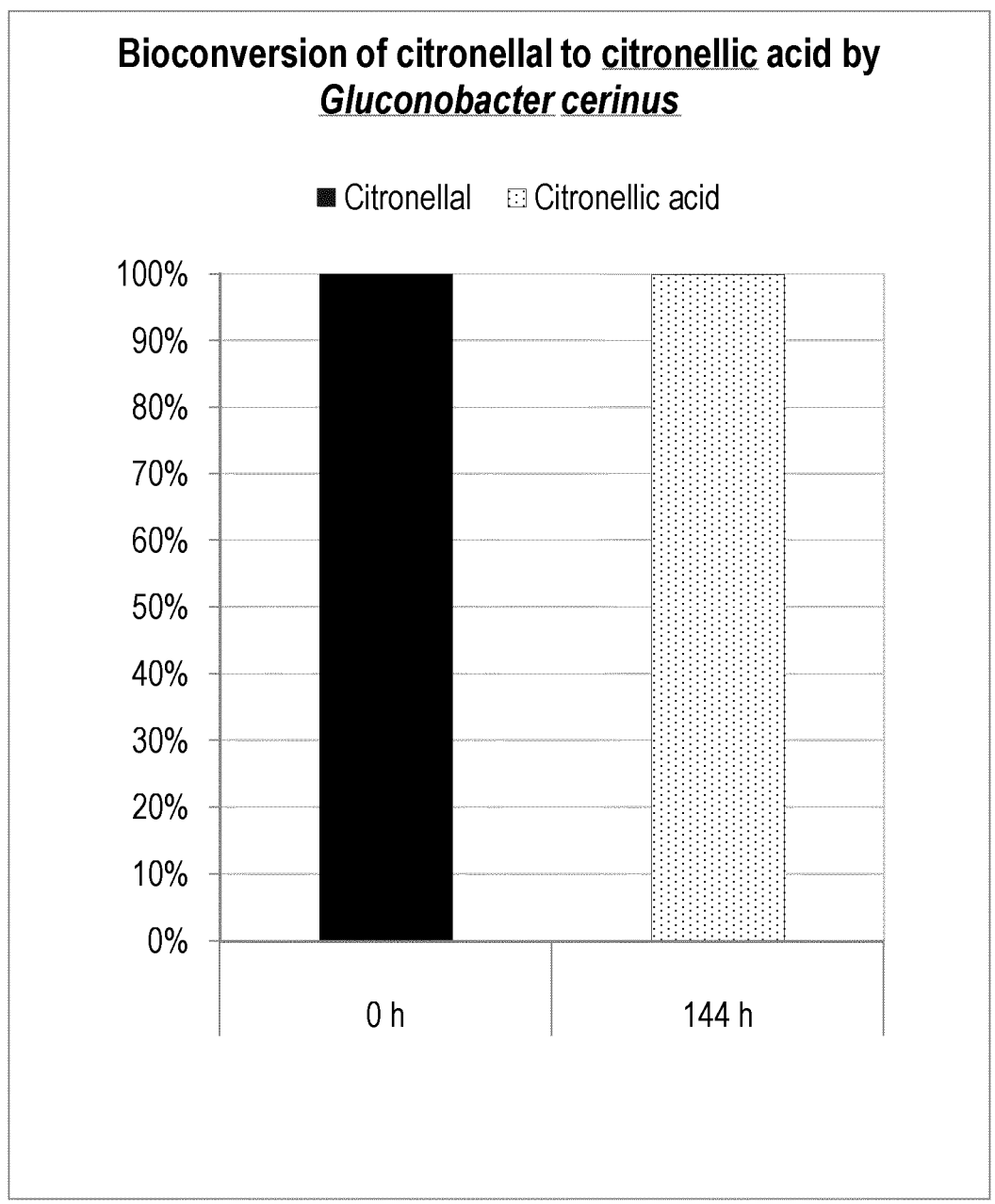
FIG. 22 shows the results from bioconversion of citronellal into citronellic acid. The oxidizing bacteria *Gluconobacter cerinus* converted 100% of the citronellal into citronellic acid after 144 hours.

The example identifies that the oxidizing activity of the oxidizing bacteria *Gluconobacter cerinus* converts citronellal produced by recombinant microorganisms into citronellic acid, and demonstrates an approach of bioconversion of citronellal into citronellic acid. The oxidizing bacteria *Gluconobacter cerinus* converted 100% of the citronellal into citronellic acid after 144 hours (see FIG. 22).

Example 28. Bioconversion of Citronellol to Citronellic Acid by Oxidizing Bacteria Citronellol produced by recombinant microorganisms ("strains from NCCB") were contacted with the oxidizing bacteria *Gluconobacter cerinus* or *Gluconobacter frateurii* to perform the bioconversion of citronellol to citronellic acid. The oxidizing bacteria were cultured in a glycerol medium with 2.5% glycerol, 0.5% yeast extract, and 0.3% peptone. Cultures were harvested and resuspended in 50 mM acetate (pH 5), and supplemented with 10% v/v isopropylmyristate secondary phase containing 0.5 g/L citronellol to decrease toxicity of the substrate and the product. Bioconversion was performed for 144 hours. IPM samples were analyzed by UPCs-UV to detect products.

Figure 23:
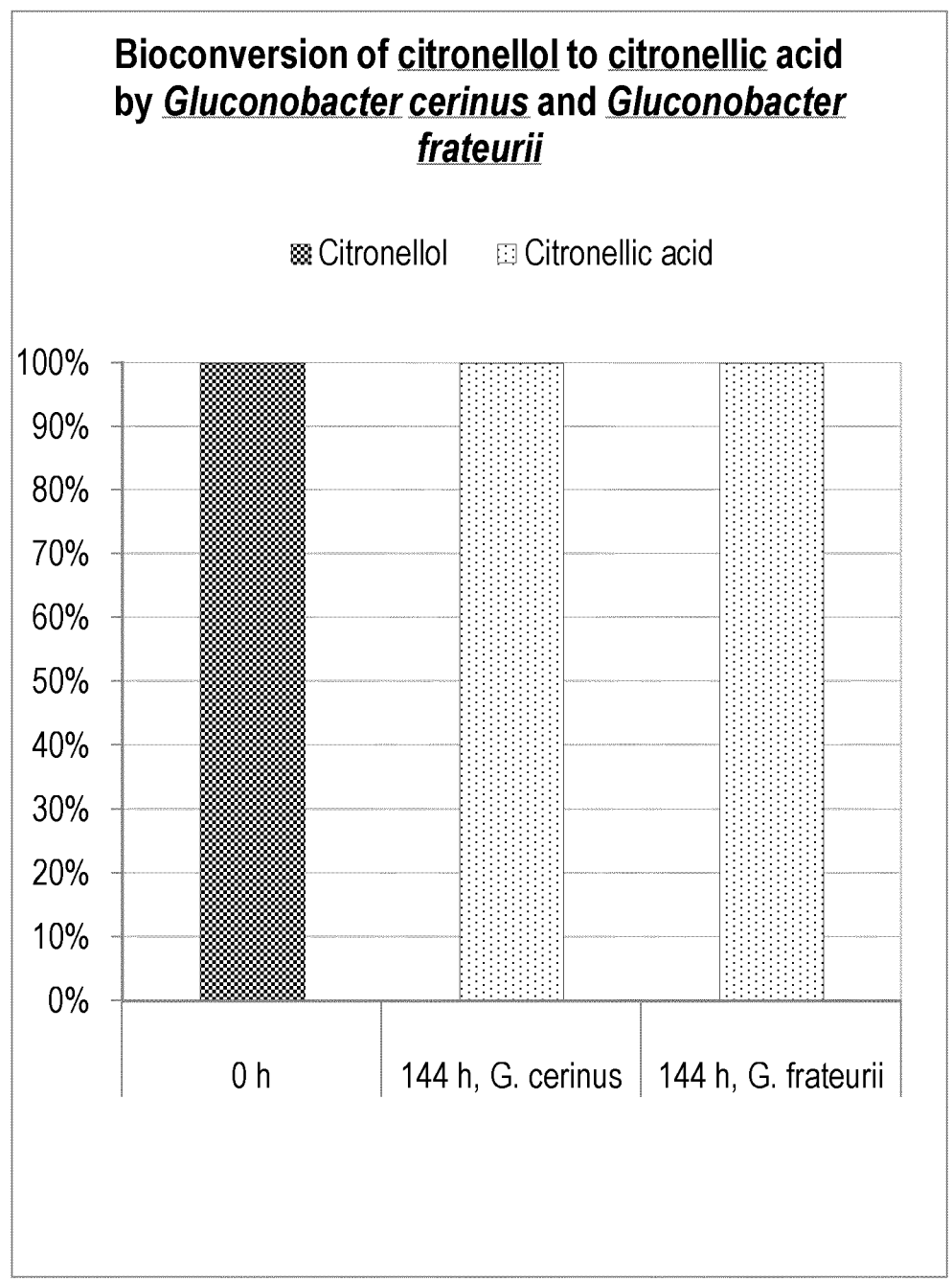
FIG. 23 shows the results from bioconversion of citronellol into citronellic acid. The oxidizing bacteria *Gluconobacter cerinus* or *Gluconobacter frateurii* converted 100% of the citronellol into citronellic acid after 144 hours.

The example identifies that the oxidizing activity of the oxidizing bacteria *Gluconobacter cerinus* or *Gluconobacter frateurii* converts citronellol produced by recombinant microorganisms into citronellic acid, and demonstrates an approach of bioconversion of citronellol into citronellic acid. The oxidizing bacteria *Gluconobacter cerinus* or *Gluconobacter frateurii* converted 100% of the citronellol into citronellic acid after 144 hours (see FIG. 23).

TABLE 1

| | Sequence listing key. |
|---|---|
| SEQ ID NO: 1 | Amino acid sequence<br>Origin: *Castellaniella defragrans*.<br>Enzyme activity: Geraniol dehydrogenase.<br>Cd_GeDH. Codon optimized for *S. cerevisiae* |
| SEQ ID NO: 2 | Amino acid sequence<br>Origin: *Rhodococcus* sp. RD6.2.<br>Enzyme activity: Geraniol dehydrogenase.<br>Rs_GeDH. Codon optimized for *S. cerevisiae* |
| SEQ ID NO: 3 | Amino acid sequence<br>Origin: *Sphingopyxis macrogoltabida*.<br>Enzyme activity: Geraniol dehydrogenase.<br>Sm_GeDH. Codon optimized for *S. cerevisiae* |
| SEQ ID NO: 4 | Amino acid sequence<br>Origin: *Acinetobacter calcoaceticus*.<br>Enzyme activity: Geraniol dehydrogenase.<br>Ac_GeDH. Codon optimized for *S. cerevisiae* |
| SEQ ID NO: 5 | Amino acid sequence<br>Origin: *Thauera terpenica* 58Eu.<br>Enzyme activity: Geraniol dehydrogenase.<br>Tt_GeDH. Codon optimized for *S. cerevisiae* |
| SEQ ID NO: 6 | Amino acid sequence<br>Origin: *Pseudomonas putida*.<br>Enzyme activity: Geraniol dehydrogenase.<br>Pp_GeDH. Codon optimized for *S. cerevisiae* |
| SEQ ID NO: 7 | Amino acid sequence<br>Origin: *Kluyveromyces lactis*.<br>Enzyme activity: Ene reductase.<br>Kl_KYE1. Codon optimized for *S. cerevisiae* |
| SEQ ID NO: 8 | Amino acid sequence<br>Origin: *Pichia stipitis*. Enzyme activity: Ene reductase.<br>Ps_OYE2.6. Codon optimized for *S. cerevisiae* |
| SEQ ID NO: 9 | Amino acid sequence<br>Origin: *Zymomonas mobilis* subsp. *Mobilis*.<br>Enzyme activity: Ene reductase.<br>Zm_OYE. Codon optimized for *S. cerevisiae* |
| SEQ ID NO: 10 | Amino acid sequence<br>Origin: *Escherichia coli* MG1655.<br>Enzyme activity: Acetyl-CoA acetyltransferase.<br>Ec_atoB. |
| SEQ ID NO: 11 | Amino acid sequence<br>Origin: *Staphylococcus aureus*.<br>Enzyme activity: HMG-CoA synthase.<br>Sa_mvaS. Codon optimized for *E. coli*. |
| SEQ ID NO: 12 | Amino acid sequence<br>Origin: *Staphylococcus aureus*.<br>Enzyme activity: HMG-CoA reductase.<br>Sa_mvaA. Codon optimized for *E. coli*. |
| SEQ ID NO: 13 | Amino acid sequence<br>Origin: *Saccharomyces cerevisiae*.<br>Enzyme Activity: Mevalonate kinase (MK).<br>Sc_erg12. Codon optimized for *E. coli*. |
| SEQ ID NO: 14 | Amino acid sequence<br>Origin: *Saccharomyces cerevisiae*.<br>Enzyme activity: Phospho mevalonate kinase (PMK).<br>Sc_erg8. Codon optimized for *E. coli*. |
| SEQ ID NO: 15 | Amino acid sequence<br>Origin: *Saccharomyces cerevisiae*. |

TABLE 1-continued

Sequence listing key.

|  |  |
|---|---|
|  | Enzyme activity: Diphosphomevalonate decarboxylase (PMD). Sc_erg19. Codon optimized for *E. coli*. |
| SEQ ID NO: 16 | Amino acid sequence<br>Origin: *E. coli*.<br>Enzyme Activity: Isopentenyl diphosphate isomerase.<br>Ec_idi. |
| SEQ ID NO: 17 | Amino acid sequence<br>Origin: *Abies grandis*.<br>Enzyme activity: Geranyl diphosphate synthase.<br>Ag_GPPS2. Codon optimized for *E. coli*. |
| SEQ ID NO: 18 | Amino acid sequence<br>Origin: *Catharanthus roseus*.<br>Enzyme activity: Geraniol synthase.<br>Cr_GES |
| SEQ ID NO: 19 | Amino acid sequence<br>Origin: *Castellaniella defragrans*.<br>Enzyme activity: Geraniol dehydrogenase.<br>Cd_GeDH. Codon optimized for *E. coli*. |
| SEQ ID NO: 20 | Amino acid sequence<br>Origin: *Rhodococcus* sp. RD6.2.<br>Enzyme activity: Geraniol dehydrogenase.<br>Rs_GeDH. Codon optimized for *E. coli*. |
| SEQ ID NO: 21 | Amino acid sequence<br>Origin: *Kluyveromyces lactis*.<br>Enzyme activity: Ene reductase.<br>Kl_KYE1. Codon optimized for *E. coli*. |
| SEQ ID NO: 22 | Amino acid sequence<br>Origin: *Pichia stipitis*.<br>Enzyme activity: Ene reductase.<br>Ps_OYE2.6. Codon optimized for *E. coli*. |
| SEQ ID NO: 24 | Amino acid sequence<br>Origin: *Carpoglyphus lactis*.<br>Enzyme Activity: geraniol dehydrogenase.<br>Cl_GeDH |
| SEQ ID NO: 25 | Amino acid sequence<br>Origin: *Aedes aergypti*.<br>Enzyme Activity: geraniol dehydrogenase.<br>Aa_SDR-1 |
| SEQ ID NO: 26 | Amino acid sequence<br>Origin: *Ocimum basilicum*.<br>Enzyme Activity: geraniol dehydrogenase.<br>Ob_CAD1 |
| SEQ ID NO: 27 | Amino acid sequence<br>Origin: *Ziniber officinale*.<br>Enzyme Activity: geraniol dehydrogenase.<br>Zo_GeDH |
| SEQ ID NO: 28 | Amino acid sequence<br>Origin: *Camellia sinensis*.<br>Enzyme Activity: geraniol dehydrogenase.<br>Cc_putCAD. |
| SEQ ID NO: 29 | Amino acid sequence<br>Orgin: *Sphingopyxis granuli*.<br>Enzyme Activity: geraniol dehydrogenase.<br>Sg_GeDH |
| SEQ ID NO: 30 | Amino acid sequence<br>Origin: *Microbacterium trichothecenolyticium*.<br>Enzyme Activity: geraniol dehydrogenase.<br>Mt_GeDH |
| SEQ ID NO: 31 | Amino acid sequence<br>Origin: *Escherichia coli*.<br>Enzyme Activity: aldehyde reductase.<br>Ec_Ahr |
| SEQ ID NO: 32 | Amino acid sequence<br>Origin: *Escherichia coli*.<br>Enzyme Activity: aldehyde reductase.<br>Ec_YahK |
| SEQ ID NO: 33 | Amino acid sequence<br>Origin: *Saccharomyces cerevisiae*.<br>Enzyme Activity: Ene reductase.<br>Sc_OYE2 |
| SEQ ID NO: 34 | Amino acid sequence<br>Origin: *Rubus idaeus*.<br>Enzyme Activity: Ene reductase.<br>Ri_ENR |
| SEQ ID NO: 37 | Amino acid sequence<br>Origin: *Pseudomonas putida*.<br>Enzyme Activity: Ene reductase.<br>Pp_XenA |

TABLE 1-continued

| Sequence listing key. | |
|---|---|
| SEQ ID NO: 44 | Amino acid sequence<br>Origin: *Kluyveromyces marxianus*.<br>Enzyme Activity: Ene Reductase.<br>Km_OYE |
| SEQ ID NO: 45 | Amino acid sequence<br>Origin: *Gluconobacter mobifer*.<br>Enzyme Activity: Ene Reductase.<br>Gm_ENR |
| SEQ ID NO: 46 | Amino acid sequence<br>Origin: *Tanticharoenia sakaeratensis*.<br>Enzyme Activity: Ene Reductase.<br>Ts_ENR. |
| SEQ ID NO: 47 | Amino acid sequence<br>Origin: *Zymomonas mobilis*.<br>Enzyme Activity: Ene Reductase.<br>Zm_ENR |
| SEQ ID NO: 48 | Amino acid sequence<br>Origin: *Escherichia coli*.<br>Enzyme Activity: Ene Reductase.<br>Ec_NemA |
| SEQ ID NO: 49 | Amino acid sequence<br>Origin: *Pseudomonas citronellolis*.<br>Enzyme Activity: citronellol/citronellal dehydrogenase.<br>Pc_atuB |
| SEQ ID NO: 50 | Amino acid sequence<br>Origin: *Pseudomonas citronellolis*.<br>Enzyme Activity: citronellol/citronellal dehydrogenase.<br>Pc_atuG |
| SEQ ID NO: 51 | Amino acid sequence<br>Origin: *Pseudomonas* sp. Ag1.<br>Enzyme Activity: citronellol/citronellal dehydrogenase. Ps_atuB |
| SEQ ID NO: 52 | Amino acid sequence<br>Origin: *Bradyrhizobium* sp. DFCI-1.<br>Enzyme Activity: citronellol/citronellal dehydrogenase.<br>Bs_CiDH |
| SEQ ID NO: 53 | Amino acid sequence<br>Origin: *Solanum lycopersicum*.<br>Enzyme Activity: neryl diphosphate (NPP) synthase.<br>Sl_NDSP1 (CTP1) (Uniprot: C1K5M2) |
| SEQ ID NO: 54 | Amino acid sequence<br>Origin: *Olea europae*.<br>Enzyme Activity: Iridoid synthase (ISY).<br>Oe_ISY |
| SEQ ID NO: 55 | Amino acid sequence<br>Origin: *Catharanthus roseus*.<br>Enzyme Activity: Iridoid synthase (ISY).<br>Cr_ISY |
| SEQ ID NO: 56 | Amino acid sequence<br>Origin: *Glycine max*.<br>Enzyme Activity: Nerol Synthase (NES).<br>Gm_NES (Uniprot: T2DP90) |
| SEQ ID NO: 57 | Amino acid sequence<br>Origin: *Phaseolus vulgaris*.<br>Enzyme Activity: Nerol Synthase (NES).<br>Pv_NES_1 (Uniprot: R4HEK6; also hypothetical protein<br>PHAVU_006G195700g [*Phaseolus vulgaris*] XP_007148288.1) |
| SEQ ID NO: 58 | Amino acid sequence<br>Origin: *Persicaria minor*.<br>Enzyme Activity: Nerol Synthase (NES).<br>Pm_NES |
| SEQ ID NO: 59 | Amino acid sequence<br>Origin: *Picea abies*.<br>Enzyme Activity: Geranyl diphosphate synthase.<br>Pa_GPPS2 |
| SEQ ID NO: 60 | Amino acid sequence<br>Origin: *Coffea canephora*.<br>Enzyme Activity: Geranyl diphosphate Synthase.<br>Cc_GPPS |
| SEQ ID NO: 61 | Amino acid sequence<br>Origin: *Physcomitrella patens*.<br>Enzyme Activity: Geranyl diphosphate Synthase.<br>Pp_GPPS |
| SEQ ID NO: 62 | Amino acid sequence<br>Origin: *Picea glauca*.<br>Enzyme Activity: Geranyl diphosphate synthase.<br>Pg_GPPS |
| SEQ ID NO: 63 | Amino acid sequence<br>Origin: *Ocimum basilicum*. |

TABLE 1-continued

Sequence listing key.

|  |  |
|---|---|
|  | Enzyme Activity: Geraniol synthase.<br>Ob_GES |
| SEQ ID NO: 64 | Amino acid sequence<br>Origin: *Phyla dulcis*.<br>Enzyme Activity: Geraniol synthase.<br>Pd_GES |
| SEQ ID NO: 65 | Amino acid sequence<br>Origin: *Perilla setoyenis*.<br>Enzyme Activity: Geraniol synthase.<br>Ps_GES |
| SEQ ID NO: 66 | Amino acid sequence<br>Origin: *Valeriana officinalis*.<br>Enzyme Activity: Geraniol synthase.<br>Vo_GES |
| SEQ ID NO: 67 | Amino acid sequence<br>Origin: *Lycopersicon esculentum*.<br>Enzyme Activity: Ene Reductase.<br>Le_OPR3 |
| SEQ ID NO: 68 | Amino acid sequence<br>Origin: *Saccharomyces cerevisiae*.<br>Enzyme Activity: Alcohol Dehydrogenase.<br>Sc_ADH6 |
| SEQ ID NO: 69 | Amino acid sequence<br>Origin: *Streptococcus pneumoniae*<br>Enzyme Activity: NADH oxidase<br>Sp_NADHoxi (Uniprot: O84925) |
| SEQ ID NO: 70 | Amino acid sequence<br>Origin: *Mycobacterium marinum*<br>Enzyme Activity: carboxylic acid reductase (CAR)<br>Mm_CAR (Uniprot: B2HN69) |
| SEQ ID NO: 71 | Amino acid sequence<br>Origin: *Bacillus subtilis*<br>Enzyme Activity: phosphopantetheine transferase (PPTase)<br>Bs_SFP (Uniprot: P39135) |
| SEQ ID NO: 74 | Amino acid sequence<br>Origin: *Solanum tuberosum*<br>Enzyme Activity: Dimethylallylcistransferase<br>St_NDPS (XP_006361580.1) |
| SEQ ID NO: 75 | Amino acid sequence<br>Origin: *Solanum pennillii*<br>Enzyme Activity: Dimethylallylcistransferase<br>Sp_NDPS (XP_015085612.1) |
| SEQ ID NO: 77 | Amino acid sequence<br>Origin: *Phaseolus vulgaris*<br>Enzyme Activity: Nerol synthase<br>Pv_NES_2 (Uniprot: R4HEK6; also hypothetical protein HAVU_006G195600g [*Phaseolus vulgaris*] XP_007148287.1) |
| SEQ ID NO: 78 | Amino acid sequence<br>Origin: *Gossypium hirsutum*<br>Enzyme Activity: Nerol synthase<br>Gh_NES_1 (Uniprot: A0A1N7T9S3-1) |
| SEQ ID NO: 79 | Amino acid sequence<br>Origin: *Gossypium hirsutum*<br>Enzyme Activity: Nerol synthase<br>Gh_NES_2 (Uniprot: A0A1N7T9S6-1) |
| SEQ ID NO: 80 | Amino acid sequence<br>Origin: *Lactobacillus casei*<br>Enzyme Activity: 3-hydroxy-3-methylglutaryl coenzyme A reductase<br>Lc_MvA (Uniprot: K0MWE8_LACCA) |
| SEQ ID NO: 81 | Amino acid sequence<br>Origin: *Lactobacillus casei*<br>Enzyme Activity: hydroxymethylglutaryl-CoA synthase<br>Lc_MvaS (Uniprot: K0N9K3_LACCA) |
| SEQ ID NO: 82 | Amino acid sequence<br>Origin: *Methanosarcina mazei*<br>Enzyme Activity: mevalonate kinase<br>Mm_MK (Uniprot: Q8PW39_METMA) |
| SEQ ID NO: 83 | Amino acid sequence<br>Origin: *Saccharomyces cerevisiae*<br>Enzyme Activity: aldehyde reductase<br>Sc_Gre2 (Uniprot: GRE2_YEAST) |
| SEQ ID NO: 84 | Amino acid sequence<br>Origin: *Saccharomyces cerevisiae*<br>Enzyme Activity: aldehyde reductase<br>Sc_Ari1 (Uniprot: ARI1_YEAST) |

TABLE 1-continued

Sequence listing key.

| | |
|---|---|
| SEQ ID NO: 85 | Amino acid sequence<br>Origin: *Saccharomyces cerevisiae*<br>Enzyme Activity: aldehyde reductase<br>Sc_Gcy1 (Uniprot: GCY1_YEAST) |
| SEQ ID NO: 86 | Amino acid sequence<br>Origin: *Saccharomyces cerevisiae*<br>Enzyme Activity: aldehyde reductase<br>Sc_Ayr1 (Uniprot: AYR1_YEAST) |
| SEQ ID NO: 87 | Amino acid sequence<br>Origin: *Saccharomyces cerevisiae*<br>Enzyme Activity: farnesyl diphosphate synthase/<br>dimethylallyltranstransferase<br>Sc_Erg20 (Uniprot: P08524 (FPPS_YEAST) |
| SEQ ID NO: 88 | Amino acid sequence<br>Origin: *Saccharomyces cerevisiae*<br>Enzyme Activity: farnesyl diphosphate synthase/<br>dimethylallyltranstransferase<br>Ec_IspA (Uniprot: P22939 (ISPA_ECOLI) |

TABLE 2

Sequences disclosed herein.

```
Cd_GeDH       MNDTQDFISA QAAVLRQVGG PLAVEPVRIS MPKGDEVLIR IAGVGVCHTD LVCRDGFPVP    60
(SEQ          LPIVLGHEGS GTVEAVGEQV RILKPGDAVV LSFNSCGHCG NCHDGHPSNC LQMLPLNFGG   120
NO: 1)        AQRVDGGQVL DGAGHPVQSM FFGQSSFGTH AVAREINAVK VGDDLPLELL GPLGCGIQTG   180
              AGAAINSLGI GPGQSLAIFG GGVGLSALL  GARAVGADRV VVIEPNAARR ALALELGASH   240
              ALDPHAEGDL VAAIKAATGG GATHSLDTTG LPPVIGSAIA CTLPGGTVGM VGLPAPDAPV   300
              PATLLDDLSK SVTLRPITEG DADPQRFIPR MLDFHRAGKE PFDRLITRYR FDQINEALHA   360
              TEKGEAIKPV LVF                                                     373

Rs_GeDH       MGRAARAAVL GAYGEPLEIR DVEVGDLRDD EVLIRIAGVG ICHTDLTAAA GGVPVPVPAV    60
(SEQ          LGHEGAGVVE AVGGAVDSLV PGDHVLLSYS ACRDCVNCAN GHPAYCTRFA LANYSGRRAD   120
NO: 2)        GSTTLSMDSV ALQGNWFGQS SFATHAVVAA SDAVQVAGDL PIELLGPLGC GIQTGAGAVL   180
              RVLRPRIGSS IVVFGGGAVG LAAVLAAVVA ECSTIVVVDP LPTRRELALS LGATAVFDSA   240
              EPDLAKQLRA ATGGGADHTV DAVSTPEVLA TAVAVLRSPG SCVTVGLRGG RNPVTLDQSA   300
              LLMGRSVTGV IEGDADPQQF LPELIALWRA GKFPFDKLIT TFDFDDLHAA LEATRSGAAV   360
              KPVLTFASSE GQA                                                     373

Sm_GeDH       MKASAAIVRN VGGPFVIEDI EVAEPRGAEV RVRMVGVGMC HTDLVARDGF PVPLPIVLGH    60
(SEQ          EGSGVVEAVG PEITDLAAGD HVVLSFDSCA ACPTCDEGLP AYCHQFLGKN FAGVRLEDGS   120
NO: 3)        SPLSQTGAVI HGNFFGQSSF GIYAIAHRRN TVKVDKDLPL EILGPLGCGV MTGAGAAVIS   180
              LGLRPGQSLA IFGGGAVGLS ALLGARAVDA GTVVVVEPNA ERRALALELG ASHVIDPAAT   240
              DDVLAAVKEL SGGGVNLALD TTGIPAVVAV AVETTIAHGT VGLVAVPPPE AMLPANMMSM   300
              LVRGTIIKYI TEGDADPQTF IPQMITWYKA GKFPFDRLLK TFPFDQINEA AKASEDGSAI   360
              KPVLTF                                                             366

Ac_GeDH       MSELKDIIAA VTPCKGADFE LQALKIRQPQ GDEVLVKVVA TGMCHTDLIV RDQYYPVPLP    60
(SEQ ID       AVLGHEGSGI IEAIGPNVTE LQVGDHVVLS YGYCGKCTQC NIGNPAYCSE FFGRNFSGAD   120
NO: 4)        SEGNHALCTH DQGVVNDHFF AQSSFATYAL SRENNIVKVT KDVPIELLGP LGCGIQTGAG   180
              ACINALKVTP ASSLVTWGAG AVGLSALLAA KVCGASIIIA VDIVESRLEL AKQLGATHVI   240
              NSKTQDPVAA IKEITDGGVN FALESTGRPE ILKQGVDALG ILGKIAVVGA PQLGTTAQFD   300
              VNDLLLGGKT ILGVVEGSGS PKKFIPELVR LYQQGKFPFD QLVKFLAFDE INQAAIDSHK   360
              GITLKPIIKI A                                                       371

Tt_GeDH       MCSNHDFTAARAAVLAKVGGPLEIEDVRISAPKGDEVLVRMVGVGVCHTDLVCRDAFPVPLPIVLGHEGAGIVEAVG
(SEQ ID       EGVRSLEPGDRVVLSFNSCGRCGNCGSGHPSNCLQMLPLNFGGAQRVDGGRMLDAAGNAVQGLFFGQSSFGTYAIAR
NO: 5)        EINAVKVAEDLPLEILGPLGCGIQTGAGAAINSLGIGPGQSLAIFGGGVGLSALLGARAVGAAQVVVEPNAARRA
              LALELGASHAFDPFAGDDLVAAIRAATGGGATHALDTTGLPSVIGNAIDCTLPGGIVGMVGMPAPDAAVPATLLDLL
              TKSVILRPITEGDADPQAFIPQMLRFYREGKFPFDRLITRYREDQINEALHATEKGGAIKPVLVF

Pp_GeDH       MEMEIKAAIV RQKNGPFLLE HVALNEPAED QVLVALVATG LCHTDLVCRD QHYPVPLPMV    60
(SEQ ID       FGHEGAGVVE RVGSAVKKVQ PGDHVVLTFY TCGSCDACLS GDPTSCANSF GPNFMGRSVT   120
NO: 6)        GECTIHDHQG AEVGASFFGQ SSFATYALSY ERNIVKVIKD VPLELLGPLG CGIQTGAGSV   180
              LNALNPPAGS SIAIFGAGAV GLSAVMAAVV AGCTKIIVVD VKENRLKLAD ELGATHVINA   240
              ASSDPVEKIK EICAGGVPYV LETSGLPSVL QQAILSSAIG GEIGIVGAPP MGATIPVDIN   300
              FLLENRKLRG IVEGOSISDI FIPRLVELYR QGKFPFDKLL KFTSFDEINQ AAEDSENGIT   360
              LKPVLRIS                                                           368

Kl_KYE1       MSFMNFEPKPLADTDIFKPIKIGNTELKHRVVMPALTRMRALHPGNVPNPDWAVEYYRQRSQYPGIMIITEGAFPSA
(SEQ ID       QSGGYDNAPGVWSEEQLAQWRKIFKAIHDNKSFVWVQLWVLGRQAFADNLARDGLRYDSASDEVYMGEDEKERAIRS
NO: 7)        NNPQHGITKDEIKQYIRDYVDAAKKCIDAGADGVEIHSANGYLLNQFLDPISNKRIDEYGGSIENRARFVLEVVDAV
              VDAVGAERTSIRFSPYGVEGTMSGVSDPVLVAQFAYVLAELEKRAKAGKRLAYVDLVEPRVISPFQPEFEGWYKGGT
              NEFVYSVWKGNVLAVGNYALDPDAAITDSKNPNTLIGYGRAFIANPDLVERLEKGLPLNQYDRPSFYKMSAEGYIDY
              PTYEEAVAKGYKK
```

TABLE 2-continued

Sequences disclosed herein.

```
Ps_OYE2.6   MSSVKISPLK DSEAFQSIKV GNNTLQTKIV YPPTIRFRAL EDHTPSDLQL QYYGDRSTFP    60
(SEQ ID     GILLITEATF VSPQASGYEG AAPGIWTDKH AKAWKVITDK VHANGSFVST QLIFLGRVAD   120
NO: 8)      PAVMKTRGLN PVSASATYES DAAKEAAEAV GNPVRALTTQ EVKDLVYETY TNAAQKAMDA   180
            GFDYIELHAA HGYLLDQFLQ PCINQRTDEY GGSIENRARL ILELIDHLST IVGADKIGIR   240
            ISPWATFQNM KAHKDTVHPL TIFSYLVHEL QQRADKGQGI AYISVVEPRV SGNVDVSEED   300
            QAGDNEFVSK IWKGVILKAG NYSYDAPEFK TLKEDIADKR TLVGFSRYFT SNPNLVWKLR   360
            DGIDLVPYDR NTFYSDNNYG YNIFSMDSEE VDKELEIKRV PSAIEAL                 407

Zm_OYE      MPSLFDPIRF GAFTAKNRIW MAPLTRGRAT RDHVPTEIMA ELYAQRASAG LIISEATGIS    60
(SEQ ID     QEGLGWPYAP GIWSDAQVEA WLPITQAVHD AGGLIFAQLW HMGRMVPSNV SGMQPVAPSA   120
NO: 9)      SQAPGLGHTY DGKKPYDVAR ALRLDEIPRL LDDYEKAARH ALKAGFDGVQ IHAANGYLID   180
            EFIRDSTNHR HDEYGGAVEN RIALLKDVIE RVIATIGKER TAVRLSPNGE IQGTVDSHPE   240
            QVFIPAAKML SDLDIAFLGM REGAVDGTFG KTDQPKLSPE IRKVFKPPLV LNQDYTFETA   300
            QAALDSGVAD AISFGRPFIG NPDLPRRFFE KAPLTKDVIE TWYTQTPKGY TDYPLLGD     358

Ec_atoB     MKNCVIVSAV RTAIGSFNGS LASTSAIDLG ATVIKAAIER AKIDSQHVDE VIMGNVLQAG    60
(SEQ ID     LGQNPARQAL LKSGLAETVC GFTVNKVCGS GLKSVALAAQ AIQAGQAQSI VAGGMENMSL   120
NO: 10)     APYLLDAKAR SGYRLGDGQV YDVILRDGLM CATHGYHMGI TAENVAKEYG ITREMQDELA   180
            LHSQRKAAAA IESGAFTAEI VPVNVVTRKK TFVFSQDEFP KANSTAEALG ALRPAFDKAG   240
            TVTAGNASGI NDGAAALVIM EESAALAAGL TPLARIKSYA SGGVPPALMG MGPVPATQKA   300
            LQLAGLQLAD IDLIEANEAF AAQFLAVGKN LGFDSEKVNV NGGAIALGHP IGASGARILV   360
            TLLHAMQARD KTLGLATLCI GGGQGIAMVI ERLN                              394

Sa_mvaS     MTIGIDKINF YVPKYYVDMA KLAEARQVDP NKFLIGIGQT EMAVSPVNQD IVSMGANAAK    60
(SEQ ID     DIITDEDKKK IGMVIVATES AVDAAKAAAV QIHNLLGIQP FARCFEMKEA CYAATPAIQL   120
NO: 11)     AKDYLATRPN EKVLVIATDT ARYGLNSGGE PTQGAGAVAM VIAHNPSILA LNEDAVAYTE   180
            DVYDFWRPTG HKYPLVDGAL SKDAYIRSFQ QSWNEYAKRQ GKSLADFASL CFHVPFTKMG   240
            KKALESIIDN ADETTQERLR SGYEDAVDYN RYVGNILIGS LYLSLISLLE NRDLQAGETI   300
            GLFSYGSGSV VEFYSATLVV GYKDHLDQAA HKALLNNATE VSVDAYETFF KRFDDVEFDE   360
            EQDAVHEDRH IFYLSNIENN VREYHRPE                                     388

Sa_mvaA     MQSLDKNFRH LSRQQKLQQL VDKQWLSECQ FDILLNHPLI DEEVANSLIE NVIAQGALPV    60
(SEQ ID     GLLPNIIVDD KAYVVPMMVE EPSVVAAASY GAKLVNQTGG FKTVSSERIM IGQIVFDGVD   120
NO: 12)     DTEKLSADIK ALEKQIHKIA DEAYPSIKAR GGGYQRIAID TFPEQQLLSL KVFVDTKDAM   180
            GANMLNTILE AITAFLKNES PQSDILMSIL SNHATASVVK IQGEIDVKDL ARGERTGEEV   240
            AKRMERASVL AQVDIHRAAT HNKGVMNGIH AVVLATGNDT RGAEASAHAY ASRDGQYRGI   300
            ATWRYDQKRQ RLIGTIEVPM TLAIVGGGIK VLPIAKASLE LLNVDSAQEL GHVVAAVGLA   360
            QNFAACRALV SEGIQQGHMS LQYKSLAIVV GAKGDEIAQV AEALKQEPRA NTQVAERILQ   420
            EIRQQ                                                             425

Sc_erg12    MSLPFLTSAP GKVIIFGEHS AVYNKPAVAA SVSALRTYLL ISESSAPDTI ELDFPDISFN    60
(SEQ ID     HKWSINDFNA ITEDQVNSQK LAKAQQATDG LSQELVSLLD PLLAQLSESF HYHAAFCFLY   120
NO: 13)     MFVCLCPHAK NIKESLKSTL PIGAGLGSSA SISVSLALAM AYLGGLIGSN DLEKLSENDK   180
            HIVNQWAFIG EKCIHGTPSG IDNAVATYGN ALLFEKDSHN GTINTNNKIF LDDFPAIPMI   240
            LTYTRIPRST KDLVARVRVL VTEKEPEVMK PILDAMGECA LQGLEIMTKL SKCKGTDDEA   300
            VETNNELYEQ LLELIRINHG LLVSIGVSHP GLELIKNLSD DLRIGSTKLT GAGGGGCSLT   360
            LLRRDITQEQ IDSFKKKLQD DESTETFETD LGGTGCCLLS AKNLNKDLKI KSLVFQLFEN   420
            KITTKQQIDD LLLPGNTNLP WTS                                          443

Sc_erg8     MSELRAFSAP GKALLAGGYL VLDTKYEAFV VGLSARMHAV AHPYGSLQGS DKFEVRVKSK    60
(SEQ ID     QFKDGEWLYH ISPKSGFIPV SIGGSKNPFI EKVIANVESY FKPNMDDYCN RNLFVIDIFS   120
NO: 14)     DDAYHSQEDS VIEHRGNARL SFHSHRIEEV PKTGLGSSAG LVTVLITALA SFFVSDLENN   180
            VDKYREVIHN LAQVAHCQAQ GKIGSGFDVA AAAYGSIRYR RFPPALISNL PDIGSATYGS   240
            KLAHLVDEED WNITIKSNHL PSGLTLWMGD IKNGSETVKL VQKVKNWYDS HMPESLKILT   300
            ELDHANSRFM DGLSKLDRLH ETHDDYSDQI FESLERNDCT CQKYPEITEV RDAVATIRRS   360
            FRKITKESGA DIEPPVQTSL LDDCQTLKGV LTCLIPGAGG YDAIAVITKQ DVDLRAQTAN   420
            DKRFSKVQWL DVTQADWGVR KEKDPETYLD K                                 451

Sc_erg19    MTVYTASVTA PVNIATLKYW GKRDTKLNLP INSSISVILS QDDLRILTSA ATAPEFERDT    60
(SEQ ID     LWLNGEPHSI DNERTQNCLR DLRQLRKEME SKDASLPTLS QWKLHIVSEN NEPTAAGLAS   120
NO: 15)     SAAGFAALVS AIAKLYQLPQ STSEISRIAR KGSGSACRSL FGGYVAWEMG KAEDGHDSMA   180
            VQIADSSDWP QMKACVLVVS DIKKDVSSTQ GMQLTVATSE LFKERIEHVV PKRFEVMRKA   240
            IVEKDFATFA KETMMDSNSF HATCLDSFPP IFYMNDTSKR IISWCHTINQ FYGETIVAYT   300
            FDAGPNAVLY YLAENESKLF AFIYKLEGSV PGWDKKFTTE QLEAFNHQFE SSNFTARELD   360
            LELQKDVARV ILTQVGSGPQ ETNESLIDAK TGLPKE                            396

Ec_idi      MQTEHVILLN AQGVPIGTLE KYAAHTADTR LHLAFSSWLF NAKGQLLVTR RALSKKAWPG    60
(SEQ ID     VWTNSVCGHP QLGESNEDAV IRRCRYELGV EITPPESILP DFRYRATDPS GIVENEVCPV   120
NO: 16)     FAARTTSALQ INDDEVMDYQ WCDLADVLHG IDATPWAFSP WMVMQATNRE ARKRLSAFTQ   180
            LK                                                                182

Ag_GPPS     MAYSAMATMG YNGMAASCHT LHPTSPLKPF HGASTLEAF NGEHMGLLRG YSKRKLSSYK     60
(SEQ ID     NPASRSSNAT VAQLLNPPQK GKKAVEFDFN KYMDSKAMTV NEALNKAIPL RYPQKIYESM   120
NO: 17)     RYSLLAGGKR VRPVLCIAAC ELVGGTEELA IPTACAIEMI HTMSLMHDDL PCIDNDDLRR   180
            GKPINHKIFG EDTAVTAGNA LHSYAFEHIA VSTSKTVGAD RILRMVSELG RATGSEGVMG   240
            GQMVDIASEG DPSIDLQTLE WIHIHKTAML LECSVVCGAI IGGASEIVIE RARRYARCVG   300
```

|  |  |  |  |  |  |  |
|---|---|---|---|---|---|---|
|  | LLFQVVDDIL | DVTKSSDELG | KTAGKDLISD | KATYPKLMGL | EKAKEFSDEL | LNRAKGELSC | 360 |
|  | FDPVKAAPLL | GLADYVAFRQ | N |  |  |  | 381 |
| Cr_GES | MAATISNLSF | LAKSRALSRP | SSSSLSWLER | PKTSSTICMS | MPSSSSSSSS | SSMSLPLATP | 60 |
| (SEQ ID | LIKDNESLIK | FLRQPLVLPH | EVDDSTKRRE | LLERTRKELE | LNAEKPLEAL | KMIDIIQRLG | 120 |
| NO: 18) | LSYHFEDDIN | SILTGESNIS | SQTHEDLLTA | SLCFRLLRHN | GHKINPDIFQ | KFMDNNGKFK | 180 |
|  | DSLKDDTLGM | LSLYEASYLG | ANGEEILMEA | QEFTKTHLKN | SLPAMAPSLS | KKVSQALEQP | 240 |
|  | RHRRMLRLEA | RRFIEEYGAE | NDHNPDLLEL | AKLDYNKVQS | LHQMELSEIT | RWWKQLGLVD | 300 |
|  | KLTFARDRPL | ECFLWTVGLL | PEPKYSGCRI | ELAKTIAILL | VIDDIFDTHG | ILDELLLFIN | 360 |
|  | AIKRQDLEAM | EDLPEYMRIC | YMALYNTTNE | ICYKVLKENG | WSVLPYLKAT | WIDMIEGFMV | 420 |
|  | EAEWENSDYV | PNMEEYVENG | VRTAGSYMAL | VHLFFLIGQG | VTEDNVKLLI | KPYPKLFSSS | 480 |
|  | GRILRLWDDL | GTAKEEQERG | DLASSIQLFM | REKEIKSEEE | GRKGILEIIE | NLWKELNGEL | 540 |
|  | VYREEMPLAI | IKTAFNMARA | SQVVYQHEED | TYFSSVDNYV | KALFFTPCF |  | 589 |
| Cd_GeDH | MNDTQDFISA | QAAVLRQVGG | PLAVEPVRIS | MPKGDEVLIR | IAGVGVCHTD | LVCRDGFPVP | 60 |
| (SEQ ID | LPIVLGHEGS | GTVEAVGEQV | RILKPGDAVV | LSFNSCGHCG | NCHDGHPSNC | LQMLPLNFGG | 120 |
| NO: 19) | AQRVDGGQVL | DGAGHPVQSM | FFGQSSFGTH | AVAREINAVK | VGDDLPLELL | GPLGCGIQTG | 180 |
|  | AGAAINSLGI | GPGQSLAIFG | GGVGLSALL | GARAVGADRV | VVIEPNAARR | ALALELGASH | 240 |
|  | ALDPHAEGDL | VAAIKAATGG | GATHSLDTTG | LPPVIGSAIA | CTLPGGTVGM | VGLPAPDAPV | 300 |
|  | PATLLDLLSK | SVTLRPITEG | DADPQRFIPR | MKTENRAGKE | PFDRLITRYR | FDQINEALHA | 360 |
|  | TEKGEAIKPV | LVF |  |  |  |  | 373 |
| Rs_GeDH | MGRAARAAVL | GAYGEPLEIR | DVEVGDLRDD | EVLIRIAGVG | ICHTDLTAAA | GGVPVPVPAV | 60 |
| (SEQ ID | LGHEGAGVVE | AVGGAVDSLV | PGDHVLLSYS | ACRDCVNCAN | GHPAYCTRFA | LRNYSGRRAD | 120 |
| NO: 20) | GSTTLSMDSV | ALQGNWFGQS | SPATHAVVAA | SDAVQVAGDL | PIELLGPLGC | GIQTGAGAVL | 180 |
|  | RVLRPRIGSS | IVVFGGGAVG | LAAVLAAVVA | ECSTIVVVDP | LPTRRELALS | LGATAVFDSA | 240 |
|  | EPDLAKQLRA | ATGGGADHTV | DAVSTPEVLA | TAVAVLRSPG | SCVTVGLRGG | RNPVTLDQSA | 300 |
|  | LLMGRSVTGV | IEGDADPQQF | LPELIALWRA | GKFPFDKLIT | TFDFDDLHAA | LEATRSGAAV | 360 |
|  | KPVLTFASSE | GQA |  |  |  |  | 373 |
| Kl_KYE1 | MSFMNFEPKP | LADTDIFKPI | KIGNTELKHR | VVMPALTRMR | ALHPGNVPNP | DWAVEYYRQR | 60 |
| (SEQ ID | SQLPGIMIIT | EGAFPSAQSG | GYDNAPGVWS | EEQLAQWRKI | FKAIHDNKSF | VWVQLWVLGR | 120 |
| NO: 21) | QAFADNLARD | GLRYDSASDE | VYMGEDEKER | AIRSNNPQHG | ITKDEIKQYI | RDYVDAAKKC | 180 |
|  | IDAGADGVEI | HSANGYLLNQ | FLDPISNKRT | DEYGGSIENR | ARFVLEVVDA | VVDAVGAERT | 240 |
|  | SIRFSPYGVF | GTMSGGSDPV | LVAQFAYVLA | ELEKRAKAGK | RLAYVDLVEP | RVISPFQPEF | 300 |
|  | EGWYKGGTNE | FVYSVWKGNV | LRVGNYALDP | DAAITDSKNP | NTLIGYGRAF | IANPDLVERL | 360 |
|  | EKGLPLNQYD | RPSFYKMSAE | GYIDYPTYEE | AVAKGYKK |  |  | 398 |
| Ps_OYE2.6 | MSSVKISPLK | DSEAFQSIKV | GNNTLQTKIV | YPPTIRFRAL | EDHTPSDLQL | QYYGDRSTFP | 60 |
| (SEQ ID | GILLITEATF | VSPQASGYEG | AAPGIWTDKH | AKAWKVITDK | VHANGSFVST | QLIFLGRVAD | 120 |
| NO: 22) | PAVMKTRGLN | PVSASATYES | DAAKEAAEAV | GNPVRALTIQ | EVKDLVYETY | TNAAQKAMDA | 180 |
|  | GFDYIELHAA | HGYLLDQFLQ | PCINQRTDEY | GGSIENRARL | ILELIDHLST | IVGADKIGIR | 240 |
|  | ISPWATFQNM | KAHKDTVHPL | TIFSYLVHEL | QQRADKGQGI | AYISVVEPRV | SGNVDVSEED | 300 |
|  | QAGDNEFVSK | IWKGVILKAG | NYSYDAPEFK | TLKEDIADKR | TLVGFSRYFT | SNPNLVWKLR | 360 |
|  | DGIDLVPYDR | NTFYSDNNYG | YNIFSMDSEE | VDKELEIKRV | PSAIEAL |  | 407 |
| Cl_GeDH | MVQNPGASAI | QCRAAVLRKE | GQPMKIEQVL | IQAPGPNQVR | VKMVSSGLCA | TDAHLVWGEQ | 60 |
| (SEQ ID | KISDLGGIGC | PAIAGHEGAG | IVESVGENVT | EFVPGDSVLT | SFQPQCGQCE | SCLRPSTNIC | 120 |
| NO: 24) | KKYDLIKSTT | DVSTARTLDG | QPITSLFGLG | VYSELITTTE | HHVFKVNKAA | NLEHASIISC | 180 |
|  | SVGIGFYSAT | NLAAVYEGST | CAVWGLGGIG | INTLFGCKYN | KAKHIIGIDV | NEDKREIAAE | 240 |
|  | FGCTEFINPK | TLGQPVEQYL | MDKFGGVDFA | FDCVGYKPIL | DQAAVSLAID | GTMVIIGAAA | 300 |
|  | KEVKFEMPAF | NFLENRKVVG | GLLGSKKTKV | AYQELCDMYV | DGLYDVDRLV | SNKFSLDQIN | 360 |
|  | EAFQTLKDGN | CIRSIVVFK |  |  |  |  | 379 |
| Aa_SDR-1 | MDRWAGKVAV | VTGASSGIGA | AITTDLAKAG | MVVVGLARRV | ERVEALKANL | PESAKPRLHA | 60 |
| (SEQ ID | VKCDVSKEED | ITQVFKWVEE | KFGGVDVLVN | NAGILRQTDL | LGIDNGQMLR | EVLDTNVGAL | 120 |
| NO: 25) | VLCSQKAYQS | MKKRSVDGHI | VHINSVVGHK | VFDFPQSNIY | PASKHAVTAI | TETMRNELRN | 180 |
|  | AGSRIKVISI | SPGVVRTEIL | PESIIEGGHS | LLESEDISEA | VLYVLGTPPR | VQVHELTIKP | 240 |
|  | VGEKF |  |  |  |  |  | 245 |
| Ob_CAD1 | MGSLEVERKT | VGWAARDPSG | VLSPLETTLR | NTGPQDVYVE | VMCCGICHTD | VHQIKNDLGM | 60 |
| (SEQ ID | SNYPMVPGHE | VVGEVVEVGS | EVTKFRAGDV | VGVGCIVGSC | GNCRPCNSDI | EQYCNKKIWS | 120 |
| NO: 26) | YNDVYPDGKP | TQGGFAGAMV | VDQKFVVKIP | DGMAPEQAAP | LLCAGVTVYS | PLNHFGLKQS | 180 |
|  | GLRGGILGLG | GVGHMGVKIA | KAMGHHVTVI | SSSDKKRAEA | LDHLGADDYL | VSSDAARMQE | 240 |
|  | AADSLDYIID | TVPVFHPLEP | YLSLLKIDGK | LILMGVVNTP | LQFVSPMVML | GRKSITGSFI | 300 |
|  | GSMKELAEML | EFCKEKDLSS | TIEIVKMDYI | NTAFERLEKN | DVRYRFVVDV | AGSKLYQ |  | 357 |
| Zo_GeDH | MAELGNGKKQ | ASPEEVHPRK | AFGWAAKDKS | GVLSPFAFSR | RNTGADDVTI | KILYCGICHS | 60 |
| (SEQ ID | DLHTAKNEWS | NAIYPMVPGH | EIVGVVTEVG | QNVQNFKVGE | KVGVGCIVNS | CLSCQNCNRD | 120 |
| NO: 27) | YENYCPRIIL | TYNSLDVDGT | MTYGGYSNMV | VVNQHFVIRF | PENLPLDKGA | PLLCAGITVY | 180 |
|  | SPLKEHGLDV | PGKHLGVVGL | GGLGHVAVKF | GKAFGMKVTV | ISTSLKKEKE | AIERLGADAF | 240 |
|  | LVSSNAEQMQ | AAMGTMDGII | NTVSADHSIA | PLAFLLKTHG | KMIMVGAPEK | PLQLPIFSLI | 300 |
|  | LGGKTLAGSC | IGGIKATQEM | IDFAAKNNIT | ADIELIPISY | LNEAMERLTK | ADVRYRFVID | 360 |
|  | IGNSLTEA |  |  |  |  |  | 368 |
| Cc_putCAD. | MAQTTPNHTQ | TVSGWAAHDS | SGKITPYTFK | RRENGINDVT | IDILYCGICH | TDLHHVANDW | 60 |
| (SEQ ID | GITMYPVVPG | HEITGLISKV | GSNVSKFKIG | DRVGVGCLAA | SCLECEFCKD | SQENYCDQIQ | 120 |
| NO: 28) | FTYNGIFWDG | SITYGGYSKM | LVADQRYVVH | VPENLPMDAA | APLLCAGVTV | FCPLKDNNML | 180 |

TABLE 2-continued

Sequences disclosed herein.

```
              ELDSPPKKLG VVGLGGLGHV AVKFGKAFGH HVIVISTSPS KEDEAKHRLG ADDFIVSTDL   240
              AQMQAKKRSL DLILDTVAAK HSLGSYLELL KVNGTLVIVG APDKPIDLPS FPLIFGKRVV   300
              KGSMTGSMKE TQEMMDVCGK YNIKCDIEKT TPNKINEALD RLSKNDVKYR FVIDIASADK   360

Sg_GeDH       MKCKAAIARE DVAEFGWSEV ELDEPRADEI LVRIAGVGLC HTDLIARDQF IPVGSPAVLG    60
(SEQ ID       HEGAGEVVKV GSAVTKVGPG DRVALSFRSC GACRSCADHM PSYCQHFGGL NMSGARPDGS   120
NO: 29)       KAVRLDGQPI SSNFFGQSSF AEYALAYESN VVRIDDDEVP LELLGPLGCG IQTGAGGVMR   180
              SLACPAGSSL LVVGGSVGL AAVMGGAVQR CGTIIVVEPH AARRDLALEL GATHAIDPIG   240
              NDVAAAVRDI LPDGVDYAFD TTGRPDSFAA VLASLAVRGH FGMVSAQAAD TTITLDVNSF   300
              ILAGHHVQGI IEGDSDPDVF IPELIAHYKA GRFPYDRLVT TYPLADINRA IEDQHAGRCI   360
              KAVLIPDHGK GAAHD                                                    375

Mt_GeDH       MTAAVAALVR ERGGSVALTD VALRSPDPRE LVVKVMASGV CPTDLEGIDG GAGDREPAVF    60
(SEQ ID       GHEGAGIVEA VGAEVIRVRP GDRVVLGEGS CGACGPCRDG HPAYCDRFAE LNYAPRSDAA   120
NO: 30)       TAGGEHVTTG WMAQSSWATR IVVHESSAVP IGDDVPWAVA ALLGCGILIG AGTVLNVLRP   180
              APGDALLVLG AGTTGLAVM AAAHRGVARI VVSDPVEARR TLALEVGATE VIAPDDLAAL   240
              RPAPSFSHVL DTAGTQPSID AALAAVAPRG IAATVALKPG ANPVAVSQSR LLWGRILIGV   300
              IEGDADIARD VPLLAALWRA GRLPVERLVG TYAFADAQAA IADARAGRLV KPVLEMETVT   360
              VTDAAAASV RSLVDRLREG VSDDDLAALW RSLPAVGTAQ LRLWQGWAV TRDHHAGRLL   420
              ERSRWYGKLF RSDDDVAPIV CETDDGALLA DTDLARGGAT LRTIVHDGVA TASMVYDGQP   480
              IIDHFVALGA DTVLGVMTGR DTDDRGRAFY FVLEHVEDRP VAARDTTPTT AHRS          534

Ec_Ahr        MSMIKSYAAK EAGGELEVYE YDPGELRPQD VEVQVDYCGI CHSDLSMIDN EWGESQYPLV    60
(SEQ ID       AGHEVIGRVV ALGSAAQDKG LQVGQRVGIG WTARSCGHCD ACISGNQINC EQGAVPTIMN   120
NO: 31)       RGGFAEKLRA DWQWVIPLPE NIDIESAGPL LCGGITVFKP LLMHHITATS RVGVIGIGGL   180
              GHIAIKLLHA MGCEVTAFSS NPAKEQVLA MGADKVVNSR DPQALKALAG QFDLIINTVN   240
              VSLDWQPYFE ALTYGGNFHT VGAVLTPLSV PAFTLIAGDR SVSGSAIGTP YELRKLMRFA   300
              ARSKVAPTTE LFPMSKINDA IQHVRDGKAR YRVVLKADF                          339

Ec_YahK       MKIKAVGAYS AKQPLEPMDI TRREPGPNDV KIEIALCGVC HSDLHQVRSE WAGTVYPCVP    60
(SEQ ID       GHEIVGRVVA VGDQVEKTAP GDLVGVGCIV DSCKHCEECE DGLENYCDHM TGTYNSPTPD   120
NO: 32)       EPGHTLGGYS QQIVVHERYV LRIRHPQEQL AAVPALLCAG ITTYSPLRHW QAGPGKKVGV   180
              VGIGGLGHMG IKLAHAMGAH VVAFTTSEAK REAAKALGAD EVVNSRNADE MAAHLKSFDF   240
              ILNTVAAPHN LDDETTLLKR DGIMILVGAP ATPHKSPEVF NLIMKRRAIA GSMIGGIPET   300
              QEMLDFCAEH GIVADIEMIR ADQINEAYER MLRGDVKYRF VIDNRILTD              349

Sc_OYE2       MPFVKDFKPQ ALGDINLFKP IKIGNNELLH RAVIPPLTRM RAQHPGNIPN RDWAVEYYAQ    60
(SEQ ID       RAQRPGTLII TEGTFPSPQS GGYDNAPGIW SEEQIKEWTK IFKAIHENKS FAWVQLWVLG   120
NO: 33)       WAAFPDTLAR DGLRYDSASD NVYMNAEQEE KAKKANNPQH SITKDEIKQY VKEYVQAAKN   180
              SIAAGADGVE IHSANGYLLN QFLDPHSNNR TDEYGGSIEN RARFTLEVVD AVVDAIGPEK   240
              VGLRLSPYGV FNSMSGGAET GIVAQYAYVL GELERRAKAG KRLAFVHLVE PRVINPFLTE   300
              GEGEYNGGSN KFAYSIWKGP IIRAGNFALH PEVVREEVKD PRTLIGYGRF FISNPDLVDR   360
              LEKGLPLNKY DRDTFYKMSA EGYIDYPTYE EALKLGWDKN                         400

Ri_ENR        MASGGEMQVS NKQVIFRDYV TGFPKESDME LTIRSITLKL PQGSTGLLLK NLYLSCDPYM    60
(SEQ ID       RARMINHHRL SYVDSFKPGS PIIGYGVARV LESGNPKFNP GDLVWGFTGW EEYSVITATE   120
NO: 34)       SLFKIHNTDV PLSYYTGLLG MPGMTAYAGF YEICSPKKGE TVYVSAASGA VGQLVGQFAK   180
              LTGCYVVGSA GSKEKVDLLK NKFGFDEAFN YKEEADLSAL LRRYFPDGID IYFENVGGKM   240
              LDAVLPNMRP KGRIAVCGMI SQYNLEQPEG VRNLMALIVK QVRMEGFMVF SYTHLYGKEL   300
              ETVLPYIKQG KITYVEDVVD GLDNAPAALI GLYSGRNVGK QVVVVSRE              348

Pp_XenA       MSALFEPYIL KDVILRNRIA IPPMCQYMAE DGMINDWHHV HLAGLARGGA GLLVVEATAV    60
(SEQ ID       APEGRITPGC AGIWSDAHAQ AFVPVVQAIK AAGSVPGIQI AHAGRKASAN RPWEGDDHIA   120
NO: 37)       ADDARGWETI APSAIAFGAH LPKVPREMIL DDIARVKQDF VDAARRARDA GFEWIELHFA   180
              HGYLGQSFFS EHSNKRTDAY GGSFDNRSRF LLETLAAVRE VWPENLPLTA RFGVLEYDGR   240
              DEQTLEESIE LARRFKAGGL DLLSVSVGFT IPDTNIPWGP AFMGPIAERV RREAKLPVTS   300
              AWGEGTPQLA EAALQANQLD LVSVGRAHLA DPHWAYFAAK ELGVEKASWT LPAPYAHWLE   360
              RR                                                                  363

Km_OYE        MSYMNFDPKP LGDTNIFKPI KIGNNELKHR VVMPALTRMR AIAPGNIPNT EWAEEYYRQR    60
(SEQ ID       SQLPGILIIT EGTFPSAQSG GYPNVPGIWS KEQLAEWKKI FNAIHENKSF VQVQLWVLGR   120
NO: 44)       QAWPEVLKKE GLRYDSATDD LYMGEEEKER ALKANNPQHG ITKEEIKQYI KEYVDAAKKA   180
              IDAGADVQI HSANGYLLNQ FLDPISNNRT DEYGGSIENR ARFTLEVVDA VVDAVGAERT   240
              SIRFSPYGTF GTMSGGENPG IVAQYAYVIG ELEKRARAGK RLAFIDLVEP RVTDPFLPEF   300
              EKWFKEGINE FILSIWKGPV LRVGNYALDP DQATLDSKKP NTLIGYGRSF IANPDLVYRL   360
              EKGLPLNKYD RNIFYIFTKE GYTDYPSYEE SVAKGYKKEE KKY                     403

Gm_ENR        MPTLFDPVEL GTIHARNRIL MAPLTRGRAD KNGVPSALMV ELYAQRASAG LIISEATGIS    60
(SEQ ID       REGLGWPFAP GIWSDEQVAA WKPVTHESSV HGGKIVCQLW HMGRLVHSSV TGGQPVSCSA   120
NO: 45)       TTGPDEVHTY EGKKPYEQAR ALRLDEIPRI LNDYENAARN ALKAGFDGVQ IHGANGYLID   180
              EFLRDGTNHR TDEYGGSPEN RTRFLRHVVE RVIATIGADR TAIRLSPNGE TQGCIDSAPE   240
              KVFILAAEIL QDLGIAWLEL REPGPNGTFG KTDQPKLSPQ IRKVFHKPLV LNQDYTFEGA   300
              EAAVSEGRAD AIAFGRKFIA NPDLPERFRQ HAPLQADDMK TWYSQGPEGY TDYPFLSA    358

Ts_ENR.       MTTLFDPIKL GAIAAPNRII MAPLIRGASS RGHVPSALMA ELYAQRASAG LIITEATGIS    60
(SEQ ID       QEGLGWPYAP GIWSDEQVEA WKPIVRAVHD KGGRIVMQLW HMGRMVHSNV TGLQPVSASP   120
NO: 46)       TTAPGEAHTY DGKKPYEQAR ALDISEIPRL LADYENATRN ALAAGFDVQ IHAANGYLID   180
              EFLRDSTNKR TDAYGGEPEN RIALLREVIE RVISVAGADR TAVRLSPNGE TQGTIDSNPI   240
```

TABLE 2-continued

Sequences disclosed herein.

```
              SVFVPAAKML YDLGLAWLEL REPGPNGTFG RTDQPKLSPQ IRQVFKAPLV LNSDYTLEEA  300
              ETAVLEDRAD AISFGRKFLA NPDLPHRFKS GLPLNRDEMK TWYSQGPQGY VDTPAAS     357

Zm_ENR        MPTLFDPIRL GAVTAKNRIL MAPLTRGRAT RDHVPTDIMI KLYAQRASAG LIISEATGIS   60
(SEQ ID       QEGLGWPYAP GIWNEAQTQA WIPITQAVHD AGGLIFVQLW HMGRLVPSSV SGMQPVSASA  120
NO: 47)       TKAPDLAHTY EGKKPFDVAR PLEIAEIPRL LDDYERATRN AISAGFDGVQ IHAANGYLID  180
              EFLRDGTNLR KDAYGGTPEH RIALLREVIE RVISVIGADR TSVRLSPNGE IQGASDSHPE  240
              NIFLPAARML SDLGIAFLGL REGTPEGTFG RTDQPKLSPK IREVFNPPLI LNQDYNLETA  300
              QEALDSGVAD AISFGRLFIS NPDLPRRFFE GSPLIKDNIA TWYTQGAEGY TDYPLIGNEI  360
              PA                                                                362

Ec_NemA       MSSEKLYSPL KVGAITAANR IFMAPLTRLR SIEPGDIPTP LMAEYYRQRA SAGLIISEAT   60
(SEQ ID       QISAQAKGYA GAPGIHSPEQ IAAWKKITAG VHAENGHMAV QLWHTGRISH ASLQPGGQAP  120
NO: 48)       VAPSALSAGT RTSLRDENGQ AIRVETSMPR ALELEEIPGI VNDFRQAIAN AREAGFDLVE  180
              LHSAHGYLLH QFLSPSSNHR TDQYGGSVEN RARLVLEVVD AGIEEWGADR IGIRVSPIGT  240
              FQNTDNGPNE EADALYLIEQ LGKRGIAYLH MSEPDWAGGE PYTDAFREKV RARFHGPIIG  300
              AGAYTVEKAE TLIGKGLIDA VAFGRDWIAN PDLVARLQRK AELNPQRAES FYGGGAEGYT  360
              DYPTL                                                             365

Pc_atuB       MAYDSIFKPG LFAGQTVIVT GGGSGIGRCT AHELAALGAH VVLVGRKAEK LEKTAGEIVE   60
(SEQ ID       DGGSANWHSC DIRDEEAVKA LVAQVLVERG PIHHLVNNAG GQYPAPLASI NLKGFEAVVR  120
NO: 49)       INLVGGELMA REVFNQSMSK HGGSIVNMLA DMWGGMPGMG HSGAARAGME NFTKTAAVEW  180
              GHAGVRVNAV APGWIASSGM DIYEGAFKAV IPTLREHVPL KRIGTESEVA SAIVFLLSPG  240
              AAFISGNTIR IDGAASQGSR AFPLSKAKPG QSRSYNGEHR AYLPDVLKDQ E           291

Pc_atuG       MSLNAKTLFI TGASRGIGRE IALRAARDGA NVVIAAKSAE PHPKLAGTIH SVAEEVEAAG   60
(SEQ ID       GKALALQLDV RDENAVREAM ARAAEHFGGI DGLVNNAGAI KLVGVERLEP KRFDLMFQIN  120
NO: 50)       TRAVMVCSQA ALPYLKQSQG HILSLSPPLN LAEKWFAQHG PYTVTKYGMS MLTLGMHEEF  180
              RKYGISVNAL WPKTMIATAA IEFELGSRDA FKRARTPAIM ADAAHAILGS TGRSISGRLL  240
              IDEDILREQG VSDFEQYRETT PQGGPLVPDL FLD                              273

Ps_atuB       MAFDSIFKAD LFGGQIIIVT GGGSGIGRCT AHELAALGAH VILVGRKPEK LQTVAAEISE   60
(SEQ ID       DGGRASWQAC DIRDEEAVKA LVGQVLQEHG PIHGLVNNAG GQYPSPLASI NQKGFETVLR  120
NO: 51)       INLVGGELMA REVFNQSMSK HGGSIVNMLA DMWGGMPGMG HSGAARSGMD NLIKTAAVEW  180
              GYAGVRVNAV APGWIASSGM DIYEGAFKAV IPTLREHVPL KRIGTESEVS AAIVFLLSPA  240
              AAFVSGSTLR IDGAASLGSR AWPLHKAQPP SVSENGEHRA YLPDVLKEEK             290

Bs_CiDH       MLRFARNDAG RQQATTLSAL GSARAAAGVL AFVIGGVEGT YIGWRPAFGI LIAVSAIVFL   60
(SEQ ID       LSFRLKPDRG RPDIEIDLVG VALAAGAIIL ISFGENNLIG WGLALARPNA PFDLLGVSPA  120
NO: 52)       PIMIVIGIVL GQAFLSWTHR QQAAGKTPLL ALEVIDSPEE RCAVYALFTV VALEAALNFT  180
              VPLYIQIVQG RSPIATAIAM MPFNLTVFFS AMLIVNLYDR LTPRQIGRFG FALCTIALLW  240
              LAFVVRNDWS EIPVLFGLVL FGIGQGSLVT LLFNVLVTAS PKVLAGDVGS LRGITQNLAA  300
              AVGTAVAGAL LVGLLSTIAL GKITASPVLT KELQSQVDLD NITFVSNDRL RSVLEATSGT  360
              PQQVEEAVRV NTEARLRALK IGLLIMAGLA LLAVIPAGQL PNYRPGEIPD DNAAGHRERT  420
              S                                                                 421

Sl_NDSP1      MSSLVLQCWK LSSPSLILQQ NTSISMGAFK GIHKLQIPNS PLTVSARGLN KISCSLNLQT   60
(CTP1)        EKLCYEDNDN DLDEELMPKH IALIMDGNRR WAKDKGLEVY EGHKHIIPKL KEICDISSKL  120
(SEQ ID       GIQIITAFAF STENWKRSKE EVDFLLQMFE EIYDEFSRSG VRVSIIGCKS DLPMTLQKCI  180
NO: 53)       ALTEETTKGN KGLHLVIALN YGGYYDILQA TKSIVNKAMN GLLDVEDINK NLFDQELESK  240
              CPNPDLLIRT GGEQRVSNFL LWQLAYTEFY FINTLFPDFG EEDLKEAIMN FQQAHRREGG  300
              HTY                                                               303

Oe_ISY        MSWWFNRSVN GCKQKKIQEN GVQQQQNGDI QSFKSVALIV GVTGIVGSSL SEILQYTDTP   60
(SEQ ID       GGPWKVYGVA RRPRPTWLAK SHVEYVQCDV TNTEETISKI SPLTDITHIF YVSWMGNEDC  120
NO: 54)       SMNAVMFQNI LNSVIPNAPN LQHICLQTGS KHYIGLFETD TPESHDTPYS EDLARLKGDN  180
              FYHNLEDILF EETAKKGLTW SVHRPALIFG FSPCSLMNIV STLSVYAAIC KHENKPLVYP  240
              GSKASWNCFV DAADAELAAE HQIWAAVDPN AKNQAFNCIN GDLFKWKHIW KVLANQFDLE  300
              MVGYIEGNEQ VSMEELMKDK DSVWDEIVKK NNLMPTKLKE IAAFWFADIA FCLENVLSST  360
              HKNALHGEMG FRNTYTSFVS CIDKMRAYRF IP                                392

Cr_ISY        MSWVWKRSIG AGKNLPNQNK ENGVCKSYKS VALVVGVTGI VGSSLAEVLK LPDTPGGPWK   60
(SEQ ID       VYGVARRPCP VWLAKKPVEY IQCDVSDNQE TISKLSPLKD ITHIFYVSWI GSEDCQTNAT  120
NO: 55)       MFKNILNSVI PNASNLQHVC LQTGIKHYFG IFEEGSKVVP HDSPFTEDLP RLNVPNEYHD  180
              LEDILYEETG KNNLTWSVHR PALVFGESPC SMMNIVSTLC VYATICKHEN KALVYPGSKN  240
              SWNCYADAVD ADLVAEHEIW AAVDPKAKNQ VLNCNNGDVF KWKHIWKKLA EEFGIEMVGY  300
              VEGKEQVSLA ELMKDKDQVW DEIVKKNNLV PTKLKEIAAF WFADIAFCSE NLISSMNKSK  360
              ELGELGERNS MKSFVSCIDK MRDYRFIP                                     388

Gm_NES        MDNIYIKQAL VLKEVKHVFQ KLIGEDPMES MYMVDTIQRL GIEHHFEEEI EAALQKQHLI   60
(SEQ ID       FSSHLSDFAN NHKLCEVALP FALLRQRGHY VLADVFDNLK SNKKEFREKH GEDVKGLISL  120
NO: 56)       YEATQLGIEG EDSLDDAGYL CHQLLHAWLT RHEEHNEAMY VAKTLQHPLH YDLSRFRDDT  180
              SILLNDFKIK REWECLEELA EINSSIVRFV NQNEITQVYK WWKDLGLNNE VKFARYQPLK  240
              WYMWPMACFT DPRFSEQRIE LTKPISLVYI IDDIFDVYGT LDQLTLFTDA IKRWELASTE  300
              QLPDFMKMCL RVLYEITNDF AEKICKKHGF NPIETLKRSW VALLNAFLEE AHWLNSGHLP  360
              RSAEYLNNGI VSTGVHVVLV HSFFLMDYSI NNEIVAIVDN VPQIIHSVAK ILRLSDDLEG  420
              AKSEDQNGLD GSYIDCYMNE HQDVSAGDAQ RHVAHLISCE WKRLNREILT QNQLPSSFTN  480
              FCLNAARMVP LMYHYRSNPG LSTLQEHVKL LSNNAVAGAE RHVVHILCLQ FVIE         534
```

TABLE 2-continued

Sequences disclosed herein.

| | | |
|---|---|---|
| Pv_NES_1 (SEQ ID NO: 57) | MQGPLCSVAS ATSPTCSKDS FFRFLQRSQN THFFQIHSNH PFLKACPKPK SVSLKAYSST<br>DVIYVKQASL LKEAKHLSNK LIRENPMESL HMIDIIQRLG IEHHFEQEIQ LVLQKQQLIL<br>SNHPCDFDFF SSHDQLYEVA LAFRLLRQGG YYVNADLFDI LKNEKRKFKE IYGEDVKVLS<br>ALYEASQLGV QEDSVDDVGY LSLQLLHAWL RRHEEHPQAI HVTKTLHSPL HHGESRFRDA<br>NIFPIQFNIN NEWIGCLEEL AEINSCVVSL MNQKEITEVY KWWKTLEMAK EEKFRSYQPL<br>KWYMWPMACL INPCLSQQRI QLTKFISLIY IVDDIFDAYG ILDQLTLFTD AIIRWELGGT<br>EQLPGFMKMC LSVLYDTTND FAEEVYKKHG LNPIDILKRS WVALLNAFME EAHWLKGGDL<br>PRSEEYLNNG IVSSGVHVLL LYAFFLLDQS INMESVAVMD NFPQIITSVA KILRLSDDLE<br>GAKKKDEKGV DGSYLDCYMN EHQHVSAEDA QNHVSHLIQS EWKRLNQQIL TQNQLSSSFA<br>NICLNGARMV PLMYHTTNNP YLSIMQEHVM ILLHTAGAET V | 60<br>120<br>180<br>240<br>300<br>360<br>420<br>480<br>540<br>581 |
| Pm_NES (SEQ ID NO: 58) | MEMGNGTEEH TVKAVGWAAR DPSGHLSPFT FSRRATGELD VTFKVLYCGI CHSDLHYIKN<br>EWSNTIYPAL PGHEIVGEVT EVGSKVNKFK VGDKVGVGCI VGSCHSCPNC NNHLENYCPN<br>RILTEGSRLY DGTLNHGGYS DLMVVQEHFA VRIPDALPLD SAAPLLCAGI TVYSPLRYYG<br>LDKPGLHVGV VGLGGLGHMA VKFAKAFGVK VTVVSTSPAK KEDAISGLGA HSFILSTDAE<br>QMQAAVGTMD GIIDTVSASH PLPPLISLLK SHGKLVMVGD PPKPLELPVF PLLLGRKMVA<br>GSAIGGMKET QEMIDFAAKE GVRADVEVIP MDYVNTAMQR VSKSDVKYRF VIDIGNTEND<br>SLISSE | 60<br>120<br>180<br>240<br>300<br>360<br>366 |
| Pa_GPPS2 (SEQ ID NO: 59) | MGYNGMVVSS NLGLYYLNIA SRECNLKRIS IPSPFHGVST SLGSSTSKHL GLRGHLKKEL<br>LSHRLLLSST RSSKALVQLA DLSEQVKNVV EFDFDKYMHS KAIAVNEALD KVIPPRYPQK<br>IYESMRYSLL AGGKRVRPIL CIAACELMGG TEELAMPTAC AIEMIHTMSL IHDDLPYIDN<br>DDLARGKPIN HKVFGEDTAI IAGDALLSLA FEHVAVSTSR TLGTDIILRL LSEIGRATGS<br>EGVMGGQVVD IESEGDPSID LETLEWVHIH KTAVLLECSV VCGAIMGGAS EDDIERARRY<br>ARCVGLLFQV VDDILDVSQS SEELGKTAGK DLISDKATYP KLMGLEKAKE FADELLNRGK<br>QELSCFDPIK AAPLFALADY IASRQN | 60<br>120<br>180<br>240<br>300<br>360<br>386 |
| Cc_GPPS (SEQ ID NO: 60) | MAISATISSR YGGSFLQQNL DHFKISVQTI PRSQNIRMIV PKKINPASHV ANSSALEAAQ<br>VQEKKPLSLD SPFPDFRFDE YMNTKAISVN KALDDAIPLQ EPIKIHEAMR YSLLAGGKRV<br>RPMLCIASCE LVGGDESLAM PMACAVEMIH TMSLIHDDLP CMDNDDLRRG KPTNHKVYGE<br>ETAVLAGDAL LSLAFEHVAA KTGNVEASRV VRAIAELASS VGSQGLVAGQ IVDLSSEGEQ<br>VDLNHLEYIH VHKTSKLLEA AVVCGAIVGG ANEAEIERMR NYAKCIGLLF QVVDDILDVT<br>KSSEELGKTA GKDLATDKAT YPKLMGLERA KKFADELVAV ATEELSHFDA VKAAPLYHLA<br>NYIAYRQN | 60<br>120<br>180<br>240<br>300<br>360<br>368 |
| Pp_GPPS (SEQ ID NO: 61) | MKSKAQAVNV ALDKAVPMQY PEKIREAMRY SLLAGGKRVR PALCIAACEL VGGNEEMSMP<br>AACAMEMVHT MSLIHDDLPC MDNDDLRRGK PINHKVEGED TAVLAGDALL TYAFEHIARD<br>TTGVPADRVL RVIAHLGKAV GSEGLVAGQI VDIASEGDPT VGLETLEYVH THKTAVLLES<br>SVVCGAILGG ASEDEISRLS KYARNVGLLF QVVDDILDVT KSSAELGKTA GKDLLADKAT<br>YPKLLGLEKS KAFAEELTRK AKDQLSVFDQ QKAAPLLGLA DYIAYRQN | 60<br>120<br>180<br>240<br>288 |
| Pg_GPPS (SEQ ID NO: 62) | SMAPSC HCLHFMNIVS QECNLKRVSI QSARFRGLST SLWSSGGFQG HLKRELSAYR<br>HLVSSLRCSN TNAQLANLSE QVKEKVEEFD FKEYMRSKAM SVNEALDRAV PLRYPEKIHE<br>AMRYSLLAGG KRVRPILCIA ACELVGGSEE LAMPTACAME IIHTMSLIHD DLPPMDNDDL<br>ARGKPINHKV FGEGTAVLAG DALLSFAFEH IAVSTSKTVE SDRVLRVVSE LGRAIGSEGV<br>AGGQVADITS QGNPSVGLET LEWIHIHKTA VLLECSVASG AIIGGASEDE IERVRKYARC<br>VGLLFQVVDD ILDVTKSSEE LGKTAAKDLL SDKATYPKLM GLEKAKEFAD ELLGKAKEEL<br>SFENPIKAAP LLGLADYIAQ RQN | 60<br>120<br>180<br>240<br>300<br>360<br>383 |
| Ob_GES (SEQ ID NO: 63) | MSCARITVTL PYRSAKTSIQ RGITHYPALI RPRFSACTPL ASAMPLSSTP LINGDNSQRK<br>NTRQHMEESS SKRREYLLEE TTRKLQRNDT ESVEKLKLID NIQQLGIGYY FEDAINAVLR<br>SPFSTGEEDL FTAALRFRLL RHNGIEISPE IFLKFKDERG KFDESDTLGL LSLYEASNLG<br>VAGEEILEEA MEFAEARLRR SLSEPAAPLH GEVAQALDVP RHLRMARLEA RRFIEQYGKQ<br>SDHDGDLLEL AILDYNQVQA QHQSELTEII RWWKELGLVD KLSFGRDRPL ECFLWTVGLL<br>PEPKYSSVRI ELAKAISILL VIDDIFDTYG EMDDLILFTD AIRRWDLEAM EGLPEYMKIC<br>YMALYNTTNE VCYKVLRDTG RIVLLNLKST WIDMIEGFME EAKNENGGSA PKLEEYIENG<br>VSTAGAYMAF AHIFFLIGEG VTHQNSQLFT QKPYPKVESA AGRILRLWDD LGTAKEEQER<br>GDLASCVQLF MKEKSLTEEE ARSRILEEIK GLWRDLNGEL VYNKNLPLSI IKVALNMARA<br>SQVVYKHDQD TYFSSVDNYV DALFFTQ | 60<br>120<br>180<br>240<br>300<br>360<br>420<br>480<br>540<br>567 |
| Pd_GES (SEQ ID NO: 64) | MASARSTISL SSQSSHHGFS KNSFPWQLRH SRFVMGSRAR TCACMSSSVS LPTATTSSSV<br>ITGNDALLKY IRQPMVIPLK EKEGTKRREY LLEKTARELQ GTTEAAEKLK FIDTIQRLGI<br>SCYFEDEING ILQAELSDID QLEDGLFTTA LRFRLLRHYG YQIAPDVFLK FIDQNGEKEKE<br>SLADDTQGLV SLYEASYMGA NGENILEEAM ELPFRHLRMA QHAMREVAFL LELPRHLRMA<br>RLEARRYIEQ YGTMIGHDKD LLELVILDYN NVQAQHQAEL AEIARWWKEL GLVDKLTFAR<br>DRPLECFLWT VGLLPEPKYS ACRIELAKTI AILLVIDDIF DTYGKMEELA LFTEAIRRWD<br>LEAMETLPEY MKICYMALYN TTNEICYKVL KKNGWSVLPY LRYTWMDMIE GEMVEAKNEN<br>GGSAPNLEEY IENGVSTAGA YMALVHLFFL IGEGVSAQNA QILLKKPYPK LFSAAGRILR<br>LWDDLGTAKE EEGRGDLASS IRFLMKEKNL TTEEEGRNGI QEEIYSLWKD LNGELISKGR<br>MPLAIIKVAL NMARASQVVY KHDEDSYFSC VDNYVEALFF TPLL | 60<br>120<br>180<br>240<br>300<br>360<br>420<br>480<br>540<br>584 |
| Ps_GES (SEQ ID NO: 65) | MCSISQKVVI GLNKAAANNC LQNLDRAGEK TRRVSSSEAA SCLRASSSLQ LDVKPVEEGR<br>RSGNYQPSIW DENYVQSLNT PYKEERYLTR HAELIVQVKP LLEKKMEATQ QLELIDDLNN<br>LGLSYFFQDR IKQILSFIYD ENQCFHSNIN DQAEKRDLYF TALGETULRQ HGENVSQEVF<br>DCFKNDKGSD FKASLSGNTK GLLQLYEASF LVREGEDTLE LARQFATKFL RRKLDEIDDN<br>HLLSRIHHSL EIPLHWRIQR LEARWFLDAY ATRHDMNPII LELAKLDFNI IQATHQEELK<br>DVSRWWQNTR LAEKLPFVRD RLVESYFWAI ALFEPHQYGY QRRVAAKIIT LATSIDDVYD | 60<br>120<br>180<br>240<br>300<br>360 |

TABLE 2-continued

Sequences disclosed herein.

```
             IYGILDELQL FIDNFRAWDT ESLGGLPYSM QLFYMVIHNF VSELAYEILK EKGFIAIPYL  420
             QRSWVDLAES FLKEANWYYS GYIPSLEELI DNGSISIGAV AVLSQVYFTL ANSIEKPKIE  480
             SMYKYHHILR LSGLLVRLHD DLGTSLFEKK RGDVPKAVEI CMKERNDTEE EAEEHVKYLI  540
             REAWKEMNTA TAAAGCPFMD ELNVAAANLG RAAQFVYLDG DGHGVQHSKI HQQMGGLMFK  600
             PYV                                                                603

Vo_GES       MITSSSSVRS LCCPKTSIIS GKLLPSLLLT NVINVSNGTS SRACVSMSSL PVSKSTASSI   60
(SEQ ID      AAPLVRDNGS ALNFFPQAPQ VEIDESSRIM ELVEATRRIL RNESSDSTEK MRLIDSLQRL  120
NO: 66)      GLNHHFEQDI KEMLQDFANE HKNINQDLFT TSLRFRLLRH NGENVTPDVF NKFTEENGKF  180
             KESLGEDTIG ILSLYEASYL GGKGEEILSE AMKESESKLR ESSGHVAXHI RRQIFQSLEL  240
             PRHLRMARLE SRRYIEEDYS NEIGADSSLL ELAKLDFNSV QALHQMELTE ISRWWKQLGL  300
             SDKLPFARDR PLECFLWTVG LLPEPKYSGC RIELAKTIAV LLVIDDIFDT YGSYDQLILF  360
             TNAIRRWDLD AMDELPEYMK ICYMALYNTT NEICYKVLKE NGWSVLPYLE RTWIDMVEGF  420
             MLEAKWLNSG EQPNLEAYIE NGVTTAGSYM ALVHLFFLIG DGVNDENVKL LLDPYPKLFS  480
             SAGRILRLWD DLGTAKEEQE RGDVSSSIQL YMKEKNVRSE SEGREGIVEI IYNLWKDMNG  540
             ELIGSNALPQ AIIETSFNMA RTSQVVYQHE DDTYFSSVDN YVQSLFFTPV SVSV         594

Le_OPR3      MASSAQDGNN PLFSPYKMGK FNLSHRVVLA PMTRCRALNN IPQAALGEYY EQRATAGGFL   60
(SEQ ID      ITEGTMISPT SAGFPHVPGI FTKEQVREWK KIVDVVHAKG AVIFCQLWHV GRASHEVYQP  120
NO: 67)      AGAAPISSTE KPISNRWRIL MPDGTHGIYP KPRAIGLYEI SQVVEDYRRS ALNAIEAGED  180
             GIEIHGAHGY LIDQFLKDGI NDRIDEYGGS LANRCKFITQ VVQAVVSAIG ADRVGVRVSP  240
             AIDHLDAMDS NPLSLGLAVV ERLNKIQLHS GSKLAYLHVT QPRYVAYGQT EAGRLGSEEE  300
             EARLMRTLRN AYQGTFICSG GYTRELGIEA VAQGDADLVS YGRLFISNPD LVMRIKLNAP  360
             LNKYNRKTFY TQDPVVGYTD YPFLQGNGSN GPLSRL                             396

Sc_ADH6      MSYPEKFEGI AIQSHEDWKN PKKTYDPKP FYDHDIDIKI EACGVCGSDI HCAAGHWGNM    60
(SEQ ID      KMPLVVGHEI VGKVVKLGPK SNSGLKVGQR VGVGAQVFSC LECDRCKNDN EPYCIKKATT  120
NO: 68)      YSQPYEDGYV SQGGYANYVR VHEHFVVPIP ENIPSHLAAP LLCGGLTVYS PLVRNGCGPG  180
             KKVGIVGLGG IGSMGTLISK AMGAETYVIS RSSRKREDAM KMGADHYRAT LEEGDWGEKY  240
             FDTFDLIVVC ASSLTDIDEN IMPKAMKVGG RIVSISIPEQ HEMLSLKPYG LKAVSISYSA  300
             LGSIKELNQL LKLVSEKDIK IWVETLPVGE AGVHEAFERM EKGDVRYRFT LVGYDKEFSD  360

Sp_NADHoxi   MSKIVVVGANHAGTACINTMLDNFGNENEIVVFDQNSNISFLGCGMALWIGEQIDGAEGLFYSDKEKLEAKGAKVYM
(SEQ ID      NSPVLSIDYDNKVVTAEVEGKEHKESYEKLIFAIGSTPILPPIEGVEIVKGNREFKATLENVQFVKLYQNAEEVINK
NO: 69)      LSDKSQHLDRIAVVGGGYIGVELAEAFERLGKEVVLVDIVDTVLNGYYDKKDFTQMMAKNLEDHNIRLALGQTVKAIE
             GDGKVERLITDKESFDVDMVILAVGFRPNTALADGKIELFRNGAFLVDKKQETSIPGVYAVGDCATVYDNARKDISY
             IALASNAVRTGIVGAYNACGHELEGIGVQGSNGIGISIYGLHMVSTGLTLEKAKAAGYNATETGENDLQKPEFMKHDNH
             EVAIKIVETIKDSREILGAQMVSHDIAISMGIHMESLAIQEHVTIDKLALTDLEFLPHENKPYNYITMAALTAEK Mm_CAR       MSPITREERLERRIQDLYANDPQFAAAKPATATIAAIERPGLPLPQIIETVMTGYADRPALAQRSVEFVTDAGIGHT
(SEQ ID      TLALLPHFETISYGELWDRISALADVLSTEQTVKPGDRVCLLGENSVDTATIDMILARLGAVAVPLQTSAAITQLQP
NO: 70)      IVAETQPTMIAASVDALADATELALSGQTATRVLVFDHHRQVDAHRAAVESARERLAGSAVVETLAEAIARGDVPRG
             ASAGSAPGTDVSDDSLALLITTSGSTGAPKGAMYPRRNVATEWRKRTWEEGGYEPSITLNEMPMSHVMGRQILYGIL
             CNGGTAYFVAKSDLSTLFEDLALVRPTELTFVPRVWDMVFDEFQSEVDRALVDGADRVALEAQVKAEIRNDVLGGRY
             TSALIGSAPISDEMKAWVEELLDMHLVEGYGSTEAGMILIDGAIRRPAVLDYKLVDVPDLGYFLTDRPHPRGELLVK
             TDSLFPGYYQRAEVTADVFDADGFYRTGDIMAEVGPEQFVYLDRANNVLKLSQGEFVTVSKLEAVEGDSPLVRQIYI
             YGNSARAYLLAVIVPIQEALDAVPVEELKARLGDSLQEVAKAAGLQSYEIPRDFIIETTPWILENGLLIGIRKLARP
             QLKKHYGELLEQIYTDLAHGQADELRSLRQSGADAPVLVTVCRAAAALLGGSASDVQPDAHFIDLGGDSLSALSFIN
             LLHEIFDIEVPVGVIVSPANDLQALADYVEAARKPGSSRPTFASVHGASNGQVIEVHAGDLSLDKFIDAATLAEAPR
             LPAANTQVRTVLLTGATGELGRYLAEWLERMDLVDGKLICLVRAKSDTEARARLDKTEDSGDPELLAHYRALAGDH
             LEVLAGDKGEADLGLDRQTWQRLADTVDLIVDPAALVNHVLPYSQLFGPNALGTAELLRLALTSKIKPYSYTSTIGV
             ADQIPPSAFTEDADIRVISATRAVDDSTANGYSNSKWAGEVLLREAHDLCGLPVAVERCDMILADTTWAGQLNVPDM
             FIRMILSLAATGIAPGSFYELAADGARQRAHYDGLPVEFIAEAISTLGAQSQDGFHTYHVMNPYDDGIGLDEFVDWL
             NESGCPIQRIADYGDWLQRFETALRALPDRQRHSSLPLLHNYRQPERPVRGSIAPTDRFRAAVQEAKIGPDKDIPH
             VGAPIIVKYVSDLRLLGLL Bs_SFP       MKIYGIYMDRPLSQEENERFMSFISPEKREKCARFYHKEDAHRTLLGDVLRSVISRQYQLDKSDIRESTQEYGKPC
(SEQ ID      IPDLPDAHFNISHSGRWVICAFDSQPIGIDIEKTKPISLEIAKRFFSKTEYSDLLAKDKDEQTDYFYHLWSMKESFI
NO: 71)      KQEGKGLSLPLDSFSVALHQDGQVSIELPDSHSPCYIKTLEVDPGYKMAVCAAHPDFPEDITMVSYEELL St_NDPS      MSFSLVSQHFISLKSSSLGLQCWKSSSPSLILQRNTSISMGAFKGMHKLQILNSPLIVSARGLNKISCSLNLQTEKFC
(SEQ ID      DDDNDNDDLYLDEELMPKHIALIMDGNRRWAKAKGLEVYEGHKLIIPKLKEICHISSSKLGIQGITAFAFSTENWKRS
NO: 74)      KEEVDFLMQLFEEFFDEFSRSGVRVSVIGCKSNLPLTLQKCIALTEETTKGNKGLHLVIALNYGGYYDILQATKSIA
             NKVMNGLLHVEDINKNLFEQELESKCPNPDLLIRTGGEQRVSNELLWQLAYTEFYFINTLFPDFGEKDLKEAILNFQ
             QRHRRFGGHTY Sp_NDPS      MNSSLVFQHLIPSKSSLGLKSQKSSSPSLILRANTSITMGEFKGTHDKQLQILNLPLIVSACRLNKISSSFSLQTEK
(SEQ ID      LCYDNDNDDDNDDLELHEELIPKHIALIMDGNRRWAKAKGLEVYEGHKLIIPKLKEICDISSKLGIQIITAFAFSTEN
NO: 75)      WKRSKEEVDLLMQLFEEFFDAFSREGVRVSVIGCKSNLPMTLQKCIELTEETTKGNKGLHLVIALNYGGYYDILQAT
             KSIVNKAMNGLLDVEDINKSLFEQELESKCPNPDLLIRTGGEQRVSNELLWQLAYTEFYFINTLFPDFGEKDLKEAI
             MNFQQAHRREGGHTY Pv_NES_2     MDLSDDILLEQALVLKEVKQAFQKLVSEDYMECFYVIDIIQRLGIEHHFQEEIEALLQNQCSIFISHISDFANHHKL
(SEQ ID      YELALLFALLRQRGYHVPADVFEGLKSNKREFRAKHGEDVKSLIALHEAAQLSIEGEDSLDDAGELCCQLLHSWLKR
NO: 77)      HREHHEAILVANTLQNPLHYGLSRFRDITSLALSDYKTKKEWICIEKLAEINSCIVRMMNQNEIIQVYRWWKDVGMV
             REEKFCMYEPLKWYLWPMACFTDPRESDQRIELIKSISLIYIIDDIFDVYGILDQLTLFRDAVYRWELGGAEQLPDF
```

TABLE 2-continued

Sequences disclosed herein.

|  |  |
|---|---|
|  | MKMCLSVLYDITNDFAEKVYKRHGLNPIDTLKRSWVALLNAFMEEAHWLKGGDLPRSEELLNNGIVSSGVHVVLLHA FFLFDHSINMESVAVMDNFPQIITSVAKILRLSDDLEGAKKKDEKGVDGSYLDCYMNEHQHVSAEDAQNHVSHLIQS EWKRLNEQILTQNELPSSFINFCLNAARMVPLMYDYTTNNPCLSIMREELKMVLNVDSGHM |
| Gh_NES_1 (SEQ ID NO: 78) | MECSRQVQVVDDKQQVVSCHMKSAAFDEIQQRRSANYKANIWQYDFLQSLPTIYNGVEYTLRVENLKENVKDMFVEA KDQLAKLELIDIIRKLGLGDLFAEETHKALQTVVSSMKNNKNGEEEELYMTALRFKLLRLHGYDVSQDVFNAVSITK CSDIKGLLELFEASYLAFEGETILDEAKAFSMEALRNVYPILDLNLAKEVAHALELPMHWRVQWEDVKWRITMYETY NKNIDKRFLELAKLNENTVQAILQKDLREISRWWRNLRIMEGLNPFIRDRLAESFLCSVGLITEPQYSCFRKCLIKIT IMILIIDDVYDVYGSIEELEQFTEAVDRWDSSKTQDLPECMKTCFQALYDITNEIALDIQELNGWQVQALLHLRKAW AGFCKALFVEAKWYNKGYSPSLEELLSNALISSGAIVISIHTMLSVGSTDEKIINLLGKDEDLAYNISIITRLYNDL GTSMAEKERGDAPSSIHCYAREMNVSEKEAEEHIKNMINNTWKKINGQCLNNQSHNLLPCSFVKVTTNVARMVQCLY QFGDGEGIQDRETRNHISSLLIEPINLDKTAKD |
| Gh_NES_2 (SEQ ID NO: 79) | MAPTSQSLNEEQRRSANYHPSIWDPTAIQSFTTPYTTELYATQLEDLKQKVRKLLASTKDTAALLKLIDSMKRLGVA YHFQEQIQQALNQLNPDLNLVSNDLSTVALHFRILREDCYPITADVLEKFKGDDGRFMGSLCGDVEGLLGLNEASSM AIQGEKILEEAKAFSSENLKNVIGKLEKVEAKQVQRSLEVPLYWRMERIEARNFIDSTAMDDSNSSVLLDQAKLDYN LIQSVYKQELKQLAEWWSELNFKEKLSFSRDRLMEILFWATGLSFEAQYAKCRICETKYACLATVVDDILDIYGSLE ELECETKAVTGWDVKVIQELPEYMRVMESAISDFINELAQQTLKDHGLDVLPYIKEQWAILCRAHITEARWFYGGQI PTFDEYIENAWISIGSLGGLVLLCFVEADSIVNQFPNCLKDYSQLFYWSSLITRLSDDLGTSKAEMERGDIPKAVQT YMIEKGVSEETARNHVKELISNSWKKINEEILDNRFSRAIVNLSKNMARTAQCIYQHGDGFGTSTGVIKDCIISSIL RPIPI |
| Lc_mvaA (SEQ ID NO: 80) | MKEWELSPEKRADQLVQEGWLITQDAALLAGTHSLPEVTGARLIENAIGEFPLPLGVARNLLVNGQLHQVPIADEEP SVIAAASNGARLATANGGVRTHVAAHRVVAEVVLINLIDLVQARQTILAHQTDIQRVIAVAHPSMIQRGGGLDQLTV ESLGAQFLKIRLILDPQQAMGANYANTVAEAVAAAVISWVDGDVLVSILTNAPTELVTAEVSLEPVSLATKAVSGDV IAKKIVQLSDLAFVDAERAVIHNKGILNGIIGAVLAIGNDTRAVAASIGAFACASGRYQPLSRWYMDQGHLVGHLQL PLPMGAVGGAIGALPMAQVVRALGGYQNLAIMQQVIAALGLVQNLAAMRALAGPGIQAGHMKLQANALAIAAGATET ELPMLVNALRQGSMDLKHAQQYLITIRLNKKVGQSKDENRD |
| Lc_mvaS (SEQ ID NO: 81) | MKIGIDAIAMDTPDFLVDLVKLAQVAGDDPDKYTIGIGQDEQAVPPSSQDIVIMGANAATKLLTPAIRASLGMVLVG TESGVDASKSAALFIHDLLALPEWVRAVELKEACYGGTAALMMARDYIAAHPDKTVLVIAADIARYGLATAGEVTQG AGAVAMLIKAEPHIMTIEDDSVYRSESIDDFWRPVYQDTAIAQGKYSTEQYLAFFQAIWSRYQTQRHHTASDFAAMT FHLPYTKNGKKALKLVLPDTDEATGERLQRRFEASTRYCRRVGNITTGSLYLGLLSLLDNDTSLKAGDRIGLFSYGS GAVAEFFSGILQPDFAAQLHAANHAKMLADRQELTVPEYEAVFSDKVPYDPEDYRSDPTYYMGQFVLIGVIGQEROY QQR |
| Mm_MK (SEQ ID NO: 82) | MVSCSAPGKIYLFGEHAVVYGETAIACAVELRTRVRAELNDSITIQSQIGRTGLDFEKHPYVSAVIEKMRKSIPING VFLTVDSDIPVGSGLGSSAAVTIASIGALNELFGFGLSLQEIAKLGHEIEIKVGQAASPTDTYVSTFGGVVTIPEAR KLKTPDCGIVIGDTGVESSTKELVANVRQLRESYPDLIEPLMTSIGKISRIGEQLVLSGDYASIGRLMNVNQGLLDA LGVNILELSQLIYSARAAGAFGAKITGAGGGGCMVALTAPEKCNQVAEAVAGAGGKVTITKPTEQGLKVD |
| Sc_Gre2 (SEQ ID NO: 83) | MSVEVSGANGFIAQHIVDLLLKEDYKAPIGSARSQEKAENLTEAFGNNPKFSMEWTDISKLDAFDHVFQKHGKDIKI VLIPTASPECEDITDSERDLLIPAVNGVKGILHSIKKYAADSVERWYTSSTAAVEDMAKENDKSLTFNEESWNPATW ESCQSDPVNALCGSKKFAEKAAWEFLEENRDSVKFELTAVNPVYVEGPQMFDKDVKKHLNTSCELVNSLMHLSPEDK IPELFGGYIDVRDVAKAHLVAFQKRETIGQRLIVSEARFTMQDVLDILNEDFPVLKGNIPVGKPGSGATHNTLGATL DNKKSKKLLGEKERNLKETIDDTASQILKFEGRI |
| Sc_Ari1 (SEQ ID NO: 84) | MTTDTTVFVSGATGFIALHIMNDLLKAGYTVIGSGRSQEKNDGLIKKENNNPKLSMEIVEDIAAPNAFDEVFKKHGK EIKIVLHTASPFHFETTNFEKDLLTPAVNGTKSILEAIKKARADTVEKVIVTSSTAALVTPTDMNKGDLVITEESWN KDTWDSCQANAVAATCGSKKFAEKTAWEFLKENKSSVKFTLSTINPGFVFGPQMFADSLKHGINTSSGIVSELIHSK VGGEFYNYCGPFIDVADVSKAHLVAIEKPECTGQRLVLSEGLFCCQEIVDILNEEFPQLKGKIATGEPATGPSFLEK NSCKFDNSKTKKLLGFQFYNLKDCIVDTAAQMLEVQNEA |
| Sc_GCY1 (SEQ ID NO: 85) | MPATLHDSTKILSLNTGAQIPQIGLGTWQSKENDAYKAVLTALKDGYRHIDTAAIYRNEDQVGQAIKDSGVPREEIF VTTKLWCTQHHEPEVALDQSLKRLGLDYVDLYLMHWPARLDPAYIKNEDILSVPTKKDGSRAVDITNWNFIKTWELM QELPKTGKTKAVGVSNFSINNLKDLLASQGNKLTPAANQVEIHPLLPQDELINFCKSKGIVVEAYSPLGSTDAPLLK EPVILEIAKKNNVQPGHVVISWHVQRGYVVLPKSVNPDRIKTNRKIFTLSTEDFEAINNISKEKGEKRVVHPNWSPF EVFK |
| Sc_AYR1 (SEQ ID NO: 86) | MSELQSQPKKIPSNTGASGGIGYEVTKELARNGYLVYACPRRLEPMAQLAIQFGNDSIKPYKLDISKPEEIVTFSGE LRANLPDGKLDLLYNNAGQSCTFPALDATDAAVEQCFKVNVFGHINMCRELSEFLIKAKGTIVFIGSLAGVVSFPFG SIYSASKAAIHQYARGLHLEMKPFNVRVINAITGGVATDIADKRPLPETSITNFPEGREAFNSRKTMAKDNKPMPAD AYAKQLVKDILSTSDPVDVYRGTFANIMRFVMIFVPYWLLEKGLSKKFKLDKVNNALKSKQNKDD |
| Sc_ERG20 (SEQ ID NO: 87) | MASEKEIRRERELNVFPKLVEELNASLLAYGMPKEACDWYAHSLNYNTPGGKLNRGLSVVDTYAILSNKTVEQLGQE EYEKVAILGWCIELLQAYFLVADDMMDKSITRRGQPCWYKVPEVGEIAINDAFMLEAAILKLLKSHFRNEKLYIDIT ELFHEVTFQTELGQLMDLITAPEDKVDLSKFSLKKHSFIVTFKTAYYSFYLPVALAMYVAGITDEKDLKQARDVLIP LGEYFQIQDDYLDCFGTPEQIGKIGTDIQDNKCSWVINKALELASAEQRKTLDENYGKKDSVAEAKCKKIFNDLKIE QLTHEYEESIAKDLKAKISQVDESRGFKADVITAFLNKAPYKRSK |
| Ec_IspA (SEQ ID NO: 88) | MDFPQQLEACVKQPNQALSRFIAPLPFQNTPVVETMQYGALLGGKRLRPFLVYATGHMFGVSTNTLDAPAAAVECIH AYSLIHDDLPAPDDDDLRRGLPTCHVKFGEANAILAGDALQTLAFSILSDADMPEVSDRDRISMISELASASGIAGM CGGQALDLDAEGKHVPLDALERIHRHKTGALIRAAVRLGALSAGDKGRRALPVLDKYAESIGLAFQVQDDILDVVGD TATLGKRQGADQQLGKSTYPALLGLEQARKKARDLIDDARQSLKQLAEQSLDTSALEALADYIIQRNK |

What is claimed is:

1. A recombinant host cell capable of producing a citronellal and/or a citronellol, comprising:
   (a) a gene encoding a geranyl diphosphate synthase (Ag_GPPS) polypeptide comprising a polypeptide having the amino acid sequence set forth in SEQ ID NO: 17;
   (b) a gene encoding a geraniol synthase (Cr_GES) polypeptide comprising a polypeptide having the amino acid sequence set forth in SEQ ID NO: 18;
   (c) a gene encoding an ene reductase (Kl_KYE1) polypeptide comprising a polypeptide having the amino acid sequence set forth in SEQ ID NO: 7; and
   (d) a gene encoding a geraniol dehydrogenase (Rs_GeDH) polypeptide comprising a polypeptide having the amino acid sequence set forth in SEQ ID NO: 2 or SEQ ID NO: 20,
   wherein the recombinant host cell is an *Escherichia coli* cell.

2. The recombinant host cell of claim 1, wherein the citronellal is d-citronellal, l-citronellal, or a combination thereof.

3. The recombinant host cell of claim 1, wherein the citronellol is d-citronellol, l-citronellol, or a combination thereof.

4. A method of producing a citronellal, a citronellol, or a citronellic acid, comprising growing the recombinant host cell of claim 1 in a cell culture broth, under conditions in which the genes are expressed, wherein the citronellal, citronellol, or citronellic acid is produced by the recombinant host cell.

5. The method of claim 4, wherein at least one of the recombinant genes is integrated within the host cell genome.

6. The recombinant host cell of claim 1, wherein the geraniol dehydrogenase (Rs_GeDH) polypeptide comprises a polypeptide having the amino acid sequence set forth in SEQ ID NO: 2.

* * * * *

SEQUENCE LISTING

<160> NUMBER OF SEQ ID NOS: 88

<210> SEQ ID NO 1
<211> LENGTH: 373
<212> TYPE: PRT
<213> ORGANISM: Castellaniella defragrans

<400> SEQUENCE: 1

```
Met Asn Asp Thr Gln Asp Phe Ile Ser Ala Gln Ala Val Leu Arg
1               5                   10                  15

Gln Val Gly Gly Pro Leu Ala Val Glu Pro Val Arg Ile Ser Met Pro
                20                  25                  30

Lys Gly Asp Glu Val Leu Ile Arg Ile Ala Gly Val Gly Val Cys His
                35                  40                  45

Thr Asp Leu Val Cys Arg Asp Gly Phe Pro Val Pro Leu Pro Ile Val
            50                  55                  60

Leu Gly His Glu Gly Ser Gly Thr Val Glu Ala Val Gly Glu Gln Val
65                  70                  75                  80

Arg Thr Leu Lys Pro Gly Asp Arg Val Val Leu Ser Phe Asn Ser Cys
                85                  90                  95

Gly His Cys Gly Asn Cys His Asp Gly His Pro Ser Asn Cys Leu Gln
                100                 105                 110

Met Leu Pro Leu Asn Phe Gly Gly Ala Gln Arg Val Asp Gly Gly Gln
                115                 120                 125

Val Leu Asp Gly Ala Gly His Pro Val Gln Ser Met Phe Phe Gly Gln
            130                 135                 140

Ser Ser Phe Gly Thr His Ala Val Ala Arg Glu Ile Asn Ala Val Lys
145                 150                 155                 160

Val Gly Asp Asp Leu Pro Leu Glu Leu Leu Gly Pro Leu Gly Cys Gly
                165                 170                 175

Ile Gln Thr Gly Ala Gly Ala Ala Ile Asn Ser Leu Gly Ile Gly Pro
                180                 185                 190

Gly Gln Ser Leu Ala Ile Phe Gly Gly Gly Val Gly Leu Ser Ala
                195                 200                 205

Leu Leu Gly Ala Arg Ala Val Gly Ala Asp Arg Val Val Ile Glu
            210                 215                 220

Pro Asn Ala Ala Arg Arg Ala Leu Ala Leu Glu Leu Gly Ala Ser His
225                 230                 235                 240

Ala Leu Asp Pro His Ala Glu Gly Asp Leu Val Ala Ala Ile Lys Ala
                245                 250                 255

Ala Thr Gly Gly Gly Ala Thr His Ser Leu Asp Thr Thr Gly Leu Pro
                260                 265                 270

Pro Val Ile Gly Ser Ala Ile Ala Cys Thr Leu Pro Gly Gly Thr Val
            275                 280                 285

Gly Met Val Gly Leu Pro Ala Pro Asp Ala Pro Val Pro Ala Thr Leu
                290                 295                 300

Leu Asp Leu Leu Ser Lys Ser Val Thr Leu Arg Pro Ile Thr Glu Gly
305                 310                 315                 320

Asp Ala Asp Pro Gln Arg Phe Ile Pro Arg Met Leu Asp Phe His Arg
                325                 330                 335

Ala Gly Lys Phe Pro Phe Asp Arg Leu Ile Thr Arg Tyr Arg Phe Asp
                340                 345                 350

Gln Ile Asn Glu Ala Leu His Ala Thr Glu Lys Gly Glu Ala Ile Lys
            355                 360                 365
```

Pro Val Leu Val Phe
    370

<210> SEQ ID NO 2
<211> LENGTH: 373
<212> TYPE: PRT
<213> ORGANISM: Rhodococcus sp. RD6.2

<400> SEQUENCE: 2

Met Gly Arg Ala Ala Arg Ala Ala Val Leu Gly Ala Tyr Gly Glu Pro
1               5                   10                  15

Leu Glu Ile Arg Asp Val Glu Val Gly Asp Leu Arg Asp Asp Glu Val
            20                  25                  30

Leu Ile Arg Ile Ala Gly Val Gly Ile Cys His Thr Asp Leu Thr Ala
        35                  40                  45

Ala Ala Gly Gly Val Pro Val Pro Val Pro Ala Val Leu Gly His Glu
    50                  55                  60

Gly Ala Gly Val Val Glu Ala Val Gly Gly Ala Val Asp Ser Leu Val
65                  70                  75                  80

Pro Gly Asp His Val Leu Leu Ser Tyr Ser Ala Cys Arg Asp Cys Val
                85                  90                  95

Asn Cys Ala Asn Gly His Pro Ala Tyr Cys Thr Arg Phe Ala Leu Arg
            100                 105                 110

Asn Tyr Ser Gly Arg Arg Ala Asp Gly Ser Thr Thr Leu Ser Met Asp
        115                 120                 125

Ser Val Ala Leu Gln Gly Asn Trp Phe Gly Gln Ser Ser Phe Ala Thr
    130                 135                 140

His Ala Val Val Ala Ala Ser Asp Ala Val Gln Val Ala Gly Asp Leu
145                 150                 155                 160

Pro Ile Glu Leu Leu Gly Pro Leu Gly Cys Gly Ile Gln Thr Gly Ala
                165                 170                 175

Gly Ala Val Leu Arg Val Leu Arg Pro Arg Thr Gly Ser Ser Ile Val
            180                 185                 190

Val Phe Gly Gly Gly Ala Val Gly Leu Ala Ala Val Leu Ala Ala Val
        195                 200                 205

Val Ala Glu Cys Ser Thr Ile Val Val Asp Pro Leu Pro Thr Arg
    210                 215                 220

Arg Glu Leu Ala Leu Ser Leu Gly Ala Thr Ala Val Phe Asp Ser Ala
225                 230                 235                 240

Glu Pro Asp Leu Ala Lys Gln Leu Arg Ala Ala Thr Gly Gly Gly Ala
                245                 250                 255

Asp His Thr Val Asp Ala Val Ser Thr Pro Glu Val Leu Ala Thr Ala
            260                 265                 270

Val Ala Val Leu Arg Ser Pro Gly Ser Cys Val Thr Val Gly Leu Arg
        275                 280                 285

Gly Gly Arg Asn Pro Val Thr Leu Asp Gln Ser Ala Leu Leu Met Gly
    290                 295                 300

Arg Ser Val Thr Gly Val Ile Glu Gly Asp Ala Asp Pro Gln Gln Phe
305                 310                 315                 320

Leu Pro Glu Leu Ile Ala Leu Trp Arg Ala Gly Lys Phe Pro Phe Asp
                325                 330                 335

Lys Leu Ile Thr Thr Phe Asp Phe Asp Asp Leu His Ala Ala Leu Glu
            340                 345                 350

Ala Thr Arg Ser Gly Ala Ala Val Lys Pro Val Leu Thr Phe Ala Ser
        355                 360                 365

Ser Glu Gly Gln Ala
    370

<210> SEQ ID NO 3
<211> LENGTH: 366
<212> TYPE: PRT
<213> ORGANISM: Sphingopyxis macrogoltabida

<400> SEQUENCE: 3

Met Lys Ala Ser Ala Ala Ile Val Arg Asn Val Gly Gly Pro Phe Val
1               5                   10                  15

Ile Glu Asp Ile Glu Val Ala Glu Pro Arg Gly Ala Glu Val Arg Val
            20                  25                  30

Arg Met Val Gly Val Gly Met Cys His Thr Asp Leu Val Ala Arg Asp
        35                  40                  45

Gly Phe Pro Val Pro Leu Pro Ile Val Leu Gly His Glu Gly Ser Gly
    50                  55                  60

Val Val Glu Ala Val Gly Pro Glu Ile Thr Asp Leu Ala Ala Gly Asp
65                  70                  75                  80

His Val Val Leu Ser Phe Asp Ser Cys Ala Ala Cys Pro Thr Cys Asp
                85                  90                  95

Glu Gly Leu Pro Ala Tyr Cys His Gln Phe Leu Gly Lys Asn Phe Ala
            100                 105                 110

Gly Val Arg Leu Glu Asp Gly Ser Ser Pro Leu Ser Gln Thr Gly Ala
        115                 120                 125

Val Ile His Gly Asn Phe Phe Gly Gln Ser Ser Phe Gly Thr Tyr Ala
    130                 135                 140

Ile Ala His Arg Arg Asn Thr Val Lys Val Asp Lys Asp Leu Pro Leu
145                 150                 155                 160

Glu Ile Leu Gly Pro Leu Gly Cys Gly Val Met Thr Gly Ala Gly Ala
                165                 170                 175

Ala Val Ile Ser Leu Gly Leu Arg Pro Gly Gln Ser Leu Ala Ile Phe
            180                 185                 190

Gly Gly Gly Ala Val Gly Leu Ser Ala Leu Leu Gly Ala Arg Ala Val
        195                 200                 205

Asp Ala Gly Thr Val Val Val Glu Pro Asn Ala Glu Arg Arg Ala
    210                 215                 220

Leu Ala Leu Glu Leu Gly Ala Ser His Val Ile Asp Pro Ala Ala Thr
225                 230                 235                 240

Asp Asp Val Leu Ala Val Lys Glu Leu Ser Gly Gly Val Asn
                245                 250                 255

Leu Ala Leu Asp Thr Thr Gly Ile Pro Ala Val Val Ala Val Ala Val
            260                 265                 270

Glu Thr Thr Ile Ala His Gly Thr Val Gly Leu Val Ala Val Pro Pro
        275                 280                 285

Pro Glu Ala Met Leu Pro Ala Asn Met Met Ser Met Leu Val Arg Gly
    290                 295                 300

Thr Ile Ile Lys Tyr Ile Thr Glu Gly Asp Ala Asp Pro Gln Thr Phe
305                 310                 315                 320

Ile Pro Gln Met Ile Thr Trp Tyr Lys Ala Gly Lys Phe Pro Phe Asp
                325                 330                 335

Arg Leu Leu Lys Thr Phe Pro Phe Asp Gln Ile Asn Glu Ala Ala Lys
            340                 345                 350

Ala Ser Glu Asp Gly Ser Ala Ile Lys Pro Val Leu Thr Phe

```
                355                 360                 365

<210> SEQ ID NO 4
<211> LENGTH: 371
<212> TYPE: PRT
<213> ORGANISM: Acinetobacter calcoaceticus

<400> SEQUENCE: 4

Met Ser Glu Leu Lys Asp Ile Ile Ala Ala Val Thr Pro Cys Lys Gly
1               5                   10                  15

Ala Asp Phe Glu Leu Gln Ala Leu Lys Ile Arg Gln Pro Gln Gly Asp
            20                  25                  30

Glu Val Leu Val Lys Val Ala Thr Gly Met Cys His Thr Asp Leu
        35                  40                  45

Ile Val Arg Asp Gln Tyr Tyr Pro Val Pro Leu Pro Ala Val Leu Gly
    50                  55                  60

His Glu Gly Ser Gly Ile Ile Glu Ala Ile Gly Pro Asn Val Thr Glu
65                  70                  75                  80

Leu Gln Val Gly Asp His Val Val Leu Ser Tyr Gly Tyr Cys Gly Lys
                85                  90                  95

Cys Thr Gln Cys Asn Thr Gly Asn Pro Ala Tyr Cys Ser Glu Phe Phe
            100                 105                 110

Gly Arg Asn Phe Ser Gly Ala Asp Ser Glu Gly Asn His Ala Leu Cys
        115                 120                 125

Thr His Asp Gln Gly Val Val Asn Asp His Phe Phe Ala Gln Ser Ser
    130                 135                 140

Phe Ala Thr Tyr Ala Leu Ser Arg Glu Asn Asn Thr Val Lys Val Thr
145                 150                 155                 160

Lys Asp Val Pro Ile Glu Leu Leu Gly Pro Leu Gly Cys Gly Ile Gln
                165                 170                 175

Thr Gly Ala Gly Ala Cys Ile Asn Ala Leu Lys Val Thr Pro Ala Ser
            180                 185                 190

Ser Leu Val Thr Trp Gly Ala Gly Ala Val Gly Leu Ser Ala Leu Leu
        195                 200                 205

Ala Ala Lys Val Cys Gly Ala Ser Ile Ile Ile Ala Val Asp Ile Val
    210                 215                 220

Glu Ser Arg Leu Glu Leu Ala Lys Gln Leu Gly Ala Thr His Val Ile
225                 230                 235                 240

Asn Ser Lys Thr Gln Asp Pro Val Ala Ala Ile Lys Glu Ile Thr Asp
                245                 250                 255

Gly Gly Val Asn Phe Ala Leu Glu Ser Thr Gly Arg Pro Glu Ile Leu
            260                 265                 270

Lys Gln Gly Val Asp Ala Leu Gly Ile Leu Gly Lys Ile Ala Val Val
        275                 280                 285

Gly Ala Pro Gln Leu Gly Thr Thr Ala Gln Phe Asp Val Asn Asp Leu
    290                 295                 300

Leu Leu Gly Gly Lys Thr Ile Leu Gly Val Val Glu Gly Ser Gly Ser
305                 310                 315                 320

Pro Lys Lys Phe Ile Pro Glu Leu Val Arg Leu Tyr Gln Gln Gly Lys
                325                 330                 335

Phe Pro Phe Asp Gln Leu Val Lys Phe Tyr Ala Phe Asp Glu Ile Asn
            340                 345                 350

Gln Ala Ala Ile Asp Ser His Lys Gly Ile Thr Leu Lys Pro Ile Ile
        355                 360                 365
```

Lys Ile Ala
    370

<210> SEQ ID NO 5
<211> LENGTH: 373
<212> TYPE: PRT
<213> ORGANISM: Thauera terpenica 58Eu

<400> SEQUENCE: 5

Met Cys Ser Asn His Asp Phe Thr Ala Ala Arg Ala Ala Val Leu Arg
1               5                   10                  15

Lys Val Gly Gly Pro Leu Glu Ile Glu Asp Val Arg Ile Ser Ala Pro
            20                  25                  30

Lys Gly Asp Glu Val Leu Val Arg Met Val Gly Val Gly Val Cys His
        35                  40                  45

Thr Asp Leu Val Cys Arg Asp Ala Phe Pro Val Pro Leu Pro Ile Val
    50                  55                  60

Leu Gly His Glu Gly Ala Gly Ile Val Glu Ala Val Gly Glu Gly Val
65                  70                  75                  80

Arg Ser Leu Glu Pro Gly Asp Arg Val Val Leu Ser Phe Asn Ser Cys
                85                  90                  95

Gly Arg Cys Gly Asn Cys Gly Ser Gly His Pro Ser Asn Cys Leu Gln
            100                 105                 110

Met Leu Pro Leu Asn Phe Gly Ala Gln Arg Val Asp Gly Gly Arg
        115                 120                 125

Met Leu Asp Ala Ala Gly Asn Ala Val Gln Gly Leu Phe Phe Gly Gln
    130                 135                 140

Ser Ser Phe Gly Thr Tyr Ala Ile Ala Arg Glu Ile Asn Ala Val Lys
145                 150                 155                 160

Val Ala Glu Asp Leu Pro Leu Glu Ile Leu Gly Pro Leu Gly Cys Gly
                165                 170                 175

Ile Gln Thr Gly Ala Gly Ala Ala Ile Asn Ser Leu Gly Ile Gly Pro
            180                 185                 190

Gly Gln Ser Leu Ala Val Phe Gly Gly Gly Val Gly Leu Ser Ala
        195                 200                 205

Leu Leu Gly Ala Arg Ala Val Gly Ala Ala Gln Val Val Val Val Glu
    210                 215                 220

Pro Asn Ala Ala Arg Arg Ala Leu Ala Leu Glu Leu Gly Ala Ser His
225                 230                 235                 240

Ala Phe Asp Pro Phe Ala Gly Asp Leu Val Ala Ala Ile Arg Ala
                245                 250                 255

Ala Thr Gly Gly Gly Ala Thr His Ala Leu Asp Thr Gly Leu Pro
            260                 265                 270

Ser Val Ile Gly Asn Ala Ile Asp Cys Thr Leu Pro Gly Gly Thr Val
        275                 280                 285

Gly Met Val Gly Met Pro Ala Pro Asp Ala Ala Val Pro Ala Thr Leu
    290                 295                 300

Leu Asp Leu Leu Thr Lys Ser Val Thr Leu Arg Pro Ile Thr Glu Gly
305                 310                 315                 320

Asp Ala Asp Pro Gln Ala Phe Ile Pro Gln Met Leu Arg Phe Tyr Arg
                325                 330                 335

Glu Gly Lys Phe Pro Phe Asp Arg Leu Ile Thr Arg Tyr Arg Phe Asp
            340                 345                 350

Gln Ile Asn Glu Ala Leu His Ala Thr Glu Lys Gly Gly Ala Ile Lys
        355                 360                 365

Pro Val Leu Val Phe
    370

<210> SEQ ID NO 6
<211> LENGTH: 368
<212> TYPE: PRT
<213> ORGANISM: Pseudomonas putida

<400> SEQUENCE: 6

Met Glu Met Glu Ile Lys Ala Ala Ile Val Arg Gln Lys Asn Gly Pro
1               5                   10                  15

Phe Leu Leu Glu His Val Ala Leu Asn Glu Pro Ala Glu Asp Gln Val
            20                  25                  30

Leu Val Arg Leu Val Ala Thr Gly Leu Cys His Thr Asp Leu Val Cys
        35                  40                  45

Arg Asp Gln His Tyr Pro Val Pro Leu Pro Met Val Phe Gly His Glu
    50                  55                  60

Gly Ala Gly Val Val Glu Arg Val Gly Ser Ala Val Lys Lys Val Gln
65                  70                  75                  80

Pro Gly Asp His Val Val Leu Thr Phe Tyr Thr Cys Gly Ser Cys Asp
                85                  90                  95

Ala Cys Leu Ser Gly Asp Pro Thr Ser Cys Ala Asn Ser Phe Gly Pro
            100                 105                 110

Asn Phe Met Gly Arg Ser Val Thr Gly Glu Cys Thr Ile His Asp His
        115                 120                 125

Gln Gly Ala Glu Val Gly Ala Ser Phe Phe Gly Gln Ser Ser Phe Ala
130                 135                 140

Thr Tyr Ala Leu Ser Tyr Glu Arg Asn Thr Val Lys Val Thr Lys Asp
145                 150                 155                 160

Val Pro Leu Glu Leu Leu Gly Pro Leu Gly Cys Gly Ile Gln Thr Gly
                165                 170                 175

Ala Gly Ser Val Leu Asn Ala Leu Asn Pro Pro Ala Gly Ser Ser Ile
            180                 185                 190

Ala Ile Phe Gly Ala Gly Ala Val Gly Leu Ser Ala Val Met Ala Ala
        195                 200                 205

Val Val Ala Gly Cys Thr Lys Ile Ile Val Asp Val Lys Glu Asn
210                 215                 220

Arg Leu Lys Leu Ala Asp Glu Leu Gly Ala Thr His Val Ile Asn Ala
225                 230                 235                 240

Ala Ser Ser Asp Pro Val Glu Lys Ile Lys Glu Ile Cys Ala Gly Gly
                245                 250                 255

Val Pro Tyr Val Leu Glu Thr Ser Gly Leu Pro Ser Val Leu Gln Gln
            260                 265                 270

Ala Ile Leu Ser Ser Ala Ile Gly Gly Glu Ile Gly Ile Val Gly Ala
        275                 280                 285

Pro Pro Met Gly Ala Thr Ile Pro Val Asp Ile Asn Phe Leu Leu Phe
    290                 295                 300

Asn Arg Lys Leu Arg Gly Ile Val Glu Gly Gln Ser Ile Ser Asp Ile
305                 310                 315                 320

Phe Ile Pro Arg Leu Val Glu Leu Tyr Arg Gln Gly Lys Phe Pro Phe
                325                 330                 335

Asp Lys Leu Leu Lys Phe Tyr Ser Phe Asp Glu Ile Asn Gln Ala Ala
            340                 345                 350

Glu Asp Ser Glu Asn Gly Ile Thr Leu Lys Pro Val Leu Arg Ile Ser

```
                355                 360                 365

<210> SEQ ID NO 7
<211> LENGTH: 398
<212> TYPE: PRT
<213> ORGANISM: Kluyveromyces lactis

<400> SEQUENCE: 7

Met Ser Phe Met Asn Phe Glu Pro Lys Pro Leu Ala Asp Thr Asp Ile
1               5                   10                  15

Phe Lys Pro Ile Lys Ile Gly Asn Thr Glu Leu Lys His Arg Val Val
                20                  25                  30

Met Pro Ala Leu Thr Arg Met Arg Ala Leu His Pro Gly Asn Val Pro
            35                  40                  45

Asn Pro Asp Trp Ala Val Glu Tyr Tyr Arg Gln Arg Ser Gln Tyr Pro
        50                  55                  60

Gly Thr Met Ile Ile Thr Glu Gly Ala Phe Pro Ser Ala Gln Ser Gly
65                  70                  75                  80

Gly Tyr Asp Asn Ala Pro Gly Val Trp Ser Glu Gln Leu Ala Gln
                85                  90                  95

Trp Arg Lys Ile Phe Lys Ala Ile His Asp Asn Lys Ser Phe Val Trp
            100                 105                 110

Val Gln Leu Trp Val Leu Gly Arg Gln Ala Phe Ala Asp Asn Leu Ala
        115                 120                 125

Arg Asp Gly Leu Arg Tyr Asp Ser Ala Ser Asp Glu Val Tyr Met Gly
130                 135                 140

Glu Asp Glu Lys Glu Arg Ala Ile Arg Ser Asn Pro Gln His Gly
145                 150                 155                 160

Ile Thr Lys Asp Glu Ile Lys Gln Tyr Ile Arg Asp Tyr Val Asp Ala
                165                 170                 175

Ala Lys Lys Cys Ile Asp Ala Gly Ala Asp Gly Val Glu Ile His Ser
            180                 185                 190

Ala Asn Gly Tyr Leu Leu Asn Gln Phe Leu Asp Pro Ile Ser Asn Lys
        195                 200                 205

Arg Thr Asp Glu Tyr Gly Gly Ser Ile Glu Asn Arg Ala Arg Phe Val
210                 215                 220

Leu Glu Val Val Asp Ala Val Asp Ala Val Gly Ala Glu Arg Thr
225                 230                 235                 240

Ser Ile Arg Phe Ser Pro Tyr Gly Val Phe Gly Thr Met Ser Gly Gly
                245                 250                 255

Ser Asp Pro Val Leu Val Ala Gln Phe Ala Tyr Val Leu Ala Glu Leu
            260                 265                 270

Glu Lys Arg Ala Lys Ala Gly Lys Arg Leu Ala Tyr Val Asp Leu Val
        275                 280                 285

Glu Pro Arg Val Thr Ser Pro Phe Gln Pro Glu Phe Glu Gly Trp Tyr
290                 295                 300

Lys Gly Gly Thr Asn Glu Phe Val Tyr Ser Val Trp Lys Gly Asn Val
305                 310                 315                 320

Leu Arg Val Gly Asn Tyr Ala Leu Asp Pro Asp Ala Ala Ile Thr Asp
                325                 330                 335

Ser Lys Asn Pro Asn Thr Leu Ile Gly Tyr Gly Arg Ala Phe Ile Ala
            340                 345                 350

Asn Pro Asp Leu Val Glu Arg Leu Glu Lys Gly Leu Pro Leu Asn Gln
        355                 360                 365
```

```
Tyr Asp Arg Pro Ser Phe Tyr Lys Met Ser Ala Glu Gly Tyr Ile Asp
    370                 375                 380

Tyr Pro Thr Tyr Glu Glu Ala Val Ala Lys Gly Tyr Lys Lys
385                 390                 395
```

<210> SEQ ID NO 8
<211> LENGTH: 407
<212> TYPE: PRT
<213> ORGANISM: Pichia stipitis

<400> SEQUENCE: 8

```
Met Ser Ser Val Lys Ile Ser Pro Leu Lys Asp Ser Glu Ala Phe Gln
1               5                   10                  15

Ser Ile Lys Val Gly Asn Asn Thr Leu Gln Thr Lys Ile Val Tyr Pro
                20                  25                  30

Pro Thr Thr Arg Phe Arg Ala Leu Glu Asp His Thr Pro Ser Asp Leu
            35                  40                  45

Gln Leu Gln Tyr Tyr Gly Asp Arg Ser Thr Phe Pro Gly Thr Leu Leu
        50                  55                  60

Ile Thr Glu Ala Thr Phe Val Ser Pro Gln Ala Ser Gly Tyr Glu Gly
65                  70                  75                  80

Ala Ala Pro Gly Ile Trp Thr Asp Lys His Ala Lys Ala Trp Lys Val
                85                  90                  95

Ile Thr Asp Lys Val His Ala Asn Gly Ser Phe Val Ser Thr Gln Leu
            100                 105                 110

Ile Phe Leu Gly Arg Val Ala Asp Pro Ala Val Met Lys Thr Arg Gly
        115                 120                 125

Leu Asn Pro Val Ser Ala Ser Ala Thr Tyr Glu Ser Asp Ala Ala Lys
130                 135                 140

Glu Ala Ala Glu Ala Val Gly Asn Pro Val Arg Ala Leu Thr Thr Gln
145                 150                 155                 160

Glu Val Lys Asp Leu Val Tyr Glu Thr Tyr Thr Asn Ala Ala Gln Lys
                165                 170                 175

Ala Met Asp Ala Gly Phe Asp Tyr Ile Glu Leu His Ala Ala His Gly
            180                 185                 190

Tyr Leu Leu Asp Gln Phe Leu Gln Pro Cys Thr Asn Gln Arg Thr Asp
        195                 200                 205

Glu Tyr Gly Gly Ser Ile Glu Asn Arg Ala Arg Leu Ile Leu Glu Leu
210                 215                 220

Ile Asp His Leu Ser Thr Ile Val Gly Ala Asp Lys Ile Gly Ile Arg
225                 230                 235                 240

Ile Ser Pro Trp Ala Thr Phe Gln Asn Met Lys Ala His Lys Asp Thr
                245                 250                 255

Val His Pro Leu Thr Thr Phe Ser Tyr Leu Val His Glu Leu Gln Gln
            260                 265                 270

Arg Ala Asp Lys Gly Gln Gly Ile Ala Tyr Ile Ser Val Val Glu Pro
        275                 280                 285

Arg Val Ser Gly Asn Val Asp Val Ser Glu Glu Asp Gln Ala Gly Asp
290                 295                 300

Asn Glu Phe Val Ser Lys Ile Trp Lys Gly Val Ile Leu Lys Ala Gly
305                 310                 315                 320

Asn Tyr Ser Tyr Asp Ala Pro Glu Phe Lys Thr Leu Lys Glu Asp Ile
                325                 330                 335

Ala Asp Lys Arg Thr Leu Val Gly Phe Ser Arg Tyr Phe Thr Ser Asn
            340                 345                 350
```

Pro Asn Leu Val Trp Lys Leu Arg Asp Gly Ile Asp Leu Val Pro Tyr
            355                 360                 365

Asp Arg Asn Thr Phe Tyr Ser Asp Asn Asn Tyr Gly Tyr Asn Thr Phe
        370                 375                 380

Ser Met Asp Ser Glu Glu Val Asp Lys Glu Leu Glu Ile Lys Arg Val
385                 390                 395                 400

Pro Ser Ala Ile Glu Ala Leu
                405

<210> SEQ ID NO 9
<211> LENGTH: 358
<212> TYPE: PRT
<213> ORGANISM: Zymomonasmobilis subsp. mobilis

<400> SEQUENCE: 9

Met Pro Ser Leu Phe Asp Pro Ile Arg Phe Gly Ala Phe Thr Ala Lys
1               5                   10                  15

Asn Arg Ile Trp Met Ala Pro Leu Thr Arg Gly Arg Ala Thr Arg Asp
            20                  25                  30

His Val Pro Thr Glu Ile Met Ala Glu Tyr Tyr Ala Gln Arg Ala Ser
            35                  40                  45

Ala Gly Leu Ile Ile Ser Glu Ala Thr Gly Ile Ser Gln Glu Gly Leu
        50                  55                  60

Gly Trp Pro Tyr Ala Pro Gly Ile Trp Ser Asp Ala Gln Val Glu Ala
65                  70                  75                  80

Trp Leu Pro Ile Thr Gln Ala Val His Asp Ala Gly Gly Leu Ile Phe
                85                  90                  95

Ala Gln Leu Trp His Met Gly Arg Met Val Pro Ser Asn Val Ser Gly
            100                 105                 110

Met Gln Pro Val Ala Pro Ser Ala Ser Gln Ala Pro Gly Leu Gly His
            115                 120                 125

Thr Tyr Asp Gly Lys Lys Pro Tyr Asp Val Ala Arg Ala Leu Arg Leu
        130                 135                 140

Asp Glu Ile Pro Arg Leu Leu Asp Asp Tyr Glu Lys Ala Ala Arg His
145                 150                 155                 160

Ala Leu Lys Ala Gly Phe Asp Gly Val Gln Ile His Ala Ala Asn Gly
                165                 170                 175

Tyr Leu Ile Asp Glu Phe Ile Arg Asp Ser Thr Asn His Arg His Asp
            180                 185                 190

Glu Tyr Gly Gly Ala Val Glu Asn Arg Ile Arg Leu Leu Lys Asp Val
        195                 200                 205

Thr Glu Arg Val Ile Ala Thr Ile Gly Lys Glu Arg Thr Ala Val Arg
    210                 215                 220

Leu Ser Pro Asn Gly Glu Ile Gln Gly Thr Val Asp Ser His Pro Glu
225                 230                 235                 240

Gln Val Phe Ile Pro Ala Ala Lys Met Leu Ser Asp Leu Asp Ile Ala
                245                 250                 255

Phe Leu Gly Met Arg Glu Gly Ala Val Asp Gly Thr Phe Gly Lys Thr
            260                 265                 270

Asp Gln Pro Lys Leu Ser Pro Glu Ile Arg Lys Val Phe Lys Pro Pro
        275                 280                 285

Leu Val Leu Asn Gln Asp Tyr Thr Phe Glu Thr Ala Gln Ala Ala Leu
    290                 295                 300

Asp Ser Gly Val Ala Asp Ala Ile Ser Phe Gly Arg Pro Phe Ile Gly

```
                305                 310                 315                 320
Asn Pro Asp Leu Pro Arg Arg Phe Phe Glu Lys Ala Pro Leu Thr Lys
                    325                 330                 335

Asp Val Ile Glu Thr Trp Tyr Thr Gln Thr Pro Lys Gly Tyr Thr Asp
                    340                 345                 350

Tyr Pro Leu Leu Gly Asp
                355

<210> SEQ ID NO 10
<211> LENGTH: 394
<212> TYPE: PRT
<213> ORGANISM: Escherichia coli MG1655

<400> SEQUENCE: 10

Met Lys Asn Cys Val Ile Val Ser Ala Val Arg Thr Ala Ile Gly Ser
1               5                   10                  15

Phe Asn Gly Ser Leu Ala Ser Thr Ser Ala Ile Asp Leu Gly Ala Thr
                20                  25                  30

Val Ile Lys Ala Ala Ile Glu Arg Ala Lys Ile Asp Ser Gln His Val
            35                  40                  45

Asp Glu Val Ile Met Gly Asn Val Leu Gln Ala Gly Leu Gly Gln Asn
        50                  55                  60

Pro Ala Arg Gln Ala Leu Leu Lys Ser Gly Leu Ala Glu Thr Val Cys
65                  70                  75                  80

Gly Phe Thr Val Asn Lys Val Cys Gly Ser Gly Leu Lys Ser Val Ala
                85                  90                  95

Leu Ala Ala Gln Ala Ile Gln Ala Gly Gln Ala Gln Ser Ile Val Ala
            100                 105                 110

Gly Gly Met Glu Asn Met Ser Leu Ala Pro Tyr Leu Leu Asp Ala Lys
        115                 120                 125

Ala Arg Ser Gly Tyr Arg Leu Gly Asp Gly Gln Val Tyr Asp Val Ile
    130                 135                 140

Leu Arg Asp Gly Leu Met Cys Ala Thr His Gly Tyr His Met Gly Ile
145                 150                 155                 160

Thr Ala Glu Asn Val Ala Lys Glu Tyr Gly Ile Thr Arg Glu Met Gln
                165                 170                 175

Asp Glu Leu Ala Leu His Ser Gln Arg Lys Ala Ala Ala Ala Ile Glu
            180                 185                 190

Ser Gly Ala Phe Thr Ala Glu Ile Val Pro Val Asn Val Val Thr Arg
        195                 200                 205

Lys Lys Thr Phe Val Phe Ser Gln Asp Glu Phe Pro Lys Ala Asn Ser
    210                 215                 220

Thr Ala Glu Ala Leu Gly Ala Leu Arg Pro Ala Phe Asp Lys Ala Gly
225                 230                 235                 240

Thr Val Thr Ala Gly Asn Ala Ser Gly Ile Asn Asp Gly Ala Ala Ala
                245                 250                 255

Leu Val Ile Met Glu Glu Ser Ala Leu Ala Ala Gly Leu Thr Pro
            260                 265                 270

Leu Ala Arg Ile Lys Ser Tyr Ala Ser Gly Gly Val Pro Pro Ala Leu
        275                 280                 285

Met Gly Met Gly Pro Val Pro Ala Thr Gln Lys Ala Leu Gln Leu Ala
    290                 295                 300

Gly Leu Gln Leu Ala Asp Ile Asp Leu Ile Glu Ala Asn Glu Ala Phe
305                 310                 315                 320
```

Ala Ala Gln Phe Leu Ala Val Gly Lys Asn Leu Gly Phe Asp Ser Glu
             325                 330                 335

Lys Val Asn Val Asn Gly Gly Ala Ile Ala Leu Gly His Pro Ile Gly
         340                 345                 350

Ala Ser Gly Ala Arg Ile Leu Val Thr Leu Leu His Ala Met Gln Ala
     355                 360                 365

Arg Asp Lys Thr Leu Gly Leu Ala Thr Leu Cys Ile Gly Gly Gly Gln
370                 375                 380

Gly Ile Ala Met Val Ile Glu Arg Leu Asn
385                 390

<210> SEQ ID NO 11
<211> LENGTH: 388
<212> TYPE: PRT
<213> ORGANISM: Staphylococcus aureus

<400> SEQUENCE: 11

Met Thr Ile Gly Ile Asp Lys Ile Asn Phe Tyr Val Pro Lys Tyr Tyr
1               5                   10                  15

Val Asp Met Ala Lys Leu Ala Glu Ala Arg Gln Val Asp Pro Asn Lys
            20                  25                  30

Phe Leu Ile Gly Ile Gly Gln Thr Glu Met Ala Val Ser Pro Val Asn
        35                  40                  45

Gln Asp Ile Val Ser Met Gly Ala Asn Ala Ala Lys Asp Ile Ile Thr
    50                  55                  60

Asp Glu Asp Lys Lys Lys Ile Gly Met Val Ile Val Ala Thr Glu Ser
65                  70                  75                  80

Ala Val Asp Ala Ala Lys Ala Ala Val Gln Ile His Asn Leu Leu
                85                  90                  95

Gly Ile Gln Pro Phe Ala Arg Cys Phe Glu Met Lys Glu Ala Cys Tyr
            100                 105                 110

Ala Ala Thr Pro Ala Ile Gln Leu Ala Lys Asp Tyr Leu Ala Thr Arg
        115                 120                 125

Pro Asn Glu Lys Val Leu Val Ile Ala Thr Asp Thr Ala Arg Tyr Gly
    130                 135                 140

Leu Asn Ser Gly Gly Glu Pro Thr Gln Gly Ala Gly Ala Val Ala Met
145                 150                 155                 160

Val Ile Ala His Asn Pro Ser Ile Leu Ala Leu Asn Glu Asp Ala Val
                165                 170                 175

Ala Tyr Thr Glu Asp Val Tyr Asp Phe Trp Arg Pro Thr Gly His Lys
            180                 185                 190

Tyr Pro Leu Val Asp Gly Ala Leu Ser Lys Asp Ala Tyr Ile Arg Ser
        195                 200                 205

Phe Gln Gln Ser Trp Asn Glu Tyr Ala Lys Arg Gln Gly Lys Ser Leu
    210                 215                 220

Ala Asp Phe Ala Ser Leu Cys Phe His Val Pro Phe Thr Lys Met Gly
225                 230                 235                 240

Lys Lys Ala Leu Glu Ser Ile Ile Asp Asn Ala Asp Glu Thr Thr Gln
                245                 250                 255

Glu Arg Leu Arg Ser Gly Tyr Glu Asp Ala Val Asp Tyr Asn Arg Tyr
            260                 265                 270

Val Gly Asn Ile Tyr Thr Gly Ser Leu Tyr Leu Ser Leu Ile Ser Leu
        275                 280                 285

Leu Glu Asn Arg Asp Leu Gln Ala Gly Glu Thr Ile Gly Leu Phe Ser
    290                 295                 300

Tyr Gly Ser Gly Ser Val Val Glu Phe Tyr Ser Ala Thr Leu Val Val
305                 310                 315                 320

Gly Tyr Lys Asp His Leu Asp Gln Ala Ala His Lys Ala Leu Leu Asn
                325                 330                 335

Asn Arg Thr Glu Val Ser Val Asp Ala Tyr Glu Thr Phe Phe Lys Arg
            340                 345                 350

Phe Asp Asp Val Glu Phe Asp Glu Gln Asp Ala Val His Glu Asp
            355                 360                 365

Arg His Ile Phe Tyr Leu Ser Asn Ile Glu Asn Asn Val Arg Glu Tyr
        370                 375                 380

His Arg Pro Glu
385

<210> SEQ ID NO 12
<211> LENGTH: 425
<212> TYPE: PRT
<213> ORGANISM: Staphylococcus aureus

<400> SEQUENCE: 12

Met Gln Ser Leu Asp Lys Asn Phe Arg His Leu Ser Arg Gln Gln Lys
1               5                   10                  15

Leu Gln Gln Leu Val Asp Lys Gln Trp Leu Ser Glu Asp Gln Phe Asp
            20                  25                  30

Ile Leu Leu Asn His Pro Leu Ile Asp Glu Val Ala Asn Ser Leu
        35                  40                  45

Ile Glu Asn Val Ile Ala Gln Gly Ala Leu Pro Val Gly Leu Leu Pro
50                  55                  60

Asn Ile Ile Val Asp Asp Lys Ala Tyr Val Val Pro Met Met Val Glu
65                  70                  75                  80

Glu Pro Ser Val Ala Ala Ala Ser Tyr Gly Ala Lys Leu Val Asn
            85                  90                  95

Gln Thr Gly Gly Phe Lys Thr Val Ser Ser Glu Arg Ile Met Ile Gly
            100                 105                 110

Gln Ile Val Phe Asp Gly Val Asp Asp Thr Glu Lys Leu Ser Ala Asp
            115                 120                 125

Ile Lys Ala Leu Glu Lys Gln Ile His Lys Ile Ala Asp Glu Ala Tyr
        130                 135                 140

Pro Ser Ile Lys Ala Arg Gly Gly Gly Tyr Gln Arg Ile Ala Ile Asp
145                 150                 155                 160

Thr Phe Pro Glu Gln Gln Leu Leu Ser Leu Lys Val Phe Val Asp Thr
                165                 170                 175

Lys Asp Ala Met Gly Ala Asn Met Leu Asn Thr Ile Leu Glu Ala Ile
            180                 185                 190

Thr Ala Phe Leu Lys Asn Glu Ser Pro Gln Ser Asp Ile Leu Met Ser
        195                 200                 205

Ile Leu Ser Asn His Ala Thr Ala Ser Val Val Lys Val Gln Gly Glu
        210                 215                 220

Ile Asp Val Lys Asp Leu Ala Arg Gly Glu Arg Thr Gly Glu Val
225                 230                 235                 240

Ala Lys Arg Met Glu Arg Ala Ser Val Leu Ala Gln Val Asp Ile His
                245                 250                 255

Arg Ala Ala Thr His Asn Lys Gly Val Met Asn Gly Ile His Ala Val
            260                 265                 270

Val Leu Ala Thr Gly Asn Asp Thr Arg Gly Ala Glu Ala Ser Ala His

```
                275                 280                 285
Ala Tyr Ala Ser Arg Asp Gly Gln Tyr Arg Gly Ile Ala Thr Trp Arg
    290                 295                 300

Tyr Asp Gln Lys Arg Gln Arg Leu Ile Gly Thr Ile Glu Val Pro Met
305                 310                 315                 320

Thr Leu Ala Ile Val Gly Gly Thr Lys Val Leu Pro Ile Ala Lys
                    325                 330                 335

Ala Ser Leu Glu Leu Leu Asn Val Asp Ser Ala Gln Glu Leu Gly His
                340                 345                 350

Val Val Ala Ala Val Gly Leu Ala Gln Asn Phe Ala Ala Cys Arg Ala
                355                 360                 365

Leu Val Ser Glu Gly Ile Gln Gln Gly His Met Ser Leu Gln Tyr Lys
            370                 375                 380

Ser Leu Ala Ile Val Val Gly Ala Lys Gly Asp Glu Ile Ala Gln Val
385                 390                 395                 400

Ala Glu Ala Leu Lys Gln Glu Pro Arg Ala Asn Thr Gln Val Ala Glu
                405                 410                 415

Arg Ile Leu Gln Glu Ile Arg Gln Gln
                420                 425

<210> SEQ ID NO 13
<211> LENGTH: 443
<212> TYPE: PRT
<213> ORGANISM: Saccharomyces cerevisiae

<400> SEQUENCE: 13

Met Ser Leu Pro Phe Leu Thr Ser Ala Pro Gly Lys Val Ile Ile Phe
1               5                   10                  15

Gly Glu His Ser Ala Val Tyr Asn Lys Pro Ala Val Ala Ala Ser Val
                20                  25                  30

Ser Ala Leu Arg Thr Tyr Leu Leu Ile Ser Glu Ser Ser Ala Pro Asp
            35                  40                  45

Thr Ile Glu Leu Asp Phe Pro Asp Ile Ser Phe Asn His Lys Trp Ser
    50                  55                  60

Ile Asn Asp Phe Asn Ala Ile Thr Glu Asp Gln Val Asn Ser Gln Lys
65                  70                  75                  80

Leu Ala Lys Ala Gln Gln Ala Thr Asp Gly Leu Ser Gln Glu Leu Val
                85                  90                  95

Ser Leu Leu Asp Pro Leu Leu Ala Gln Leu Ser Glu Ser Phe His Tyr
                100                 105                 110

His Ala Ala Phe Cys Phe Leu Tyr Met Phe Val Cys Leu Cys Pro His
            115                 120                 125

Ala Lys Asn Ile Lys Phe Ser Leu Lys Ser Thr Leu Pro Ile Gly Ala
    130                 135                 140

Gly Leu Gly Ser Ser Ala Ser Ile Ser Val Ser Leu Ala Leu Ala Met
145                 150                 155                 160

Ala Tyr Leu Gly Gly Leu Ile Gly Ser Asn Asp Leu Glu Lys Leu Ser
                165                 170                 175

Glu Asn Asp Lys His Ile Val Asn Gln Trp Ala Phe Ile Gly Glu Lys
                180                 185                 190

Cys Ile His Gly Thr Pro Ser Gly Ile Asp Asn Ala Val Ala Thr Tyr
            195                 200                 205

Gly Asn Ala Leu Leu Phe Glu Lys Asp Ser His Asn Gly Thr Ile Asn
    210                 215                 220
```

Thr Asn Asn Phe Lys Phe Leu Asp Asp Phe Pro Ala Ile Pro Met Ile
225                 230                 235                 240

Leu Thr Tyr Thr Arg Ile Pro Arg Ser Thr Lys Asp Leu Val Ala Arg
            245                 250                 255

Val Arg Val Leu Val Thr Glu Lys Phe Pro Glu Val Met Lys Pro Ile
        260                 265                 270

Leu Asp Ala Met Gly Glu Cys Ala Leu Gln Gly Leu Glu Ile Met Thr
        275                 280                 285

Lys Leu Ser Lys Cys Lys Gly Thr Asp Asp Glu Ala Val Glu Thr Asn
290                 295                 300

Asn Glu Leu Tyr Glu Gln Leu Leu Glu Leu Ile Arg Ile Asn His Gly
305                 310                 315                 320

Leu Leu Val Ser Ile Gly Val Ser His Pro Gly Leu Glu Leu Ile Lys
            325                 330                 335

Asn Leu Ser Asp Asp Leu Arg Ile Gly Ser Thr Lys Leu Thr Gly Ala
            340                 345                 350

Gly Gly Gly Gly Cys Ser Leu Thr Leu Leu Arg Arg Asp Ile Thr Gln
        355                 360                 365

Glu Gln Ile Asp Ser Phe Lys Lys Lys Leu Gln Asp Asp Phe Ser Tyr
        370                 375                 380

Glu Thr Phe Glu Thr Asp Leu Gly Gly Thr Gly Cys Cys Leu Leu Ser
385                 390                 395                 400

Ala Lys Asn Leu Asn Lys Asp Leu Lys Ile Lys Ser Leu Val Phe Gln
                405                 410                 415

Leu Phe Glu Asn Lys Thr Thr Thr Lys Gln Gln Ile Asp Asp Leu Leu
            420                 425                 430

Leu Pro Gly Asn Thr Asn Leu Pro Trp Thr Ser
            435                 440

<210> SEQ ID NO 14
<211> LENGTH: 451
<212> TYPE: PRT
<213> ORGANISM: Saccharomyces cerevisiae

<400> SEQUENCE: 14

Met Ser Glu Leu Arg Ala Phe Ser Ala Pro Gly Lys Ala Leu Leu Ala
1               5                   10                  15

Gly Gly Tyr Leu Val Leu Asp Thr Lys Tyr Glu Ala Phe Val Val Gly
            20                  25                  30

Leu Ser Ala Arg Met His Ala Val Ala His Pro Tyr Gly Ser Leu Gln
        35                  40                  45

Gly Ser Asp Lys Phe Glu Val Arg Val Lys Ser Lys Gln Phe Lys Asp
    50                  55                  60

Gly Glu Trp Leu Tyr His Ile Ser Pro Lys Ser Gly Phe Ile Pro Val
65                  70                  75                  80

Ser Ile Gly Gly Ser Lys Asn Pro Phe Ile Glu Lys Val Ile Ala Asn
                85                  90                  95

Val Phe Ser Tyr Phe Lys Pro Asn Met Asp Asp Tyr Cys Asn Arg Asn
            100                 105                 110

Leu Phe Val Ile Asp Ile Phe Ser Asp Asp Ala Tyr His Ser Gln Glu
        115                 120                 125

Asp Ser Val Thr Glu His Arg Gly Asn Arg Arg Leu Ser Phe His Ser
    130                 135                 140

His Arg Ile Glu Glu Val Pro Lys Thr Gly Leu Gly Ser Ser Ala Gly
145                 150                 155                 160

```
Leu Val Thr Val Leu Thr Thr Ala Leu Ala Ser Phe Phe Val Ser Asp
                165                 170                 175

Leu Glu Asn Asn Val Asp Lys Tyr Arg Glu Val Ile His Asn Leu Ala
            180                 185                 190

Gln Val Ala His Cys Gln Ala Gln Gly Lys Ile Gly Ser Gly Phe Asp
        195                 200                 205

Val Ala Ala Ala Ala Tyr Gly Ser Ile Arg Tyr Arg Arg Phe Pro Pro
    210                 215                 220

Ala Leu Ile Ser Asn Leu Pro Asp Ile Gly Ser Ala Thr Tyr Gly Ser
225                 230                 235                 240

Lys Leu Ala His Leu Val Asp Glu Glu Asp Trp Asn Ile Thr Ile Lys
                245                 250                 255

Ser Asn His Leu Pro Ser Gly Leu Thr Leu Trp Met Gly Asp Ile Lys
            260                 265                 270

Asn Gly Ser Glu Thr Val Lys Leu Val Gln Lys Val Lys Asn Trp Tyr
        275                 280                 285

Asp Ser His Met Pro Glu Ser Leu Lys Ile Tyr Thr Glu Leu Asp His
    290                 295                 300

Ala Asn Ser Arg Phe Met Asp Gly Leu Ser Lys Leu Asp Arg Leu His
305                 310                 315                 320

Glu Thr His Asp Asp Tyr Ser Asp Gln Ile Phe Glu Ser Leu Glu Arg
                325                 330                 335

Asn Asp Cys Thr Cys Gln Lys Tyr Pro Glu Ile Thr Glu Val Arg Asp
            340                 345                 350

Ala Val Ala Thr Ile Arg Arg Ser Phe Arg Lys Ile Thr Lys Glu Ser
        355                 360                 365

Gly Ala Asp Ile Glu Pro Pro Val Gln Thr Ser Leu Leu Asp Asp Cys
    370                 375                 380

Gln Thr Leu Lys Gly Val Leu Thr Cys Leu Ile Pro Gly Ala Gly Gly
385                 390                 395                 400

Tyr Asp Ala Ile Ala Val Ile Thr Lys Gln Asp Val Asp Leu Arg Ala
                405                 410                 415

Gln Thr Ala Asn Asp Lys Arg Phe Ser Lys Val Gln Trp Leu Asp Val
            420                 425                 430

Thr Gln Ala Asp Trp Gly Val Arg Lys Glu Lys Asp Pro Glu Thr Tyr
        435                 440                 445

Leu Asp Lys
450

<210> SEQ ID NO 15
<211> LENGTH: 396
<212> TYPE: PRT
<213> ORGANISM: Saccharomyces cerevisiae

<400> SEQUENCE: 15

Met Thr Val Tyr Thr Ala Ser Val Thr Ala Pro Val Asn Ile Ala Thr
1               5                   10                  15

Leu Lys Tyr Trp Gly Lys Arg Asp Thr Lys Leu Asn Leu Pro Thr Asn
            20                  25                  30

Ser Ser Ile Ser Val Thr Leu Ser Gln Asp Asp Leu Arg Thr Leu Thr
        35                  40                  45

Ser Ala Ala Thr Ala Pro Glu Phe Glu Arg Asp Thr Leu Trp Leu Asn
    50                  55                  60

Gly Glu Pro His Ser Ile Asp Asn Glu Arg Thr Gln Asn Cys Leu Arg
```

Asp Leu Arg Gln Leu Arg Lys Glu Met Glu Ser Lys Asp Ala Ser Leu
            85                  90                  95

Pro Thr Leu Ser Gln Trp Lys Leu His Ile Val Ser Glu Asn Asn Phe
        100                 105                 110

Pro Thr Ala Ala Gly Leu Ala Ser Ala Ala Gly Phe Ala Ala Leu
        115                 120                 125

Val Ser Ala Ile Ala Lys Leu Tyr Gln Leu Pro Gln Ser Thr Ser Glu
130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175

Asp Ser Met Ala Val Gln Ile Ala Asp Ser Ser Asp Trp Pro Gln Met
            180                 185                 190

Lys Ala Cys Val Leu Val Val Ser Asp Ile Lys Lys Asp Val Ser Ser
        195                 200                 205

Thr Gln Gly Met Gln Leu Thr Val Ala Thr Ser Glu Leu Phe Lys Glu
210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
            260                 265                 270

Tyr Met Asn Asp Thr Ser Lys Arg Ile Ile Ser Trp Cys His Thr Ile
        275                 280                 285

Asn Gln Phe Tyr Gly Glu Thr Ile Val Ala Tyr Thr Phe Asp Ala Gly
        290                 295                 300

Pro Asn Ala Val Leu Tyr Tyr Leu Ala Glu Asn Glu Ser Lys Leu Phe
305                 310                 315                 320

Ala Phe Ile Tyr Lys Leu Phe Gly Ser Val Pro Gly Trp Asp Lys Lys
                325                 330                 335

Phe Thr Thr Glu Gln Leu Glu Ala Phe Asn His Gln Phe Glu Ser Ser
            340                 345                 350

Asn Phe Thr Ala Arg Glu Leu Asp Leu Glu Leu Gln Lys Asp Val Ala
        355                 360                 365

Arg Val Ile Leu Thr Gln Val Gly Ser Gly Pro Gln Glu Thr Asn Glu
370                 375                 380

Ser Leu Ile Asp Ala Lys Thr Gly Leu Pro Lys Glu
385                 390                 395

<210> SEQ ID NO 16
<211> LENGTH: 182
<212> TYPE: PRT
<213> ORGANISM: Escherichia coli

<400> SEQUENCE: 16

Met Gln Thr Glu His Val Ile Leu Leu Asn Ala Gln Gly Val Pro Thr
1               5                   10                  15

Gly Thr Leu Glu Lys Tyr Ala Ala His Thr Ala Asp Thr Arg Leu His
            20                  25                  30

Leu Ala Phe Ser Ser Trp Leu Phe Asn Ala Lys Gly Gln Leu Leu Val
        35                  40                  45

```
Thr Arg Arg Ala Leu Ser Lys Lys Ala Trp Pro Gly Val Trp Thr Asn
 50                  55                  60

Ser Val Cys Gly His Pro Gln Leu Gly Glu Ser Asn Glu Asp Ala Val
 65                  70                  75                  80

Ile Arg Arg Cys Arg Tyr Glu Leu Gly Val Glu Ile Thr Pro Pro Glu
                 85                  90                  95

Ser Ile Tyr Pro Asp Phe Arg Tyr Arg Ala Thr Asp Pro Ser Gly Ile
            100                 105                 110

Val Glu Asn Glu Val Cys Pro Val Phe Ala Ala Arg Thr Thr Ser Ala
        115                 120                 125

Leu Gln Ile Asn Asp Asp Glu Val Met Asp Tyr Gln Trp Cys Asp Leu
130                 135                 140

Ala Asp Val Leu His Gly Ile Asp Ala Thr Pro Trp Ala Phe Ser Pro
145                 150                 155                 160

Trp Met Val Met Gln Ala Thr Asn Arg Glu Ala Arg Lys Arg Leu Ser
                165                 170                 175

Ala Phe Thr Gln Leu Lys
            180

<210> SEQ ID NO 17
<211> LENGTH: 381
<212> TYPE: PRT
<213> ORGANISM: Abies grandis

<400> SEQUENCE: 17

Met Ala Tyr Ser Ala Met Ala Thr Met Gly Tyr Asn Gly Met Ala Ala
  1               5                  10                  15

Ser Cys His Thr Leu His Pro Thr Ser Pro Leu Lys Pro Phe His Gly
                 20                  25                  30

Ala Ser Thr Ser Leu Glu Ala Phe Asn Gly Glu His Met Gly Leu Leu
             35                  40                  45

Arg Gly Tyr Ser Lys Arg Lys Leu Ser Ser Tyr Lys Asn Pro Ala Ser
 50                  55                  60

Arg Ser Ser Asn Ala Thr Val Ala Gln Leu Leu Asn Pro Pro Gln Lys
 65                  70                  75                  80

Gly Lys Lys Ala Val Glu Phe Asp Phe Asn Lys Tyr Met Asp Ser Lys
                 85                  90                  95

Ala Met Thr Val Asn Glu Ala Leu Asn Lys Ala Ile Pro Leu Arg Tyr
            100                 105                 110

Pro Gln Lys Ile Tyr Glu Ser Met Arg Tyr Ser Leu Leu Ala Gly Gly
        115                 120                 125

Lys Arg Val Arg Pro Val Leu Cys Ile Ala Ala Cys Glu Leu Val Gly
130                 135                 140

Gly Thr Glu Glu Leu Ala Ile Pro Thr Ala Cys Ala Ile Glu Met Ile
145                 150                 155                 160

His Thr Met Ser Leu Met His Asp Asp Leu Pro Cys Ile Asp Asn Asp
                165                 170                 175

Asp Leu Arg Arg Gly Lys Pro Thr Asn His Lys Ile Phe Gly Glu Asp
            180                 185                 190

Thr Ala Val Thr Ala Gly Asn Ala Leu His Ser Tyr Ala Phe Glu His
        195                 200                 205

Ile Ala Val Ser Thr Ser Lys Thr Val Gly Ala Asp Arg Ile Leu Arg
    210                 215                 220

Met Val Ser Glu Leu Gly Arg Ala Thr Gly Ser Glu Gly Val Met Gly
225                 230                 235                 240
```

```
Gly Gln Met Val Asp Ile Ala Ser Glu Gly Asp Pro Ser Ile Asp Leu
                245                 250                 255

Gln Thr Leu Glu Trp Ile His Ile His Lys Thr Ala Met Leu Leu Glu
            260                 265                 270

Cys Ser Val Val Cys Gly Ala Ile Ile Gly Gly Ala Ser Glu Ile Val
        275                 280                 285

Ile Glu Arg Ala Arg Arg Tyr Ala Arg Cys Val Gly Leu Leu Phe Gln
    290                 295                 300

Val Val Asp Asp Ile Leu Asp Val Thr Lys Ser Ser Asp Glu Leu Gly
305                 310                 315                 320

Lys Thr Ala Gly Lys Asp Leu Ile Ser Asp Lys Ala Thr Tyr Pro Lys
                325                 330                 335

Leu Met Gly Leu Glu Lys Ala Lys Glu Phe Ser Asp Glu Leu Leu Asn
            340                 345                 350

Arg Ala Lys Gly Glu Leu Ser Cys Phe Asp Pro Val Lys Ala Ala Pro
        355                 360                 365

Leu Leu Gly Leu Ala Asp Tyr Val Ala Phe Arg Gln Asn
    370                 375                 380

<210> SEQ ID NO 18
<211> LENGTH: 589
<212> TYPE: PRT
<213> ORGANISM: Catharanthus roseus

<400> SEQUENCE: 18

Met Ala Ala Thr Ile Ser Asn Leu Ser Phe Leu Ala Lys Ser Arg Ala
1               5                   10                  15

Leu Ser Arg Pro Ser Ser Ser Leu Ser Trp Leu Glu Arg Pro Lys
            20                  25                  30

Thr Ser Ser Thr Ile Cys Met Ser Met Pro Ser Ser Ser Ser Ser
            35                  40                  45

Ser Ser Ser Ser Met Ser Leu Pro Leu Ala Thr Pro Leu Ile Lys Asp
    50                  55                  60

Asn Glu Ser Leu Ile Lys Phe Leu Arg Gln Pro Leu Val Leu Pro His
65                  70                  75                  80

Glu Val Asp Asp Ser Thr Lys Arg Arg Glu Leu Leu Glu Arg Thr Arg
                85                  90                  95

Lys Glu Leu Glu Leu Asn Ala Glu Lys Pro Leu Glu Ala Leu Lys Met
            100                 105                 110

Ile Asp Ile Ile Gln Arg Leu Gly Leu Ser Tyr His Phe Glu Asp Asp
        115                 120                 125

Ile Asn Ser Ile Leu Thr Gly Phe Ser Asn Ile Ser Ser Gln Thr His
    130                 135                 140

Glu Asp Leu Leu Thr Ala Ser Leu Cys Phe Arg Leu Leu Arg His Asn
145                 150                 155                 160

Gly His Lys Ile Asn Pro Asp Ile Phe Gln Lys Phe Met Asp Asn Asn
                165                 170                 175

Gly Lys Phe Lys Asp Ser Leu Lys Asp Asp Thr Leu Gly Met Leu Ser
            180                 185                 190

Leu Tyr Glu Ala Ser Tyr Leu Gly Ala Asn Gly Glu Gly Ile Leu Met
        195                 200                 205

Glu Ala Gln Glu Phe Thr Lys Thr His Leu Lys Asn Ser Leu Pro Ala
    210                 215                 220

Met Ala Pro Ser Leu Ser Lys Lys Val Ser Gln Ala Leu Glu Gln Pro
```

```
            225                 230                 235                 240

Arg His Arg Arg Met Leu Arg Leu Glu Ala Arg Arg Phe Ile Glu Glu
                245                 250                 255

Tyr Gly Ala Glu Asn Asp His Asn Pro Asp Leu Leu Glu Leu Ala Lys
                260                 265                 270

Leu Asp Tyr Asn Lys Val Gln Ser Leu His Gln Met Glu Leu Ser Glu
                275                 280                 285

Ile Thr Arg Trp Trp Lys Gln Leu Gly Leu Val Asp Lys Leu Thr Phe
                290                 295                 300

Ala Arg Asp Arg Pro Leu Glu Cys Phe Leu Trp Thr Val Gly Leu Leu
305                 310                 315                 320

Pro Glu Pro Lys Tyr Ser Gly Cys Arg Ile Glu Leu Ala Lys Thr Ile
                325                 330                 335

Ala Ile Leu Leu Val Ile Asp Asp Ile Phe Asp Thr His Gly Thr Leu
                340                 345                 350

Asp Glu Leu Leu Leu Phe Thr Asn Ala Ile Lys Arg Trp Asp Leu Glu
                355                 360                 365

Ala Met Glu Asp Leu Pro Glu Tyr Met Arg Ile Cys Tyr Met Ala Leu
                370                 375                 380

Tyr Asn Thr Thr Asn Glu Ile Cys Tyr Lys Val Leu Lys Glu Asn Gly
385                 390                 395                 400

Trp Ser Val Leu Pro Tyr Leu Lys Ala Thr Trp Ile Asp Met Ile Glu
                405                 410                 415

Gly Phe Met Val Glu Ala Glu Trp Phe Asn Ser Asp Tyr Val Pro Asn
                420                 425                 430

Met Glu Glu Tyr Val Glu Asn Gly Val Arg Thr Ala Gly Ser Tyr Met
                435                 440                 445

Ala Leu Val His Leu Phe Phe Leu Ile Gly Gln Gly Val Thr Glu Asp
                450                 455                 460

Asn Val Lys Leu Leu Ile Lys Pro Tyr Pro Lys Leu Phe Ser Ser Ser
465                 470                 475                 480

Gly Arg Ile Leu Arg Leu Trp Asp Asp Leu Gly Thr Ala Lys Glu Glu
                485                 490                 495

Gln Glu Arg Gly Asp Leu Ala Ser Ser Ile Gln Leu Phe Met Arg Glu
                500                 505                 510

Lys Glu Ile Lys Ser Glu Glu Gly Arg Lys Gly Ile Leu Glu Ile
                515                 520                 525

Ile Glu Asn Leu Trp Lys Glu Leu Asn Gly Glu Leu Val Tyr Arg Glu
                530                 535                 540

Glu Met Pro Leu Ala Ile Ile Lys Thr Ala Phe Asn Met Ala Arg Ala
545                 550                 555                 560

Ser Gln Val Val Tyr Gln His Glu Glu Asp Thr Tyr Phe Ser Ser Val
                565                 570                 575

Asp Asn Tyr Val Lys Ala Leu Phe Phe Thr Pro Cys Phe
                580                 585

<210> SEQ ID NO 19
<211> LENGTH: 373
<212> TYPE: PRT
<213> ORGANISM: Castellaniella defragrans

<400> SEQUENCE: 19

Met Asn Asp Thr Gln Asp Phe Ile Ser Ala Gln Ala Ala Val Leu Arg
1               5                   10                  15
```

```
Gln Val Gly Gly Pro Leu Ala Val Glu Pro Val Arg Ile Ser Met Pro
             20                  25                  30

Lys Gly Asp Glu Val Leu Ile Arg Ile Ala Gly Val Gly Val Cys His
         35                  40                  45

Thr Asp Leu Val Cys Arg Asp Gly Phe Pro Val Pro Leu Pro Ile Val
     50                  55                  60

Leu Gly His Glu Gly Ser Gly Thr Val Glu Ala Val Gly Glu Gln Val
 65                  70                  75                  80

Arg Thr Leu Lys Pro Gly Asp Arg Val Val Leu Ser Phe Asn Ser Cys
                 85                  90                  95

Gly His Cys Gly Asn Cys His Asp Gly His Pro Ser Asn Cys Leu Gln
            100                 105                 110

Met Leu Pro Leu Asn Phe Gly Gly Ala Gln Arg Val Asp Gly Gly Gln
        115                 120                 125

Val Leu Asp Gly Ala Gly His Pro Val Gln Ser Met Phe Phe Gly Gln
    130                 135                 140

Ser Ser Phe Gly Thr His Ala Val Ala Arg Glu Ile Asn Ala Val Lys
145                 150                 155                 160

Val Gly Asp Asp Leu Pro Leu Glu Leu Leu Gly Pro Leu Gly Cys Gly
                165                 170                 175

Ile Gln Thr Gly Ala Gly Ala Ala Ile Asn Ser Leu Gly Ile Gly Pro
            180                 185                 190

Gly Gln Ser Leu Ala Ile Phe Gly Gly Gly Val Gly Leu Ser Ala
        195                 200                 205

Leu Leu Gly Ala Arg Ala Val Gly Ala Asp Arg Val Val Ile Glu
    210                 215                 220

Pro Asn Ala Ala Arg Arg Ala Leu Ala Leu Glu Leu Gly Ala Ser His
225                 230                 235                 240

Ala Leu Asp Pro His Ala Glu Gly Asp Leu Val Ala Ala Ile Lys Ala
                245                 250                 255

Ala Thr Gly Gly Gly Ala Thr His Ser Leu Asp Thr Thr Gly Leu Pro
            260                 265                 270

Pro Val Ile Gly Ser Ala Ile Ala Cys Thr Leu Pro Gly Gly Thr Val
        275                 280                 285

Gly Met Val Gly Leu Pro Ala Pro Asp Ala Pro Val Pro Ala Thr Leu
    290                 295                 300

Leu Asp Leu Leu Ser Lys Ser Val Thr Leu Arg Pro Ile Thr Glu Gly
305                 310                 315                 320

Asp Ala Asp Pro Gln Arg Phe Ile Pro Arg Met Leu Asp Phe His Arg
                325                 330                 335

Ala Gly Lys Phe Pro Phe Asp Arg Leu Ile Thr Arg Tyr Arg Phe Asp
            340                 345                 350

Gln Ile Asn Glu Ala Leu His Ala Thr Glu Lys Gly Glu Ala Ile Lys
        355                 360                 365

Pro Val Leu Val Phe
    370

<210> SEQ ID NO 20
<211> LENGTH: 373
<212> TYPE: PRT
<213> ORGANISM: Rhodococcus sp. RD6.2

<400> SEQUENCE: 20

Met Gly Arg Ala Ala Arg Ala Ala Val Leu Gly Ala Tyr Gly Glu Pro
1               5                  10                  15
```

```
Leu Glu Ile Arg Asp Val Glu Val Gly Asp Leu Arg Asp Asp Glu Val
         20                  25                  30
Leu Ile Arg Ile Ala Gly Val Gly Ile Cys His Thr Asp Leu Thr Ala
         35                  40                  45
Ala Ala Gly Gly Val Pro Val Pro Val Pro Ala Val Leu Gly His Glu
 50                  55                  60
Gly Ala Gly Val Val Glu Ala Val Gly Gly Ala Val Asp Ser Leu Val
 65                  70                  75                  80
Pro Gly Asp His Val Leu Leu Ser Tyr Ser Ala Cys Arg Asp Cys Val
                 85                  90                  95
Asn Cys Ala Asn Gly His Pro Ala Tyr Cys Thr Arg Phe Ala Leu Arg
                100                 105                 110
Asn Tyr Ser Gly Arg Arg Ala Asp Gly Ser Thr Thr Leu Ser Met Asp
            115                 120                 125
Ser Val Ala Leu Gln Gly Asn Trp Phe Gly Gln Ser Ser Phe Ala Thr
130                 135                 140
His Ala Val Val Ala Ala Ser Asp Ala Val Gln Val Ala Gly Asp Leu
145                 150                 155                 160
Pro Ile Glu Leu Leu Gly Pro Leu Gly Cys Gly Ile Gln Thr Gly Ala
                165                 170                 175
Gly Ala Val Leu Arg Val Leu Arg Pro Arg Thr Gly Ser Ser Ile Val
            180                 185                 190
Val Phe Gly Gly Gly Ala Val Gly Leu Ala Ala Val Leu Ala Ala Val
        195                 200                 205
Val Ala Glu Cys Ser Thr Ile Val Val Asp Pro Leu Pro Thr Arg
210                 215                 220
Arg Glu Leu Ala Leu Ser Leu Gly Ala Thr Ala Val Phe Asp Ser Ala
225                 230                 235                 240
Glu Pro Asp Leu Ala Lys Gln Leu Arg Ala Thr Gly Gly Ala
                245                 250                 255
Asp His Thr Val Asp Ala Val Ser Thr Pro Glu Val Leu Ala Thr Ala
            260                 265                 270
Val Ala Val Leu Arg Ser Pro Gly Ser Cys Val Thr Val Gly Leu Arg
        275                 280                 285
Gly Gly Arg Asn Pro Val Thr Leu Asp Gln Ser Ala Leu Leu Met Gly
290                 295                 300
Arg Ser Val Thr Gly Val Ile Glu Gly Asp Ala Asp Pro Gln Gln Phe
305                 310                 315                 320
Leu Pro Glu Leu Ile Ala Leu Trp Arg Ala Gly Lys Phe Pro Phe Asp
                325                 330                 335
Lys Leu Ile Thr Thr Phe Asp Phe Asp Leu His Ala Ala Leu Glu
            340                 345                 350
Ala Thr Arg Ser Gly Ala Ala Val Lys Pro Val Leu Thr Phe Ala Ser
        355                 360                 365
Ser Glu Gly Gln Ala
    370

<210> SEQ ID NO 21
<211> LENGTH: 398
<212> TYPE: PRT
<213> ORGANISM: Kluyveromyces lactis

<400> SEQUENCE: 21

Met Ser Phe Met Asn Phe Glu Pro Lys Pro Leu Ala Asp Thr Asp Ile
```

```
               1               5                  10                 15
         Phe Lys Pro Ile Lys Ile Gly Asn Thr Glu Leu Lys His Arg Val Val
                         20                 25                 30

Met Pro Ala Leu Thr Arg Met Arg Ala Leu His Pro Gly Asn Val Pro
                         35                 40                 45

Asn Pro Asp Trp Ala Val Glu Tyr Tyr Arg Gln Arg Ser Gln Tyr Pro
                 50                 55                 60

Gly Thr Met Ile Ile Thr Glu Gly Ala Phe Pro Ser Ala Gln Ser Gly
         65                 70                 75                 80

Gly Tyr Asp Asn Ala Pro Gly Val Trp Ser Glu Glu Leu Ala Gln
                         85                 90                 95

Trp Arg Lys Ile Phe Lys Ala Ile His Asp Asn Lys Ser Phe Val Trp
                         100                105                110

Val Gln Leu Trp Val Leu Gly Arg Gln Ala Phe Ala Asp Asn Leu Ala
                         115                120                125

Arg Asp Gly Leu Arg Tyr Asp Ser Ala Ser Asp Glu Val Tyr Met Gly
                 130                135                140

Glu Asp Glu Lys Glu Arg Ala Ile Arg Ser Asn Asn Pro Gln His Gly
         145                150                155                160

Ile Thr Lys Asp Glu Ile Lys Gln Tyr Ile Arg Asp Tyr Val Asp Ala
                         165                170                175

Ala Lys Lys Cys Ile Asp Ala Gly Ala Asp Gly Val Glu Ile His Ser
                         180                185                190

Ala Asn Gly Tyr Leu Leu Asn Gln Phe Leu Asp Pro Ile Ser Asn Lys
                         195                200                205

Arg Thr Asp Glu Tyr Gly Gly Ser Ile Glu Asn Arg Ala Arg Phe Val
                 210                215                220

Leu Glu Val Val Asp Ala Val Val Asp Ala Val Gly Ala Glu Arg Thr
         225                230                235                240

Ser Ile Arg Phe Ser Pro Tyr Gly Val Phe Gly Thr Met Ser Gly Val
                         245                250                255

Ser Asp Pro Val Leu Val Ala Gln Phe Ala Tyr Val Leu Ala Glu Leu
                         260                265                270

Glu Lys Arg Ala Lys Ala Gly Lys Arg Leu Ala Tyr Val Asp Leu Val
                         275                280                285

Glu Pro Arg Val Thr Ser Pro Phe Gln Pro Glu Phe Glu Gly Trp Tyr
                 290                295                300

Lys Gly Gly Thr Asn Glu Phe Val Tyr Ser Val Trp Lys Gly Asn Val
         305                310                315                320

Leu Arg Val Gly Asn Tyr Ala Leu Asp Pro Asp Ala Ala Ile Thr Asp
                         325                330                335

Ser Lys Asn Pro Asn Thr Leu Ile Gly Tyr Gly Arg Ala Phe Ile Ala
                         340                345                350

Asn Pro Asp Leu Val Glu Arg Leu Glu Lys Gly Leu Pro Leu Asn Gln
                         355                360                365

Tyr Asp Arg Pro Ser Phe Tyr Lys Met Ser Ala Glu Gly Tyr Ile Asp
                 370                375                380

Tyr Pro Thr Tyr Glu Glu Ala Val Ala Lys Gly Tyr Lys Lys
         385                390                395

<210> SEQ ID NO 22
<211> LENGTH: 407
<212> TYPE: PRT
<213> ORGANISM: Pichia stipitis
```

<400> SEQUENCE: 22

```
Met Ser Ser Val Lys Ile Ser Pro Leu Lys Asp Ser Glu Ala Phe Gln
1               5                   10                  15

Ser Ile Lys Val Gly Asn Asn Thr Leu Gln Thr Lys Ile Val Tyr Pro
            20                  25                  30

Pro Thr Thr Arg Phe Arg Ala Leu Glu Asp His Thr Pro Ser Asp Leu
        35                  40                  45

Gln Leu Gln Tyr Tyr Gly Asp Arg Ser Thr Phe Pro Gly Thr Leu Leu
    50                  55                  60

Ile Thr Glu Ala Thr Phe Val Ser Pro Gln Ala Ser Gly Tyr Glu Gly
65                  70                  75                  80

Ala Ala Pro Gly Ile Trp Thr Asp Lys His Ala Lys Ala Trp Lys Val
                85                  90                  95

Ile Thr Asp Lys Val His Ala Asn Gly Ser Phe Val Ser Thr Gln Leu
            100                 105                 110

Ile Phe Leu Gly Arg Val Ala Asp Pro Ala Val Met Lys Thr Arg Gly
        115                 120                 125

Leu Asn Pro Val Ser Ala Ser Ala Thr Tyr Glu Ser Asp Ala Ala Lys
    130                 135                 140

Glu Ala Glu Ala Val Gly Asn Pro Val Arg Ala Leu Thr Thr Gln
145                 150                 155                 160

Glu Val Lys Asp Leu Val Tyr Glu Thr Tyr Thr Asn Ala Ala Gln Lys
                165                 170                 175

Ala Met Asp Ala Gly Phe Asp Tyr Ile Glu Leu His Ala His Gly
            180                 185                 190

Tyr Leu Leu Asp Gln Phe Leu Gln Pro Cys Thr Asn Gln Arg Thr Asp
        195                 200                 205

Glu Tyr Gly Gly Ser Ile Glu Asn Arg Ala Arg Leu Ile Leu Glu Leu
    210                 215                 220

Ile Asp His Leu Ser Thr Ile Val Gly Ala Asp Lys Ile Gly Ile Arg
225                 230                 235                 240

Ile Ser Pro Trp Ala Thr Phe Gln Asn Met Lys Ala His Lys Asp Thr
                245                 250                 255

Val His Pro Leu Thr Thr Phe Ser Tyr Leu Val His Glu Leu Gln Gln
            260                 265                 270

Arg Ala Asp Lys Gly Gln Gly Ile Ala Tyr Ile Ser Val Glu Pro
        275                 280                 285

Arg Val Ser Gly Asn Val Asp Val Ser Glu Asp Gln Ala Gly Asp
    290                 295                 300

Asn Glu Phe Val Ser Lys Ile Trp Lys Gly Val Ile Leu Lys Ala Gly
305                 310                 315                 320

Asn Tyr Ser Tyr Asp Ala Pro Glu Phe Lys Thr Leu Lys Glu Asp Ile
            325                 330                 335

Ala Asp Lys Arg Thr Leu Val Gly Phe Ser Arg Tyr Phe Thr Ser Asn
        340                 345                 350

Pro Asn Leu Val Trp Lys Leu Arg Asp Gly Ile Asp Leu Val Pro Tyr
    355                 360                 365

Asp Arg Asn Thr Phe Tyr Ser Asp Asn Asn Tyr Gly Tyr Asn Thr Phe
        370                 375                 380

Ser Met Asp Ser Glu Glu Val Asp Lys Glu Leu Glu Ile Lys Arg Val
385                 390                 395                 400

Pro Ser Ala Ile Glu Ala Leu
```

<210> SEQ ID NO 23

<400> SEQUENCE: 23

000

<210> SEQ ID NO 24
<211> LENGTH: 379
<212> TYPE: PRT
<213> ORGANISM: Carpoglyphus lactis

<400> SEQUENCE: 24

```
Met Val Gln Asn Pro Gly Ala Ser Ala Ile Gln Cys Arg Ala Ala Val
1               5                   10                  15

Leu Arg Lys Glu Gly Gln Pro Met Lys Ile Glu Gln Val Leu Ile Gln
            20                  25                  30

Ala Pro Gly Pro Asn Gln Val Arg Val Lys Met Val Ser Ser Gly Leu
        35                  40                  45

Cys Ala Thr Asp Ala His Leu Val Trp Gly Glu Gln Lys Ile Ser Asp
    50                  55                  60

Leu Gly Gly Ile Gly Cys Pro Ala Ile Ala Gly His Glu Gly Ala Gly
65                  70                  75                  80

Ile Val Glu Ser Val Gly Glu Asn Val Thr Glu Phe Val Pro Gly Asp
                85                  90                  95

Ser Val Leu Thr Ser Phe Gln Pro Gln Cys Gly Gln Cys Glu Ser Cys
            100                 105                 110

Leu Arg Pro Ser Thr Asn Ile Cys Lys Lys Tyr Asp Leu Ile Lys Ser
        115                 120                 125

Thr Thr Asp Val Ser Thr Ala Arg Thr Leu Asp Gly Gln Pro Ile Thr
    130                 135                 140

Ser Leu Phe Gly Leu Gly Val Tyr Ser Glu Tyr Ile Thr Thr Thr Glu
145                 150                 155                 160

His His Val Phe Lys Val Asn Lys Ala Ala Asn Leu Glu His Ala Ser
                165                 170                 175

Ile Ile Ser Cys Ser Val Gly Thr Gly Phe Tyr Ser Ala Thr Asn Leu
            180                 185                 190

Ala Ala Val Tyr Glu Gly Ser Thr Cys Ala Val Trp Gly Leu Gly Gly
        195                 200                 205

Ile Gly Ile Asn Thr Leu Phe Gly Cys Lys Tyr Asn Lys Ala Lys His
    210                 215                 220

Ile Ile Gly Ile Asp Val Asn Glu Asp Lys Arg Glu Ile Ala Ala Glu
225                 230                 235                 240

Phe Gly Cys Thr Glu Phe Ile Asn Pro Lys Thr Leu Gly Gln Pro Val
                245                 250                 255

Glu Gln Tyr Leu Met Asp Lys Phe Gly Gly Val Asp Phe Ala Phe Asp
            260                 265                 270

Cys Val Gly Tyr Lys Pro Ile Leu Asp Gln Ala Ala Val Ser Leu Ala
        275                 280                 285

Ile Asp Gly Thr Met Val Ile Gly Ala Ala Lys Glu Val Lys
    290                 295                 300

Phe Glu Met Pro Ala Phe Asn Phe Leu Phe Asn Arg Lys Val Val Gly
305                 310                 315                 320

Gly Leu Leu Gly Ser Lys Lys Thr Lys Val Ala Tyr Gln Glu Leu Cys
                325                 330                 335
```

```
Asp Met Tyr Val Asp Gly Thr Tyr Asp Val Asp Arg Leu Val Ser Asn
            340                 345                 350

Lys Phe Ser Leu Asp Gln Ile Asn Glu Ala Phe Gln Thr Leu Lys Asp
            355                 360                 365

Gly Asn Cys Ile Arg Ser Ile Val Val Phe Lys
            370                 375

<210> SEQ ID NO 25
<211> LENGTH: 245
<212> TYPE: PRT
<213> ORGANISM: Aedes aegypti

<400> SEQUENCE: 25

Met Asp Arg Trp Ala Gly Lys Val Ala Val Thr Gly Ala Ser Ser
1               5                   10                  15

Gly Ile Gly Ala Ala Ile Thr Thr Asp Leu Ala Lys Ala Gly Met Val
            20                  25                  30

Val Val Gly Leu Ala Arg Arg Val Glu Arg Val Glu Ala Leu Lys Ala
            35                  40                  45

Asn Leu Pro Glu Ser Ala Lys Pro Arg Leu His Ala Val Lys Cys Asp
        50                  55                  60

Val Ser Lys Glu Glu Asp Ile Thr Gln Val Phe Lys Trp Val Glu Glu
65                  70                  75                  80

Lys Phe Gly Gly Val Asp Leu Val Asn Asn Ala Gly Ile Leu Arg
            85                  90                  95

Gln Thr Asp Leu Leu Gly Thr Asp Asn Gly Gln Met Leu Arg Glu Val
            100                 105                 110

Leu Asp Thr Asn Val Met Gly Leu Val Leu Cys Ser Gln Lys Ala Tyr
            115                 120                 125

Gln Ser Met Lys Lys Arg Ser Val Asp Gly His Ile Val His Ile Asn
        130                 135                 140

Ser Val Val Gly His Lys Val Phe Asp Phe Pro Gln Ser Asn Ile Tyr
145                 150                 155                 160

Pro Ala Ser Lys His Ala Val Thr Ala Ile Thr Glu Thr Met Arg Asn
            165                 170                 175

Glu Leu Arg Asn Ala Gly Ser Arg Ile Lys Val Thr Ser Ile Ser Pro
            180                 185                 190

Gly Val Val Arg Thr Glu Ile Leu Pro Glu Ser Ile Ile Glu Gly Gly
            195                 200                 205

His Ser Leu Leu Glu Ser Glu Asp Ile Ser Glu Ala Val Leu Tyr Val
        210                 215                 220

Leu Gly Thr Pro Pro Arg Val Gln Val His Glu Leu Thr Ile Lys Pro
225                 230                 235                 240

Val Gly Glu Lys Phe
            245

<210> SEQ ID NO 26
<211> LENGTH: 357
<212> TYPE: PRT
<213> ORGANISM: Ocimum basilicum

<400> SEQUENCE: 26

Met Gly Ser Leu Glu Val Glu Arg Lys Thr Val Gly Trp Ala Ala Arg
1               5                   10                  15

Asp Pro Ser Gly Val Leu Ser Pro Tyr Glu Tyr Thr Leu Arg Asn Thr
            20                  25                  30
```

Gly Pro Gln Asp Val Tyr Val Glu Val Met Cys Cys Gly Ile Cys His
           35                  40                  45

Thr Asp Val His Gln Ile Lys Asn Asp Leu Gly Met Ser Asn Tyr Pro
 50                  55                  60

Met Val Pro Gly His Glu Val Val Gly Val Val Glu Val Gly Ser
 65                  70                  75                  80

Glu Val Thr Lys Phe Arg Ala Gly Asp Val Val Gly Val Gly Cys Ile
                 85                  90                  95

Val Gly Ser Cys Gly Asn Cys Arg Pro Cys Asn Ser Asp Ile Glu Gln
            100                 105                 110

Tyr Cys Asn Lys Lys Ile Trp Ser Tyr Asn Asp Val Tyr Pro Asp Gly
        115                 120                 125

Lys Pro Thr Gln Gly Gly Phe Ala Gly Ala Met Val Val Asp Gln Lys
    130                 135                 140

Phe Val Val Lys Ile Pro Asp Gly Met Ala Pro Glu Gln Ala Ala Pro
145                 150                 155                 160

Leu Leu Cys Ala Gly Val Thr Val Tyr Ser Pro Leu Asn His Phe Gly
                165                 170                 175

Leu Lys Gln Ser Gly Leu Arg Gly Gly Ile Leu Gly Leu Gly Gly Val
            180                 185                 190

Gly His Met Gly Val Lys Ile Ala Lys Ala Met Gly His His Val Thr
        195                 200                 205

Val Ile Ser Ser Ser Asp Lys Lys Arg Ala Glu Ala Leu Asp His Leu
    210                 215                 220

Gly Ala Asp Asp Tyr Leu Val Ser Ser Asp Ala Ala Arg Met Gln Glu
225                 230                 235                 240

Ala Ala Asp Ser Leu Asp Tyr Ile Ile Asp Thr Val Pro Val Phe His
                245                 250                 255

Pro Leu Glu Pro Tyr Leu Ser Leu Leu Lys Ile Asp Gly Lys Leu Ile
            260                 265                 270

Leu Met Gly Val Val Asn Thr Pro Leu Gln Phe Val Ser Pro Met Val
        275                 280                 285

Met Leu Gly Arg Lys Ser Ile Thr Gly Ser Phe Ile Gly Ser Met Lys
    290                 295                 300

Glu Leu Ala Glu Met Leu Glu Phe Cys Lys Glu Lys Asp Leu Ser Ser
305                 310                 315                 320

Thr Ile Glu Ile Val Lys Met Asp Tyr Ile Asn Thr Ala Phe Glu Arg
                325                 330                 335

Leu Glu Lys Asn Asp Val Arg Tyr Arg Phe Val Val Asp Val Ala Gly
            340                 345                 350

Ser Lys Leu Tyr Gln
        355

<210> SEQ ID NO 27
<211> LENGTH: 368
<212> TYPE: PRT
<213> ORGANISM: Zingiber officinale

<400> SEQUENCE: 27

Met Ala Glu Leu Gly Asn Gly Lys Lys Gln Ala Ser Pro Glu Glu Val
1               5                   10                  15

His Pro Arg Lys Ala Phe Gly Trp Ala Ala Lys Asp Lys Ser Gly Val
            20                  25                  30

Leu Ser Pro Phe Ala Phe Ser Arg Arg Asn Thr Gly Ala Asp Asp Val

```
            35                  40                  45
Thr Ile Lys Ile Leu Tyr Cys Gly Ile Cys His Ser Asp Leu His Thr
         50                  55                  60
Ala Lys Asn Glu Trp Ser Asn Ala Ile Tyr Pro Met Val Pro Gly His
 65                  70                  75                  80
Glu Ile Val Gly Val Thr Glu Val Gly Gln Asn Val Gln Asn Phe
                 85                  90                  95
Lys Val Gly Lys Val Gly Val Gly Cys Ile Val Asn Ser Cys Leu
            100                 105                 110
Ser Cys Gln Asn Cys Asn Arg Asp Tyr Glu Asn Tyr Cys Pro Arg Ile
            115                 120                 125
Ile Leu Thr Tyr Asn Ser Leu Asp Val Asp Gly Thr Met Thr Tyr Gly
        130                 135                 140
Gly Tyr Ser Asn Met Val Val Asn Gln His Phe Val Ile Arg Phe
145                 150                 155                 160
Pro Glu Asn Leu Pro Leu Asp Lys Gly Ala Pro Leu Leu Cys Ala Gly
                165                 170                 175
Ile Thr Val Tyr Ser Pro Leu Lys Glu His Gly Leu Asp Val Pro Gly
            180                 185                 190
Lys His Leu Gly Val Val Gly Leu Gly Gly Leu Gly His Val Ala Val
        195                 200                 205
Lys Phe Gly Lys Ala Phe Gly Met Lys Val Thr Val Ile Ser Thr Ser
    210                 215                 220
Leu Lys Lys Glu Lys Glu Ala Ile Glu Arg Leu Gly Ala Asp Ala Phe
225                 230                 235                 240
Leu Val Ser Ser Asn Ala Glu Gln Met Gln Ala Ala Met Gly Thr Met
                245                 250                 255
Asp Gly Ile Ile Asn Thr Val Ser Ala Asp His Ser Ile Ala Pro Leu
            260                 265                 270
Ala Phe Leu Leu Lys Thr His Gly Lys Met Ile Met Val Gly Ala Pro
        275                 280                 285
Glu Lys Pro Leu Gln Leu Pro Ile Phe Ser Leu Ile Leu Gly Gly Lys
    290                 295                 300
Thr Leu Ala Gly Ser Cys Ile Gly Gly Ile Lys Ala Thr Gln Glu Met
305                 310                 315                 320
Ile Asp Phe Ala Ala Lys Asn Ile Thr Ala Asp Ile Glu Leu Ile
                325                 330                 335
Pro Ile Ser Tyr Leu Asn Glu Ala Met Glu Arg Leu Thr Lys Ala Asp
            340                 345                 350
Val Arg Tyr Arg Phe Val Ile Asp Ile Gly Asn Ser Leu Thr Glu Ala
        355                 360                 365

<210> SEQ ID NO 28
<211> LENGTH: 360
<212> TYPE: PRT
<213> ORGANISM: Camellia sinensis

<400> SEQUENCE: 28

Met Ala Gln Thr Thr Pro Asn His Thr Gln Thr Val Ser Gly Trp Ala
 1               5                  10                  15
Ala His Asp Ser Ser Gly Lys Ile Thr Pro Tyr Thr Phe Lys Arg Arg
                20                  25                  30
Glu Asn Gly Ile Asn Asp Val Thr Ile Asp Ile Leu Tyr Cys Gly Ile
            35                  40                  45
```

Cys His Thr Asp Leu His His Val Arg Asn Asp Trp Gly Ile Thr Met
            50                  55                  60

Tyr Pro Val Val Pro Gly His Glu Ile Thr Gly Leu Ile Ser Lys Val
 65                  70                  75                  80

Gly Ser Asn Val Ser Lys Phe Lys Ile Gly Asp Arg Val Gly Val Gly
                 85                  90                  95

Cys Leu Ala Ala Ser Cys Leu Glu Cys Glu Phe Cys Lys Asp Ser Gln
            100                 105                 110

Glu Asn Tyr Cys Asp Gln Ile Gln Phe Thr Tyr Asn Gly Ile Phe Trp
            115                 120                 125

Asp Gly Ser Ile Thr Tyr Gly Gly Tyr Ser Lys Met Leu Val Ala Asp
            130                 135                 140

Gln Arg Tyr Val Val His Val Pro Glu Asn Leu Pro Met Asp Ala Ala
145                 150                 155                 160

Ala Pro Leu Leu Cys Ala Gly Val Thr Val Phe Cys Pro Leu Lys Asp
                165                 170                 175

Asn Asn Met Leu Glu Leu Asp Ser Pro Pro Lys Leu Gly Val Val
            180                 185                 190

Gly Leu Gly Gly Leu Gly His Val Ala Val Lys Phe Gly Lys Ala Phe
            195                 200                 205

Gly His His Val Thr Val Ile Ser Thr Ser Pro Ser Lys Glu Asp Glu
            210                 215                 220

Ala Lys His Arg Leu Gly Ala Asp Asp Phe Ile Val Ser Thr Asp Leu
225                 230                 235                 240

Ala Gln Met Gln Ala Lys Lys Arg Ser Leu Asp Leu Ile Leu Asp Thr
                245                 250                 255

Val Ala Ala Lys His Ser Leu Gly Ser Tyr Leu Glu Leu Leu Lys Val
            260                 265                 270

Asn Gly Thr Leu Val Ile Val Gly Ala Pro Asp Lys Pro Ile Asp Leu
            275                 280                 285

Pro Ser Phe Pro Leu Ile Phe Gly Lys Arg Val Val Lys Gly Ser Met
            290                 295                 300

Thr Gly Ser Met Lys Glu Thr Gln Glu Met Met Asp Val Cys Gly Lys
305                 310                 315                 320

Tyr Asn Ile Lys Cys Asp Ile Glu Lys Thr Thr Pro Asn Lys Ile Asn
                325                 330                 335

Glu Ala Leu Asp Arg Leu Ser Lys Asn Asp Val Lys Tyr Arg Phe Val
            340                 345                 350

Ile Asp Ile Ala Ser Ala Asp Lys
            355                 360

<210> SEQ ID NO 29
<211> LENGTH: 375
<212> TYPE: PRT
<213> ORGANISM: Sphingopyxis granuli

<400> SEQUENCE: 29

Met Lys Cys Lys Ala Ala Ile Ala Arg Glu Asp Val Ala Glu Phe Gly
 1               5                  10                  15

Trp Ser Glu Val Glu Leu Asp Glu Pro Arg Ala Asp Glu Ile Leu Val
                 20                  25                  30

Arg Ile Ala Gly Val Gly Leu Cys His Thr Asp Leu Ile Ala Arg Asp
             35                  40                  45

Gln Phe Ile Pro Val Gly Ser Pro Ala Val Leu Gly His Glu Gly Ala
         50                  55                  60

-continued

Gly Glu Val Val Lys Val Gly Ser Ala Val Thr Lys Val Gly Pro Gly
65 70 75 80

Asp Arg Val Ala Leu Ser Phe Arg Ser Cys Gly Ala Cys Arg Ser Cys
85 90 95

Ala Asp His Met Pro Ser Tyr Cys Gln His Phe Gly Gly Leu Asn Met
100 105 110

Ser Gly Ala Arg Pro Asp Gly Ser Lys Ala Val Arg Leu Asp Gly Gln
115 120 125

Pro Ile Ser Ser Asn Phe Phe Gly Gln Ser Ser Phe Ala Glu Tyr Ala
130 135 140

Leu Ala Tyr Glu Ser Asn Val Val Arg Ile Asp Asp Asp Glu Val Pro
145 150 155 160

Leu Glu Leu Leu Gly Pro Leu Gly Cys Gly Ile Gln Thr Gly Ala Gly
165 170 175

Gly Val Met Arg Ser Leu Ala Cys Pro Ala Gly Ser Ser Leu Leu Val
180 185 190

Val Gly Gly Gly Ser Val Gly Leu Ala Ala Val Met Gly Gly Ala Val
195 200 205

Gln Arg Cys Gly Thr Ile Ile Val Val Glu Pro His Ala Ala Arg Arg
210 215 220

Asp Leu Ala Leu Glu Leu Gly Ala Thr His Ala Ile Asp Pro Ile Gly
225 230 235 240

Asn Asp Val Ala Ala Ala Val Arg Asp Ile Leu Pro Asp Gly Val Asp
245 250 255

Tyr Ala Phe Asp Thr Thr Gly Arg Pro Asp Ser Phe Ala Ala Val Leu
260 265 270

Ala Ser Leu Ala Val Arg Gly His Phe Gly Met Val Ser Ala Gln Ala
275 280 285

Ala Asp Thr Thr Ile Thr Leu Asp Val Asn Ser Phe Ile Leu Ala Gly
290 295 300

His His Val Gln Gly Ile Ile Glu Gly Asp Ser Asp Pro Asp Val Phe
305 310 315 320

Ile Pro Glu Leu Ile Ala His Tyr Lys Ala Gly Arg Phe Pro Tyr Asp
325 330 335

Arg Leu Val Thr Thr Tyr Pro Leu Ala Asp Ile Asn Arg Ala Ile Glu
340 345 350

Asp Gln His Ala Gly Arg Cys Ile Lys Ala Val Leu Ile Pro Asp His
355 360 365

Gly Lys Gly Ala Ala His Asp
370 375

<210> SEQ ID NO 30
<211> LENGTH: 534
<212> TYPE: PRT
<213> ORGANISM: Microbacterium trichothecenolyticum

<400> SEQUENCE: 30

Met Thr Ala Ala Val Ala Ala Leu Val Arg Glu Arg Gly Gly Ser Val
1 5 10 15

Ala Leu Thr Asp Val Ala Leu Arg Ser Pro Asp Pro Arg Glu Leu Val
20 25 30

Val Lys Val Met Ala Ser Gly Val Cys Pro Thr Asp Leu Phe Gly Ile
35 40 45

Asp Gly Gly Ala Gly Asp Arg Phe Pro Ala Val Phe Gly His Glu Gly

```
            50                  55                  60
Ala Gly Ile Val Glu Ala Val Gly Ala Glu Val Thr Arg Val Arg Pro
 65                  70                  75                  80

Gly Asp Arg Val Val Leu Gly Phe Gly Ser Cys Gly Ala Cys Gly Pro
                 85                  90                  95

Cys Arg Asp Gly His Pro Ala Tyr Cys Asp Arg Phe Ala Glu Leu Asn
                100                 105                 110

Tyr Ala Pro Arg Ser Asp Ala Ala Thr Ala Gly Gly Glu His Val Thr
            115                 120                 125

Thr Gly Trp Met Ala Gln Ser Ser Trp Ala Thr Arg Ile Val Val His
        130                 135                 140

Glu Ser Ser Ala Val Pro Ile Gly Asp Asp Val Pro Trp Ala Val Ala
145                 150                 155                 160

Ala Thr Leu Gly Cys Gly Ile Leu Thr Gly Ala Gly Thr Val Leu Asn
                165                 170                 175

Val Leu Arg Pro Ala Pro Gly Asp Ala Leu Leu Val Leu Gly Ala Gly
            180                 185                 190

Thr Thr Gly Leu Ala Ala Val Met Ala Ala Ala His Arg Gly Val Ala
        195                 200                 205

Arg Ile Val Val Ser Asp Pro Val Glu Ala Arg Arg Thr Leu Ala Leu
210                 215                 220

Glu Val Gly Ala Thr Glu Val Ile Ala Pro Asp Asp Leu Ala Ala Leu
225                 230                 235                 240

Arg Pro Ala Pro Ser Phe Ser His Val Leu Asp Thr Ala Gly Thr Gln
                245                 250                 255

Pro Ser Ile Asp Ala Ala Leu Ala Ala Val Ala Pro Arg Gly Ile Ala
            260                 265                 270

Ala Thr Val Ala Leu Lys Pro Gly Ala Asn Pro Val Ala Val Ser Gln
        275                 280                 285

Ser Arg Leu Leu Trp Gly Arg Thr Leu Thr Gly Val Ile Glu Gly Asp
290                 295                 300

Ala Asp Ile Ala Arg Asp Val Pro Leu Leu Ala Ala Leu Trp Arg Ala
305                 310                 315                 320

Gly Arg Leu Pro Val Glu Arg Leu Val Gly Thr Tyr Ala Phe Ala Asp
                325                 330                 335

Ala Gln Ala Ala Ile Ala Asp Ala Arg Ala Gly Arg Leu Val Lys Pro
            340                 345                 350

Val Leu Glu Met Glu Thr Val Thr Val Thr Asp Ala Ala Ala Ala Ala
        355                 360                 365

Ser Val Arg Ser Leu Val Asp Arg Leu Arg Glu Gly Val Ser Asp Asp
370                 375                 380

Asp Leu Ala Ala Leu Trp Arg Ser Leu Pro Ala Val Gly Thr Ala Gln
385                 390                 395                 400

Leu Arg Gly Leu Trp Gln Gly Trp Ala Val Thr Arg Asp His His Ala
                405                 410                 415

Gly Arg Leu Leu Glu Arg Ser Arg Trp Tyr Gly Lys Leu Phe Arg Ser
            420                 425                 430

Asp Asp Asp Val Ala Pro Ile Val Cys Glu Thr Asp Asp Gly Ala Leu
        435                 440                 445

Leu Ala Asp Thr Asp Leu Ala Arg Gly Gly Ala Thr Leu Arg Thr Ile
450                 455                 460

Val His Asp Gly Val Ala Thr Ala Ser Met Val Tyr Asp Gly Gln Pro
465                 470                 475                 480
```

Ile Ile Asp His Phe Val Arg Leu Gly Ala Asp Thr Val Leu Gly Val
            485                 490                 495

Met Thr Gly Arg Asp Thr Asp Arg Gly Arg Ala Phe Tyr Phe Val
        500                 505                 510

Leu Glu His Val Glu Asp Arg Pro Val Ala Ala Arg Asp Thr Thr Pro
        515                 520                 525

Thr Thr Ala His Arg Ser
    530

<210> SEQ ID NO 31
<211> LENGTH: 339
<212> TYPE: PRT
<213> ORGANISM: Escherichia coli

<400> SEQUENCE: 31

Met Ser Met Ile Lys Ser Tyr Ala Ala Lys Glu Ala Gly Gly Glu Leu
1               5                   10                  15

Glu Val Tyr Glu Tyr Asp Pro Gly Glu Leu Arg Pro Gln Asp Val Glu
            20                  25                  30

Val Gln Val Asp Tyr Cys Gly Ile Cys His Ser Asp Leu Ser Met Ile
        35                  40                  45

Asp Asn Glu Trp Gly Phe Ser Gln Tyr Pro Leu Val Ala Gly His Glu
    50                  55                  60

Val Ile Gly Arg Val Val Ala Leu Gly Ser Ala Ala Gln Asp Lys Gly
65                  70                  75                  80

Leu Gln Val Gly Gln Arg Val Gly Ile Gly Trp Thr Ala Arg Ser Cys
                85                  90                  95

Gly His Cys Asp Ala Cys Ile Ser Gly Asn Gln Ile Asn Cys Glu Gln
            100                 105                 110

Gly Ala Val Pro Thr Ile Met Asn Arg Gly Gly Phe Ala Glu Lys Leu
        115                 120                 125

Arg Ala Asp Trp Gln Trp Val Ile Pro Leu Pro Glu Asn Ile Asp Ile
    130                 135                 140

Glu Ser Ala Gly Pro Leu Leu Cys Gly Gly Ile Thr Val Phe Lys Pro
145                 150                 155                 160

Leu Leu Met His His Ile Thr Ala Thr Ser Arg Val Gly Val Ile Gly
                165                 170                 175

Ile Gly Gly Leu Gly His Ile Ala Ile Lys Leu Leu His Ala Met Gly
            180                 185                 190

Cys Glu Val Thr Ala Phe Ser Ser Asn Pro Ala Lys Glu Gln Glu Val
        195                 200                 205

Leu Ala Met Gly Ala Asp Lys Val Val Asn Ser Arg Asp Pro Gln Ala
    210                 215                 220

Leu Lys Ala Leu Ala Gly Gln Phe Asp Leu Ile Ile Asn Thr Val Asn
225                 230                 235                 240

Val Ser Leu Asp Trp Gln Pro Tyr Phe Glu Ala Leu Thr Tyr Gly Gly
                245                 250                 255

Asn Phe His Thr Val Gly Ala Val Leu Thr Pro Leu Ser Val Pro Ala
            260                 265                 270

Phe Thr Leu Ile Ala Gly Asp Arg Ser Val Ser Gly Ser Ala Thr Gly
        275                 280                 285

Thr Pro Tyr Glu Leu Arg Lys Leu Met Arg Phe Ala Ala Arg Ser Lys
    290                 295                 300

Val Ala Pro Thr Thr Glu Leu Phe Pro Met Ser Lys Ile Asn Asp Ala

```
305                 310                 315                 320
Ile Gln His Val Arg Asp Gly Lys Ala Arg Tyr Arg Val Val Leu Lys
                325                 330                 335

Ala Asp Phe

<210> SEQ ID NO 32
<211> LENGTH: 349
<212> TYPE: PRT
<213> ORGANISM: Escherichia coli

<400> SEQUENCE: 32

Met Lys Ile Lys Ala Val Gly Ala Tyr Ser Ala Lys Gln Pro Leu Glu
1               5                   10                  15

Pro Met Asp Ile Thr Arg Arg Glu Pro Gly Pro Asn Asp Val Lys Ile
                20                  25                  30

Glu Ile Ala Tyr Cys Gly Val Cys His Ser Asp Leu His Gln Val Arg
                35                  40                  45

Ser Glu Trp Ala Gly Thr Val Tyr Pro Cys Val Pro Gly His Glu Ile
        50                  55                  60

Val Gly Arg Val Val Ala Val Gly Asp Gln Val Glu Lys Tyr Ala Pro
65                  70                  75                  80

Gly Asp Leu Val Gly Val Gly Cys Ile Val Asp Ser Cys Lys His Cys
                85                  90                  95

Glu Glu Cys Glu Asp Gly Leu Glu Asn Tyr Cys Asp His Met Thr Gly
                100                 105                 110

Thr Tyr Asn Ser Pro Thr Pro Asp Glu Pro Gly His Thr Leu Gly Gly
                115                 120                 125

Tyr Ser Gln Gln Ile Val Val His Glu Arg Tyr Val Leu Arg Ile Arg
        130                 135                 140

His Pro Gln Glu Gln Leu Ala Ala Val Ala Pro Leu Leu Cys Ala Gly
145                 150                 155                 160

Ile Thr Thr Tyr Ser Pro Leu Arg His Trp Gln Ala Gly Pro Gly Lys
                165                 170                 175

Lys Val Gly Val Val Gly Ile Gly Gly Leu Gly His Met Gly Ile Lys
                180                 185                 190

Leu Ala His Ala Met Gly Ala His Val Val Ala Phe Thr Thr Ser Glu
        195                 200                 205

Ala Lys Arg Glu Ala Ala Lys Ala Leu Gly Ala Asp Glu Val Val Asn
210                 215                 220

Ser Arg Asn Ala Asp Glu Met Ala Ala His Leu Lys Ser Phe Asp Phe
225                 230                 235                 240

Ile Leu Asn Thr Val Ala Ala Pro His Asn Leu Asp Asp Phe Thr Thr
                245                 250                 255

Leu Leu Lys Arg Asp Gly Thr Met Thr Leu Val Gly Ala Pro Ala Thr
                260                 265                 270

Pro His Lys Ser Pro Glu Val Phe Asn Leu Ile Met Lys Arg Arg Ala
                275                 280                 285

Ile Ala Gly Ser Met Ile Gly Gly Ile Pro Glu Thr Gln Glu Met Leu
        290                 295                 300

Asp Phe Cys Ala Glu His Gly Ile Val Ala Asp Ile Glu Met Ile Arg
305                 310                 315                 320

Ala Asp Gln Ile Asn Glu Ala Tyr Glu Arg Met Leu Arg Gly Asp Val
                325                 330                 335

Lys Tyr Arg Phe Val Ile Asp Asn Arg Thr Leu Thr Asp
```

<210> SEQ ID NO 33
<211> LENGTH: 400
<212> TYPE: PRT
<213> ORGANISM: Saccharomyces cerevisiae

<400> SEQUENCE: 33

Met Pro Phe Val Lys Asp Phe Lys Pro Gln Ala Leu Gly Asp Thr Asn
1               5                   10                  15

Leu Phe Lys Pro Ile Lys Ile Gly Asn Asn Glu Leu Leu His Arg Ala
            20                  25                  30

Val Ile Pro Pro Leu Thr Arg Met Arg Ala Gln His Pro Gly Asn Ile
        35                  40                  45

Pro Asn Arg Asp Trp Ala Val Glu Tyr Tyr Ala Gln Arg Ala Gln Arg
    50                  55                  60

Pro Gly Thr Leu Ile Ile Thr Glu Gly Thr Phe Pro Ser Pro Gln Ser
65                  70                  75                  80

Gly Gly Tyr Asp Asn Ala Pro Gly Ile Trp Ser Glu Glu Gln Ile Lys
                85                  90                  95

Glu Trp Thr Lys Ile Phe Lys Ala Ile His Glu Asn Lys Ser Phe Ala
            100                 105                 110

Trp Val Gln Leu Trp Val Leu Gly Trp Ala Ala Phe Pro Asp Thr Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asn Pro Phe Leu Thr Glu Gly Glu Gly Glu
    290                 295                 300

Tyr Asn Gly Gly Ser Asn Lys Phe Ala Tyr Ser Ile Trp Lys Gly Pro
305                 310                 315                 320

Ile Ile Arg Ala Gly Asn Phe Ala Leu His Pro Glu Val Val Arg Glu
                325                 330                 335

Glu Val Lys Asp Pro Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
        355                 360                 365

```
Lys Tyr Asp Arg Asp Thr Phe Tyr Lys Met Ser Ala Glu Gly Tyr Ile
370                 375                 380

Asp Tyr Pro Thr Tyr Glu Glu Ala Leu Lys Leu Gly Trp Asp Lys Asn
385                 390                 395                 400

<210> SEQ ID NO 34
<211> LENGTH: 348
<212> TYPE: PRT
<213> ORGANISM: Rubus idaeus

<400> SEQUENCE: 34

Met Ala Ser Gly Gly Glu Met Gln Val Ser Asn Lys Gln Val Ile Phe
1               5                   10                  15

Arg Asp Tyr Val Thr Gly Phe Pro Lys Glu Ser Asp Met Glu Leu Thr
                20                  25                  30

Thr Arg Ser Ile Thr Leu Lys Leu Pro Gln Gly Ser Thr Gly Leu Leu
        35                  40                  45

Leu Lys Asn Leu Tyr Leu Ser Cys Asp Pro Tyr Met Arg Ala Arg Met
50                  55                  60

Thr Asn His His Arg Leu Ser Tyr Val Asp Ser Phe Lys Pro Gly Ser
65                  70                  75                  80

Pro Ile Ile Gly Tyr Gly Val Ala Arg Val Leu Glu Ser Gly Asn Pro
                85                  90                  95

Lys Phe Asn Pro Gly Asp Leu Val Trp Gly Phe Thr Gly Trp Glu Glu
                100                 105                 110

Tyr Ser Val Ile Thr Ala Thr Glu Ser Leu Phe Lys Ile His Asn Thr
            115                 120                 125

Asp Val Pro Leu Ser Tyr Tyr Thr Gly Leu Leu Gly Met Pro Gly Met
130                 135                 140

Thr Ala Tyr Ala Gly Phe Tyr Glu Ile Cys Ser Pro Lys Lys Gly Glu
145                 150                 155                 160

Thr Val Tyr Val Ser Ala Ala Ser Gly Ala Val Gly Gln Leu Val Gly
                165                 170                 175

Gln Phe Ala Lys Leu Thr Gly Cys Tyr Val Val Gly Ser Ala Gly Ser
            180                 185                 190

Lys Glu Lys Val Asp Leu Leu Lys Asn Lys Phe Gly Phe Asp Glu Ala
        195                 200                 205

Phe Asn Tyr Lys Glu Glu Ala Asp Leu Asp Ala Ala Leu Arg Arg Tyr
210                 215                 220

Phe Pro Asp Gly Ile Asp Ile Tyr Phe Glu Asn Val Gly Gly Lys Met
225                 230                 235                 240

Leu Asp Ala Val Leu Pro Asn Met Arg Pro Lys Gly Arg Ile Ala Val
                245                 250                 255

Cys Gly Met Ile Ser Gln Tyr Asn Leu Glu Gln Pro Glu Gly Val Arg
            260                 265                 270

Asn Leu Met Ala Leu Ile Val Lys Gln Val Arg Met Glu Gly Phe Met
        275                 280                 285

Val Phe Ser Tyr Tyr His Leu Tyr Gly Lys Phe Leu Glu Thr Val Leu
290                 295                 300

Pro Tyr Ile Lys Gln Gly Lys Ile Thr Tyr Val Glu Asp Val Val Asp
305                 310                 315                 320

Gly Leu Asp Asn Ala Pro Ala Ala Leu Ile Gly Leu Tyr Ser Gly Arg
                325                 330                 335

Asn Val Gly Lys Gln Val Val Val Ser Arg Glu
            340                 345
```

<210> SEQ ID NO 35

<400> SEQUENCE: 35

000

<210> SEQ ID NO 36

<400> SEQUENCE: 36

000

<210> SEQ ID NO 37
<211> LENGTH: 363
<212> TYPE: PRT
<213> ORGANISM: Pseudomonas putida

<400> SEQUENCE: 37

```
Met Ser Ala Leu Phe Glu Pro Tyr Thr Leu Lys Asp Val Thr Leu Arg
 1               5                  10                  15

Asn Arg Ile Ala Ile Pro Pro Met Cys Gln Tyr Met Ala Glu Asp Gly
                20                  25                  30

Met Ile Asn Asp Trp His His Val His Leu Ala Gly Leu Ala Arg Gly
            35                  40                  45

Gly Ala Gly Leu Leu Val Val Glu Ala Thr Ala Val Ala Pro Glu Gly
        50                  55                  60

Arg Ile Thr Pro Gly Cys Ala Gly Ile Trp Ser Asp Ala His Ala Gln
65                  70                  75                  80

Ala Phe Val Pro Val Val Gln Ala Ile Lys Ala Ala Gly Ser Val Pro
                85                  90                  95

Gly Ile Gln Ile Ala His Ala Gly Arg Lys Ala Ser Ala Asn Arg Pro
            100                 105                 110

Trp Glu Gly Asp Asp His Ile Ala Ala Asp Ala Arg Gly Trp Glu
        115                 120                 125

Thr Ile Ala Pro Ser Ala Ile Ala Phe Gly Ala His Leu Pro Lys Val
    130                 135                 140

Pro Arg Glu Met Thr Leu Asp Asp Ile Ala Arg Val Lys Gln Asp Phe
145                 150                 155                 160

Val Asp Ala Ala Arg Ala Arg Asp Ala Gly Phe Glu Trp Ile Glu
                165                 170                 175

Leu His Phe Ala His Gly Tyr Leu Gly Gln Ser Phe Ser Glu His
            180                 185                 190

Ser Asn Lys Arg Thr Asp Ala Tyr Gly Gly Ser Phe Asp Asn Arg Ser
        195                 200                 205

Arg Phe Leu Leu Glu Thr Leu Ala Ala Val Arg Glu Val Trp Pro Glu
    210                 215                 220

Asn Leu Pro Leu Thr Ala Arg Phe Gly Val Leu Glu Tyr Asp Gly Arg
225                 230                 235                 240

Asp Glu Gln Thr Leu Glu Glu Ser Ile Glu Leu Ala Arg Arg Phe Lys
                245                 250                 255

Ala Gly Gly Leu Asp Leu Leu Ser Val Ser Val Gly Phe Thr Ile Pro
            260                 265                 270

Asp Thr Asn Ile Pro Trp Gly Pro Ala Phe Met Gly Pro Ile Ala Glu
        275                 280                 285

Arg Val Arg Arg Glu Ala Lys Leu Pro Val Thr Ser Ala Trp Gly Phe
    290                 295                 300
```

Gly Thr Pro Gln Leu Ala Glu Ala Ala Leu Gln Ala Asn Gln Leu Asp
305                 310                 315                 320

Leu Val Ser Val Gly Arg Ala His Leu Ala Asp Pro His Trp Ala Tyr
            325                 330                 335

Phe Ala Ala Lys Glu Leu Gly Val Glu Lys Ala Ser Trp Thr Leu Pro
        340                 345                 350

Ala Pro Tyr Ala His Trp Leu Glu Arg Tyr Arg
    355                 360

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44
<211> LENGTH: 403
<212> TYPE: PRT
<213> ORGANISM: Kluyveromyces marxianus

<400> SEQUENCE: 44

Met Ser Tyr Met Asn Phe Asp Pro Lys Pro Leu Gly Asp Thr Asn Ile
1               5                   10                  15

Phe Lys Pro Ile Lys Ile Gly Asn Asn Glu Leu Lys His Arg Val Val
            20                  25                  30

Met Pro Ala Leu Thr Arg Met Arg Ala Ile Ala Pro Gly Asn Ile Pro
        35                  40                  45

Asn Thr Glu Trp Ala Glu Glu Tyr Tyr Arg Gln Arg Ser Gln Tyr Pro
    50                  55                  60

Gly Thr Leu Ile Ile Thr Glu Gly Thr Phe Pro Ser Ala Gln Ser Gly
65                  70                  75                  80

Gly Tyr Pro Asn Val Pro Gly Ile Trp Ser Lys Glu Gln Leu Ala Glu

```
                        85                  90                  95
Trp Lys Lys Ile Phe Asn Ala Ile His Glu Asn Lys Ser Phe Val Trp
                100                 105                 110
Val Gln Leu Trp Val Leu Gly Arg Gln Ala Trp Pro Glu Val Leu Lys
            115                 120                 125
Lys Glu Gly Leu Arg Tyr Asp Ser Ala Thr Asp Leu Tyr Met Gly
        130                 135                 140
Glu Glu Glu Lys Glu Arg Ala Leu Lys Ala Asn Asn Pro Gln His Gly
145                 150                 155                 160
Ile Thr Lys Glu Glu Ile Lys Gln Tyr Ile Lys Glu Tyr Val Asp Ala
                165                 170                 175
Ala Lys Lys Ala Ile Asp Ala Gly Ala Asp Gly Val Gln Ile His Ser
            180                 185                 190
Ala Asn Gly Tyr Leu Leu Asn Gln Phe Leu Asp Pro Ile Ser Asn Asn
        195                 200                 205
Arg Thr Asp Glu Tyr Gly Gly Ser Ile Glu Asn Arg Ala Arg Phe Thr
    210                 215                 220
Leu Glu Val Val Asp Ala Val Val Asp Ala Val Gly Ala Glu Arg Thr
225                 230                 235                 240
Ser Ile Arg Phe Ser Pro Tyr Gly Thr Phe Gly Thr Met Ser Gly Gly
                245                 250                 255
Glu Asn Pro Gly Ile Val Ala Gln Tyr Ala Tyr Val Ile Gly Glu Leu
            260                 265                 270
Glu Lys Arg Ala Arg Ala Gly Lys Arg Leu Ala Phe Ile Asp Leu Val
        275                 280                 285
Glu Pro Arg Val Thr Asp Pro Phe Leu Pro Glu Phe Glu Lys Trp Phe
    290                 295                 300
Lys Glu Gly Thr Asn Glu Phe Ile Tyr Ser Ile Trp Lys Gly Pro Val
305                 310                 315                 320
Leu Arg Val Gly Asn Tyr Ala Leu Asp Pro Asp Gln Ala Thr Leu Asp
                325                 330                 335
Ser Lys Lys Pro Asn Thr Leu Ile Gly Tyr Gly Arg Ser Phe Ile Ala
            340                 345                 350
Asn Pro Asp Leu Val Tyr Arg Leu Glu Lys Gly Leu Pro Leu Asn Lys
        355                 360                 365
Tyr Asp Arg Asn Thr Phe Tyr Thr Phe Thr Lys Glu Gly Tyr Thr Asp
    370                 375                 380
Tyr Pro Ser Tyr Glu Glu Ser Val Ala Lys Gly Tyr Lys Lys Glu Glu
385                 390                 395                 400
Lys Lys Tyr

<210> SEQ ID NO 45
<211> LENGTH: 358
<212> TYPE: PRT
<213> ORGANISM: Gluconobacter morbifer

<400> SEQUENCE: 45

Met Pro Thr Leu Phe Asp Pro Val Glu Leu Gly Thr Ile His Ala Arg
1               5                   10                  15
Asn Arg Ile Leu Met Ala Pro Leu Thr Arg Gly Arg Ala Asp Lys Asn
            20                  25                  30
Gly Val Pro Ser Ala Leu Met Val Glu Tyr Tyr Ala Gln Arg Ala Ser
        35                  40                  45
Ala Gly Leu Ile Ile Ser Glu Ala Thr Gly Ile Ser Arg Glu Gly Leu
```

```
            50                  55                  60
Gly Trp Pro Phe Ala Pro Gly Ile Trp Ser Asp Glu Gln Val Ala Ala
 65                  70                  75                  80

Trp Lys Pro Val Thr Glu Ala Val His Ala Lys Gly Gly Lys Ile Val
                 85                  90                  95

Cys Gln Leu Trp His Met Gly Arg Leu Val His Ser Val Thr Gly
            100                 105                 110

Gln Gln Pro Val Ser Cys Ser Ala Thr Thr Gly Pro Asp Glu Val His
            115                 120                 125

Thr Tyr Glu Gly Lys Lys Pro Tyr Glu Gln Ala Arg Ala Leu Arg Leu
            130                 135                 140

Asp Glu Ile Pro Arg Ile Leu Asn Asp Tyr Glu Asn Ala Ala Arg Asn
145                 150                 155                 160

Ala Leu Lys Ala Gly Phe Asp Gly Val Gln Ile His Gly Ala Asn Gly
                165                 170                 175

Tyr Leu Ile Asp Glu Phe Leu Arg Asp Gly Thr Asn His Arg Thr Asp
            180                 185                 190

Glu Tyr Gly Gly Ser Pro Glu Asn Arg Thr Arg Phe Leu Arg His Val
            195                 200                 205

Val Glu Arg Val Ile Ala Thr Ile Gly Ala Asp Arg Thr Ala Ile Arg
210                 215                 220

Leu Ser Pro Asn Gly Glu Thr Gln Gly Cys Ile Asp Ser Ala Pro Glu
225                 230                 235                 240

Lys Val Phe Ile Leu Ala Ala Glu Ile Leu Gln Asp Leu Gly Ile Ala
                245                 250                 255

Trp Leu Glu Leu Arg Glu Pro Gly Pro Asn Gly Thr Phe Gly Lys Thr
            260                 265                 270

Asp Gln Pro Lys Leu Ser Pro Gln Ile Arg Lys Val Phe His Lys Pro
            275                 280                 285

Leu Val Leu Asn Gln Asp Tyr Thr Phe Glu Gly Glu Ala Ala Val
            290                 295                 300

Ser Glu Gly Arg Ala Asp Ala Ile Ala Phe Gly Arg Lys Phe Ile Ala
305                 310                 315                 320

Asn Pro Asp Leu Pro Glu Arg Phe Arg Gln His Ala Pro Leu Gln Ala
                325                 330                 335

Asp Asp Met Lys Thr Trp Tyr Ser Gln Gly Pro Glu Gly Tyr Thr Asp
            340                 345                 350

Tyr Pro Phe Leu Ser Ala
            355

<210> SEQ ID NO 46
<211> LENGTH: 357
<212> TYPE: PRT
<213> ORGANISM: Tanticharoenia sakaeratensis

<400> SEQUENCE: 46

Met Thr Thr Leu Phe Asp Pro Ile Lys Leu Gly Ala Ile Ala Ala Pro
 1               5                  10                  15

Asn Arg Ile Ile Met Ala Pro Leu Thr Arg Gly Arg Ser Ser Arg Gly
                 20                  25                  30

His Val Pro Ser Ala Leu Met Ala Glu Tyr Tyr Ala Gln Arg Ala Ser
             35                  40                  45

Ala Gly Leu Ile Ile Thr Glu Ala Thr Gly Ile Ser Gln Glu Gly Leu
 50                  55                  60
```

```
Gly Trp Pro Tyr Ala Pro Gly Ile Trp Ser Asp Glu Gln Val Glu Ala
 65                  70                  75                  80

Trp Lys Pro Ile Val Arg Ala Val His Asp Lys Gly Arg Ile Val
                 85                  90                  95

Met Gln Leu Trp His Met Gly Arg Met Val His Ser Asn Val Thr Gly
            100                 105                 110

Leu Gln Pro Val Ser Ala Ser Pro Thr Thr Ala Pro Gly Glu Ala His
        115                 120                 125

Thr Tyr Asp Gly Lys Lys Pro Tyr Glu Gln Ala Arg Ala Leu Asp Ile
    130                 135                 140

Ser Glu Ile Pro Arg Leu Leu Ala Asp Tyr Glu Asn Ala Thr Arg Asn
145                 150                 155                 160

Ala Leu Ala Ala Gly Phe Asp Gly Val Gln Ile His Ala Ala Asn Gly
                165                 170                 175

Tyr Leu Ile Asp Glu Phe Leu Arg Asp Ser Thr Asn Lys Arg Thr Asp
            180                 185                 190

Ala Tyr Gly Gly Glu Pro Glu Asn Arg Ile Arg Leu Leu Arg Glu Val
        195                 200                 205

Thr Glu Arg Val Ile Ser Val Ala Gly Ala Asp Arg Thr Ala Val Arg
    210                 215                 220

Leu Ser Pro Asn Gly Glu Thr Gln Gly Thr Ile Asp Ser Asn Pro Ile
225                 230                 235                 240

Ser Val Phe Val Pro Ala Ala Lys Met Leu Tyr Asp Leu Gly Leu Ala
                245                 250                 255

Trp Leu Glu Leu Arg Glu Pro Gly Pro Asn Gly Thr Phe Gly Arg Thr
            260                 265                 270

Asp Gln Pro Lys Leu Ser Pro Gln Ile Arg Gln Val Phe Lys Ala Pro
        275                 280                 285

Leu Val Leu Asn Ser Asp Tyr Thr Leu Glu Glu Ala Glu Thr Ala Val
    290                 295                 300

Leu Glu Asp Arg Ala Asp Ala Ile Ser Phe Gly Arg Lys Phe Leu Ala
305                 310                 315                 320

Asn Pro Asp Leu Pro His Arg Phe Lys Ser Gly Leu Pro Leu Asn Arg
                325                 330                 335

Asp Glu Met Lys Thr Trp Tyr Ser Gln Gly Pro Gln Gly Tyr Val Asp
            340                 345                 350

Tyr Pro Ala Ala Ser
        355

<210> SEQ ID NO 47
<211> LENGTH: 362
<212> TYPE: PRT
<213> ORGANISM: Zymomonas mobilis

<400> SEQUENCE: 47

Met Pro Thr Leu Phe Asp Pro Ile Arg Leu Gly Ala Val Thr Ala Lys
 1               5                  10                  15

Asn Arg Ile Leu Met Ala Pro Leu Thr Arg Gly Arg Ala Thr Arg Asp
             20                  25                  30

His Val Pro Thr Asp Ile Met Ile Lys Tyr Tyr Ala Gln Arg Ala Ser
         35                  40                  45

Ala Gly Leu Ile Ile Ser Glu Ala Thr Gly Ile Ser Gln Glu Gly Leu
     50                  55                  60

Gly Trp Pro Tyr Ala Pro Gly Ile Trp Asn Glu Ala Gln Thr Gln Ala
 65                  70                  75                  80
```

-continued

Trp Ile Pro Ile Thr Gln Ala Val His Asp Ala Gly Leu Ile Phe
                85                  90                  95

Val Gln Leu Trp His Met Gly Arg Leu Val Pro Ser Val Ser Gly
            100                 105                 110

Met Gln Pro Val Ser Ala Ser Thr Lys Ala Pro Asp Leu Ala His
        115                 120                 125

Thr Tyr Glu Gly Lys Lys Pro Phe Asp Val Ala Arg Pro Leu Glu Ile
    130                 135                 140

Ala Glu Ile Pro Arg Leu Leu Asp Asp Tyr Glu Arg Ala Thr Arg Asn
145                 150                 155                 160

Ala Leu Ser Ala Gly Phe Asp Gly Val Gln Ile His Ala Ala Asn Gly
                165                 170                 175

Tyr Leu Ile Asp Glu Phe Leu Arg Asp Gly Thr Asn Leu Arg Lys Asp
            180                 185                 190

Ala Tyr Gly Gly Thr Pro Glu His Arg Ile Arg Leu Leu Arg Glu Val
        195                 200                 205

Thr Glu Arg Val Ile Ser Val Ile Gly Ala Asp Arg Thr Ser Val Arg
    210                 215                 220

Leu Ser Pro Asn Gly Glu Ile Gln Gly Ala Ser Asp Ser His Pro Glu
225                 230                 235                 240

Asn Ile Phe Leu Pro Ala Ala Arg Met Leu Ser Asp Leu Gly Ile Ala
                245                 250                 255

Phe Leu Gly Leu Arg Glu Gly Thr Pro Glu Gly Thr Phe Gly Arg Thr
            260                 265                 270

Asp Gln Pro Lys Leu Ser Pro Lys Ile Arg Glu Val Phe Asn Pro Pro
        275                 280                 285

Leu Ile Leu Asn Gln Asp Tyr Asn Leu Glu Thr Ala Gln Glu Ala Leu
    290                 295                 300

Asp Ser Gly Val Ala Asp Ala Ile Ser Phe Gly Arg Leu Phe Ile Ser
305                 310                 315                 320

Asn Pro Asp Leu Pro Arg Arg Phe Phe Glu Gly Ser Pro Leu Ile Lys
                325                 330                 335

Asp Asn Ile Ala Thr Trp Tyr Thr Gln Gly Ala Glu Gly Tyr Thr Asp
            340                 345                 350

Tyr Pro Leu Ile Gly Asn Glu Ile Pro Ala
        355                 360

<210> SEQ ID NO 48
<211> LENGTH: 365
<212> TYPE: PRT
<213> ORGANISM: Escherichia coli

<400> SEQUENCE: 48

Met Ser Ser Glu Lys Leu Tyr Ser Pro Leu Lys Val Gly Ala Ile Thr
1               5                   10                  15

Ala Ala Asn Arg Ile Phe Met Ala Pro Leu Thr Arg Leu Arg Ser Ile
                20                  25                  30

Glu Pro Gly Asp Ile Pro Thr Pro Leu Met Ala Glu Tyr Tyr Arg Gln
            35                  40                  45

Arg Ala Ser Ala Gly Leu Ile Ile Ser Glu Ala Thr Gln Ile Ser Ala
        50                  55                  60

Gln Ala Lys Gly Tyr Ala Gly Ala Pro Gly Ile His Ser Pro Glu Gln
65                  70                  75                  80

Ile Ala Ala Trp Lys Lys Ile Thr Ala Gly Val His Ala Glu Asn Gly 85                  90                  95
His Met Ala Val Gln Leu Trp His Thr Gly Arg Ile Ser His Ala Ser
                100                 105                 110
Leu Gln Pro Gly Gly Gln Ala Pro Val Ala Pro Ser Ala Leu Ser Ala
                115                 120                 125
Gly Thr Arg Thr Ser Leu Arg Asp Glu Asn Gly Gln Ala Ile Arg Val
            130                 135                 140
Glu Thr Ser Met Pro Arg Ala Leu Glu Leu Glu Glu Ile Pro Gly Ile
145                 150                 155                 160
Val Asn Asp Phe Arg Gln Ala Ile Ala Asn Ala Arg Glu Ala Gly Phe
                165                 170                 175
Asp Leu Val Glu Leu His Ser Ala His Gly Tyr Leu Leu His Gln Phe
                180                 185                 190
Leu Ser Pro Ser Ser Asn His Arg Thr Asp Gln Tyr Gly Gly Ser Val
                195                 200                 205
Glu Asn Arg Ala Arg Leu Val Leu Glu Val Val Asp Ala Gly Ile Glu
            210                 215                 220
Glu Trp Gly Ala Asp Arg Ile Gly Ile Arg Val Ser Pro Ile Gly Thr
225                 230                 235                 240
Phe Gln Asn Thr Asp Asn Gly Pro Asn Glu Glu Ala Asp Ala Leu Tyr
                245                 250                 255
Leu Ile Glu Gln Leu Gly Lys Arg Gly Ile Ala Tyr Leu His Met Ser
                260                 265                 270
Glu Pro Asp Trp Ala Gly Gly Glu Pro Tyr Thr Asp Ala Phe Arg Glu
                275                 280                 285
Lys Val Arg Ala Arg Phe His Gly Pro Ile Ile Gly Ala Gly Ala Tyr
                290                 295                 300
Thr Val Glu Lys Ala Glu Thr Leu Ile Gly Lys Gly Leu Ile Asp Ala
305                 310                 315                 320
Val Ala Phe Gly Arg Asp Trp Ile Ala Asn Pro Asp Leu Val Ala Arg
                325                 330                 335
Leu Gln Arg Lys Ala Glu Leu Asn Pro Gln Arg Ala Glu Ser Phe Tyr
                340                 345                 350
Gly Gly Gly Ala Glu Gly Tyr Thr Asp Tyr Pro Thr Leu
                355                 360                 365

<210> SEQ ID NO 49
<211> LENGTH: 291
<212> TYPE: PRT
<213> ORGANISM: Pseudomonas citronellolis

<400> SEQUENCE: 49

Met Ala Tyr Asp Ser Ile Phe Lys Pro Gly Leu Phe Ala Gly Gln Thr
1               5                   10                  15
Val Ile Val Thr Gly Gly Ser Gly Ile Gly Arg Cys Thr Ala His
            20                  25                  30
Glu Leu Ala Ala Leu Gly Ala His Val Val Leu Val Gly Arg Lys Ala
        35                  40                  45
Glu Lys Leu Glu Lys Thr Ala Gly Glu Ile Val Glu Asp Gly Gly Ser
    50                  55                  60
Ala Asn Trp His Ser Cys Asp Ile Arg Asp Glu Glu Ala Val Lys Ala
65                  70                  75                  80
Leu Val Ala Gln Val Leu Val Glu Arg Gly Pro Ile His His Leu Val
                85                  90                  95

```
Asn Asn Ala Gly Gly Gln Tyr Pro Ala Pro Leu Ala Ser Ile Asn Leu
            100                 105                 110

Lys Gly Phe Glu Ala Val Val Arg Thr Asn Leu Val Gly Gly Phe Leu
        115                 120                 125

Met Ala Arg Glu Val Phe Asn Gln Ser Met Ser Lys His Gly Gly Ser
130                 135                 140

Ile Val Asn Met Leu Ala Asp Met Trp Gly Met Pro Gly Met Gly
145                 150                 155                 160

His Ser Gly Ala Ala Arg Ala Gly Met Glu Asn Phe Thr Lys Thr Ala
                165                 170                 175

Ala Val Glu Trp Gly His Ala Gly Val Arg Val Asn Ala Val Ala Pro
            180                 185                 190

Gly Trp Ile Ala Ser Ser Gly Met Asp Thr Tyr Glu Gly Ala Phe Lys
        195                 200                 205

Ala Val Ile Pro Thr Leu Arg Glu His Val Pro Leu Lys Arg Ile Gly
    210                 215                 220

Thr Glu Ser Glu Val Ala Ser Ala Ile Val Phe Leu Leu Ser Pro Gly
225                 230                 235                 240

Ala Ala Phe Ile Ser Gly Asn Thr Ile Arg Ile Asp Gly Ala Ala Ser
                245                 250                 255

Gln Gly Ser Arg Ala Phe Pro Leu Ser Lys Ala Lys Pro Gly Gln Ser
            260                 265                 270

Arg Ser Tyr Asn Gly Phe His Arg Ala Tyr Leu Pro Asp Val Leu Lys
        275                 280                 285

Asp Gln Glu
    290

<210> SEQ ID NO 50
<211> LENGTH: 273
<212> TYPE: PRT
<213> ORGANISM: Pseudomonas citronellolis

<400> SEQUENCE: 50

Met Ser Leu Asn Ala Lys Thr Leu Phe Ile Thr Gly Ala Ser Arg Gly
1               5                   10                  15

Ile Gly Arg Glu Ile Ala Leu Arg Ala Ala Arg Asp Gly Ala Asn Val
            20                  25                  30

Val Ile Ala Ala Lys Ser Ala Glu Pro His Pro Lys Leu Ala Gly Thr
        35                  40                  45

Ile His Ser Val Ala Glu Glu Val Glu Ala Ala Gly Gly Lys Ala Leu
    50                  55                  60

Ala Leu Gln Leu Asp Val Arg Asp Glu Asn Ala Val Arg Glu Ala Met
65                  70                  75                  80

Ala Arg Ala Ala Glu His Phe Gly Gly Ile Asp Gly Leu Val Asn Asn
                85                  90                  95

Ala Gly Ala Ile Lys Leu Val Gly Val Glu Arg Leu Glu Pro Lys Arg
            100                 105                 110

Phe Asp Leu Met Phe Gln Ile Asn Thr Arg Ala Val Met Val Cys Ser
        115                 120                 125

Gln Ala Ala Leu Pro Tyr Leu Lys Gln Ser Gln Gly His Ile Leu Ser
    130                 135                 140

Leu Ser Pro Pro Leu Asn Leu Ala Glu Lys Trp Phe Ala Gln His Gly
145                 150                 155                 160

Pro Tyr Thr Val Thr Lys Tyr Gly Met Ser Met Leu Thr Leu Gly Met
                165                 170                 175
```

```
His Glu Glu Phe Arg Lys Tyr Gly Ile Ser Val Asn Ala Leu Trp Pro
                180                 185                 190

Lys Thr Met Ile Ala Thr Ala Ala Ile Glu Phe Glu Leu Gly Ser Arg
            195                 200                 205

Asp Ala Phe Lys Arg Ala Arg Thr Pro Ala Ile Met Asp Ala Ala
        210                 215                 220

His Ala Ile Leu Gly Ser Thr Gly Arg Ser Ile Ser Gly Arg Leu Leu
225                 230                 235                 240

Ile Asp Glu Asp Ile Leu Arg Glu Gln Gly Val Ser Asp Phe Glu Gln
                245                 250                 255

Tyr Arg Phe Asp Pro Gln Gly Gly Pro Leu Val Pro Asp Leu Phe Leu
            260                 265                 270

Asp

<210> SEQ ID NO 51
<211> LENGTH: 290
<212> TYPE: PRT
<213> ORGANISM: Pseudomonas sp. Ag1

<400> SEQUENCE: 51

Met Ala Phe Asp Ser Ile Phe Lys Ala Asp Leu Phe Gln Gly Gln Thr
1               5                   10                  15

Ile Ile Val Thr Gly Gly Gly Ser Gly Ile Gly Arg Cys Thr Ala His
            20                  25                  30

Glu Leu Ala Ala Leu Gly Ala His Val Ile Leu Val Gly Arg Lys Pro
        35                  40                  45

Glu Lys Leu Gln Thr Val Ala Ala Glu Ile Ser Glu Asp Gly Gly Arg
    50                  55                  60

Ala Ser Trp Gln Ala Cys Asp Ile Arg Asp Glu Ala Val Lys Ala
65                  70                  75                  80

Leu Val Gly Gln Val Leu Gln Glu His Gly Pro Ile His Gly Leu Val
                85                  90                  95

Asn Asn Ala Gly Gly Gln Tyr Pro Ser Pro Leu Ala Ser Ile Asn Gln
            100                 105                 110

Lys Gly Phe Glu Thr Val Leu Arg Thr Asn Leu Val Gly Gly Phe Leu
        115                 120                 125

Met Ala Arg Glu Val Phe Asn Gln Ser Met Ser Lys His Gly Gly Ser
    130                 135                 140

Ile Val Asn Met Leu Ala Asp Met Trp Gly Gly Met Pro Gly Met Gly
145                 150                 155                 160

His Ser Gly Ala Ala Arg Ser Gly Met Asp Asn Leu Thr Lys Thr Ala
                165                 170                 175

Ala Val Glu Trp Gly Tyr Ala Gly Val Arg Val Asn Ala Val Ala Pro
            180                 185                 190

Gly Trp Ile Ala Ser Ser Gly Met Asp Thr Tyr Glu Gly Ala Phe Lys
        195                 200                 205

Ala Val Ile Pro Thr Leu Arg Glu His Val Pro Leu Lys Arg Ile Gly
    210                 215                 220

Thr Glu Ser Glu Val Ser Ala Ile Val Phe Leu Leu Ser Pro Ala
225                 230                 235                 240

Ala Ala Phe Val Ser Gly Ser Thr Leu Arg Ile Asp Gly Ala Ala Ser
                245                 250                 255

Leu Gly Ser Arg Ala Trp Pro Leu His Lys Ala Gln Pro Pro Ser Val
            260                 265                 270
```

-continued

Ser Phe Asn Gly Phe His Arg Ala Tyr Leu Pro Asp Val Leu Lys Glu
        275                 280                 285

Glu Lys
    290

<210> SEQ ID NO 52
<211> LENGTH: 421
<212> TYPE: PRT
<213> ORGANISM: Bradyrhizobium sp. DFC1-1

<400> SEQUENCE: 52

Met Leu Arg Phe Ala Arg Asn Asp Ala Gly Arg Gln Gln Ala Thr Thr
1               5                   10                  15

Leu Ser Ala Leu Gly Ser Ala Arg Ala Ala Ala Gly Val Leu Ala Phe
            20                  25                  30

Val Ile Gly Gly Val Phe Gly Thr Tyr Ile Gly Trp Arg Pro Ala Phe
        35                  40                  45

Gly Ile Leu Ile Ala Val Ser Ala Ile Val Phe Leu Leu Ser Phe Arg
    50                  55                  60

Leu Lys Pro Asp Arg Gly Arg Pro Asp Ile Glu Ile Asp Leu Val Gly
65                  70                  75                  80

Val Ala Leu Ala Ala Gly Ala Ile Ile Leu Ile Ser Phe Gly Phe Asn
            85                  90                  95

Asn Leu Ile Gly Trp Gly Leu Ala Leu Ala Arg Pro Asn Ala Pro Phe
            100                 105                 110

Asp Leu Leu Gly Val Ser Pro Ala Pro Ile Met Ile Val Ile Gly Ile
        115                 120                 125

Val Leu Gly Gln Ala Phe Leu Ser Trp Thr His Arg Gln Gln Ala Ala
    130                 135                 140

Gly Lys Thr Pro Leu Leu Ala Leu Glu Val Ile Asp Ser Pro Glu Glu
145                 150                 155                 160

Arg Cys Ala Val Tyr Ala Leu Phe Thr Val Ala Leu Glu Ala Ala
                165                 170                 175

Leu Asn Phe Thr Val Pro Leu Tyr Ile Gln Ile Val Gln Gly Arg Ser
            180                 185                 190

Pro Ile Ala Thr Ala Ile Ala Met Met Pro Phe Asn Leu Thr Val Phe
        195                 200                 205

Phe Ser Ala Met Leu Ile Val Asn Leu Tyr Asp Arg Leu Thr Pro Arg
    210                 215                 220

Gln Ile Gly Arg Phe Gly Phe Ala Leu Cys Thr Ile Ala Leu Leu Trp
225                 230                 235                 240

Leu Ala Phe Val Val Arg Asn Asp Trp Ser Glu Ile Pro Val Leu Phe
                245                 250                 255

Gly Leu Val Leu Phe Gly Ile Gly Gln Gly Ser Leu Val Thr Leu Leu
            260                 265                 270

Phe Asn Val Leu Val Thr Ala Ser Pro Lys Val Leu Ala Gly Asp Val
        275                 280                 285

Gly Ser Leu Arg Gly Thr Thr Gln Asn Leu Ala Ala Val Gly Thr
    290                 295                 300

Ala Val Ala Gly Ala Leu Leu Val Gly Leu Ser Thr Ile Ala Leu
305                 310                 315                 320

Gly Lys Ile Thr Ala Ser Pro Val Leu Thr Lys Glu Leu Gln Ser Gln
                325                 330                 335

Val Asp Leu Asp Asn Ile Thr Phe Val Ser Asn Asp Arg Leu Arg Ser

```
                 340                 345                 350
Val Leu Glu Ala Thr Ser Gly Thr Pro Gln Gln Val Glu Glu Ala Val
            355                 360                 365

Arg Val Asn Thr Glu Ala Arg Leu Arg Ala Leu Lys Ile Gly Leu Leu
        370                 375                 380

Ile Met Ala Gly Leu Ala Leu Leu Ala Val Ile Pro Ala Gly Gln Leu
385                 390                 395                 400

Pro Asn Tyr Arg Pro Gly Glu Ile Pro Asp Asp Asn Ala Ala Gly His
            405                 410                 415

Arg Glu Arg Thr Ser
            420

<210> SEQ ID NO 53
<211> LENGTH: 303
<212> TYPE: PRT
<213> ORGANISM: Solanum lycopersicum

<400> SEQUENCE: 53

Met Ser Ser Leu Val Leu Gln Cys Trp Lys Leu Ser Ser Pro Ser Leu
1               5                   10                  15

Ile Leu Gln Gln Asn Thr Ser Ile Ser Met Gly Ala Phe Lys Gly Ile
            20                  25                  30

His Lys Leu Gln Ile Pro Asn Ser Pro Leu Thr Val Ser Ala Arg Gly
        35                  40                  45

Leu Asn Lys Ile Ser Cys Ser Leu Asn Leu Gln Thr Glu Lys Leu Cys
    50                  55                  60

Tyr Glu Asp Asn Asp Asn Leu Asp Glu Leu Met Pro Lys His
65                  70                  75                  80

Ile Ala Leu Ile Met Asp Gly Asn Arg Arg Trp Ala Lys Asp Lys Gly
                85                  90                  95

Leu Glu Val Tyr Glu Gly His Lys His Ile Ile Pro Lys Leu Lys Glu
            100                 105                 110

Ile Cys Asp Ile Ser Ser Lys Leu Gly Ile Gln Ile Ile Thr Ala Phe
        115                 120                 125

Ala Phe Ser Thr Glu Asn Trp Lys Arg Ser Lys Glu Glu Val Asp Phe
    130                 135                 140

Leu Leu Gln Met Phe Glu Glu Ile Tyr Asp Glu Phe Ser Arg Ser Gly
145                 150                 155                 160

Val Arg Val Ser Ile Ile Gly Cys Lys Ser Asp Leu Pro Met Thr Leu
                165                 170                 175

Gln Lys Cys Ile Ala Leu Thr Glu Glu Thr Thr Lys Gly Asn Lys Gly
            180                 185                 190

Leu His Leu Val Ile Ala Leu Asn Tyr Gly Gly Tyr Tyr Asp Ile Leu
        195                 200                 205

Gln Ala Thr Lys Ser Ile Val Asn Lys Ala Met Asn Gly Leu Leu Asp
    210                 215                 220

Val Glu Asp Ile Asn Lys Asn Leu Phe Asp Gln Glu Leu Glu Ser Lys
225                 230                 235                 240

Cys Pro Asn Pro Asp Leu Leu Ile Arg Thr Gly Gly Glu Gln Arg Val
                245                 250                 255

Ser Asn Phe Leu Leu Trp Gln Leu Ala Tyr Thr Glu Phe Tyr Phe Thr
            260                 265                 270

Asn Thr Leu Phe Pro Asp Phe Gly Glu Glu Asp Leu Lys Glu Ala Ile
        275                 280                 285
```

```
Met Asn Phe Gln Gln Arg His Arg Arg Phe Gly Gly His Thr Tyr
    290                 295                 300
```

<210> SEQ ID NO 54
<211> LENGTH: 392
<212> TYPE: PRT
<213> ORGANISM: Olea europaea

<400> SEQUENCE: 54

```
Met Ser Trp Trp Phe Asn Arg Ser Val Asn Gly Cys Lys Gln Lys Lys
1               5                   10                  15

Ile Gln Glu Asn Gly Val Gln Gln Gln Asn Gly Asp Ile Gln Ser
            20                  25                  30

Phe Lys Ser Val Ala Leu Ile Val Gly Val Thr Gly Ile Val Gly Ser
                35                  40                  45

Ser Leu Ser Glu Ile Leu Gln Tyr Thr Asp Thr Pro Gly Gly Pro Trp
50                  55                  60

Lys Val Tyr Gly Val Ala Arg Arg Pro Arg Pro Thr Trp Leu Ala Lys
65                  70                  75                  80

Ser His Val Glu Tyr Val Gln Cys Asp Val Thr Asn Thr Glu Glu Thr
                85                  90                  95

Ile Ser Lys Ile Ser Pro Leu Thr Asp Ile Thr His Ile Phe Tyr Val
            100                 105                 110

Ser Trp Met Gly Asn Glu Asp Cys Ser Met Asn Ala Val Met Phe Gln
        115                 120                 125

Asn Ile Leu Asn Ser Val Ile Pro Asn Ala Pro Asn Leu Gln His Ile
    130                 135                 140

Cys Leu Gln Thr Gly Ser Lys His Tyr Ile Gly Leu Phe Glu Thr Asp
145                 150                 155                 160

Thr Pro Glu Ser His Asp Thr Pro Tyr Ser Glu Asp Leu Ala Arg Leu
                165                 170                 175

Lys Gln Pro Asn Phe Tyr His Asn Leu Glu Asp Ile Leu Phe Glu Glu
            180                 185                 190

Thr Ala Lys Lys Gly Leu Thr Trp Ser Val His Arg Pro Ala Leu Ile
        195                 200                 205

Phe Gly Phe Ser Pro Cys Ser Leu Met Asn Ile Val Ser Thr Leu Ser
    210                 215                 220

Val Tyr Ala Ala Ile Cys Lys His Glu Asn Lys Pro Leu Val Tyr Pro
225                 230                 235                 240

Gly Ser Lys Ala Ser Trp Asn Cys Phe Val Asp Ala Ala Asp Ala Glu
                245                 250                 255

Leu Ala Ala Glu His Gln Ile Trp Ala Ala Val Asp Pro Asn Ala Lys
            260                 265                 270

Asn Gln Ala Phe Asn Cys Thr Asn Gly Asp Leu Phe Lys Trp Lys His
        275                 280                 285

Ile Trp Lys Val Leu Ala Asn Gln Phe Asp Leu Glu Met Val Gly Tyr
    290                 295                 300

Ile Glu Gly Asn Glu Gln Val Ser Met Glu Glu Leu Met Lys Asp Lys
305                 310                 315                 320

Asp Ser Val Trp Asp Glu Ile Val Lys Lys Asn Asn Leu Met Pro Thr
                325                 330                 335

Lys Leu Lys Glu Ile Ala Ala Phe Trp Phe Ala Asp Ile Ala Phe Cys
            340                 345                 350

Leu Glu Asn Val Leu Ser Ser Thr His Lys Asn Arg Leu His Gly Phe
        355                 360                 365
```

Met Gly Phe Arg Asn Thr Tyr Thr Ser Phe Val Ser Cys Ile Asp Lys
        370                 375                 380

Met Arg Ala Tyr Arg Phe Ile Pro
385                 390

<210> SEQ ID NO 55
<211> LENGTH: 388
<212> TYPE: PRT
<213> ORGANISM: Catharanthus roseus

<400> SEQUENCE: 55

Met Ser Trp Trp Trp Lys Arg Ser Ile Gly Ala Gly Lys Asn Leu Pro
1               5                   10                  15

Asn Gln Asn Lys Glu Asn Gly Val Cys Lys Ser Tyr Lys Ser Val Ala
            20                  25                  30

Leu Val Val Gly Val Thr Gly Ile Val Gly Ser Ser Leu Ala Glu Val
        35                  40                  45

Leu Lys Leu Pro Asp Thr Pro Gly Gly Pro Trp Lys Val Tyr Gly Val
    50                  55                  60

Ala Arg Arg Pro Cys Pro Val Trp Leu Ala Lys Lys Pro Val Glu Tyr
65                  70                  75                  80

Ile Gln Cys Asp Val Ser Asp Asn Gln Glu Thr Ile Ser Lys Leu Ser
                85                  90                  95

Pro Leu Lys Asp Ile Thr His Ile Phe Tyr Val Ser Trp Ile Gly Ser
            100                 105                 110

Glu Asp Cys Gln Thr Asn Ala Thr Met Phe Lys Asn Ile Leu Asn Ser
        115                 120                 125

Val Ile Pro Asn Ala Ser Asn Leu Gln His Val Cys Leu Gln Thr Gly
    130                 135                 140

Ile Lys His Tyr Phe Gly Ile Phe Glu Glu Gly Ser Lys Val Val Pro
145                 150                 155                 160

His Asp Ser Pro Phe Thr Glu Asp Leu Pro Arg Leu Asn Val Pro Asn
                165                 170                 175

Phe Tyr His Asp Leu Glu Asp Ile Leu Tyr Glu Glu Thr Gly Lys Asn
            180                 185                 190

Asn Leu Thr Trp Ser Val His Arg Pro Ala Leu Val Phe Gly Phe Ser
        195                 200                 205

Pro Cys Ser Met Met Asn Ile Val Ser Thr Leu Cys Val Tyr Ala Thr
    210                 215                 220

Ile Cys Lys His Glu Asn Lys Ala Leu Val Tyr Pro Gly Ser Lys Asn
225                 230                 235                 240

Ser Trp Asn Cys Tyr Ala Asp Ala Val Asp Ala Asp Leu Val Ala Glu
                245                 250                 255

His Glu Ile Trp Ala Ala Val Asp Pro Lys Ala Lys Asn Gln Val Leu
            260                 265                 270

Asn Cys Asn Asn Gly Asp Val Phe Lys Trp Lys His Ile Trp Lys Lys
        275                 280                 285

Leu Ala Glu Glu Phe Gly Ile Glu Met Val Gly Tyr Val Glu Gly Lys
    290                 295                 300

Glu Gln Val Ser Leu Ala Glu Leu Met Lys Asp Lys Asp Gln Val Trp
305                 310                 315                 320

Asp Glu Ile Val Lys Lys Asn Asn Leu Val Pro Thr Lys Leu Lys Glu
                325                 330                 335

Ile Ala Ala Phe Trp Phe Ala Asp Ile Ala Phe Cys Ser Glu Asn Leu

```
              340                 345                 350
Ile Ser Ser Met Asn Lys Ser Lys Glu Leu Gly Phe Leu Gly Phe Arg
            355                 360                 365

Asn Ser Met Lys Ser Phe Val Ser Cys Ile Asp Lys Met Arg Asp Tyr
            370                 375                 380

Arg Phe Ile Pro
385

<210> SEQ ID NO 56
<211> LENGTH: 534
<212> TYPE: PRT
<213> ORGANISM: Glycine max

<400> SEQUENCE: 56

Met Asp Asn Ile Tyr Ile Lys Gln Ala Leu Val Leu Lys Glu Val Lys
  1               5                  10                  15

His Val Phe Gln Lys Leu Ile Gly Glu Asp Pro Met Glu Ser Met Tyr
                 20                  25                  30

Met Val Asp Thr Ile Gln Arg Leu Gly Ile Glu His His Phe Glu Glu
             35                  40                  45

Glu Ile Glu Ala Ala Leu Gln Lys Gln His Leu Ile Phe Ser Ser His
 50                  55                  60

Leu Ser Asp Phe Ala Asn Asn His Lys Leu Cys Glu Val Ala Leu Pro
 65                  70                  75                  80

Phe Arg Leu Leu Arg Gln Arg Gly His Tyr Val Leu Ala Asp Val Phe
                 85                  90                  95

Asp Asn Leu Lys Ser Asn Lys Lys Glu Phe Arg Glu Lys His Gly Glu
            100                 105                 110

Asp Val Lys Gly Leu Ile Ser Leu Tyr Glu Ala Thr Gln Leu Gly Ile
        115                 120                 125

Glu Gly Glu Asp Ser Leu Asp Asp Ala Gly Tyr Leu Cys His Gln Leu
130                 135                 140

Leu His Ala Trp Leu Thr Arg His Glu Glu His Asn Glu Ala Met Tyr
145                 150                 155                 160

Val Ala Lys Thr Leu Gln His Pro Leu His Tyr Asp Leu Ser Arg Phe
                165                 170                 175

Arg Asp Asp Thr Ser Ile Leu Leu Asn Asp Phe Lys Thr Lys Arg Glu
            180                 185                 190

Trp Glu Cys Leu Glu Glu Leu Ala Glu Ile Asn Ser Ser Ile Val Arg
        195                 200                 205

Phe Val Asn Gln Asn Glu Ile Thr Gln Val Tyr Lys Trp Trp Lys Asp
210                 215                 220

Leu Gly Leu Asn Asn Glu Val Lys Phe Ala Arg Tyr Gln Pro Leu Lys
225                 230                 235                 240

Trp Tyr Met Trp Pro Met Ala Cys Phe Thr Asp Pro Arg Phe Ser Glu
                245                 250                 255

Gln Arg Ile Glu Leu Thr Lys Pro Ile Ser Leu Val Tyr Ile Ile Asp
            260                 265                 270

Asp Ile Phe Asp Val Tyr Gly Thr Leu Asp Gln Leu Thr Leu Phe Thr
        275                 280                 285

Asp Ala Ile Lys Arg Trp Glu Leu Ala Ser Thr Glu Gln Leu Pro Asp
290                 295                 300

Phe Met Lys Met Cys Leu Arg Val Leu Tyr Glu Ile Thr Asn Asp Phe
305                 310                 315                 320
```

Ala Glu Lys Ile Cys Lys Lys His Gly Phe Asn Pro Ile Glu Thr Leu
            325                 330                 335

Lys Arg Ser Trp Val Arg Leu Leu Asn Ala Phe Leu Glu Glu Ala His
        340                 345                 350

Trp Leu Asn Ser Gly His Leu Pro Arg Ser Ala Glu Tyr Leu Asn Asn
            355                 360                 365

Gly Ile Val Ser Thr Gly Val His Val Leu Val His Ser Phe Phe
    370                 375                 380

Leu Met Asp Tyr Ser Ile Asn Asn Glu Ile Val Ala Ile Val Asp Asn
385                 390                 395                 400

Val Pro Gln Ile Ile His Ser Val Ala Lys Ile Leu Arg Leu Ser Asp
                405                 410                 415

Asp Leu Glu Gly Ala Lys Ser Glu Asp Gln Asn Gly Leu Asp Gly Ser
            420                 425                 430

Tyr Ile Asp Cys Tyr Met Asn Glu His Gln Asp Val Ser Ala Gly Asp
        435                 440                 445

Ala Gln Arg His Val Ala His Leu Ile Ser Cys Glu Trp Lys Arg Leu
    450                 455                 460

Asn Arg Glu Ile Leu Thr Gln Asn Gln Leu Pro Ser Ser Phe Thr Asn
465                 470                 475                 480

Phe Cys Leu Asn Ala Ala Arg Met Val Pro Leu Met Tyr His Tyr Arg
                485                 490                 495

Ser Asn Pro Gly Leu Ser Thr Leu Gln Glu His Val Lys Leu Leu Ser
            500                 505                 510

Asn Asn Ala Val Ala Gly Ala Glu Arg His Val Val His Ile Leu Cys
        515                 520                 525

Leu Gln Phe Val Ile Glu
    530

<210> SEQ ID NO 57
<211> LENGTH: 581
<212> TYPE: PRT
<213> ORGANISM: Phaseolus vulgaris

<400> SEQUENCE: 57

Met Gln Gly Pro Leu Cys Ser Val Ala Ser Ala Thr Ser Pro Thr Cys
1               5                   10                  15

Ser Lys Asp Ser Phe Phe Arg Phe Leu Gln Arg Ser Gln Asn Thr His
            20                  25                  30

Phe Phe Gln Ile His Ser Asn His Pro Phe Leu Lys Ala Cys Pro Lys
        35                  40                  45

Pro Lys Ser Val Ser Leu Lys Ala Tyr Ser Ser Thr Asp Val Ile Tyr
    50                  55                  60

Val Lys Gln Ala Ser Leu Leu Lys Glu Ala Lys His Leu Ser Asn Lys
65                  70                  75                  80

Leu Ile Arg Glu Asn Pro Met Glu Ser Leu His Met Ile Asp Ile Ile
                85                  90                  95

Gln Arg Leu Gly Ile Glu His His Phe Glu Gln Glu Ile Gln Leu Val
            100                 105                 110

Leu Gln Lys Gln Leu Ile Leu Ser Asn His Pro Cys Asp Phe Asp
        115                 120                 125

Phe Phe Ser Ser His Asp Gln Leu Tyr Glu Val Ala Leu Ala Phe Arg
    130                 135                 140

Leu Leu Arg Gln Gly Gly Tyr Tyr Val Asn Ala Asp Leu Phe Asp Ile
145                 150                 155                 160

-continued

Leu Lys Asn Glu Lys Arg Lys Phe Lys Glu Ile Tyr Gly Glu Asp Val
            165                 170                 175

Lys Val Leu Ser Ala Leu Tyr Glu Ala Ser Gln Leu Gly Val Gln Glu
            180                 185                 190

Asp Ser Val Asp Val Gly Tyr Leu Ser Leu Gln Leu Leu His Ala
            195                 200                 205

Trp Leu Arg Arg His Glu Glu His Pro Gln Ala Ile His Val Thr Lys
    210                 215                 220

Thr Leu His Ser Pro Leu His His Gly Phe Ser Arg Phe Arg Asp Ala
225                 230                 235                 240

Asn Ile Phe Pro Ile Gln Phe Asn Thr Asn Asn Glu Trp Ile Gly Cys
            245                 250                 255

Leu Glu Glu Leu Ala Glu Ile Asn Ser Cys Val Val Ser Leu Met Asn
            260                 265                 270

Gln Lys Glu Ile Thr Glu Val Tyr Lys Trp Lys Thr Leu Glu Met
        275                 280                 285

Ala Lys Glu Glu Lys Phe Arg Ser Tyr Gln Pro Leu Lys Trp Tyr Met
        290                 295                 300

Trp Pro Met Ala Cys Leu Thr Asn Pro Cys Leu Ser Gln Gln Arg Ile
305                 310                 315                 320

Gln Leu Thr Lys Phe Ile Ser Leu Ile Tyr Ile Val Asp Asp Ile Phe
                325                 330                 335

Asp Ala Tyr Gly Thr Leu Asp Gln Leu Thr Leu Phe Thr Asp Ala Ile
            340                 345                 350

Ile Arg Trp Glu Leu Gly Gly Thr Glu Gln Leu Pro Gly Phe Met Lys
        355                 360                 365

Met Cys Leu Ser Val Leu Tyr Asp Thr Thr Asn Asp Phe Ala Glu Glu
370                 375                 380

Val Tyr Lys Lys His Gly Leu Asn Pro Ile Asp Thr Leu Lys Arg Ser
385                 390                 395                 400

Trp Val Arg Leu Leu Asn Ala Phe Met Glu Glu Ala His Trp Leu Lys
            405                 410                 415

Gly Gly Asp Leu Pro Arg Ser Glu Glu Tyr Leu Asn Asn Gly Ile Val
            420                 425                 430

Ser Ser Gly Val His Val Leu Leu Leu Tyr Ala Phe Phe Leu Leu Asp
        435                 440                 445

Gln Ser Ile Asn Met Glu Ser Val Ala Val Met Asp Asn Phe Pro Gln
        450                 455                 460

Ile Ile Tyr Ser Val Ala Lys Ile Leu Arg Leu Ser Asp Asp Leu Glu
465                 470                 475                 480

Gly Ala Lys Lys Lys Asp Glu Lys Gly Val Asp Gly Ser Tyr Leu Asp
                485                 490                 495

Cys Tyr Met Asn Glu His Gln His Val Ser Ala Glu Asp Ala Gln Asn
            500                 505                 510

His Val Ser His Leu Ile Gln Ser Glu Trp Lys Arg Leu Asn Gln Gln
        515                 520                 525

Ile Leu Thr Gln Asn Gln Leu Ser Ser Ser Phe Ala Asn Ile Cys Leu
    530                 535                 540

Asn Gly Ala Arg Met Val Pro Leu Met Tyr His Thr Thr Asn Asn Pro
545                 550                 555                 560

Tyr Leu Ser Ile Met Gln Glu His Val Met Thr Leu Leu His Thr Ala
                565                 570                 575

Gly Ala Glu Thr Val
            580

<210> SEQ ID NO 58
<211> LENGTH: 366
<212> TYPE: PRT
<213> ORGANISM: Persicaria minor

<400> SEQUENCE: 58

Met Glu Met Gly Asn Gly Thr Glu His Thr Val Lys Ala Val Gly
1               5                   10                  15

Trp Ala Ala Arg Asp Pro Ser Gly His Leu Ser Pro Phe Thr Phe Ser
                20                  25                  30

Arg Arg Ala Thr Gly Glu Leu Asp Val Thr Phe Lys Val Leu Tyr Cys
            35                  40                  45

Gly Ile Cys His Ser Asp Leu His Tyr Ile Lys Asn Glu Trp Ser Asn
    50                  55                  60

Thr Ile Tyr Pro Ala Leu Pro Gly His Glu Ile Val Gly Val Thr
65                  70                  75                  80

Glu Val Gly Ser Lys Val Asn Lys Phe Lys Val Gly Asp Lys Val Gly
                85                  90                  95

Val Gly Cys Ile Val Gly Ser Cys His Ser Cys Pro Asn Cys Asn Asn
            100                 105                 110

His Leu Glu Asn Tyr Cys Pro Asn Arg Ile Leu Thr Phe Gly Ser Arg
        115                 120                 125

Tyr Tyr Asp Gly Thr Leu Asn His Gly Gly Tyr Ser Asp Leu Met Val
    130                 135                 140

Val Gln Glu His Phe Ala Val Arg Ile Pro Asp Ala Leu Pro Leu Asp
145                 150                 155                 160

Ser Ala Ala Pro Leu Leu Cys Ala Gly Ile Thr Val Tyr Ser Pro Leu
                165                 170                 175

Arg Tyr Tyr Gly Leu Asp Lys Pro Gly Leu His Val Gly Val Val Gly
            180                 185                 190

Leu Gly Gly Leu Gly His Met Ala Val Lys Phe Ala Lys Ala Phe Gly
        195                 200                 205

Val Lys Val Thr Val Val Ser Thr Ser Pro Ala Lys Lys Glu Asp Ala
    210                 215                 220

Ile Ser Gly Leu Gly Ala His Ser Phe Ile Leu Ser Thr Asp Ala Glu
225                 230                 235                 240

Gln Met Gln Ala Ala Val Gly Thr Met Asp Gly Ile Ile Asp Thr Val
                245                 250                 255

Ser Ala Ser His Pro Leu Pro Pro Leu Ile Ser Leu Leu Lys Ser His
            260                 265                 270

Gly Lys Leu Val Met Val Gly Asp Pro Pro Lys Pro Leu Glu Leu Pro
        275                 280                 285

Val Phe Pro Leu Leu Leu Gly Arg Lys Met Val Ala Gly Ser Ala Ile
    290                 295                 300

Gly Gly Met Lys Glu Thr Gln Glu Met Ile Asp Phe Ala Ala Lys Glu
305                 310                 315                 320

Gly Val Arg Ala Asp Val Glu Val Ile Pro Met Asp Tyr Val Asn Thr
                325                 330                 335

Ala Met Gln Arg Val Ser Lys Ser Asp Val Lys Tyr Arg Phe Val Ile
            340                 345                 350

Asp Ile Gly Asn Thr Phe Asn Asp Ser Leu Ile Ser Ser Glu
        355                 360                 365

<210> SEQ ID NO 59
<211> LENGTH: 386
<212> TYPE: PRT
<213> ORGANISM: Picea abies

<400> SEQUENCE: 59

```
Met Gly Tyr Asn Gly Met Val Val Ser Ser Asn Leu Gly Leu Tyr Tyr
1               5                   10                  15

Leu Asn Ile Ala Ser Arg Glu Cys Asn Leu Lys Arg Ile Ser Ile Pro
            20                  25                  30

Ser Pro Phe His Gly Val Ser Thr Ser Leu Gly Ser Ser Thr Ser Lys
        35                  40                  45

His Leu Gly Leu Arg Gly His Leu Lys Lys Glu Leu Leu Ser His Arg
    50                  55                  60

Leu Leu Leu Ser Ser Thr Arg Ser Ser Lys Ala Leu Val Gln Leu Ala
65                  70                  75                  80

Asp Leu Ser Glu Gln Val Lys Asn Val Val Glu Phe Asp Phe Asp Lys
                85                  90                  95

Tyr Met His Ser Lys Ala Ile Ala Val Asn Glu Ala Leu Asp Lys Val
            100                 105                 110

Ile Pro Pro Arg Tyr Pro Gln Lys Ile Tyr Glu Ser Met Arg Tyr Ser
        115                 120                 125

Leu Leu Ala Gly Gly Lys Arg Val Arg Pro Ile Leu Cys Ile Ala Ala
    130                 135                 140

Cys Glu Leu Met Gly Gly Thr Glu Glu Leu Ala Met Pro Thr Ala Cys
145                 150                 155                 160

Ala Ile Glu Met Ile His Thr Met Ser Leu Ile His Asp Asp Leu Pro
                165                 170                 175

Tyr Ile Asp Asn Asp Asp Leu Arg Arg Gly Lys Pro Thr Asn His Lys
            180                 185                 190

Val Phe Gly Glu Asp Thr Ala Ile Ile Ala Gly Asp Ala Leu Leu Ser
        195                 200                 205

Leu Ala Phe Glu His Val Ala Val Ser Thr Ser Arg Thr Leu Gly Thr
    210                 215                 220

Asp Ile Ile Leu Arg Leu Leu Ser Glu Ile Gly Arg Ala Thr Gly Ser
225                 230                 235                 240

Glu Gly Val Met Gly Gly Gln Val Val Asp Ile Glu Ser Glu Gly Asp
                245                 250                 255

Pro Ser Ile Asp Leu Glu Thr Leu Glu Trp Val His Ile His Lys Thr
            260                 265                 270

Ala Val Leu Leu Glu Cys Ser Val Val Cys Gly Ala Ile Met Gly Gly
        275                 280                 285

Ala Ser Glu Asp Asp Ile Glu Arg Ala Arg Arg Tyr Ala Arg Cys Val
    290                 295                 300

Gly Leu Leu Phe Gln Val Val Asp Asp Ile Leu Asp Val Ser Gln Ser
305                 310                 315                 320

Ser Glu Glu Leu Gly Lys Thr Ala Gly Lys Asp Leu Ile Ser Asp Lys
                325                 330                 335

Ala Thr Tyr Pro Lys Leu Met Gly Leu Glu Lys Ala Lys Glu Phe Ala
            340                 345                 350

Asp Glu Leu Leu Asn Arg Gly Lys Gln Glu Leu Ser Cys Phe Asp Pro
        355                 360                 365

Thr Lys Ala Ala Pro Leu Phe Ala Leu Ala Asp Tyr Ile Ala Ser Arg
```

Gln Asn
385

<210> SEQ ID NO 60
<211> LENGTH: 368
<212> TYPE: PRT
<213> ORGANISM: Coffea canephora

<400> SEQUENCE: 60

Met Ala Ile Ser Ala Thr Ile Ser Ser Arg Tyr Gly Gly Ser Phe Leu
1               5                   10                  15

Gln Gln Asn Leu Asp His Phe Lys Ile Ser Val Gln Thr Ile Pro Arg
            20                  25                  30

Ser Gln Asn Ile Arg Met Ile Val Pro Lys Lys Ile Asn Pro Ala Ser
        35                  40                  45

His Val Ala Asn Ser Ser Ala Leu Glu Ala Ala Gln Val Gln Glu Lys
    50                  55                  60

Lys Pro Leu Ser Leu Asp Ser Pro Phe Pro Asp Phe Arg Phe Asp Glu
65                  70                  75                  80

Tyr Met Asn Thr Lys Ala Ile Ser Val Asn Lys Ala Leu Asp Asp Ala
                85                  90                  95

Ile Pro Leu Gln Glu Pro Ile Lys Ile His Glu Ala Met Arg Tyr Ser
            100                 105                 110

Leu Leu Ala Gly Gly Lys Arg Val Arg Pro Met Leu Cys Ile Ala Ser
        115                 120                 125

Cys Glu Leu Val Gly Gly Asp Glu Ser Leu Ala Met Pro Met Ala Cys
130                 135                 140

Ala Val Glu Met Ile His Thr Met Ser Leu Ile His Asp Asp Leu Pro
145                 150                 155                 160

Cys Met Asp Asn Asp Asp Leu Arg Arg Gly Lys Pro Thr Asn His Lys
                165                 170                 175

Val Tyr Gly Glu Glu Thr Ala Val Leu Ala Gly Asp Ala Leu Leu Ser
            180                 185                 190

Leu Ala Phe Glu His Val Ala Ala Lys Thr Gly Asn Val Glu Ala Ser
        195                 200                 205

Arg Val Val Arg Ala Ile Ala Glu Leu Ala Ser Ser Val Gly Ser Gln
    210                 215                 220

Gly Leu Val Ala Gly Gln Ile Val Asp Leu Ser Ser Glu Gly Glu Gln
225                 230                 235                 240

Val Asp Leu Asn His Leu Glu Tyr Ile His Val His Lys Thr Ser Lys
                245                 250                 255

Leu Leu Glu Ala Ala Val Val Cys Gly Ala Ile Val Gly Gly Ala Asn
            260                 265                 270

Glu Ala Glu Ile Glu Arg Met Arg Asn Tyr Ala Lys Cys Ile Gly Leu
        275                 280                 285

Leu Phe Gln Val Val Asp Asp Ile Leu Asp Val Thr Lys Ser Ser Glu
    290                 295                 300

Glu Leu Gly Lys Thr Ala Gly Lys Asp Leu Ala Thr Asp Lys Ala Thr
305                 310                 315                 320

Tyr Pro Lys Leu Met Gly Leu Glu Arg Ala Lys Lys Phe Ala Asp Glu
                325                 330                 335

Leu Val Ala Val Ala Thr Glu Glu Leu Ser His Phe Asp Ala Val Lys
            340                 345                 350

```
Ala Ala Pro Leu Tyr His Leu Ala Asn Tyr Ile Ala Tyr Arg Gln Asn
        355                 360                 365

<210> SEQ ID NO 61
<211> LENGTH: 288
<212> TYPE: PRT
<213> ORGANISM: Physcomitrella patens

<400> SEQUENCE: 61

Met Lys Ser Lys Ala Gln Ala Val Asn Val Leu Asp Lys Ala Val
1               5                   10                  15

Pro Met Gln Tyr Pro Glu Lys Ile Arg Glu Ala Met Arg Tyr Ser Leu
            20                  25                  30

Leu Ala Gly Gly Lys Arg Val Arg Pro Ala Leu Cys Ile Ala Ala Cys
        35                  40                  45

Glu Leu Val Gly Gly Asn Glu Glu Met Ser Met Pro Ala Ala Cys Ala
    50                  55                  60

Met Glu Met Val His Thr Met Ser Leu Ile His Asp Asp Leu Pro Cys
65                  70                  75                  80

Met Asp Asn Asp Asp Leu Arg Arg Gly Lys Pro Thr Asn His Lys Val
                85                  90                  95

Phe Gly Glu Asp Thr Ala Val Leu Ala Gly Asp Ala Leu Leu Thr Tyr
            100                 105                 110

Ala Phe Glu His Ile Ala Arg Asp Thr Thr Gly Val Pro Ala Asp Arg
        115                 120                 125

Val Leu Arg Val Ile Ala His Leu Gly Lys Ala Val Gly Ser Glu Gly
    130                 135                 140

Leu Val Ala Gly Gln Ile Val Asp Ile Ala Ser Glu Gly Asp Pro Thr
145                 150                 155                 160

Val Gly Leu Glu Thr Leu Glu Tyr Val His Thr His Lys Thr Ala Val
                165                 170                 175

Leu Leu Glu Ser Ser Val Val Cys Gly Ala Ile Leu Gly Gly Ala Ser
            180                 185                 190

Glu Asp Glu Ile Ser Arg Leu Ser Lys Tyr Ala Arg Asn Val Gly Leu
        195                 200                 205

Leu Phe Gln Val Val Asp Asp Ile Leu Asp Val Thr Lys Ser Ser Ala
    210                 215                 220

Glu Leu Gly Lys Thr Ala Gly Lys Asp Leu Leu Ala Asp Lys Ala Thr
225                 230                 235                 240

Tyr Pro Lys Leu Leu Gly Leu Glu Lys Ser Lys Ala Phe Ala Glu Glu
                245                 250                 255

Leu Thr Arg Lys Ala Lys Asp Gln Leu Ser Val Phe Asp Gln Gln Lys
            260                 265                 270

Ala Ala Pro Leu Leu Gly Leu Ala Asp Tyr Ile Ala Tyr Arg Gln Asn
        275                 280                 285

<210> SEQ ID NO 62
<211> LENGTH: 383
<212> TYPE: PRT
<213> ORGANISM: Picea glauca

<400> SEQUENCE: 62

Met Ala Tyr Ser Ser Met Ala Pro Ser Cys His Cys Leu His Phe Met
1               5                   10                  15

Asn Ile Val Ser Gln Glu Cys Asn Leu Lys Arg Val Ser Ile Gln Ser
            20                  25                  30
```

Arg Arg Phe Arg Gly Leu Ser Thr Ser Leu Trp Ser Gly Gly Phe
            35                  40                  45

Gln Gly His Leu Lys Arg Glu Leu Ser Ala Tyr Arg His Leu Val Ser
 50                  55                  60

Ser Leu Arg Cys Ser Asn Thr Asn Ala Gln Leu Ala Asn Leu Ser Glu
 65                  70                  75                  80

Gln Val Lys Glu Lys Val Thr Glu Phe Asp Phe Lys Glu Tyr Met Arg
                 85                  90                  95

Ser Lys Ala Met Ser Val Asn Glu Ala Leu Asp Arg Ala Val Pro Leu
            100                 105                 110

Arg Tyr Pro Glu Lys Ile His Glu Ala Met Arg Tyr Ser Leu Leu Ala
        115                 120                 125

Gly Gly Lys Arg Val Arg Pro Ile Leu Cys Ile Ala Ala Cys Glu Leu
130                 135                 140

Val Gly Gly Ser Glu Glu Leu Ala Met Pro Thr Ala Cys Ala Met Glu
145                 150                 155                 160

Ile Ile His Thr Met Ser Leu Ile His Asp Asp Leu Pro Pro Met Asp
                165                 170                 175

Asn Asp Asp Leu Arg Arg Gly Lys Pro Thr Asn His Lys Val Phe Gly
            180                 185                 190

Glu Gly Thr Ala Val Leu Ala Gly Asp Ala Leu Leu Ser Phe Ala Phe
        195                 200                 205

Glu His Ile Ala Val Ser Thr Ser Lys Thr Val Glu Ser Asp Arg Val
    210                 215                 220

Leu Arg Val Val Ser Glu Leu Gly Arg Ala Ile Gly Ser Glu Gly Val
225                 230                 235                 240

Ala Gly Gly Gln Val Ala Asp Ile Thr Ser Gln Gly Asn Pro Ser Val
                245                 250                 255

Gly Leu Glu Thr Leu Glu Trp Ile His Ile His Lys Thr Ala Val Leu
            260                 265                 270

Leu Glu Cys Ser Val Ala Ser Gly Ala Ile Ile Gly Gly Ala Ser Glu
        275                 280                 285

Asp Glu Ile Glu Arg Val Arg Lys Tyr Ala Arg Cys Val Gly Leu Leu
    290                 295                 300

Phe Gln Val Val Asp Asp Ile Leu Asp Val Thr Lys Ser Ser Glu Glu
305                 310                 315                 320

Leu Gly Lys Thr Ala Ala Lys Asp Leu Leu Ser Asp Lys Ala Thr Tyr
                325                 330                 335

Pro Lys Leu Met Gly Leu Glu Lys Ala Lys Glu Phe Ala Asp Glu Leu
            340                 345                 350

Leu Gly Lys Ala Lys Glu Glu Leu Ser Phe Phe Asn Pro Thr Lys Ala
        355                 360                 365

Ala Pro Leu Leu Gly Leu Ala Asp Tyr Ile Ala Gln Arg Gln Asn
    370                 375                 380

<210> SEQ ID NO 63
<211> LENGTH: 567
<212> TYPE: PRT
<213> ORGANISM: Ocimum basilicum

<400> SEQUENCE: 63

Met Ser Cys Ala Arg Ile Thr Val Thr Leu Pro Tyr Arg Ser Ala Lys
 1               5                  10                  15

Thr Ser Ile Gln Arg Gly Ile Thr His Tyr Pro Ala Leu Ile Arg Pro
                 20                  25                  30

-continued

```
Arg Phe Ser Ala Cys Thr Pro Leu Ala Ser Ala Met Pro Leu Ser Ser
        35                  40                  45

Thr Pro Leu Ile Asn Gly Asp Asn Ser Gln Arg Lys Asn Thr Arg Gln
 50                  55                  60

His Met Glu Glu Ser Ser Lys Arg Arg Glu Tyr Leu Leu Glu Glu
 65                  70                  75                  80

Thr Thr Arg Lys Leu Gln Arg Asn Asp Thr Glu Ser Val Glu Lys Leu
                85                  90                  95

Lys Leu Ile Asp Asn Ile Gln Gln Leu Gly Ile Gly Tyr Tyr Phe Glu
                100                 105                 110

Asp Ala Ile Asn Ala Val Leu Arg Ser Pro Phe Ser Thr Gly Glu Glu
                115                 120                 125

Asp Leu Phe Thr Ala Ala Leu Arg Phe Arg Leu Leu Arg His Asn Gly
            130                 135                 140

Ile Glu Ile Ser Pro Glu Ile Phe Leu Lys Phe Lys Asp Glu Arg Gly
145                 150                 155                 160

Lys Phe Asp Glu Ser Asp Thr Leu Gly Leu Leu Ser Leu Tyr Glu Ala
                165                 170                 175

Ser Asn Leu Gly Val Ala Gly Glu Glu Ile Leu Glu Glu Ala Met Glu
            180                 185                 190

Phe Ala Glu Ala Arg Leu Arg Arg Ser Leu Ser Glu Pro Ala Ala Pro
            195                 200                 205

Leu His Gly Glu Val Ala Gln Ala Leu Asp Val Pro Arg His Leu Arg
            210                 215                 220

Met Ala Arg Leu Glu Ala Arg Arg Phe Ile Glu Gln Tyr Gly Lys Gln
225                 230                 235                 240

Ser Asp His Asp Gly Asp Leu Leu Glu Leu Ala Ile Leu Asp Tyr Asn
                245                 250                 255

Gln Val Gln Ala Gln His Gln Ser Glu Leu Thr Glu Ile Ile Arg Trp
            260                 265                 270

Trp Lys Glu Leu Gly Leu Val Asp Lys Leu Ser Phe Gly Arg Asp Arg
            275                 280                 285

Pro Leu Glu Cys Phe Leu Trp Thr Val Gly Leu Leu Pro Glu Pro Lys
            290                 295                 300

Tyr Ser Ser Val Arg Ile Glu Leu Ala Lys Ala Ile Ser Ile Leu Leu
305                 310                 315                 320

Val Ile Asp Asp Ile Phe Asp Thr Tyr Gly Glu Met Asp Asp Leu Ile
                325                 330                 335

Leu Phe Thr Asp Ala Ile Arg Arg Trp Asp Leu Glu Ala Met Glu Gly
            340                 345                 350

Leu Pro Glu Tyr Met Lys Ile Cys Tyr Met Ala Leu Tyr Asn Thr Thr
            355                 360                 365

Asn Glu Val Cys Tyr Lys Val Leu Arg Asp Thr Gly Arg Ile Val Leu
            370                 375                 380

Leu Asn Leu Lys Ser Thr Trp Ile Asp Met Ile Glu Gly Phe Met Glu
385                 390                 395                 400

Glu Ala Lys Trp Phe Asn Gly Ser Ala Pro Lys Leu Glu Glu Tyr
            405                 410                 415

Ile Glu Asn Gly Val Ser Thr Ala Gly Ala Tyr Met Ala Phe Ala His
            420                 425                 430

Ile Phe Phe Leu Ile Gly Glu Gly Val Thr His Gln Asn Ser Gln Leu
            435                 440                 445
```

```
Phe Thr Gln Lys Pro Tyr Pro Lys Val Phe Ser Ala Ala Gly Arg Ile
            450                 455                 460

Leu Arg Leu Trp Asp Asp Leu Gly Thr Ala Lys Glu Glu Gln Glu Arg
465                 470                 475                 480

Gly Asp Leu Ala Ser Cys Val Gln Leu Phe Met Lys Glu Lys Ser Leu
                    485                 490                 495

Thr Glu Glu Glu Ala Arg Ser Arg Ile Leu Glu Glu Ile Lys Gly Leu
                500                 505                 510

Trp Arg Asp Leu Asn Gly Glu Leu Val Tyr Asn Lys Asn Leu Pro Leu
                515                 520                 525

Ser Ile Ile Lys Val Ala Leu Asn Met Ala Arg Ala Ser Gln Val Val
530                 535                 540

Tyr Lys His Asp Gln Asp Thr Tyr Phe Ser Ser Val Asp Asn Tyr Val
545                 550                 555                 560

Asp Ala Leu Phe Phe Thr Gln
                    565

<210> SEQ ID NO 64
<211> LENGTH: 584
<212> TYPE: PRT
<213> ORGANISM: Phyla dulcis

<400> SEQUENCE: 64

Met Ala Ser Ala Arg Ser Thr Ile Ser Leu Ser Ser Gln Ser Ser His
1                   5                   10                  15

His Gly Phe Ser Lys Asn Ser Phe Pro Trp Gln Leu Arg His Ser Arg
                20                  25                  30

Phe Val Met Gly Ser Arg Ala Arg Thr Cys Ala Cys Met Ser Ser Ser
            35                  40                  45

Val Ser Leu Pro Thr Ala Thr Thr Ser Ser Ser Val Ile Thr Gly Asn
        50                  55                  60

Asp Ala Leu Leu Lys Tyr Ile Arg Gln Pro Met Val Ile Pro Leu Lys
65                  70                  75                  80

Glu Lys Glu Gly Thr Lys Arg Arg Glu Tyr Leu Leu Glu Lys Thr Ala
                85                  90                  95

Arg Glu Leu Gln Gly Thr Thr Glu Ala Ala Glu Lys Leu Lys Phe Ile
            100                 105                 110

Asp Thr Ile Gln Arg Leu Gly Ile Ser Cys Tyr Phe Glu Asp Glu Ile
        115                 120                 125

Asn Gly Ile Leu Gln Ala Glu Leu Ser Asp Thr Asp Gln Leu Glu Asp
    130                 135                 140

Gly Leu Phe Thr Thr Ala Leu Arg Phe Arg Leu Leu Arg His Tyr Gly
145                 150                 155                 160

Tyr Gln Ile Ala Pro Asp Val Phe Leu Lys Phe Thr Asp Gln Asn Gly
                165                 170                 175

Lys Phe Lys Glu Ser Leu Ala Asp Asp Thr Gln Gly Leu Val Ser Leu
            180                 185                 190

Tyr Glu Ala Ser Tyr Met Gly Ala Asn Gly Glu Asn Ile Leu Glu Glu
        195                 200                 205

Ala Met Lys Phe Thr Lys Thr His Leu Gln Gly Arg Gln His Ala Met
    210                 215                 220

Arg Glu Val Ala Glu Ala Leu Glu Leu Pro Arg His Leu Arg Met Ala
225                 230                 235                 240

Arg Leu Glu Ala Arg Arg Tyr Ile Glu Gln Tyr Gly Thr Met Ile Gly
                245                 250                 255
```

His Asp Lys Asp Leu Leu Glu Leu Val Ile Leu Asp Tyr Asn Asn Val
            260                 265                 270

Gln Ala Gln His Gln Ala Glu Leu Ala Glu Ile Ala Arg Trp Trp Lys
        275                 280                 285

Glu Leu Gly Leu Val Asp Lys Leu Thr Phe Ala Arg Asp Arg Pro Leu
    290                 295                 300

Glu Cys Phe Leu Trp Thr Val Gly Leu Leu Pro Glu Pro Lys Tyr Ser
305                 310                 315                 320

Ala Cys Arg Ile Glu Leu Ala Lys Thr Ile Ala Ile Leu Leu Val Ile
                325                 330                 335

Asp Asp Ile Phe Asp Thr Tyr Gly Lys Met Glu Glu Leu Ala Leu Phe
            340                 345                 350

Thr Glu Ala Ile Arg Arg Trp Asp Leu Glu Ala Met Glu Thr Leu Pro
        355                 360                 365

Glu Tyr Met Lys Ile Cys Tyr Met Ala Leu Tyr Asn Thr Thr Asn Glu
    370                 375                 380

Ile Cys Tyr Lys Val Leu Lys Lys Asn Gly Trp Ser Val Leu Pro Tyr
385                 390                 395                 400

Leu Arg Tyr Thr Trp Met Asp Met Ile Glu Gly Phe Met Val Glu Ala
                405                 410                 415

Lys Trp Phe Asn Gly Gly Ser Ala Pro Asn Leu Glu Glu Tyr Ile Glu
            420                 425                 430

Asn Gly Val Ser Thr Ala Gly Ala Tyr Met Ala Leu Val His Leu Phe
        435                 440                 445

Phe Leu Ile Gly Glu Gly Val Ser Ala Gln Asn Ala Gln Ile Leu Leu
    450                 455                 460

Lys Lys Pro Tyr Pro Lys Leu Phe Ser Ala Ala Gly Arg Ile Leu Arg
465                 470                 475                 480

Leu Trp Asp Asp Leu Gly Thr Ala Lys Glu Glu Gly Arg Gly Asp
                485                 490                 495

Leu Ala Ser Ser Ile Arg Leu Phe Met Lys Glu Lys Asn Leu Thr Thr
            500                 505                 510

Glu Glu Glu Gly Arg Asn Gly Ile Gln Glu Glu Ile Tyr Ser Leu Trp
        515                 520                 525

Lys Asp Leu Asn Gly Glu Leu Ile Ser Lys Gly Arg Met Pro Leu Ala
    530                 535                 540

Ile Ile Lys Val Ala Leu Asn Met Ala Arg Ala Ser Gln Val Val Tyr
545                 550                 555                 560

Lys His Asp Glu Asp Ser Tyr Phe Ser Cys Val Asp Asn Tyr Val Glu
                565                 570                 575

Ala Leu Phe Phe Thr Pro Leu Leu
            580

<210> SEQ ID NO 65
<211> LENGTH: 603
<212> TYPE: PRT
<213> ORGANISM: Perilla setoyensis

<400> SEQUENCE: 65

Met Cys Ser Ile Ser Gln Lys Val Val Ile Gly Leu Asn Lys Ala Ala
1               5                   10                  15

Ala Asn Asn Cys Leu Gln Asn Leu Asp Arg Arg Gly Phe Lys Thr Arg
            20                  25                  30

Arg Val Ser Ser Ser Glu Ala Ala Ser Cys Leu Arg Ala Ser Ser Ser

```
            35                  40                  45
Leu Gln Leu Asp Val Lys Pro Val Glu Glu Gly Arg Arg Ser Gly Asn
 50                  55                  60

Tyr Gln Pro Ser Ile Trp Asp Phe Asn Tyr Val Gln Ser Leu Asn Thr
 65                  70                  75                  80

Pro Tyr Lys Glu Glu Arg Tyr Leu Thr Arg His Ala Glu Leu Ile Val
                 85                  90                  95

Gln Val Lys Pro Leu Leu Glu Lys Lys Met Glu Ala Thr Gln Gln Leu
                100                 105                 110

Glu Leu Ile Asp Asp Leu Asn Asn Leu Gly Leu Ser Tyr Phe Phe Gln
                115                 120                 125

Asp Arg Ile Lys Gln Ile Leu Ser Phe Ile Tyr Asp Glu Asn Gln Cys
            130                 135                 140

Phe His Ser Asn Ile Asn Asp Gln Ala Glu Lys Arg Asp Leu Tyr Phe
145                 150                 155                 160

Thr Ala Leu Gly Phe Arg Leu Leu Arg Gln His Gly Phe Asn Val Ser
                165                 170                 175

Gln Glu Val Phe Asp Cys Phe Lys Asn Asp Lys Gly Ser Asp Phe Lys
                180                 185                 190

Ala Ser Leu Ser Gly Asn Thr Lys Gly Leu Leu Gln Leu Tyr Glu Ala
            195                 200                 205

Ser Phe Leu Val Arg Glu Gly Glu Asp Thr Leu Glu Leu Ala Arg Gln
210                 215                 220

Phe Ala Thr Lys Phe Leu Arg Arg Lys Leu Asp Glu Ile Asp Asp Asn
225                 230                 235                 240

His Leu Leu Ser Arg Ile His His Ser Leu Glu Ile Pro Leu His Trp
                245                 250                 255

Arg Ile Gln Arg Leu Glu Ala Arg Trp Phe Leu Asp Ala Tyr Ala Thr
                260                 265                 270

Arg His Asp Met Asn Pro Ile Ile Leu Glu Leu Ala Lys Leu Asp Phe
            275                 280                 285

Asn Ile Ile Gln Ala Thr His Gln Glu Glu Leu Lys Asp Val Ser Arg
290                 295                 300

Trp Trp Gln Asn Thr Arg Leu Ala Glu Lys Leu Pro Phe Val Arg Asp
305                 310                 315                 320

Arg Leu Val Glu Ser Tyr Phe Trp Ala Ile Ala Leu Phe Glu Pro His
                325                 330                 335

Gln Tyr Gly Tyr Gln Arg Arg Val Ala Ala Lys Ile Ile Thr Leu Ala
                340                 345                 350

Thr Ser Ile Asp Asp Val Tyr Asp Ile Tyr Gly Thr Leu Asp Glu Leu
            355                 360                 365

Gln Leu Phe Thr Asp Asn Phe Arg Arg Trp Asp Thr Glu Ser Leu Gly
            370                 375                 380

Gly Leu Pro Tyr Ser Met Gln Leu Phe Tyr Met Val Ile His Asn Phe
385                 390                 395                 400

Val Ser Glu Leu Ala Tyr Glu Ile Leu Lys Glu Lys Gly Phe Ile Ala
                405                 410                 415

Ile Pro Tyr Leu Gln Arg Ser Trp Val Asp Leu Ala Glu Ser Phe Leu
                420                 425                 430

Lys Glu Ala Asn Trp Tyr Tyr Ser Gly Tyr Thr Pro Ser Leu Glu Glu
            435                 440                 445

Tyr Ile Asp Asn Gly Ser Ile Ser Ile Gly Ala Val Ala Val Leu Ser
            450                 455                 460
```

-continued

Gln Val Tyr Phe Thr Leu Ala Asn Ser Ile Glu Lys Pro Lys Ile Glu
465                 470                 475                 480

Ser Met Tyr Lys Tyr His His Ile Leu Arg Leu Ser Gly Leu Leu Val
            485                 490                 495

Arg Leu His Asp Asp Leu Gly Thr Ser Leu Phe Glu Lys Lys Arg Gly
        500                 505                 510

Asp Val Pro Lys Ala Val Glu Ile Cys Met Lys Glu Arg Asn Asp Thr
    515                 520                 525

Glu Glu Glu Ala Glu Glu His Val Lys Tyr Leu Ile Arg Glu Ala Trp
530                 535                 540

Lys Glu Met Asn Thr Ala Thr Ala Ala Ala Gly Cys Pro Phe Met Asp
545                 550                 555                 560

Glu Leu Asn Val Ala Ala Ala Asn Leu Gly Arg Ala Ala Gln Phe Val
                565                 570                 575

Tyr Leu Asp Gly Asp Gly His Gly Val Gln His Ser Lys Ile His Gln
            580                 585                 590

Gln Met Gly Gly Leu Met Phe Lys Pro Tyr Val
        595                 600

<210> SEQ ID NO 66
<211> LENGTH: 594
<212> TYPE: PRT
<213> ORGANISM: Valeriana officinalis
<220> FEATURE:
<221> NAME/KEY: misc_feature
<222> LOCATION: (228)..(228)
<223> OTHER INFORMATION: Xaa can be any naturally occurring amino acid

<400> SEQUENCE: 66

Met Ile Thr Ser Ser Ser Val Arg Ser Leu Cys Cys Pro Lys Thr
1               5                   10                  15

Ser Ile Ile Ser Gly Lys Leu Leu Pro Ser Leu Leu Leu Thr Asn Val
            20                  25                  30

Ile Asn Val Ser Asn Gly Thr Ser Ser Arg Ala Cys Val Ser Met Ser
        35                  40                  45

Ser Leu Pro Val Ser Lys Ser Thr Ala Ser Ser Ile Ala Ala Pro Leu
    50                  55                  60

Val Arg Asp Asn Gly Ser Ala Leu Asn Phe Phe Pro Gln Ala Pro Gln
65                  70                  75                  80

Val Glu Ile Asp Glu Ser Ser Arg Ile Met Glu Leu Val Glu Ala Thr
                85                  90                  95

Arg Arg Thr Leu Arg Asn Glu Ser Ser Asp Ser Thr Glu Lys Met Arg
            100                 105                 110

Leu Ile Asp Ser Leu Gln Arg Leu Gly Leu Asn His His Phe Glu Gln
        115                 120                 125

Asp Ile Lys Glu Met Leu Gln Asp Phe Ala Asn Glu His Lys Asn Thr
    130                 135                 140

Asn Gln Asp Leu Phe Thr Thr Ser Leu Arg Phe Arg Leu Leu Arg His
145                 150                 155                 160

Asn Gly Phe Asn Val Thr Pro Asp Val Phe Asn Lys Phe Thr Glu Glu
                165                 170                 175

Asn Gly Lys Phe Lys Glu Ser Leu Gly Glu Asp Thr Ile Gly Ile Leu
            180                 185                 190

Ser Leu Tyr Glu Ala Ser Tyr Leu Gly Gly Lys Gly Glu Glu Ile Leu
        195                 200                 205

Ser Glu Ala Met Lys Phe Ser Glu Lys Leu Arg Glu Ser Ser Gly
    210                 215                 220

His Val Ala Xaa His Ile Arg Arg Gln Ile Phe Gln Ser Leu Glu Leu
225                 230                 235                 240

Pro Arg His Leu Arg Met Ala Arg Leu Glu Ser Arg Arg Tyr Ile Glu
                245                 250                 255

Glu Asp Tyr Ser Asn Glu Ile Gly Ala Asp Ser Ser Leu Leu Glu Leu
            260                 265                 270

Ala Lys Leu Asp Phe Asn Ser Val Gln Ala Leu His Gln Met Glu Leu
        275                 280                 285

Thr Glu Ile Ser Arg Trp Trp Lys Gln Leu Gly Leu Ser Asp Lys Leu
    290                 295                 300

Pro Phe Ala Arg Asp Arg Pro Leu Glu Cys Phe Leu Trp Thr Val Gly
305                 310                 315                 320

Leu Leu Pro Glu Pro Lys Tyr Ser Gly Cys Arg Ile Glu Leu Ala Lys
                325                 330                 335

Thr Ile Ala Val Leu Leu Val Ile Asp Asp Ile Phe Asp Thr Tyr Gly
            340                 345                 350

Ser Tyr Asp Gln Leu Ile Leu Phe Thr Asn Ala Ile Arg Arg Trp Asp
        355                 360                 365

Leu Asp Ala Met Asp Glu Leu Pro Glu Tyr Met Lys Ile Cys Tyr Met
370                 375                 380

Ala Leu Tyr Asn Thr Thr Asn Glu Ile Cys Tyr Lys Val Leu Lys Glu
385                 390                 395                 400

Asn Gly Trp Ser Val Leu Pro Tyr Leu Glu Arg Thr Trp Ile Asp Met
                405                 410                 415

Val Glu Gly Phe Met Leu Glu Ala Lys Trp Leu Asn Ser Gly Glu Gln
            420                 425                 430

Pro Asn Leu Glu Ala Tyr Ile Glu Asn Gly Val Thr Thr Ala Gly Ser
        435                 440                 445

Tyr Met Ala Leu Val His Leu Phe Phe Leu Ile Gly Asp Gly Val Asn
    450                 455                 460

Asp Glu Asn Val Lys Leu Leu Asp Pro Tyr Pro Lys Leu Phe Ser
465                 470                 475                 480

Ser Ala Gly Arg Ile Leu Arg Leu Trp Asp Asp Leu Gly Thr Ala Lys
                485                 490                 495

Glu Glu Gln Glu Arg Gly Asp Val Ser Ser Ile Gln Leu Tyr Met
            500                 505                 510

Lys Glu Lys Asn Val Arg Ser Glu Ser Glu Gly Arg Glu Gly Ile Val
        515                 520                 525

Glu Ile Ile Tyr Asn Leu Trp Lys Asp Met Asn Gly Glu Leu Ile Gly
    530                 535                 540

Ser Asn Ala Leu Pro Gln Ala Ile Ile Glu Thr Ser Phe Asn Met Ala
545                 550                 555                 560

Arg Thr Ser Gln Val Val Tyr Gln His Glu Asp Asp Tyr Phe Ser
                565                 570                 575

Ser Val Asp Asn Tyr Val Gln Ser Leu Phe Phe Thr Pro Val Ser Val
            580                 585                 590

Ser Val

<210> SEQ ID NO 67
<211> LENGTH: 396
<212> TYPE: PRT
<213> ORGANISM: Lycopersicon esculentum

<400> SEQUENCE: 67

```
Met Ala Ser Ser Ala Gln Asp Gly Asn Asn Pro Leu Phe Ser Pro Tyr
1               5                   10                  15

Lys Met Gly Lys Phe Asn Leu Ser His Arg Val Val Leu Ala Pro Met
                20                  25                  30

Thr Arg Cys Arg Ala Leu Asn Asn Ile Pro Gln Ala Ala Leu Gly Glu
            35                  40                  45

Tyr Tyr Glu Gln Arg Ala Thr Ala Gly Gly Phe Leu Ile Thr Glu Gly
        50                  55                  60

Thr Met Ile Ser Pro Thr Ser Ala Gly Phe Pro His Val Pro Gly Ile
65                  70                  75                  80

Phe Thr Lys Glu Gln Val Arg Glu Trp Lys Lys Ile Val Asp Val Val
                85                  90                  95

His Ala Lys Gly Ala Val Ile Phe Cys Gln Leu Trp His Val Gly Arg
                100                 105                 110

Ala Ser His Glu Val Tyr Gln Pro Ala Gly Ala Ala Pro Ile Ser Ser
            115                 120                 125

Thr Glu Lys Pro Ile Ser Asn Arg Trp Arg Ile Leu Met Pro Asp Gly
130                 135                 140

Thr His Gly Ile Tyr Pro Lys Pro Arg Ala Ile Gly Thr Tyr Glu Ile
145                 150                 155                 160

Ser Gln Val Val Glu Asp Tyr Arg Arg Ser Ala Leu Asn Ala Ile Glu
                165                 170                 175

Ala Gly Phe Asp Gly Ile Glu Ile His Gly Ala His Gly Tyr Leu Ile
            180                 185                 190

Asp Gln Phe Leu Lys Asp Gly Ile Asn Asp Arg Thr Asp Glu Tyr Gly
        195                 200                 205

Gly Ser Leu Ala Asn Arg Cys Lys Phe Ile Thr Gln Val Val Gln Ala
210                 215                 220

Val Val Ser Ala Ile Gly Ala Asp Arg Val Gly Val Arg Val Ser Pro
225                 230                 235                 240

Ala Ile Asp His Leu Asp Ala Met Asp Ser Asn Pro Leu Ser Leu Gly
                245                 250                 255

Leu Ala Val Val Glu Arg Leu Asn Lys Ile Gln Leu His Ser Gly Ser
                260                 265                 270

Lys Leu Ala Tyr Leu His Val Thr Gln Pro Arg Tyr Val Ala Tyr Gly
            275                 280                 285

Gln Thr Glu Ala Gly Arg Leu Gly Ser Glu Glu Glu Ala Arg Leu
290                 295                 300

Met Arg Thr Leu Arg Asn Ala Tyr Gln Gly Thr Phe Ile Cys Ser Gly
305                 310                 315                 320

Gly Tyr Thr Arg Glu Leu Gly Ile Glu Ala Val Ala Gln Gly Asp Ala
                325                 330                 335

Asp Leu Val Ser Tyr Gly Arg Leu Phe Ile Ser Asn Pro Asp Leu Val
            340                 345                 350

Met Arg Ile Lys Leu Asn Ala Pro Leu Asn Lys Tyr Asn Arg Lys Thr
            355                 360                 365

Phe Tyr Thr Gln Asp Pro Val Gly Tyr Thr Asp Tyr Pro Phe Leu
        370                 375                 380

Gln Gly Asn Gly Ser Asn Gly Pro Leu Ser Arg Leu
385                 390                 395
```

<210> SEQ ID NO 68
<211> LENGTH: 360
<212> TYPE: PRT
<213> ORGANISM: Saccharomyces cerevisiae

<400> SEQUENCE: 68

| Met | Ser | Tyr | Pro | Glu | Lys | Phe | Glu | Gly | Ile | Ala | Ile | Gln | Ser | His | Glu |
|---|---|---|---|---|---|---|---|---|---|---|---|---|---|---|---|
| 1 | | | | 5 | | | | | 10 | | | | | 15 | |

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
        275                 280                 285

Tyr Gly Leu Lys Ala Val Ser Ile Ser Tyr Ser Ala Leu Gly Ser Ile
    290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
            340                 345                 350

Gly Tyr Asp Lys Glu Phe Ser Asp
        355                 360

<210> SEQ ID NO 69
<211> LENGTH: 459

<212> TYPE: PRT
<213> ORGANISM: Streptococcus pneumoniae

<400> SEQUENCE: 69

```
Met Ser Lys Ile Val Val Gly Ala Asn His Ala Gly Thr Ala Cys
1               5                   10                  15

Ile Asn Thr Met Leu Asp Asn Phe Gly Asn Glu Asn Glu Ile Val Val
            20                  25                  30

Phe Asp Gln Asn Ser Asn Ile Ser Phe Leu Gly Cys Gly Met Ala Leu
        35                  40                  45

Trp Ile Gly Glu Gln Ile Asp Gly Ala Glu Gly Leu Phe Tyr Ser Asp
    50                  55                  60

Lys Glu Lys Leu Glu Ala Lys Gly Ala Lys Val Tyr Met Asn Ser Pro
65                  70                  75                  80

Val Leu Ser Ile Asp Tyr Asp Asn Lys Val Thr Ala Glu Val Glu
                85                  90                  95

Gly Lys Glu His Lys Glu Ser Tyr Glu Lys Leu Ile Phe Ala Thr Gly
                100                 105                 110

Ser Thr Pro Ile Leu Pro Ile Glu Gly Val Glu Ile Val Lys Gly
                115                 120                 125

Asn Arg Glu Phe Lys Ala Thr Leu Glu Asn Val Gln Phe Val Lys Leu
130                 135                 140

Tyr Gln Asn Ala Glu Glu Val Ile Asn Lys Leu Ser Asp Lys Ser Gln
145                 150                 155                 160

His Leu Asp Arg Ile Ala Val Val Gly Gly Tyr Ile Gly Val Glu
                165                 170                 175

Leu Ala Glu Ala Phe Glu Arg Leu Gly Lys Glu Val Val Leu Val Asp
                180                 185                 190

Ile Val Asp Thr Val Leu Asn Gly Tyr Tyr Asp Lys Asp Phe Thr Gln
                195                 200                 205

Met Met Ala Lys Asn Leu Glu Asp His Asn Ile Arg Leu Ala Leu Gly
                210                 215                 220

Gln Thr Val Lys Ala Ile Glu Gly Asp Gly Lys Val Glu Arg Leu Ile
225                 230                 235                 240

Thr Asp Lys Glu Ser Phe Asp Val Asp Met Val Ile Leu Ala Val Gly
                245                 250                 255

Phe Arg Pro Asn Thr Ala Leu Ala Asp Gly Lys Ile Glu Leu Phe Arg
                260                 265                 270

Asn Gly Ala Phe Leu Val Asp Lys Lys Gln Glu Thr Ser Ile Pro Gly
                275                 280                 285

Val Tyr Ala Val Gly Asp Cys Ala Thr Val Tyr Asp Asn Ala Arg Lys
                290                 295                 300

Asp Thr Ser Tyr Ile Ala Leu Ala Ser Asn Ala Val Arg Thr Gly Ile
305                 310                 315                 320

Val Gly Ala Tyr Asn Ala Cys Gly His Glu Leu Glu Gly Ile Gly Val
                325                 330                 335

Gln Gly Ser Asn Gly Ile Ser Ile Tyr Gly Leu His Met Val Ser Thr
                340                 345                 350

Gly Leu Thr Leu Glu Lys Ala Lys Ala Gly Tyr Asn Ala Thr Glu
                355                 360                 365

Thr Gly Phe Asn Asp Leu Gln Lys Pro Glu Phe Met Lys His Asp Asn
                370                 375                 380

His Glu Val Ala Ile Lys Ile Val Phe Asp Lys Asp Ser Arg Glu Ile
385                 390                 395                 400
```

```
Leu Gly Ala Gln Met Val Ser His Asp Ile Ala Ile Ser Met Gly Ile
                405                 410                 415

His Met Phe Ser Leu Ala Ile Gln Glu His Val Thr Ile Asp Lys Leu
            420                 425                 430

Ala Leu Thr Asp Leu Phe Phe Leu Pro His Phe Asn Lys Pro Tyr Asn
        435                 440                 445

Tyr Ile Thr Met Ala Ala Leu Thr Ala Glu Lys
    450                 455

<210> SEQ ID NO 70
<211> LENGTH: 1174
<212> TYPE: PRT
<213> ORGANISM: Mycobacterium marinum

<400> SEQUENCE: 70

Met Ser Pro Ile Thr Arg Glu Glu Arg Leu Glu Arg Arg Ile Gln Asp
1               5                   10                  15

Leu Tyr Ala Asn Asp Pro Gln Phe Ala Ala Ala Lys Pro Ala Thr Ala
            20                  25                  30

Ile Thr Ala Ala Ile Glu Arg Pro Gly Leu Pro Leu Pro Gln Ile Ile
        35                  40                  45

Glu Thr Val Met Thr Gly Tyr Ala Asp Arg Pro Ala Leu Ala Gln Arg
    50                  55                  60

Ser Val Glu Phe Val Thr Asp Ala Gly Thr Gly His Thr Thr Leu Arg
65                  70                  75                  80

Leu Leu Pro His Phe Glu Thr Ile Ser Tyr Gly Glu Leu Trp Asp Arg
                85                  90                  95

Ile Ser Ala Leu Ala Asp Val Leu Ser Thr Glu Gln Thr Val Lys Pro
            100                 105                 110

Gly Asp Arg Val Cys Leu Leu Gly Phe Asn Ser Val Asp Tyr Ala Thr
        115                 120                 125

Ile Asp Met Thr Leu Ala Arg Leu Gly Ala Val Ala Val Pro Leu Gln
    130                 135                 140

Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
                165                 170                 175

Leu Ala Leu Ser Gly Gln Thr Ala Thr Arg Val Leu Val Phe Asp His
            180                 185                 190

His Arg Gln Val Asp Ala His Arg Ala Ala Val Glu Ser Ala Arg Glu
        195                 200                 205

Arg Leu Ala Gly Ser Ala Val Val Glu Thr Leu Ala Glu Ala Ile Ala
    210                 215                 220

Arg Gly Asp Val Pro Arg Gly Ala Ser Ala Gly Ser Ala Pro Gly Thr
225                 230                 235                 240

Asp Val Ser Asp Asp Ser Leu Ala Leu Leu Ile Tyr Thr Ser Gly Ser
                245                 250                 255

Thr Gly Ala Pro Lys Gly Ala Met Tyr Pro Arg Arg Asn Val Ala Thr
            260                 265                 270

Phe Trp Arg Lys Arg Thr Trp Phe Glu Gly Gly Tyr Glu Pro Ser Ile
        275                 280                 285

Thr Leu Asn Phe Met Pro Met Ser His Val Met Gly Arg Gln Ile Leu
    290                 295                 300

Tyr Gly Thr Leu Cys Asn Gly Gly Thr Ala Tyr Phe Val Ala Lys Ser
```

```
                305                 310                 315                 320
Asp Leu Ser Thr Leu Phe Glu Asp Leu Ala Leu Val Arg Pro Thr Glu
                325                 330                 335

Leu Thr Phe Val Pro Arg Val Trp Asp Met Val Phe Asp Glu Phe Gln
                340                 345                 350

Ser Glu Val Asp Arg Arg Leu Val Asp Gly Ala Asp Arg Val Ala Leu
                355                 360                 365

Glu Ala Gln Val Lys Ala Glu Ile Arg Asn Asp Val Leu Gly Gly Arg
            370                 375                 380

Tyr Thr Ser Ala Leu Thr Gly Ser Ala Pro Ile Ser Asp Glu Met Lys
385                 390                 395                 400

Ala Trp Val Glu Glu Leu Leu Asp Met His Leu Val Glu Gly Tyr Gly
                405                 410                 415

Ser Thr Glu Ala Gly Met Ile Leu Ile Asp Gly Ala Ile Arg Arg Pro
                420                 425                 430

Ala Val Leu Asp Tyr Lys Leu Val Asp Val Pro Asp Leu Gly Tyr Phe
            435                 440                 445

Leu Thr Asp Arg Pro His Pro Arg Gly Glu Leu Leu Val Lys Thr Asp
450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                485                 490                 495

Gly Pro Glu Gln Phe Val Tyr Leu Asp Arg Arg Asn Asn Val Leu Lys
                500                 505                 510

Leu Ser Gln Gly Glu Phe Val Thr Val Ser Lys Leu Glu Ala Val Phe
            515                 520                 525

Gly Asp Ser Pro Leu Val Arg Gln Ile Tyr Ile Tyr Gly Asn Ser Ala
            530                 535                 540

Arg Ala Tyr Leu Leu Ala Val Ile Val Pro Thr Gln Glu Ala Leu Asp
545                 550                 555                 560

Ala Val Pro Val Glu Glu Leu Lys Ala Arg Leu Gly Asp Ser Leu Gln
                565                 570                 575

Glu Val Ala Lys Ala Ala Gly Leu Gln Ser Tyr Glu Ile Pro Arg Asp
                580                 585                 590

Phe Ile Ile Glu Thr Thr Pro Trp Thr Leu Glu Asn Gly Leu Leu Thr
            595                 600                 605

Gly Ile Arg Lys Leu Ala Arg Pro Gln Leu Lys Lys His Tyr Gly Glu
            610                 615                 620

Leu Leu Glu Gln Ile Tyr Thr Asp Leu Ala His Gly Gln Ala Asp Glu
625                 630                 635                 640

Leu Arg Ser Leu Arg Gln Ser Gly Ala Asp Ala Pro Val Leu Val Thr
                645                 650                 655

Val Cys Arg Ala Ala Ala Ala Leu Leu Gly Gly Ser Ala Ser Asp Val
                660                 665                 670

Gln Pro Asp Ala His Phe Thr Asp Leu Gly Gly Asp Ser Leu Ser Ala
            675                 680                 685

Leu Ser Phe Thr Asn Leu Leu His Glu Ile Phe Asp Ile Glu Val Pro
            690                 695                 700

Val Gly Val Ile Val Ser Pro Ala Asn Asp Leu Gln Ala Leu Ala Asp
705                 710                 715                 720

Tyr Val Glu Ala Ala Arg Lys Pro Gly Ser Ser Arg Pro Thr Phe Ala
                725                 730                 735
```

-continued

Ser Val His Gly Ala Ser Asn Gly Gln Val Thr Glu Val His Ala Gly
                740                 745                 750

Asp Leu Ser Leu Asp Lys Phe Ile Asp Ala Ala Thr Leu Ala Glu Ala
                755                 760                 765

Pro Arg Leu Pro Ala Ala Asn Thr Gln Val Arg Thr Val Leu Leu Thr
770                 775                 780

Gly Ala Thr Gly Phe Leu Gly Arg Tyr Leu Ala Leu Glu Trp Leu Glu
785                 790                 795                 800

Arg Met Asp Leu Val Asp Gly Lys Leu Ile Cys Leu Val Arg Ala Lys
                805                 810                 815

Ser Asp Thr Glu Ala Arg Ala Arg Leu Asp Lys Thr Phe Asp Ser Gly
                820                 825                 830

Asp Pro Glu Leu Leu Ala His Tyr Arg Ala Leu Ala Gly Asp His Leu
                835                 840                 845

Glu Val Leu Ala Gly Asp Lys Gly Glu Ala Asp Leu Gly Leu Asp Arg
                850                 855                 860

Gln Thr Trp Gln Arg Leu Ala Asp Thr Val Asp Leu Ile Val Asp Pro
865                 870                 875                 880

Ala Ala Leu Val Asn His Val Leu Pro Tyr Ser Gln Leu Phe Gly Pro
                885                 890                 895

Asn Ala Leu Gly Thr Ala Glu Leu Leu Arg Leu Ala Leu Thr Ser Lys
                900                 905                 910

Ile Lys Pro Tyr Ser Tyr Thr Ser Thr Ile Gly Val Ala Asp Gln Ile
                915                 920                 925

Pro Pro Ser Ala Phe Thr Glu Asp Ala Asp Ile Arg Val Ile Ser Ala
930                 935                 940

Thr Arg Ala Val Asp Asp Ser Tyr Ala Asn Gly Tyr Ser Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Cys Asp Met Ile Leu Ala Asp Thr Thr Trp
                980                 985                 990

Ala Gly Gln Leu Asn Val Pro Asp Met Phe Thr Arg Met Ile Leu Ser
                995                 1000                1005

Leu Ala Ala Thr Gly Ile Ala Pro Gly Ser Phe Tyr Glu Leu Ala
        1010                1015                1020

Ala Asp Gly Ala Arg Gln Arg Ala His Tyr Asp Gly Leu Pro Val
        1025                1030                1035

Glu Phe Ile Ala Glu Ala Ile Ser Thr Leu Gly Ala Gln Ser Gln
        1040                1045                1050

Asp Gly Phe His Thr Tyr His Val Met Asn Pro Tyr Asp Asp Gly
        1055                1060                1065

Ile Gly Leu Asp Glu Phe Val Asp Trp Leu Asn Glu Ser Gly Cys
        1070                1075                1080

Pro Ile Gln Arg Ile Ala Asp Tyr Gly Asp Trp Leu Gln Arg Phe
        1085                1090                1095

Glu Thr Ala Leu Arg Ala Leu Pro Asp Arg Gln Arg His Ser Ser
        1100                1105                1110

Leu Leu Pro Leu Leu His Asn Tyr Arg Gln Pro Glu Arg Pro Val
        1115                1120                1125

Arg Gly Ser Ile Ala Pro Thr Asp Arg Phe Arg Ala Ala Val Gln
        1130                1135                1140

```
Glu Ala Lys Ile Gly Pro Asp Lys Asp Ile Pro His Val Gly Ala
    1145                1150                1155

Pro Ile Ile Val Lys Tyr Val Ser Asp Leu Arg Leu Leu Gly Leu
    1160                1165                1170

Leu

<210> SEQ ID NO 71
<211> LENGTH: 224
<212> TYPE: PRT
<213> ORGANISM: Bacillus subtilis

<400> SEQUENCE: 71

Met Lys Ile Tyr Gly Ile Tyr Met Asp Arg Pro Leu Ser Gln Glu Glu
1               5                   10                  15

Asn Glu Arg Phe Met Ser Phe Ile Ser Pro Glu Lys Arg Glu Lys Cys
                20                  25                  30

Arg Arg Phe Tyr His Lys Glu Asp Ala His Arg Thr Leu Leu Gly Asp
            35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Cys Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
    130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220

<210> SEQ ID NO 72

<400> SEQUENCE: 72

000

<210> SEQ ID NO 73

<400> SEQUENCE: 73

000

<210> SEQ ID NO 74
<211> LENGTH: 319
<212> TYPE: PRT
<213> ORGANISM: Solanum tuberosum

<400> SEQUENCE: 74
```

```
Met Ser Phe Ser Leu Val Ser Gln His Phe Ile Ser Leu Lys Ser Ser
1               5                   10                  15

Leu Gly Leu Gln Cys Trp Lys Ser Ser Pro Ser Leu Ile Leu Gln
            20                  25                  30

Arg Asn Thr Ser Ile Ser Met Gly Ala Phe Lys Gly Met His Lys Leu
            35                  40                  45

Gln Ile Leu Asn Ser Pro Leu Thr Val Ser Ala Arg Gly Leu Asn Lys
    50                  55                  60

Ile Ser Cys Ser Leu Asn Leu Gln Thr Glu Lys Phe Cys Asp Asp Asp
65                  70                  75                  80

Asn Asp Asn Asp Asp Leu Tyr Leu Asp Glu Glu Leu Met Pro Lys His
                85                  90                  95

Ile Ala Leu Ile Met Asp Gly Asn Arg Arg Trp Ala Lys Ala Lys Gly
                100                 105                 110

Leu Glu Val Tyr Glu Gly His Lys Leu Ile Ile Pro Lys Leu Lys Glu
            115                 120                 125

Ile Cys His Ile Ser Ser Lys Leu Gly Ile Gln Gly Ile Thr Ala Phe
    130                 135                 140

Ala Phe Ser Thr Glu Asn Trp Lys Arg Ser Lys Glu Glu Val Asp Phe
145                 150                 155                 160

Leu Met Gln Leu Phe Glu Glu Phe Phe Asp Glu Phe Ser Arg Ser Gly
                165                 170                 175

Val Arg Val Ser Val Ile Gly Cys Lys Ser Asn Leu Pro Leu Thr Leu
            180                 185                 190

Gln Lys Cys Ile Ala Leu Thr Glu Glu Thr Thr Lys Gly Asn Lys Gly
    195                 200                 205

Leu His Leu Val Ile Ala Leu Asn Tyr Gly Gly Tyr Tyr Asp Ile Leu
    210                 215                 220

Gln Ala Thr Lys Ser Ile Ala Asn Lys Val Met Asn Gly Leu Leu His
225                 230                 235                 240

Val Glu Asp Ile Asn Lys Asn Leu Phe Glu Gln Leu Glu Ser Lys
                245                 250                 255

Cys Pro Asn Pro Asp Leu Leu Ile Arg Thr Gly Gly Glu Gln Arg Val
                260                 265                 270

Ser Asn Phe Leu Leu Trp Gln Leu Ala Tyr Thr Glu Phe Tyr Phe Thr
            275                 280                 285

Asn Thr Leu Phe Pro Asp Phe Gly Glu Lys Asp Leu Lys Glu Ala Ile
            290                 295                 300

Leu Asn Phe Gln Gln Arg His Arg Arg Phe Gly Gly His Thr Tyr
305                 310                 315

<210> SEQ ID NO 75
<211> LENGTH: 323
<212> TYPE: PRT
<213> ORGANISM: Solanum pennillii

<400> SEQUENCE: 75

Met Asn Ser Ser Leu Val Phe Gln His Leu Ile Pro Ser Lys Ser Ser
1               5                   10                  15

Leu Gly Leu Lys Ser Gln Lys Ser Ser Pro Ser Leu Ile Leu Arg
            20                  25                  30

Arg Asn Thr Ser Ile Thr Met Gly Glu Phe Lys Gly Thr His Asp Lys
            35                  40                  45

Gln Leu Gln Ile Leu Asn Leu Pro Leu Thr Val Ser Ala Cys Arg Leu
```

```
            50                  55                  60
Asn Lys Ile Ser Ser Ser Phe Ser Leu Gln Thr Glu Lys Leu Cys Tyr
 65                  70                  75                  80

Asp Asn Asp Asn Asp Asn Asp Leu Glu Leu His Glu Glu Leu
                 85                  90                  95

Ile Pro Lys His Ile Ala Leu Ile Met Asp Gly Asn Arg Arg Trp Ala
                100                 105                 110

Lys Ala Lys Gly Leu Glu Val Tyr Glu Gly His Lys Leu Ile Ile Pro
                115                 120                 125

Lys Leu Lys Glu Ile Cys Asp Ile Ser Lys Leu Gly Ile Gln Ile
        130                 135                 140

Ile Thr Ala Phe Ala Phe Ser Thr Glu Asn Trp Lys Arg Ser Lys Glu
145                 150                 155                 160

Glu Val Asp Leu Leu Met Gln Leu Phe Glu Phe Phe Asp Ala Phe
                165                 170                 175

Ser Arg Phe Gly Val Arg Val Ser Val Ile Gly Cys Lys Ser Asn Leu
                180                 185                 190

Pro Met Thr Leu Gln Lys Cys Ile Glu Leu Thr Glu Glu Thr Thr Lys
            195                 200                 205

Gly Asn Lys Gly Leu His Leu Val Ile Ala Leu Asn Tyr Gly Gly Tyr
        210                 215                 220

Tyr Asp Ile Leu Gln Ala Thr Lys Ser Ile Val Asn Lys Ala Met Asn
225                 230                 235                 240

Gly Leu Leu Asp Val Glu Asp Ile Asn Lys Ser Leu Phe Glu Gln Glu
                245                 250                 255

Leu Glu Ser Lys Cys Pro Asn Pro Asp Leu Leu Ile Arg Thr Gly Gly
            260                 265                 270

Glu Gln Arg Val Ser Asn Phe Leu Leu Trp Gln Leu Ala Tyr Thr Glu
        275                 280                 285

Phe Tyr Phe Thr Asn Thr Leu Phe Pro Asp Phe Gly Glu Lys Asp Leu
        290                 295                 300

Lys Glu Ala Ile Met Asn Phe Gln Gln Arg His Arg Arg Phe Gly Gly
305                 310                 315                 320

His Thr Tyr

<210> SEQ ID NO 76

<400> SEQUENCE: 76

000

<210> SEQ ID NO 77
<211> LENGTH: 523
<212> TYPE: PRT
<213> ORGANISM: Phaseolus vulgaris

<400> SEQUENCE: 77

Met Asp Leu Ser Asp Asp Ile Tyr Leu Glu Gln Ala Leu Val Leu Lys
  1               5                  10                  15

Glu Val Lys Gln Ala Phe Gln Lys Leu Val Ser Glu Asp Tyr Met Glu
                 20                  25                  30

Cys Phe Tyr Val Ile Asp Ile Ile Gln Arg Leu Gly Ile Glu His His
                 35                  40                  45

Phe Gln Glu Glu Ile Glu Ala Leu Leu Gln Asn Gln Cys Ser Ile Phe
         50                  55                  60
```

Ile Ser His Ile Ser Asp Phe Ala Asn His His Lys Leu Tyr Glu Leu
 65                  70                  75                  80

Ala Leu Leu Phe Arg Leu Leu Arg Gln Arg Gly Tyr His Val Pro Ala
                 85                  90                  95

Asp Val Phe Glu Gly Leu Lys Ser Asn Lys Arg Glu Phe Arg Ala Lys
            100                 105                 110

His Gly Glu Asp Val Lys Ser Leu Ile Ala Leu His Glu Ala Ala Gln
        115                 120                 125

Leu Ser Ile Glu Gly Glu Asp Ser Leu Asp Asp Ala Gly Phe Leu Cys
    130                 135                 140

Cys Gln Leu Leu His Ser Trp Leu Lys Arg His Arg Glu His His Glu
145                 150                 155                 160

Ala Ile Tyr Val Ala Asn Thr Leu Gln Asn Pro Leu His Tyr Gly Leu
                165                 170                 175

Ser Arg Phe Arg Asp Thr Thr Ser Leu Ala Leu Ser Asp Tyr Lys Thr
            180                 185                 190

Lys Lys Glu Trp Thr Cys Ile Glu Lys Leu Ala Glu Ile Asn Ser Cys
        195                 200                 205

Ile Val Arg Met Met Asn Gln Asn Glu Ile Ile Gln Val Tyr Arg Trp
    210                 215                 220

Trp Lys Asp Val Gly Met Val Arg Glu Glu Lys Phe Cys Met Tyr Glu
225                 230                 235                 240

Pro Leu Lys Trp Tyr Leu Trp Pro Met Ala Cys Phe Thr Asp Pro Arg
                245                 250                 255

Phe Ser Asp Gln Arg Ile Glu Leu Thr Lys Ser Ile Ser Leu Ile Tyr
            260                 265                 270

Ile Ile Asp Asp Ile Phe Asp Val Tyr Gly Thr Leu Asp Gln Leu Thr
        275                 280                 285

Leu Phe Arg Asp Ala Val Tyr Arg Trp Glu Leu Gly Gly Ala Glu Gln
    290                 295                 300

Leu Pro Asp Phe Met Lys Met Cys Leu Ser Val Leu Tyr Asp Ile Thr
305                 310                 315                 320

Asn Asp Phe Ala Glu Lys Val Tyr Lys Arg His Gly Leu Asn Pro Ile
                325                 330                 335

Asp Thr Leu Lys Arg Ser Trp Val Arg Leu Leu Asn Ala Phe Met Glu
            340                 345                 350

Glu Ala His Trp Leu Lys Gly Gly Asp Leu Pro Arg Ser Glu Glu Tyr
        355                 360                 365

Leu Asn Asn Gly Ile Val Ser Ser Gly Val His Val Val Leu Leu His
    370                 375                 380

Ala Phe Phe Leu Phe Asp His Ser Ile Asn Met Glu Ser Val Ala Val
385                 390                 395                 400

Met Asp Asn Phe Pro Gln Ile Ile Tyr Ser Val Ala Lys Ile Leu Arg
                405                 410                 415

Leu Ser Asp Asp Leu Glu Gly Ala Lys Lys Asp Glu Lys Gly Val
            420                 425                 430

Asp Gly Ser Tyr Leu Asp Cys Tyr Met Asn Glu His Gln His Val Ser
        435                 440                 445

Ala Glu Asp Ala Gln Asn His Val Ser His Leu Ile Gln Ser Glu Trp
    450                 455                 460

Lys Arg Leu Asn Glu Gln Ile Leu Thr Gln Asn Glu Leu Pro Ser Ser
465                 470                 475                 480

Phe Thr Asn Phe Cys Leu Asn Ala Ala Arg Met Val Pro Leu Met Tyr

```
                        485                 490                 495
Asp Tyr Thr Thr Asn Asn Pro Cys Leu Ser Ile Met Arg Glu Glu Leu
                500                 505                 510

Lys Met Val Leu Asn Val Asp Ser Gly His Met
            515                 520

<210> SEQ ID NO 78
<211> LENGTH: 572
<212> TYPE: PRT
<213> ORGANISM: Gossypium hirsutum

<400> SEQUENCE: 78

Met Glu Cys Ser Arg Gln Val Gln Val Val Asp Asp Lys Gln Gln Val
1               5                   10                  15

Val Ser Cys His Met Lys Ser Ala Ala Phe Asp Glu Ile Gln Gln Arg
            20                  25                  30

Arg Ser Ala Asn Tyr Lys Ala Asn Ile Trp Gln Tyr Asp Phe Leu Gln
        35                  40                  45

Ser Leu Pro Thr Ile Tyr Asn Gly Val Glu Tyr Thr Leu Arg Val Glu
    50                  55                  60

Asn Leu Lys Glu Asn Val Lys Asp Met Phe Val Glu Ala Lys Asp Gln
65                  70                  75                  80

Leu Ala Lys Leu Glu Leu Ile Asp Ile Ile Arg Lys Leu Gly Leu Gly
                85                  90                  95

Asp Leu Phe Ala Glu Glu Thr His Lys Ala Leu Gln Thr Val Val Ser
            100                 105                 110

Ser Met Lys Asn Asn Lys Asn Gly Glu Glu Glu Leu Tyr Met Thr
        115                 120                 125

Ala Leu Arg Phe Lys Leu Leu Arg Leu His Gly Tyr Asp Val Ser Gln
    130                 135                 140

Asp Val Phe Asn Ala Val Ser Ile Thr Lys Cys Ser Asp Ile Lys Gly
145                 150                 155                 160

Leu Leu Glu Leu Phe Glu Ala Ser Tyr Leu Ala Phe Glu Gly Glu Thr
                165                 170                 175

Ile Leu Asp Glu Ala Lys Ala Phe Ser Met Glu Ala Leu Arg Asn Val
            180                 185                 190

Tyr Pro Thr Leu Asp Leu Asn Leu Ala Lys Glu Val Ala His Ala Leu
        195                 200                 205

Glu Leu Pro Met His Trp Arg Val Gln Trp Phe Asp Val Lys Trp Arg
    210                 215                 220

Ile Thr Met Tyr Glu Thr Tyr Asn Lys Asn Ile Asp Lys Arg Phe Leu
225                 230                 235                 240

Glu Leu Ala Lys Leu Asn Phe Asn Thr Val Gln Ala Ile Leu Gln Lys
                245                 250                 255

Asp Leu Arg Glu Ile Ser Arg Trp Trp Arg Asn Leu Arg Ile Met Glu
            260                 265                 270

Gly Leu Asn Phe Thr Arg Asp Arg Leu Ala Glu Ser Phe Leu Cys Ser
        275                 280                 285

Val Gly Leu Thr Tyr Glu Pro Gln Tyr Ser Cys Phe Arg Lys Cys Leu
    290                 295                 300

Thr Lys Ile Thr Thr Met Ile Leu Ile Asp Asp Val Tyr Asp Val
305                 310                 315                 320

Tyr Gly Ser Ile Glu Glu Leu Glu Gln Phe Thr Glu Ala Val Asp Arg
                325                 330                 335
```

Trp Asp Ser Ser Lys Thr Gln Asp Leu Pro Glu Cys Met Lys Thr Cys
              340                 345                 350

Phe Gln Ala Leu Tyr Asp Ile Thr Asn Glu Ile Ala Tyr Asp Ile Gln
              355                 360                 365

Glu Leu Asn Gly Trp Gln Val Gln Ala Leu Leu His Leu Arg Lys Ala
              370                 375                 380

Trp Ala Gly Phe Cys Lys Ala Leu Phe Val Glu Ala Lys Trp Tyr Asn
385                 390                 395                 400

Lys Gly Tyr Ser Pro Ser Leu Glu Glu Tyr Leu Ser Asn Ala Leu Ile
              405                 410                 415

Ser Ser Gly Ala Ile Val Ile Ser Ile His Thr Met Leu Ser Val Gly
              420                 425                 430

Ser Thr Asp Glu Lys Ile Ile Asn Leu Leu Gly Lys Asp Glu Asp Leu
              435                 440                 445

Ala Tyr Asn Ile Ser Ile Ile Thr Arg Leu Tyr Asn Asp Leu Gly Thr
              450                 455                 460

Ser Met Ala Glu Lys Glu Arg Gly Asp Ala Pro Ser Ser Ile His Cys
465                 470                 475                 480

Tyr Ala Arg Glu Met Asn Val Ser Glu Lys Glu Ala Glu His Ile
              485                 490                 495

Lys Asn Met Ile Asn Asn Thr Trp Lys Lys Ile Asn Gly Gln Cys Leu
              500                 505                 510

Asn Asn Gln Ser His Asn Leu Leu Pro Cys Ser Phe Val Lys Val Thr
              515                 520                 525

Thr Asn Val Ala Arg Met Val Gln Cys Leu Tyr Gln Phe Gly Asp Gly
              530                 535                 540

Phe Gly Ile Gln Asp Arg Glu Thr Arg Asn His Ile Ser Ser Leu Leu
545                 550                 555                 560

Ile Glu Pro Ile Asn Leu Asp Lys Thr Ala Lys Asp
              565                 570

<210> SEQ ID NO 79
<211> LENGTH: 544
<212> TYPE: PRT
<213> ORGANISM: Gossypium hirsutum

<400> SEQUENCE: 79

Met Ala Pro Thr Ser Gln Ser Leu Asn Glu Glu Gln Arg Arg Ser Ala
1               5                   10                  15

Asn Tyr His Pro Ser Ile Trp Asp Pro Thr Ala Ile Gln Ser Phe Thr
              20                  25                  30

Thr Pro Tyr Thr Tyr Glu Leu Tyr Ala Thr Gln Leu Glu Asp Leu Lys
              35                  40                  45

Gln Lys Val Arg Lys Leu Leu Ala Ser Thr Lys Asp Thr Ala Ala Leu
              50                  55                  60

Leu Lys Leu Ile Asp Ser Met Lys Arg Leu Gly Val Ala Tyr His Phe
65                  70                  75                  80

Gln Glu Gln Ile Gln Gln Ala Leu Asn Gln Leu Asn Pro Asp Leu Asn
              85                  90                  95

Leu Val Ser Asn Asp Leu Ser Thr Val Ala Leu His Phe Arg Ile Leu
              100                 105                 110

Arg Glu Asp Cys Tyr Pro Ile Thr Ala Asp Val Leu Glu Lys Phe Lys
              115                 120                 125

Gly Asp Asp Gly Arg Phe Met Gly Ser Leu Cys Gly Asp Val Glu Gly
              130                 135                 140

```
Leu Leu Gly Leu Asn Glu Ala Ser Ser Met Ala Ile Gln Gly Glu Lys
145                 150                 155                 160

Ile Leu Glu Glu Ala Lys Ala Phe Ser Ser Glu Asn Leu Lys Asn Val
            165                 170                 175

Ile Gly Lys Leu Glu Lys Val Glu Ala Lys Gln Val Gln Arg Ser Leu
            180                 185                 190

Glu Val Pro Leu Tyr Trp Arg Met Glu Arg Ile Glu Ala Arg Asn Phe
            195                 200                 205

Ile Asp Ser Tyr Ala Met Asp Asp Ser Asn Ser Ser Val Leu Leu Asp
            210                 215                 220

Gln Ala Lys Leu Asp Tyr Asn Leu Ile Gln Ser Val Tyr Lys Gln Glu
225                 230                 235                 240

Leu Lys Gln Leu Ala Glu Trp Trp Ser Glu Leu Asn Phe Lys Glu Lys
            245                 250                 255

Leu Ser Phe Ser Arg Asp Arg Leu Met Glu Ile Tyr Phe Trp Ala Thr
            260                 265                 270

Gly Leu Ser Phe Glu Ala Gln Tyr Ala Lys Cys Arg Ile Cys Phe Thr
            275                 280                 285

Lys Tyr Ala Cys Leu Ala Thr Val Val Asp Asp Ile Tyr Asp Ile Tyr
            290                 295                 300

Gly Ser Leu Glu Glu Leu Glu Cys Phe Thr Lys Ala Val Thr Gly Trp
305                 310                 315                 320

Asp Val Lys Val Ile Gln Glu Leu Pro Glu Tyr Met Arg Val Met Phe
                325                 330                 335

Ser Ala Ile Ser Asp Phe Thr Asn Glu Leu Ala Gln Gln Thr Leu Lys
                340                 345                 350

Asp His Gly Leu Asp Val Leu Pro Tyr Ile Lys Glu Gln Trp Ala Ile
                355                 360                 365

Leu Cys Arg Ala His Ile Thr Glu Ala Arg Trp Phe Tyr Gly Gly Gln
370                 375                 380

Thr Pro Thr Phe Asp Glu Tyr Ile Glu Asn Ala Trp Ile Ser Ile Gly
385                 390                 395                 400

Ser Leu Gly Gly Leu Val Leu Leu Cys Phe Val Glu Ala Asp Ser Ile
                405                 410                 415

Val Asn Gln Phe Pro Asn Cys Leu Lys Asp Tyr Ser Gln Leu Phe Tyr
                420                 425                 430

Trp Ser Ser Leu Ile Thr Arg Leu Ser Asp Asp Leu Gly Thr Ser Lys
                435                 440                 445

Ala Glu Met Glu Arg Gly Asp Ile Pro Lys Ala Val Gln Thr Tyr Met
450                 455                 460

Ile Glu Lys Gly Val Ser Glu Glu Thr Ala Arg Asn His Val Lys Glu
465                 470                 475                 480

Leu Ile Ser Asn Ser Trp Lys Lys Ile Asn Glu Glu Ile Leu Asp Asn
                485                 490                 495

Arg Phe Ser Arg Ala Ile Val Asn Leu Ser Lys Asn Met Ala Arg Thr
                500                 505                 510

Ala Gln Cys Ile Tyr Gln His Gly Asp Gly Phe Gly Thr Ser Thr Gly
                515                 520                 525

Val Thr Lys Asp Cys Ile Ile Ser Ser Ile Leu Arg Pro Ile Pro Ile
                530                 535                 540

<210> SEQ ID NO 80
<211> LENGTH: 426
```

<212> TYPE: PRT
<213> ORGANISM: Lactobacillus casei

<400> SEQUENCE: 80

| | | | | | | | | | | | | | | |
|---|---|---|---|---|---|---|---|---|---|---|---|---|---|---|
| Met | Lys | Phe | Tyr | Glu | Leu | Ser | Pro | Glu | Lys | Arg | Arg | Asp | Gln | Leu | Val |
| 1 | | | | 5 | | | | | 10 | | | | | 15 | |
| Gln | Glu | Gly | Trp | Leu | Thr | Thr | Gln | Asp | Ala | Ala | Leu | Leu | Ala | Gly | Thr |
| | | | 20 | | | | | 25 | | | | | 30 | | |
| His | Ser | Leu | Pro | Glu | Val | Thr | Gly | Ala | Arg | Leu | Ile | Glu | Asn | Ala | Ile |
| | | 35 | | | | | 40 | | | | | 45 | | | |
| Gly | Glu | Phe | Pro | Leu | Pro | Leu | Gly | Val | Ala | Arg | Asn | Leu | Leu | Val | Asn |
| | 50 | | | | | 55 | | | | | 60 | | | | |
| Gly | Gln | Leu | His | Gln | Val | Pro | Ile | Ala | Asp | Glu | Glu | Pro | Ser | Val | Ile |
| 65 | | | | | 70 | | | | | 75 | | | | | 80 |
| Ala | Ala | Ala | Ser | Asn | Gly | Ala | Arg | Leu | Ala | Thr | Ala | Asn | Gly | Gly | Val |
| | | | | 85 | | | | | 90 | | | | | 95 | |
| Arg | Thr | His | Val | Ala | Ala | His | Arg | Val | Val | Ala | Glu | Val | Val | Leu | Thr |
| | | | 100 | | | | | 105 | | | | | 110 | | |
| Asn | Leu | Thr | Asp | Leu | Val | Gln | Ala | Arg | Gln | Thr | Ile | Leu | Ala | His | Gln |
| | | 115 | | | | | 120 | | | | | 125 | | | |
| Thr | Asp | Ile | Gln | Arg | Val | Ile | Ala | Val | Ala | His | Pro | Ser | Met | Ile | Gln |
| | 130 | | | | | 135 | | | | | 140 | | | | |
| Arg | Gly | Gly | Leu | Asp | Gln | Leu | Thr | Val | Glu | Ser | Leu | Gly | Ala | Gln |
| 145 | | | | | 150 | | | | | 155 | | | | | 160 |
| Phe | Leu | Lys | Ile | Arg | Leu | Thr | Leu | Asp | Pro | Gln | Gln | Ala | Met | Gly | Ala |
| | | | | 165 | | | | | 170 | | | | | 175 | |
| Asn | Tyr | Ala | Asn | Thr | Val | Ala | Glu | Ala | Val | Ala | Ala | Val | Thr | Ser |
| | | | 180 | | | | | 185 | | | | | 190 | | |
| Trp | Val | Asp | Gly | Asp | Val | Leu | Val | Ser | Ile | Leu | Thr | Asn | Ala | Pro | Thr |
| | | | 195 | | | | | 200 | | | | | 205 | | |
| Glu | Leu | Val | Thr | Ala | Glu | Val | Ser | Leu | Glu | Pro | Val | Ser | Leu | Ala | Thr |
| | 210 | | | | | 215 | | | | | 220 | | | | |
| Lys | Ala | Val | Ser | Gly | Asp | Val | Ile | Ala | Lys | Lys | Ile | Val | Gln | Leu | Ser |
| 225 | | | | | 230 | | | | | 235 | | | | | 240 |
| Asp | Leu | Ala | Phe | Val | Asp | Ala | Glu | Arg | Ala | Val | Thr | His | Asn | Lys | Gly |
| | | | | 245 | | | | | 250 | | | | | 255 | |
| Ile | Leu | Asn | Gly | Ile | Ile | Gly | Ala | Val | Leu | Ala | Thr | Gly | Asn | Asp | Thr |
| | | | 260 | | | | | 265 | | | | | 270 | | |
| Arg | Ala | Val | Ala | Ala | Ser | Ile | Gly | Ala | Phe | Ala | Cys | Ala | Ser | Gly | Arg |
| | | 275 | | | | | 280 | | | | | 285 | | | |
| Tyr | Gln | Pro | Leu | Ser | Arg | Trp | Tyr | Met | Asp | Gln | Gly | His | Leu | Val | Gly |
| | 290 | | | | | 295 | | | | | 300 | | | | |
| His | Leu | Gln | Leu | Pro | Leu | Pro | Met | Gly | Ala | Gly | Gly | Ala | Ile | Gly |
| 305 | | | | | 310 | | | | | 315 | | | | | 320 |
| Ala | Leu | Pro | Met | Ala | Gln | Val | Val | Arg | Leu | Gly | Gly | Tyr | Gln | Asn |
| | | | | 325 | | | | | 330 | | | | | 335 | |
| Leu | Ala | Ile | Met | Gln | Gln | Val | Ile | Ala | Ala | Leu | Gly | Leu | Val | Gln | Asn |
| | | | 340 | | | | | 345 | | | | | 350 | | |
| Leu | Ala | Ala | Met | Arg | Ala | Leu | Ala | Gly | Pro | Gly | Ile | Gln | Ala | Gly | His |
| | | 355 | | | | | 360 | | | | | 365 | | | |
| Met | Lys | Leu | Gln | Ala | Asn | Ala | Leu | Ala | Ile | Ala | Gly | Ala | Thr | Glu |
| | 370 | | | | | 375 | | | | | 380 | | | | |
| Thr | Glu | Leu | Pro | Met | Leu | Val | Asn | Ala | Leu | Arg | Gln | Gly | Ser | Met | Asp |
| 385 | | | | | 390 | | | | | 395 | | | | | 400 |

```
Leu Lys His Ala Gln Gln Tyr Leu Thr Thr Ile Arg Leu Asn Lys Lys
                405                 410                 415
Val Gly Gln Ser Lys Asp Glu Asn Arg Asp
            420                 425

<210> SEQ ID NO 81
<211> LENGTH: 388
<212> TYPE: PRT
<213> ORGANISM: Lactobacillus casei

<400> SEQUENCE: 81

Met Lys Ile Gly Ile Asp Ala Ile Ala Met Asp Thr Pro Asp Phe Tyr
1               5                   10                  15
Val Asp Leu Val Lys Leu Ala Gln Val Arg Gly Asp Asp Pro Asp Lys
            20                  25                  30
Tyr Thr Ile Gly Ile Gly Gln Asp Glu Gln Ala Val Pro Pro Ser Ser
        35                  40                  45
Gln Asp Ile Val Thr Met Gly Ala Asn Ala Ala Thr Lys Leu Leu Thr
    50                  55                  60
Pro Ala Ile Arg Ala Ser Leu Gly Met Val Leu Val Gly Thr Glu Ser
65                  70                  75                  80
Gly Val Asp Ala Ser Lys Ser Ala Ala Leu Phe Ile His Asp Leu Leu
                85                  90                  95
Ala Leu Pro Glu Trp Val Arg Ala Val Glu Leu Lys Glu Ala Cys Tyr
            100                 105                 110
Gly Gly Thr Ala Ala Leu Met Met Ala Arg Asp Tyr Ile Ala Ala His
        115                 120                 125
Pro Asp Lys Thr Val Leu Val Ile Ala Ala Asp Ile Ala Arg Tyr Gly
    130                 135                 140
Leu Ala Thr Ala Gly Glu Val Thr Gln Gly Ala Gly Ala Val Ala Met
145                 150                 155                 160
Leu Ile Lys Ala Glu Pro His Ile Met Thr Ile Glu Asp Asp Ser Val
                165                 170                 175
Tyr Arg Ser Glu Ser Ile Asp Asp Phe Trp Arg Pro Val Tyr Gln Asp
            180                 185                 190
Thr Ala Ile Ala Gln Gly Lys Tyr Ser Thr Glu Gln Tyr Leu Ala Phe
        195                 200                 205
Phe Gln Ala Ile Trp Ser Arg Tyr Gln Thr Gln Arg His His Thr Ala
    210                 215                 220
Ser Asp Phe Ala Ala Met Thr Phe His Leu Pro Tyr Thr Lys Met Gly
225                 230                 235                 240
Lys Lys Ala Leu Lys Leu Val Leu Pro Asp Thr Asp Glu Ala Thr Gly
                245                 250                 255
Glu Arg Leu Gln Arg Arg Phe Glu Ala Ser Thr Arg Tyr Cys Arg Arg
            260                 265                 270
Val Gly Asn Ile Tyr Thr Gly Ser Leu Tyr Leu Gly Leu Leu Ser Leu
        275                 280                 285
Leu Asp Asn Asp Thr Ser Leu Lys Ala Gly Asp Arg Ile Gly Leu Phe
    290                 295                 300
Ser Tyr Gly Ser Gly Ala Val Ala Glu Phe Phe Ser Gly Ile Leu Gln
305                 310                 315                 320
Pro Asp Phe Ala Ala Gln Leu His Ala Ala Asn His Ala Lys Met Leu
                325                 330                 335
Ala Asp Arg Gln Glu Leu Thr Val Pro Glu Tyr Glu Ala Val Phe Ser
```

```
                    340                 345                 350
Asp Lys Val Pro Tyr Asp Pro Glu Asp Tyr Arg Ser Asp Pro Thr Tyr
        355                 360                 365

Tyr His Gly Gln Phe Val Leu Thr Gly Val Ile Gly Gln Glu Arg Gln
        370                 375                 380

Tyr Gln Gln Arg
385

<210> SEQ ID NO 82
<211> LENGTH: 301
<212> TYPE: PRT
<213> ORGANISM: Methanosarcina mazei

<400> SEQUENCE: 82

Met Val Ser Cys Ser Ala Pro Gly Lys Ile Tyr Leu Phe Gly Glu His
1               5                   10                  15

Ala Val Val Tyr Gly Glu Thr Ala Ile Ala Cys Ala Val Glu Leu Arg
            20                  25                  30

Thr Arg Val Arg Ala Glu Leu Asn Asp Ser Ile Thr Ile Gln Ser Gln
        35                  40                  45

Ile Gly Arg Thr Gly Leu Asp Phe Glu Lys His Pro Tyr Val Ser Ala
    50                  55                  60

Val Ile Glu Lys Met Arg Lys Ser Ile Pro Ile Asn Gly Val Phe Leu
65                  70                  75                  80

Thr Val Asp Ser Asp Ile Pro Val Gly Ser Gly Leu Gly Ser Ser Ala
                85                  90                  95

Ala Val Thr Ile Ala Ser Ile Gly Ala Leu Asn Glu Leu Phe Gly Phe
            100                 105                 110

Gly Leu Ser Leu Gln Glu Ile Ala Lys Leu Gly His Glu Ile Glu Ile
        115                 120                 125

Lys Val Gln Gly Ala Ala Ser Pro Thr Asp Thr Tyr Val Ser Thr Phe
    130                 135                 140

Gly Gly Val Val Thr Ile Pro Glu Arg Arg Lys Leu Lys Thr Pro Asp
145                 150                 155                 160

Cys Gly Ile Val Ile Gly Asp Thr Gly Val Phe Ser Ser Thr Lys Glu
                165                 170                 175

Leu Val Ala Asn Val Arg Gln Leu Arg Glu Ser Tyr Pro Asp Leu Ile
            180                 185                 190

Glu Pro Leu Met Thr Ser Ile Gly Lys Ile Ser Arg Ile Gly Glu Gln
        195                 200                 205

Leu Val Leu Ser Gly Asp Tyr Ala Ser Ile Gly Arg Leu Met Asn Val
    210                 215                 220

Asn Gln Gly Leu Leu Asp Ala Leu Gly Val Asn Ile Leu Glu Leu Ser
225                 230                 235                 240

Gln Leu Ile Tyr Ser Ala Arg Ala Ala Gly Ala Phe Gly Ala Lys Ile
                245                 250                 255

Thr Gly Ala Gly Gly Gly Cys Met Val Ala Leu Thr Ala Pro Glu
            260                 265                 270

Lys Cys Asn Gln Val Ala Glu Ala Val Ala Gly Ala Gly Gly Lys Val
        275                 280                 285

Thr Ile Thr Lys Pro Thr Glu Gln Gly Leu Lys Val Asp
    290                 295                 300

<210> SEQ ID NO 83
<211> LENGTH: 342
```

<212> TYPE: PRT
<213> ORGANISM: Saccharomyces cerevisiae

<400> SEQUENCE: 83

Met Ser Val Phe Val Ser Gly Ala Asn Gly Phe Ile Ala Gln His Ile
1               5                   10                  15

Val Asp Leu Leu Leu Lys Glu Asp Tyr Lys Val Ile Gly Ser Ala Arg
            20                  25                  30

Ser Gln Glu Lys Ala Glu Asn Leu Thr Glu Ala Phe Gly Asn Asn Pro
        35                  40                  45

Lys Phe Ser Met Glu Val Val Pro Asp Ile Ser Lys Leu Asp Ala Phe
    50                  55                  60

Asp His Val Phe Gln Lys His Gly Lys Asp Ile Lys Ile Val Leu His
65                  70                  75                  80

Thr Ala Ser Pro Phe Cys Phe Asp Ile Thr Asp Ser Glu Arg Asp Leu
                85                  90                  95

Leu Ile Pro Ala Val Asn Gly Val Lys Gly Ile Leu His Ser Ile Lys
            100                 105                 110

Lys Tyr Ala Ala Asp Ser Val Glu Arg Val Val Leu Thr Ser Ser Tyr
        115                 120                 125

Ala Ala Val Phe Asp Met Ala Lys Glu Asn Asp Lys Ser Leu Thr Phe
    130                 135                 140

Asn Glu Glu Ser Trp Asn Pro Ala Thr Trp Glu Ser Cys Gln Ser Asp
145                 150                 155                 160

Pro Val Asn Ala Tyr Cys Gly Ser Lys Lys Phe Ala Glu Lys Ala Ala
                165                 170                 175

Trp Glu Phe Leu Glu Glu Asn Arg Asp Ser Val Lys Phe Glu Leu Thr
            180                 185                 190

Ala Val Asn Pro Val Tyr Val Phe Gly Pro Gln Met Phe Asp Lys Asp
        195                 200                 205

Val Lys Lys His Leu Asn Thr Ser Cys Glu Leu Val Asn Ser Leu Met
    210                 215                 220

His Leu Ser Pro Glu Asp Lys Ile Pro Glu Leu Phe Gly Gly Tyr Ile
225                 230                 235                 240

Asp Val Arg Asp Val Ala Lys Ala His Leu Val Ala Phe Gln Lys Arg
                245                 250                 255

Glu Thr Ile Gly Gln Arg Leu Ile Val Ser Glu Ala Arg Phe Thr Met
            260                 265                 270

Gln Asp Val Leu Asp Ile Leu Asn Glu Asp Phe Pro Val Leu Lys Gly
        275                 280                 285

Asn Ile Pro Val Gly Lys Pro Gly Ser Gly Ala Thr His Asn Thr Leu
    290                 295                 300

Gly Ala Thr Leu Asp Asn Lys Lys Ser Lys Leu Leu Gly Phe Lys
305                 310                 315                 320

Phe Arg Asn Leu Lys Glu Thr Ile Asp Asp Thr Ala Ser Gln Ile Leu
                325                 330                 335

Lys Phe Glu Gly Arg Ile
            340

<210> SEQ ID NO 84
<211> LENGTH: 347
<212> TYPE: PRT
<213> ORGANISM: Saccharomyces cerevisiae

<400> SEQUENCE: 84

Met Thr Thr Asp Thr Thr Val Phe Val Ser Gly Ala Thr Gly Phe Ile
1               5                   10                  15

Ala Leu His Ile Met Asn Asp Leu Leu Lys Ala Gly Tyr Thr Val Ile
                20                  25                  30

Gly Ser Gly Arg Ser Gln Glu Lys Asn Asp Gly Leu Leu Lys Lys Phe
            35                  40                  45

Asn Asn Asn Pro Lys Leu Ser Met Glu Ile Val Glu Asp Ile Ala Ala
50                  55                  60

Pro Asn Ala Phe Asp Glu Val Phe Lys Lys His Gly Lys Glu Ile Lys
65                  70                  75                  80

Ile Val Leu His Thr Ala Ser Pro Phe His Phe Glu Thr Thr Asn Phe
                85                  90                  95

Glu Lys Asp Leu Leu Thr Pro Ala Val Asn Gly Thr Lys Ser Ile Leu
                100                 105                 110

Glu Ala Ile Lys Lys Tyr Ala Ala Asp Thr Val Glu Lys Val Ile Val
                115                 120                 125

Thr Ser Ser Thr Ala Ala Leu Val Thr Pro Thr Asp Met Asn Lys Gly
            130                 135                 140

Asp Leu Val Ile Thr Glu Glu Ser Trp Asn Lys Asp Thr Trp Asp Ser
145                 150                 155                 160

Cys Gln Ala Asn Ala Val Ala Ala Tyr Cys Gly Ser Lys Lys Phe Ala
                165                 170                 175

Glu Lys Thr Ala Trp Glu Phe Leu Lys Glu Asn Lys Ser Ser Val Lys
                180                 185                 190

Phe Thr Leu Ser Thr Ile Asn Pro Gly Phe Val Phe Gly Pro Gln Met
                195                 200                 205

Phe Ala Asp Ser Leu Lys His Gly Ile Asn Thr Ser Ser Gly Ile Val
                210                 215                 220

Ser Glu Leu Ile His Ser Lys Val Gly Gly Glu Phe Tyr Asn Tyr Cys
225                 230                 235                 240

Gly Pro Phe Ile Asp Val Arg Asp Val Ser Lys Ala His Leu Val Ala
                245                 250                 255

Ile Glu Lys Pro Glu Cys Thr Gly Gln Arg Leu Val Leu Ser Glu Gly
                260                 265                 270

Leu Phe Cys Cys Gln Glu Ile Val Asp Ile Leu Asn Glu Glu Phe Pro
                275                 280                 285

Gln Leu Lys Gly Lys Ile Ala Thr Gly Glu Pro Ala Thr Gly Pro Ser
                290                 295                 300

Phe Leu Glu Lys Asn Ser Cys Lys Phe Asp Asn Ser Thr Lys Lys
305                 310                 315                 320

Leu Leu Gly Phe Gln Phe Tyr Asn Leu Lys Asp Cys Ile Val Asp Thr
                325                 330                 335

Ala Ala Gln Met Leu Glu Val Gln Asn Glu Ala
                340                 345

<210> SEQ ID NO 85
<211> LENGTH: 312
<212> TYPE: PRT
<213> ORGANISM: Saccharomyces cerevisiae

<400> SEQUENCE: 85

Met Pro Ala Thr Leu His Asp Ser Thr Lys Ile Leu Ser Leu Asn Thr
1               5                   10                  15

Gly Ala Gln Ile Pro Gln Ile Gly Leu Gly Thr Trp Gln Ser Lys Glu
                20                  25                  30

```
Asn Asp Ala Tyr Lys Ala Val Leu Thr Ala Leu Lys Asp Gly Tyr Arg
            35                  40                  45

His Ile Asp Thr Ala Ala Ile Tyr Arg Asn Glu Asp Gln Val Gly Gln
 50                  55                  60

Ala Ile Lys Asp Ser Gly Val Pro Arg Glu Glu Ile Phe Val Thr Thr
 65                  70                  75                  80

Lys Leu Trp Cys Thr Gln His His Glu Pro Glu Val Ala Leu Asp Gln
                85                  90                  95

Ser Leu Lys Arg Leu Gly Leu Asp Tyr Val Asp Leu Tyr Leu Met His
            100                 105                 110

Trp Pro Ala Arg Leu Asp Pro Ala Tyr Ile Lys Asn Glu Asp Ile Leu
            115                 120                 125

Ser Val Pro Thr Lys Lys Asp Gly Ser Arg Ala Val Asp Ile Thr Asn
130                 135                 140

Trp Asn Phe Ile Lys Thr Trp Glu Leu Met Gln Glu Leu Pro Lys Thr
145                 150                 155                 160

Gly Lys Thr Lys Ala Val Gly Val Ser Asn Phe Ser Ile Asn Asn Leu
                165                 170                 175

Lys Asp Leu Leu Ala Ser Gln Gly Asn Lys Leu Thr Pro Ala Ala Asn
            180                 185                 190

Gln Val Glu Ile His Pro Leu Leu Pro Gln Asp Glu Leu Ile Asn Phe
            195                 200                 205

Cys Lys Ser Lys Gly Ile Val Val Glu Ala Tyr Ser Pro Leu Gly Ser
            210                 215                 220

Thr Asp Ala Pro Leu Leu Lys Glu Pro Val Ile Leu Glu Ile Ala Lys
225                 230                 235                 240

Lys Asn Asn Val Gln Pro Gly His Val Val Ile Ser Trp His Val Gln
                245                 250                 255

Arg Gly Tyr Val Val Leu Pro Lys Ser Val Asn Pro Asp Arg Ile Lys
            260                 265                 270

Thr Asn Arg Lys Ile Phe Thr Leu Ser Thr Glu Asp Phe Glu Ala Ile
            275                 280                 285

Asn Asn Ile Ser Lys Glu Lys Gly Glu Lys Arg Val Val His Pro Asn
            290                 295                 300

Trp Ser Pro Phe Glu Val Phe Lys
305                 310

<210> SEQ ID NO 86
<211> LENGTH: 297
<212> TYPE: PRT
<213> ORGANISM: Saccharomyces cerevisiae

<400> SEQUENCE: 86

Met Ser Glu Leu Gln Ser Gln Pro Lys Lys Ile Ala Val Val Thr Gly
  1               5                  10                  15

Ala Ser Gly Gly Ile Gly Tyr Glu Val Thr Lys Glu Leu Ala Arg Asn
                 20                  25                  30

Gly Tyr Leu Val Tyr Ala Cys Ala Arg Arg Leu Glu Pro Met Ala Gln
             35                  40                  45

Leu Ala Ile Gln Phe Gly Asn Asp Ser Ile Lys Pro Tyr Lys Leu Asp
         50                  55                  60

Ile Ser Lys Pro Glu Glu Ile Val Thr Phe Ser Gly Phe Leu Arg Ala
 65                  70                  75                  80

Asn Leu Pro Asp Gly Lys Leu Asp Leu Leu Tyr Asn Asn Ala Gly Gln
```

```
                85                  90                  95
Ser Cys Thr Phe Pro Ala Leu Asp Ala Thr Asp Ala Ala Val Glu Gln
                100                 105                 110

Cys Phe Lys Val Asn Val Phe Gly His Ile Asn Met Cys Arg Glu Leu
            115                 120                 125

Ser Glu Phe Leu Ile Lys Ala Lys Gly Thr Ile Val Phe Thr Gly Ser
    130                 135                 140

Leu Ala Gly Val Val Ser Phe Pro Phe Gly Ser Ile Tyr Ser Ala Ser
145                 150                 155                 160

Lys Ala Ala Ile His Gln Tyr Ala Arg Gly Leu His Leu Glu Met Lys
                165                 170                 175

Pro Phe Asn Val Arg Val Ile Asn Ala Ile Thr Gly Gly Val Ala Thr
            180                 185                 190

Asp Ile Ala Asp Lys Arg Pro Leu Pro Glu Thr Ser Ile Tyr Asn Phe
    195                 200                 205

Pro Glu Gly Arg Glu Ala Phe Asn Ser Arg Lys Thr Met Ala Lys Asp
210                 215                 220

Asn Lys Pro Met Pro Ala Asp Ala Tyr Ala Lys Gln Leu Val Lys Asp
225                 230                 235                 240

Ile Leu Ser Thr Ser Asp Pro Val Asp Val Tyr Arg Gly Thr Phe Ala
                245                 250                 255

Asn Ile Met Arg Phe Val Met Ile Phe Val Pro Tyr Trp Leu Leu Glu
            260                 265                 270

Lys Gly Leu Ser Lys Lys Phe Lys Leu Asp Lys Val Asn Asn Ala Leu
    275                 280                 285

Lys Ser Lys Gln Lys Asn Lys Asp Asp
290                 295

<210> SEQ ID NO 87
<211> LENGTH: 352
<212> TYPE: PRT
<213> ORGANISM: Saccharomyces cerevisiae

<400> SEQUENCE: 87

Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Asn Asp
        115                 120                 125

Ala Phe Met Leu Glu Ala Ala Ile Tyr Lys Leu Leu Lys Ser His Phe
    130                 135                 140

Arg Asn Glu Lys Tyr Tyr Ile Asp Ile Thr Glu Leu Phe His Glu Val
145                 150                 155                 160
```

Thr Phe Gln Thr Glu Leu Gly Gln Leu Met Asp Leu Ile Thr Ala Pro
            165                 170                 175

Glu Asp Lys Val Asp Leu Ser Lys Phe Ser Leu Lys Lys His Ser Phe
        180                 185                 190

Ile Val Thr Phe Lys Thr Ala Tyr Tyr Ser Phe Tyr Leu Pro Val Ala
            195                 200                 205

Leu Ala Met Tyr Val Ala Gly Ile Thr Asp Glu Lys Asp Leu Lys Gln
        210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
            245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
        290                 295                 300

Leu Lys Ile Glu Gln Leu Tyr His Glu Tyr Glu Ser Ile Ala Lys
305                 310                 315                 320

Asp Leu Lys Ala Lys Ile Ser Gln Val Asp Glu Ser Arg Gly Phe Lys
            325                 330                 335

Ala Asp Val Leu Thr Ala Phe Leu Asn Lys Val Tyr Lys Arg Ser Lys
            340                 345                 350

<210> SEQ ID NO 88
<211> LENGTH: 299
<212> TYPE: PRT
<213> ORGANISM: Saccharomyces cerevisiae

<400> SEQUENCE: 88

Met Asp Phe Pro Gln Gln Leu Glu Ala Cys Val Lys Gln Ala Asn Gln
1               5                   10                  15

Ala Leu Ser Arg Phe Ile Ala Pro Leu Pro Phe Gln Asn Thr Pro Val
            20                  25                  30

Val Glu Thr Met Gln Tyr Gly Ala Leu Leu Gly Gly Lys Arg Leu Arg
        35                  40                  45

Pro Phe Leu Val Tyr Ala Thr Gly His Met Phe Gly Val Ser Thr Asn
    50                  55                  60

Thr Leu Asp Ala Pro Ala Ala Val Glu Cys Ile His Ala Tyr Ser
65                  70                  75                  80

Leu Ile His Asp Asp Leu Pro Ala Met Asp Asp Asp Leu Arg Arg
            85                  90                  95

Gly Leu Pro Thr Cys His Val Lys Phe Gly Glu Ala Asn Ala Ile Leu
            100                 105                 110

Ala Gly Asp Ala Leu Gln Thr Leu Ala Phe Ser Ile Leu Ser Asp Ala
        115                 120                 125

Asp Met Pro Glu Val Ser Asp Arg Asp Arg Ile Ser Met Ile Ser Glu
    130                 135                 140

Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
            165                 170                 175

Ile His Arg His Lys Thr Gly Ala Leu Ile Arg Ala Ala Val Arg Leu
            180                 185                 190

-continued

```
Gly Ala Leu Ser Ala Gly Asp Lys Gly Arg Arg Ala Leu Pro Val Leu
        195             200             205

Asp Lys Tyr Ala Glu Ser Ile Gly Leu Ala Phe Gln Val Gln Asp Asp
    210             215             220

Ile Leu Asp Val Val Gly Asp Thr Ala Thr Leu Gly Lys Arg Gln Gly
225             230             235             240

Ala Asp Gln Gln Leu Gly Lys Ser Thr Tyr Pro Ala Leu Leu Gly Leu
            245             250             255

Glu Gln Ala Arg Lys Lys Ala Arg Asp Leu Ile Asp Asp Ala Arg Gln
            260             265             270

Ser Leu Lys Gln Leu Ala Glu Gln Ser Leu Asp Thr Ser Ala Leu Glu
        275             280             285

Ala Leu Ala Asp Tyr Ile Ile Gln Arg Asn Lys
        290             295
```